(12) United States Patent
Ohkawa et al.

(10) Patent No.: US 7,456,162 B2
(45) Date of Patent: Nov. 25, 2008

(54) BENZOFURAN DERIVATIVES, THEIR PRODUCTION AND USE

(75) Inventors: Shigenori Ohkawa, Takatsuki (JP); Yasuyoshi Arikawa, Hirakata (JP); Kouki Kato, Kobe (JP); Masahiro Okura, Ikeda (JP); Masaki Setoh, Suita (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 627 days.

(21) Appl. No.: 11/081,615

(22) Filed: Mar. 17, 2005

(65) Prior Publication Data

US 2005/0187238 A1 Aug. 25, 2005

Related U.S. Application Data

(62) Division of application No. 10/120,102, filed on Apr. 11, 2002, now Pat. No. 7,101,867, which is a division of application No. 09/857,293, filed as application No. PCT/JP99/06764 on Dec. 2, 1999, now Pat. No. 6,479,536.

(30) Foreign Application Priority Data

Dec. 4, 1998 (JP) .............................. 1998/345355
Dec. 4, 1998 (JP) .............................. 1998/345365

(51) Int. Cl.
  *A61K 31/33* (2006.01)
  *C07D 405/00* (2006.01)
  *C07D 411/00* (2006.01)
  *C07D 209/00* (2006.01)

(52) U.S. Cl. ................... 514/183; 549/467; 549/469; 549/491; 548/454

(58) Field of Classification Search ........... 514/183, 514/416, 414, 469; 548/454; 549/469, 467, 549/491
See application file for complete search history.

(56) References Cited

U.S. PATENT DOCUMENTS

| 4,212,865 | A | 7/1980 | Scherrer et al. |
| 4,881,967 | A | 11/1989 | Semple |
| 5,266,707 | A | 11/1993 | Matsumoto et al. |
| 6,479,536 | B1 | 11/2002 | Ohkawa et al. |

FOREIGN PATENT DOCUMENTS

| EP | 0 483 772 | 5/1992 |
| EP | 539709 | 5/1993 |
| EP | 0 632 031 | 1/1995 |
| EP | 0 685 475 | 12/1995 |
| GB | 1 312 168 | 4/1973 |
| JP | 5-194466 | 8/1993 |
| JP | 9-124633 | 5/1997 |
| WO | 95/29907 | 11/1995 |
| WO | 98/08842 | 3/1998 |
| WO | 98/55454 | 12/1998 |

OTHER PUBLICATIONS

J. Aires-de-Sousa et al., "A New Enantioselective Synthesis of N-Arylaziridines by Phase-transfer Catalysis", Tetrahedron Letters, vol. 37, No. 18, pp. 3183-3186, 1996.
E. Taylor et al., "Molecular Determinants for Recognition of RU 24969 Analogs at Central 5-Hydroxytryptamine Recognition Sites: Use of a Bilinear Function and Substituent Volumes to Describe Steric Fit", Molecular Pharmacology, vol. 34, pp. 42-53.
Delagarza, Am. Fam. Physican vol. 68, No. 7, pp. 1365-1372, 2003.
Ken-ichiro Kataoka et al., "Potent Inhibitors of Acyl-CoA:Cholesterol Acyltransferase. 2. Structure-Activity Relationships of Novel N-(2,2-Dimethyl-2,3-dihydrobenzofuran-7-yl)amides", J. Med. Chem., vol. 39, No. 6, 1996, pp. 1262-1270.
Hideo Iida et al., "One Step Synthesis of 4-Aminodihydrobenzofurans and 4-Hydroxyindoles Via Dehydrogenation-Heteromercuration of 2-Allyl-3-Aminocyclohexenones Using Mercury (II) Acetate", Tetrahedron Letters, vol. 23, No. 35, 1982, pp. 3591-3594.

(Continued)

*Primary Examiner*—James O. Wilson
*Assistant Examiner*—Paul V. Ward
(74) *Attorney, Agent, or Firm*—Wenderoth, Lind & Ponack, L.L.P.

(57) ABSTRACT

Compounds represented by the formula:

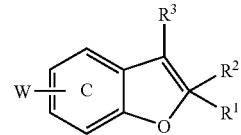

(1)

wherein $R^1$ and $R^2$ are hydrogen atom, a hydrocarbon group or a heterocyclic group, or $R^1$ and $R^2$ may form, together with the adjacent carbon atom, a 3- to 8-membered homocyclic or heterocyclic ring, W indicates a group represented by the formula:

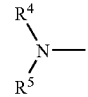

(Wb)

wherein $R^4$ indicates (1) an aliphatic hydrocarbon group, which may be substituted with an aromatic group, or (2) an acyl group containing an aromatic group, $R^5$ is hydrogen atom, a $C_{1-6}$ alkyl, or an acyl group, $R^3$ indicates a $C_{6-14}$ aryl group, or salts thereof. The compounds have an excellent action to inhibit neurodegeneration as well as an excellent brain penetrability and are low in the toxicity, thereby being useful as drugs for nerve degenerative diseases.

20 Claims, No Drawings

OTHER PUBLICATIONS

Cecil's Textbook of Medicine, vol. 2, 20th Edition, pp. 1992-1996, 1996.

Coyle et al., Science, vol. 219, pp. 1184-1190, 1983.

PubMed Abstract, 15106838, also cited as Neuroreport. 15/1, 95-8, 2004.

PubMed Abstract 14739562, also cited as Neurosignals, 12/6, 315-24, 2003.

PubMed Abstract 14724376, also cited as Neurocytol. 32/4, 329-43, 2003.

PubMed Abstract 11394871, also cited as Biochem. Biophysics res. Communic. 284/2, 261-7, 2001.

PubMed Abstract 14964575, also cited as Intern Med. 43/1, 18-29, 2004.

PubMed Abstract 15134572, also cited as Curr. Pharm. Des. 10/13, 1505-17, 2004.

PubMed Abstract 14754384, also cited as Curr. Pharm. Des. 10/3, 231-51, 2004.

Chemical Abstract DN 119:117092, also cited as EP 539709.

BENZOFURAN DERIVATIVES, THEIR PRODUCTION AND USE

This application is a divisional of Ser. No. 10/120,102 filed Apr. 11, 2002 now U.S. Pat. No. 7,101,867, which is a divisional of Ser. No. 09/857,293 filed Jun. 1, 2001, now U.S. Pat. No. 6,479,536 which is a 371 of PCT/JP99/06764 filed Dec. 2, 1999.

TECHNICAL FIELD

The present invention relates to novel benzofuran derivatives, their production, and pharmaceutical compositions containing them. More specifically, it relates to compounds having excellent pharmacological activities such as a neurotrophic factor-like activity, a neurotrophic factor activity-enhancing activity, a neurodegeneration inhibitory activity, a β-amyloid toxicity inhibitory activity and the like, and are effective as prophylactic and therapeutic drugs for neurodegenerative diseases and the like.

BACKGROUND ART

Neurodegenerative diseases are progressive diseases to cause destructive injuries such as the nerve cell death. As principal neurodegenerative diseases, there have been known central nervous diseases such as Alzheimer's disease, Parkinson's disease, amyotrophic lateral sclerosis (ALS), Hantington's disease, and the like and peripheral neuropathies such as typically diabetic neuropathy. Many of them relate to aging and, in fact, the onset increases with aging, whereas there is a case in which the onset begins even at a middle age and further at a younger age.

As a result of studies on the structure and function of brains, the roles of neurotransmitters and neurotrophic factors and so on have been gradually elucidated, but many parts of the causes of neurodegeneration are still unknown. Only for Parkinson's disease, the relation between it and a specific neurotransmitter, namely dopamine, has been clarified, whereby L-dopa that is the precursor of dopamine has been used as a drug for reducing the nervous symptoms and for recovering the function. However, L-dopa does not suppress the progress of neurodegeneration, and the effect of L-dopa is gradually lost with a progress of the disease condition, namely the degeneration and deficiency of dopamine-based nerve cells. Also, Alzheimer's disease is a disease that is caused by the degeneration and deficiency of a variety of nerve cells such as acetylcholine-based nerve cells, monoamine-based nerve cells, and the like and, as for the drugs therefor, cholinesterase inhibitors have been marketed or under development. Nevertheless, like L-dopa for Parkinson's disease, they are still within the region of symptomatic therapy to improve the nerve symptoms temporarily.

Thus, there has not been reported up to the present time any drug that protects nerve cells from the toxicity of factors causing cell death thereby suppressing the progress of neurodegenerative diseases including Alzheimer's disease and Parkinson's disease.

Moreover, it is said that the cell death in neurodegenerative diseases is caused by the toxicity of the factors that are intrinsic to the respective diseases and, for example, in Alzheimer's disease, the endogenous β-amyloid is considered to be a factor to cause the cell death. β-Amyloid is a protein constituting the senile plaque, which is a neuropathological characteristic to be seen in brain of a patient suffering from Alzheimer's disease, and is composed of 40 to 43 amino acids. It has been elucidated that the addition of this β-amyloid to a primary culture of hippocampus nerve cell causes nerve cell death [Science, Vol. 245, pp. 417-420 (1989)] and, also, it has been shown that the coagulation of β-amyloid is indispensable for the expression of its toxicity and the like [Neurobiology of Aging, Vol. 13, pp. 587-590 (1992) and Journal of Molecular Biology, Vol. 218, pp. 149-163 (1991)]. For toxicity expression mechanism of β-amyloid, there have been conceived that 1) β-amyloid forms an ion channel to allow an inflow of calcium ions, 2) β-amyloid accelerates generation of free radicals, 3) β-amyloid activates tau protein kinase I (TPK-I) to promote the phosphorylation of tau, 4) β-amyloid activates the microglia, from which the neurotoxin is secreted, and the like.

Recently, it has been elucidated that neurotrophic factors such as IGF-1 (insulin-like growth factor), NGF (nerve growth factor), and the like inhibit the apoptosis of nerve cells by β-amyloid and the like, and that, as the mechanism thereof, inhibition of TPK-I/GSK-3β (glycogen synthetase kinase 3) by activation of PI-3 kinase is concerned in the apoptosis inhibition [Journal of Neuroscience (J. Neurosci.), Vol. 11, pp. 2552-2563 (1991), Science, Vol. 267, pp. 2003-2005 (1995), and The Journal of Biological Chemistry (J. Biol. Chem.), Vol. 272, 154-161 (1997)]. When PI-3 kinase is inhibited by β-amyloid and TPK-I/GSK-3β is activated, pyruvate dehydrogenase (PDH) is inhibited, thereby affecting the synthetic reaction system of acetylcholine to lower the content of acetylcholine. This fact agrees with an observation that the content of acetylcholine is lowered in brain of a patient suffering from Alzheimer's disease. On the contrary, it is expected that the activation of PI-3 kinase results in not only the prevention of nerve cell death but also an increase in the content of acetylcholine in brain, thereby improving the nerve symptoms. In addition, it can be expected that inhibition of TPK-I/GSK-3β increases the intracerebral glucose utilization, which is lowered in Alzheimer's disease [The Journal of Biological Chemistry (J. Biol. Chem.), Vol. 269, 3568-3573 (1994) and Endocrinology, Vol. 125, pp. 314-320 (1989)].

Further, the following compounds have been reported as compounds having a fused nitrogen-containing heterocyclic group on benzene ring that is fuzed with furan ring or dihydrofuran ring.

1) As compounds having an inhibitory activity of bone resorption and bone metabolism, compounds that are represented by the formula:

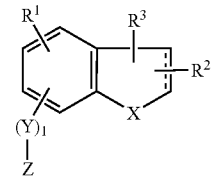

wherein $R^1$ is hydrogen, lower alkyl, acyl, amino, acylamino, nitro, halogen or hydroxy-lower alkyl that may have one or more appropriate substituents;

$R^2$ is hydrogen, lower alkyl, acyl, lower alkoxy, acyl-lower alkyl, aryl, cyano, mono- (or di- or tri-) halo-lower alkyl, lower alkylthio or hydroxy-lower alkyl that may have one or more appropriate substituents;

$R^3$ is hydrogen, lower alkyl, lower alkenyl, cyclo lower alkyl-lower alkyl, halogen, acyl, acyl-lower alkyl, acylamino, acylamino-lower alkyl, acyl-lower alkenyl, acyloxy-lower alkyl, acyl-lower alkylthio-lower alkyl, amino-lower alkyl, mono- (or di-) lower alkylamino, lower alkylthio-lower alkyl, hydroxyimino-lower alkyl that may have one or more appropriate substituents, hydroxy-lower alkyl that may have one or more appropriate substituents, hydroxy-lower alkylthio-lower alkyl, cyano-lower alkyl, mono- (or di-) lower alkoxyower alkyl that may have one or more appropriate substituents, lower alkyl substituted with aryl that may have one or more appropriate substituents, mono- (or di-) lower alkylamino-lower alkyl, lower alkyl substituted with a heterocyclic group that may have one or more appropriate substituents, a heterocyclic group that may have one or more appropriate substituents, heterocyclic thio, heterocyclic thio-lower alkyl, heterocyclic oxy, heterocyclic oxy-lower alkyl, heterocyclic aminoimino-lower alkyl, aryl, amino or nitro;

$R^2$ and $R^3$ may be combined each other to form a group of (1) lower alkylene that may have one or more appropriate substituents, (2) lower alkenylene that may have one or more appropriate substituents, or (3) the formula: $-(A^1)_m-W-(A^2)_n-$, wherein each of $A^1$ and $A^2$ is lower alkylene that may have one or more appropriate substituents or lower alkenylene that may have one or more appropriate substituents, W is —S—, —S(O)— or —N($R^5$)— (wherein $R^5$ is hydrogen, lower alkyl or acyl), and each of m and n is an integer of 0 or 1;

X is O or S, Y is vinylene or a group represented by the formula: —NHCO—, —NHSO$_2$—, —OCO—, —OCH$_2$—, —NHCOCO—, —NHCOCH=CH—, —NHCOCH$_2$—, —NHCONH— or —N($R^6$)CO— (wherein $R^6$ is lower alkyl); Z is a heterocyclic group that may have one or more appropriate substituents or aryl that may have one or more appropriate substituents; l is an integer of 0 or 1; and ----represents a single bond or a double bond, and pharmaceutically acceptable salts thereof, and specifically,

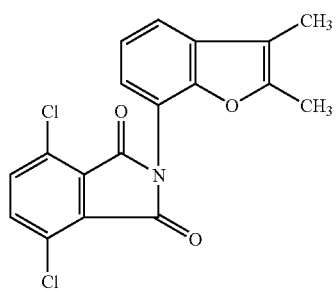

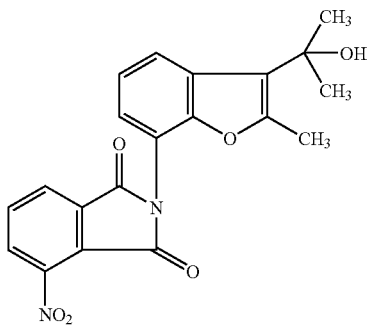

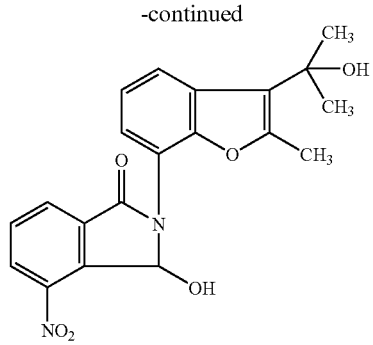

(WO 95/29907 and JP 9-512795 A).

2) As compounds having an inhibitory activity of lipid peroxide formation, 3,5-dihydroxyheptanoic acid derivatives represented by the formula:

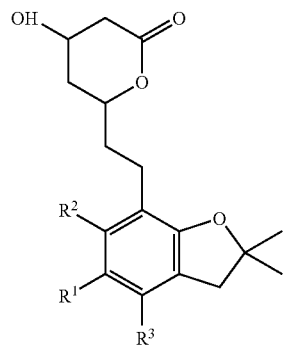

wherein $R^1$ is hydrogen, nitro, a group represented by —N($R^4$)$R^5$, wherein each of $R^4$ and $R^5$ is hydrogen, lower alkyl, lower alkenyl, aryl, aralkyl, acyl, aroyl, substituted or unsubstituted carbamoyl or substituted or unsubstituted thiocarbamoyl, or $R^4$ and $R^5$ together may form cyclic amino; each of $R^2$ and $R^3$ is hydrogen or lower alkyl], and 3,5-dihydroxyheptanoic acid derivatives represented by the formula:

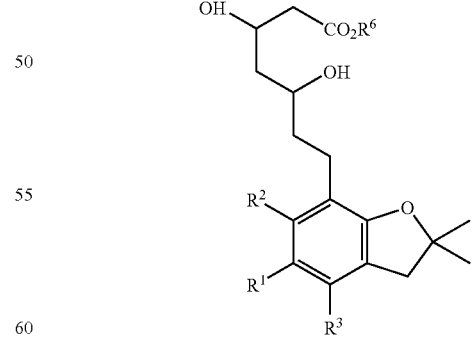

wherein $R^1$ is hydrogen, nitro, a group represented by —N($R^4$)$R^5$, wherein each of $R^4$ and $R^5$ is hydrogen, lower alkyl, lower alkenyl, aryl, aralkyl, acyl, aroyl, substituted or unsubstituted carbamoyl or substituted or unsubstituted thiocarbamoyl group, or $R^4$ and $R^5$ together may form cyclic amino; each of $R^2$ and $R^3$ is hydrogen or lower alkyl; $R^6$ is hydrogen, lower alkyl, alkali metal or alkaline earth metal (JP 5-194466 A).

3) As herbicides, compounds represented by the formula:

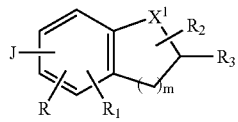

wherein R is H, Cl, F, $C_1$-$C_2$ alkyl or $C_1$-$C_2$ alkoxy; $R_1$ is H, F, Cl, Br, $CH_3$, $OCH_3$, CN, $CF_3$, $OCF_3$ or $OCF_2H$; $X^1$ is O; $R_2$ is H, $CH_3$ or $CH_2CH_3$; $R_3$ is H, $C_1$-$C_4$ haloalkyl, $CR_2R_7CN$, CN, $CR_2R_4R_7$, COCl, $COR_4$, $C(NOR_6)R_2$, $CO_2R_4$, $CONR_4R_2$, $CHR_2OH$, $CO_2(CH_2)_2Si(CH_3)_3$, $CONR_2SO_2CH_3$, $CHR_2CO_2R_4$, $CONHCH(CH_3)CONHCH(CH_3)CO_2CH_3$, $CHR_2COR_4$, $CHR_2OSO_2(C_1$-$C_4$ alkyl), $CHR_2OC(O)R_4$, $CHR_2OC(O)N(R_2)_2$, $CHR_2OC(O)N(R_2)OCH_3$, $CHR_2OC(O)N(R_2)Ph$, $HC=CH_2$ or $C\equiv CH$; $R_4$ is H, $C_1$-$C_4$ alkyl, $C_1$-$C_4$ haloalkyl, $C_2$-$C_6$ alkenyl, $C_3$-$C_6$ alkynyl, $C_2$-$C_4$ haloalkenyl, phenyl, $C_1$-$C_4$ alkylphenyl, $C_3$-$C_6$ alkoxycarbonylalkyl or $(CH_2CH_2O)_bR_2$; b is 1 to 6; m is 1, n is 1 or 2; J is

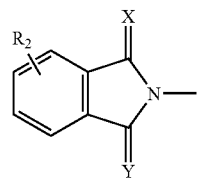

(wherein X and Y are O or S, respectively), etc. (U.S. Pat. No. 4,881,967).

4) As compounds having an antibacterial activity, compounds represented by the formula:

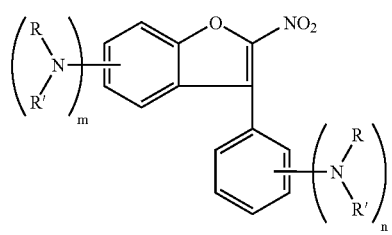

wherein each of m and n is 0 or 1 and the sum of m and n is 1; R is hydrogen or lower alkyl; R' is R,

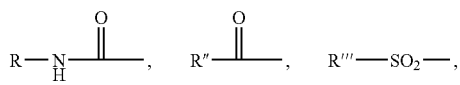

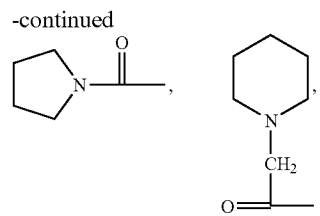

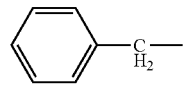

or R and R' together form $(CH_3)_2N-N=$,

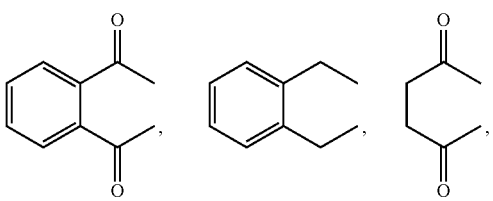

or form pyrrole or pyrrolidine; R" is R, lower alkyl, $CF_3-$, or $ClCH_2-$; and R''' is lower alkyl or $CF_3-$, or pharmacologically acceptable salts thereof (U.S. Pat. No. 4,212,865).

5) A compound that is a synthetic intermediate and is represented by the formula:

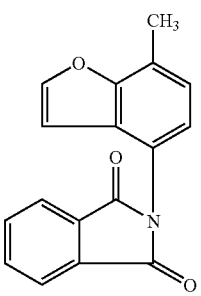

[Tetrahedron Letters, Vol. 37, No. 51, pp. 9183-9186 (1996)].

6) As compounds having an inhibitory activity of lipid peroxide formation, compounds represented by the formula:

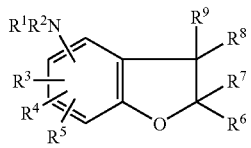

wherein $R^1$ and $R^2$ are the same or different and each is hydrogen, acyl, alkoxycarbonyl, or an aliphatic or aromatic group which respectively may be substituted; $R^3$, $R^4$, and $R^5$ are the same or different and each is hydroxyl that may be acylated, or amino, alkoxy or an aliphatic group, which respectively may be substituted, or two of $R^3$, $R^4$, and $R^5$ may form a carbon homocyclic ring that may be substituted; $R^6$ and $R^7$ are the same or different and each is an aliphatic group that may be substituted, and at least one of $R^6$ and $R^7$ has methylene at the a position; and $R^8$ and $R^9$ are the same or different and each is hydrogen, or an aliphatic or aromatic group, which respectively may be substituted, or salts thereof (EP-A-483772 and JP 5-140142 A).

7) As compounds having bone resorption inhibitory activity, compounds represented by the formula:

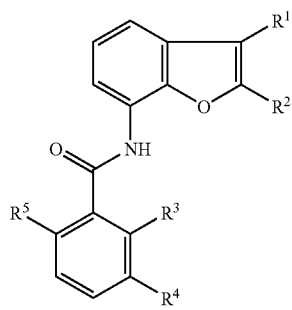

wherein $R^1$ is formyl, carbamoyl-lower alkyl, thiomorpholinocarbonyl-lower alkyl, thiomorpholinocarbonyl-lower alkyl S-oxide, pyridylaminocarbonyl-lower alkyl, pyrazolylaminocarbonyl-lower alkyl, triazolylaminocarbonyl-lower alkyl, quinolylaminocarbonyl-lower alkyl that may have one or more appropriate substituents, 3-pyridyl-lower alkylaminocarbonyl-lower alkyl, 4-pyridyl-lower alkylaminocarbonyl-lower alkyl, pyridylethylaminocarbonyl-lower alkyl, pyridyl-lower alkylaminocarbonyl-lower alkyl N-oxide, benzimidazolyl-lower alkylaminocarbonyl-lower alkyl, N-pyridyl-lower alkyl-N-acyl-lower alkylaminocarbonyl-lower alkyl, N-pyridyl-N-lower alkylaminocarbonyl-lower alkyl, lower alkylaminocarbonyl-lower alkyl, di-lower alkylaminocarbonylmethyl, quinolyl, 2-hydroxyethyl, 2-hydroxy-2-methylpropyl, cyano-lower alkyl, di-lower alkylamino-lower alkyl, pyridyl-lower alkyl, triazolyl-lower alkyl, pyrazolyl-lower alkyl that may have one or more appropriate substituents, pyrimidinyl-lower alkyl that may have one or more appropriate substituents, dihydrophthalazinyl-lower alkyl that may have one or more appropriate substituents, oxadiazolyl-lower alkyl that may have one or more appropriate substituents, heterocyclic-lower alkenyl that may have one or more appropriate substituents, lower alkoxyower alkylamino-lower alkyl that may have one or more appropriate substituents, aryl-lower alkylaminocarbonyl-lower alkyl that may have one or more appropriate substituents, arylaminocarbonyl-lower alkyl that may have one or more appropriate substituents, arylthio-lower alkyl that may have one or more appropriate substituents, lower alkyl or an imidazolyl-lower alkyl; $R^2$ is lower alkyl, protected carboxyl or cyano; $R^3$ is halogen or lower alkyl; $R^4$ is hydrogen, nitro or amino; and $R^5$ is halogen, lower alkyl or nitro; provided that, 1) when $R^1$ is methyl, $R^2$ is protected carboxyl or cyano and, 2) when $R^1$ is imidazolylmethyl, $R^2$ is protected carboxyl or cyano, or salts thereof (JP 9-124633 A).

8) As compounds having sodium channel regulating activity, compounds represented by the formula:

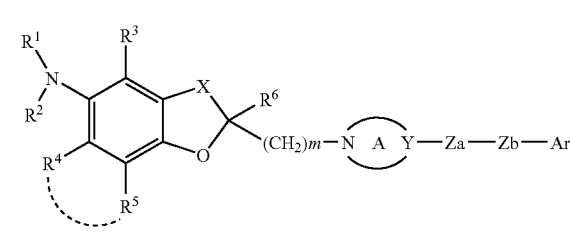

wherein each of $R^1$ and $R^2$ is hydrogen atom, lower alkyl that may be substituted or acyl;

each of $R^3$, $R^4$ and $R^5$ is lower alkyl that may be substituted or lower alkoxy that may be substituted, or $R^4$ and $R^5$ together may form a 5- or 6-membered homocyclic ring;

$R^6$ is lower alkyl;

Ar is an aromatic group that may be substituted;

ring A is a 5- to 8-membered nitrogen-containing heterocyclic ring that may be substituted;

X is a lower alkylene that may have substituents;

Y is carbon atom or nitrogen atom;

Za is a group represented by $CH_2$, $COCH(R^7)$, $OCH(R^7)$, $SCH(R^7)$, or $N(R^{10})CH(R^7)$ (wherein $R^7$ is hydrogen atom or an aromatic group that may be substituted; and $R^{10}$ is hydrogen, a hydrocarbon group that may be substituted, or acyl); Zb is a bivalent aliphatic hydrocarbon group which may have a binding bond or a substituent and may be bonded through oxygen atom, nitrogen atom or sulfur atom; and m is an integer of 1 to 3, or salts thereof (WO 98/08842).

Low-molecular weight compounds, which are excellent in intracerebral permeability and have a neurotrophic factor-like activity and a neurotrophic factor-enhancing activity, are considered to be capable of inhibiting nerve cell death in neurodegenerative diseases such as Alzheimer's disease and the like as well as of improving the symptoms. Then, it has been desired to develop compounds which have a neurotrophic factor-like activity and/or a neurotrophic factor-enhancing activity and, furthermore have excellent pharmacological activities such as a protecting activity of nerve cells by inhibiting cytotoxicity of β-amyloid, or a protecting activity of nerve cells from toxicity of a factor causing nerve cell death, and the like, thereby being useful for pharmaceuticals such as prophylactic and therapeutic drugs of neurodegenerative diseases, and the like.

DISCLOSURE OF THE INVENTION

As a result of intensive studies, the present inventors have synthesized for the first time novel compounds represented by the formula:

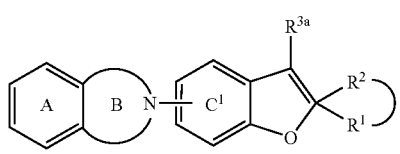

(Ia)

wherein $R^1$ and $R^2$ are the same or different and each is hydrogen atom, a hydrocarbon group that may be substituted or a heterocyclic group that may be substituted, or $R^1$ and $R^2$ may form, together with the adjacent carbon atom, a 3- to 8-membered homocyclic or heterocyclic ring that may be substituted;

$R^{3a}$ is hydrogen atom, a hydrocarbon group that may be substituted or a heterocyclic group that may be substituted;

-----is a single bond or a double bond;

ring A is benzene ring that may be substituted;

ring B is a 5- to 7-membered nitrogen-containing heterocyclic ring which may be substituted with halogen or a hydrocarbon group that may be substituted, ring $C^1$ is benzene ring which may be substituted with halogen, lower alkyl that may be halogenated, lower alkoxy that may be halogenated and lower alkylthio that may be halogenated, in addition to the group represented by the formula:

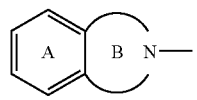

(wherein each symbol is as defined above), or salts thereof [hereinafter, sometimes, abbreviated as compounds (Ia)]. These compounds have a chemical structural characteristic in that the benzene ring condensed with the furan or dihydrofuran ring is substituted with the group represented by the formula:

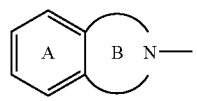

(each symbol is as defined above).

Further, unexpectedly, the present inventors have found that the compounds (Ia) have, on the basis of the specific chemical structure thereof, excellent pharmacological activities such as a neurotrophic factor-like activity, a neurotrophic factor enhancing activity, an inhibitory activity of cytotoxicity of β-amyloid, etc. The present inventors have also found that compounds including compounds (Ia) and represented by the formula:

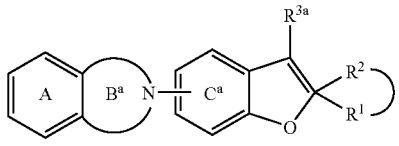

(Ia')

wherein $R^1$ and $R^2$ are the same or different and each is hydrogen atom, a hydrocarbon group that may be substituted or a heterocyclic group that may be substituted, or $R^1$ and $R^2$ may form, together with the adjacent carbon atom, a 3- to 8-membered homocyclic or heterocyclic ring that may be substituted;

$R^{3a}$ is hydrogen atom, a hydrocarbon group that may be substituted or a heterocyclic group that may be substituted;

-----is a single bond or a double bond;

ring A is benzene ring that may be substituted;

ring $B^a$ indicates a 5- to 7-membered heterocyclic ring that may be substituted;

ring $C^a$ is benzene ring that may be substituted in addition to the group represented by the formula:

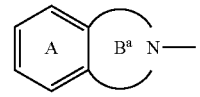

(wherein each symbol is as defined above), or salts thereof [hereinafter, sometimes, abbreviated as compounds (Ia')] have, on the basis of the specific chemical structure of the substituent on ring $C^a$,

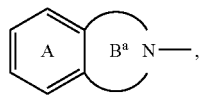

a neurotrophic factor-like activity, a neurotrophic factor enhancing activity, an inhibitory activity of cytotoxicity of β-amyloid, etc. and, further that these compounds (Ia) and compounds (Ia') have extremely low toxicity, are excellent in the brain penetrability and have an inhibitory activity of neurodegeneration, etc., thereby being fully satisfactory as pharmaceuticals.

Moreover, the present inventors have synthesized for the first time novel compounds represented by the formula:

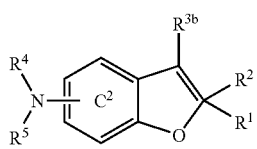

(Ib)

wherein $R^1$ and $R^2$ are the same or different and each is hydrogen atom, a hydrocarbon group that may be substituted or a heterocyclic group that may be substituted, or $R^1$ and $R^2$ may form, together with the adjacent carbon atom, a 3- to 8-membered homocyclic or heterocyclic ring that may be substituted;

$R^{3b}$ is $C_{6-14}$ aryl that may be substituted;

$R^4$ is (1) an aliphatic hydrocarbon group which may be substituted with an aromatic group that may be substituted and, further, may be substituted, or (2) acyl containing an aromatic group that may be substituted;

$R^5$ is hydrogen atom, $C_{1-6}$ alkyl or acyl;

----- indicates a single bond or a double bond;

ring $C^2$ is benzene ring that may be substituted in addition to a group represented by formula —$NR^4(R^5)$ (wherein each symbol is as defined above), or salts thereof [hereinafter, sometimes, abbreviated as compounds (Ib)]. These compounds have a chemical structural characteristic in that the benzene ring condensed with the furan or dihydrofuran ring is substituted with the group represented by formula —$NR^4(R^5)$ (wherein $R^4$ is a group containing aromatic ring) and, further, the benzofuran or dihydrofuran ring is substituted with an aryl group at the 3-position thereof.

Unexpectedly, the present inventors have further found that the thus-obtained compounds (Ib) have, on the basis of the specific chemical structure thereof, excellent pharmaceutical activities such as a neurotrophic factor-like activity, a neurotrophic factor enhancing activity, an inhibitory activity of cytotoxicity of β-amyloid, etc. and, further that these compounds have extremely low toxicity, are excellent in the brain penetrability and have an inhibitory activity of neurodegeneration, etc., thereby being fully satisfactory as pharmaceuticals.

The present inventors have further studied on the basis of these findings. As a result, the present invention has been completed. That is, the present invention provides:

1. A compound represented by the formula:

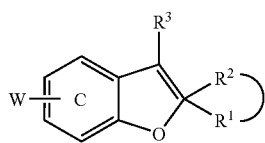

wherein $R^1$ and $R^2$ are the same or different and each is hydrogen atom, a hydrocarbon group that may be substituted or a heterocyclic group that may be substituted, or $R^1$ and $R^2$ may form, together with the adjacent carbon atom, a 3- to 8-membered homocyclic or heterocyclic ring that may be substituted

----- is a single bond or a double bond;

W is (i) a group represented by the formula:

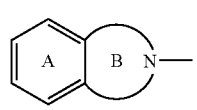

wherein ring A is benzene ring that may be substituted and ring B is a 5- to 7-membered nitrogen-containing heterocyclic ring which may be substituted with halogen or a hydrocarbon group that may be substituted, or (ii) a group represented by the formula:

wherein $R^4$ is (1) an aliphatic hydrocarbon group which is substituted with an aromatic group that may be substituted and, said, may further be substituted or (2) an acyl group containing an aromatic group that may be substituted; $R^5$ is hydrogen atom, a $C_{1-6}$ alkyl group, or an acyl group] and, when W is Wa, $R^3$ is hydrogen atom, a hydrocarbon group that may be substituted, or a heterocyclic group that may be substituted and ring C is benzene ring that may be substituted with substituent(s) selected from halogen, lower alkyl that may be halogenated, lower alkoxy that may be halogenated and lower alkylthio that may be halogenated, in addition to the group represented by Wa, and, when W is Wb, $R^3$ is a $C_{6-14}$ aryl group that may be substituted and ring C is benzene ring that may further be substituted, in addition to the group represented by Wb, provided that, when

----- is a double bond, the partial structure:

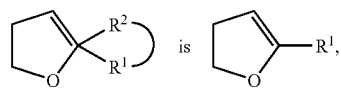

or a salt thereof;

2. A compound represented by the formula:

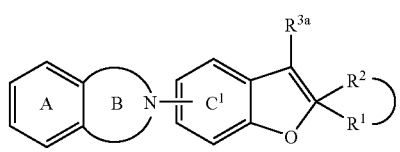

wherein $R^1$ and $R^2$ are the same or different and each is hydrogen atom, a hydrocarbon group that may be substituted or a heterocyclic group that may be substituted, or $R^1$ and $R^2$ may form, together with the adjacent carbon atom, a 3- to 8-membered homocyclic or heterocyclic ring that may be substituted;

$R^{3a}$ is hydrogen atom, a hydrocarbon group that may be substituted or a heterocyclic group that may be substituted;

----- is a single bond or a double bond;

ring A is benzene ring that may be substituted, ring B is a 5- to 7-membered nitrogen containing heterocyclic ring which may be substituted with halogen or a hydrocarbon group that may be substituted;

ring $C^1$ is benzene ring that may further be substituted with a substituent selected from halogen, lower alkyl that may be halogenated, lower alkoxy that may be halogenated and lower alkylthio that may be halogenated, in addition to the group represented by the formula:

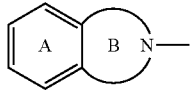

(wherein each symbol is as defined above), provided that, when

----- is a double bond, the partial structure:

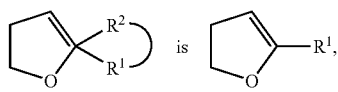

or a salt thereof;

3. A compound represented by the formula:

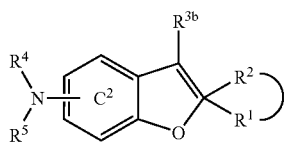

wherein $R^1$ and $R^2$ are the same or different and each is hydrogen atom, a hydrocarbon group that may be substituted or a heterocyclic group that may be substituted, or $R^1$ and $R^2$ may form, together with the adjacent carbon atom, a 3- to 8-membered homocyclic or heterocyclic ring that may be substituted;

$R^{3b}$ is a $C_{6-14}$ aryl group that may be substituted;
$R^4$ is (1) an aliphatic hydrocarbon group which is substituted with an aromatic group that may be substituted and, may further be substituted, or (2) an acyl group containing an aromatic group that may be substituted;

$R^5$ is hydrogen atom, a $C_{1-6}$ alkyl group, or an acyl group;

----- is a single bond or a double bond;
ring $C^2$ is benzene ring that may further be substituted, in addition to the group represented by $-NR^4(R^5)$ (each symbol is as defined above),
provided that, when

----- is a double bond, the partial structure:

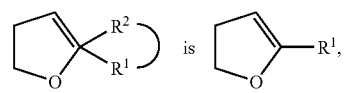

or a salt thereof;

4. The compound according to the above 1, wherein $R^1$ and $R^2$ are the same or different and each is (i) hydrogen atom, (ii) a $C_{1-6}$ alkyl group, a $C_{2-6}$ alkenyl group, a $C_{2-6}$ alkynyl group, a $C_{3-6}$ cycloalkyl group, or a $C_{6-14}$ aryl group, which respectively may have 1 to 5 substituents selected from (1) halogen, (2) $C_{1-3}$ alkylenedioxy, (3) nitro, (4) cyano, (5) $C_{1-6}$ alkyl that may be halogenated, (6) $C_{2-6}$ alkenyl that may be halogenated, (7) $C_{2-6}$ alkynyl that may be halogenated, (8) $C_{3-6}$ cycloalkyl that may be halogenated, (9) $C_{6-14}$ aryl, (10) $C_{1-6}$ alkoxy that may be halogenated, (11) $C_{1-6}$ alkylthio that may be halogenated or mercapto, (12) hydroxyl, (13) amino, (14) mono-$C_{1-6}$ alkylamino, (15) mono-$C_{6-14}$ arylamino, (16) di-$C_{1-6}$ alkylamino, (17) di-$C_{6-14}$ arylamino, (18) acyl selected from formyl, carboxyl, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5- or 6-membered heterocyclic carbonyl containing, in addition to carbon atom, 1 to 4 hetero atoms selected from nitrogen atom, sulfur atom and oxygen atom, mono-$C_{1-6}$ alkyl-carbamoyl, di-$C_{1-6}$ alkyl-carbamoyl, $C_{6-14}$ aryl-carbamoyl, thiocarbamoyl, 5- or 6-membered heterocyclic carbamoyl containing, in addition to carbon atom(s), 1 to 4 hetero atoms selected from nitrogen atom, sulfur atom and oxygen atom, $C_{1-6}$ alkylsulfonyl, $C_{6-14}$ arylsulfonyl, $C_{1-6}$ alkylsulfinyl, and $C_{6-14}$ arylsulfinyl, (19) acylamino selected from formylamino, $C_{1-6}$ alkyl-carboxamido, $C_{6-14}$ aryl-carboxamido, $C_{1-6}$ alkoxy-carboxamido, $C_{1-6}$ alkylsulfonylamino, and $C_{6-14}$ arylsulfonylamino, (20) acyloxy selected from $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-14}$ aryl-carbamoyloxy and nicotinoyloxy, (21) 5- to 7-membered saturated cyclic amino, which may have 1 to 3 substituents selected from $C_{1-6}$ alkyl, $C_{6-14}$ aryl, and 5- to 10-membered aromatic heterocyclic group containing, in addition to carbon atom(s), 1 to 4 hetero atoms selected from nitrogen atom, sulfur atom and oxygen atom, (22) 5- to 10-membered aromatic heterocyclic group containing, in addition to carbon atom(s), 1 to 4 hetero atoms selected from nitrogen atom, sulfur atom and oxygen atom, (23) sulfo, and (24) $C_{6-14}$ aryloxy, or (iii) 5- to 14-membered heterocyclic group containing, in addition to carbon atom, 1 to 4 hetero atoms selected from nitrogen atom, sulfur atom and oxygen atom, which respectively may have 1 to 5 substituents selected from (1) halogen, (2) $C_{1-3}$ alkylenedioxy, (3) nitro, (4) cyano, (5) $C_{1-6}$ alkyl that may be halogenated, (6) $C_{2-6}$ alkenyl that may be halogenated, (7) $C_{2-6}$ alkynyl that may be halogenated, (8) $C_{3-6}$ cycloalkyl that may be halogenated, (9) $C_{6-14}$ aryl, (10) $C_{1-6}$ alkoxy that may be halogenated, (11) $C_{1-6}$ alkylthio that may be halogenated or mercapto, (12) hydroxyl, (13) amino, (14) mono-$C_{1-6}$ alkylamino, (15) mono-$C_{6-14}$ arylamino, (16) di-$C_{1-6}$ alkylamino, (17) di-$C_{6-14}$ arylamino, (18) acyl selected from formyl, carboxyl, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5- or 6-membered heterocyclic carbonyl containing, in addition to carbon atom(s), 1 to 4 hetero atoms selected from nitrogen atom, sulfur atom and oxygen atom, mono-$C_{1-6}$ alkyl-carbamoyl, di-$C_{1-6}$ alkyl-carbamoyl, $C_{6-14}$ aryl-carbamoyl, thiocarbamoyl, 5- or 6-membered heterocyclic carbamoyl containing, in addition to carbon atom(s), 1 to 4 hetero atoms selected from nitrogen atom, sulfur atom and oxygen atom, $C_{1-6}$ alkylsulfonyl, $C_{6-14}$ arylsulfonyl, $C_{1-6}$ alkylsulfinyl and $C_{6-14}$ arylsulfinyl, (19) acylamino selected from formylamino, $C_{1-6}$ alkyl-carbonylamino, $C_{6-14}$ aryl-carbonylamino, $C_{1-6}$ alkoxy-carbonylamino, $C_{1-6}$ alkylsulfonylamino and $C_{6-14}$ arylsulfonylamino, (20) acyloxy selected from $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{1-14}$ arylcarbamoyloxy and nicotinoyloxy, (21) 5- to 7-membered saturated cyclic amino, which may have 1 to 3 substituents selected from $C_{1-6}$ alkyl, $C_{6-14}$ aryl and 5- to 10-membered aromatic heterocyclic group containing, in addition to carbon atom(s), 1 to 4 hetero atoms selected from nitrogen atom, sulfur atom and oxygen atom, (22) 5- to 10-membered aromatic heterocyclic group containing, in addition to carbon atom(s), 1 to 4 hetero atoms selected from nitrogen atom, sulfur atom and oxygen atom, (23) sulfo, and (24) a $C_{6-14}$ aryloxy, or (iv) $R^1$ and $R^2$ form, together with the adjacent carbon atom, $C_{3-8}$ cycloalkane or a 3- to 8-membered heterocyclic ring containing, in addition to carbon atom(s), 1 to 4 hetero atoms selected from nitrogen atom, sulfur atom and oxygen atom, which respectively may have 1 to 5 substituents selected from (1) halogen, (2) $C_{1-3}$ alkylenedioxy, (3) nitro, (4) cyano, (5) $C_{1-6}$ alkyl that may be halogenated, (6) $C_{2-6}$ alkenyl that may be halogenated, (7) $C_{2-6}$ alkynyl that may be halogenated, (8) $C_{3-6}$ cycloalkyl that may be halogenated, (9) $C_{6-14}$ aryl, (10) $C_{1-6}$ alkoxy that may be halogenated, (11) $C_{1-6}$ alkylthio that may be halogenated or mercapto, (12) hydroxyl, (13) amino, (14) mono-$C_{1-6}$ alkylamino, (15) mono-$C_{6-14}$ arylamino, (16) di-$C_{1-6}$ alkylamino, (17) di-$C_{6-14}$ arylamino, (18) acyl selected from formyl, carboxyl, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5- or 6-membered heterocyclic carbonyl containing, in addition to carbon atom, 1 to 4 heteroatoms selected from nitrogen atom, sulfur atom, and oxygen atom, mono-$C_{1-6}$ alkyl-carbamoyl, di-$C_{1-6}$ alkyl-carbamoyl, thiocarbamoyl, $C_{6-14}$ aryl-carbamoyl, 5- or 6-membered heterocyclic carbamoyl containing, in addition to carbon atom, 1 to 4 heteroatoms selected from nitrogen atom, sulfur atom and oxygen atom, $C_{1-6}$ alkylsulfonyl, $C_{6-14}$ arylsulfonyl, $C_{1-6}$ alkylsulfinyl, and $C_{6-14}$ arylsulfinyl, (19) acylamino selected from formylamino, $C_{1-6}$ alkylcarbonylamino, $C_{6-14}$ arylcarbonylamino, $C_{1-6}$ alkoxycarbonylamino, $C_{1-6}$ alkylsulfonylamino, and $C_{6-14}$ arylsulfonylamino, (20) acyloxy selected from $C_{1-6}$ alkylcarbonyloxy, $C_{6-14}$ arylcarbonyloxy, $C_{1-6}$ alkoxycarbonyloxy, mono-$C_{1-6}$ alkylcarbamoyloxy, di-$C_{1-6}$ alkylcarbamoyloxy, $C_{6-14}$ arylcarbamoyloxy and nicotinoyloxy, (21) 5- to 7-membered saturated-cyclic amino, which may have 1 to 3 substituents selected from a $C_{1-6}$ alkyl, $C_{6-14}$ aryl, and a 5- to 10-membered aromatic heterocyclic group containing, in addition to carbon atom, 1 to 4 hetero atoms selected from nitrogen atom, sulfur atom and oxygen atom, (22) a 5- to 10-membered aromatic heterocyclic group containing, in addition to carbon atom, 1 to 4 hetero atoms selected from nitrogen atom, sulfur atom, and oxygen atom, (23) sulfo, and (24) $C_{6-14}$ aryloxy;

(i) when W is Wa, $R^3$ is (i) hydrogen atom, (ii) a $C_{1-6}$ alkyl group, a $C_{2-6}$ alkenyl group, a $C_{2-6}$ alkynyl group, a $C_{3-6}$ cycloalkyl group or a $C_{6-14}$ aryl group which respectively may have 1 to 5 substituents selected from (1) halogen, (2) $C_{1-3}$ alkylenedioxy, (3) nitro, (4) cyano, (5) $C_{1-6}$ alkyl that may be halogenated, (6) $C_{2-6}$ alkenyl that may be halogenated, (7) $C_{2-6}$ alkynyl that may be halogenated, (8) $C_{3-6}$ cycloalkyl that may be halogenated, (9) $C_{6-14}$ aryl, (10) $C_{1-6}$ alkoxy that may be halogenated, (11) $C_{1-6}$ alkylthio that may be halogenated or mercapto, (12) hydroxyl, (13) amino, (14) mono-$C_{1-6}$ alkylamino, (15) mono-$C_{6-14}$ arylamino, (16) di-$C_{1-6}$ alkylamino, (17) di-$C_{6-14}$ arylamino, (18) acyl selected from formyl, carboxyl, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5- or 6-membered heterocyclic carbonyl containing, in addition to carbon atom, 1 to 4 heteroatoms selected from nitrogen atom, sulfur atom and oxygen atom, mono-$C_{1-6}$ alkyl-carbamoyl, di-$C_{1-6}$ alkyl-carbamoyl, $C_{6-14}$ aryl-carbamoyl, thiocarbamoyl, 5- or 6-membered, heterocyclic carbamoyl containing, in addition to carbon atom, 1 to 4 heteroatoms selected from nitrogen atom, sulfur atom and oxygen atom, $C_{1-6}$ alkylsulfonyl, $C_{6-14}$ arylsulfonyl, $C_{1-6}$ alkylsulfinyl and $C_{6-14}$ arylsulfinyl, (19) acylamino selected from formylamino, $C_{1-6}$ alkyl-carboxamido, $C_{6-14}$ aryl-carboxamido, $C_{1-6}$ alkoxy-carboxamido, $C_{1-6}$ alkylsulfonylamino and $C_{6-14}$ arylsulfonylamino, (20) acyloxy selected from $C_{1-6}$ alkyl-carbonyloxy, $C_{6-14}$ aryl-carbonyloxy, $C_{1-6}$ alkoxy-carbonyloxy, a mono-$C_{1-6}$ alkyl-carbamoyloxy, a di-$C_{1-6}$ alkyl-carbamoyloxy, $C_{6-14}$ aryl-carbamoyloxy and nicotinoyloxy, (21) 5- to 7-membered saturated-cyclic amino, which may have 1 to 3 substituents selected from $C_{1-6}$ alkyl, $C_{6-14}$ aryl, and a 5- to 10-membered aromatic heterocyclic group containing, in addition to carbon atom, 1 to 4 hetero atoms selected from nitrogen atom, sulfur atom and oxygen atom, (22) a 5- to 10-membered aromatic heterocyclic group containing, in addition to carbon atom, 1 to 4 hetero atoms selected from nitrogen atom, sulfur atom and oxygen atom, (23) sulfo, and (24) $C_{6-14}$ aryloxy; or (iii) a 5- to 14-membered heterocyclic group containng, in addition to carbon atom, 1 to 4 hetero atoms selected from nitrogen atom, sulfur atom and oxygen atom, which may have 1 to 5 substituents selected from (1) halogen, (2) $C_{1-3}$ alkylenedioxy, (3) nitro, (4) cyano, (5) $C_{1-6}$ alkyl that may be halogenated, (6) $C_{2-6}$ alkenyl that may be halogenated, (7) $C_{2-6}$ alkynyl that may be halogenated, (8) $C_{3-6}$ cycloalkyl that may be halogenated, (9) $C_{6-14}$ aryl, (10) $C_{1-6}$ alkoxy that may be halogenated, (11) $C_{1-6}$ alkylthio that may be halogenated or mercapto, (12) hydroxyl, (13) amino, (14) mono-$C_{1-6}$ alkylamino, (15) mono-$C_{6-14}$ arylamino, (16) di-$C_{1-6}$ alkylamino, (17) di-$C_{6-14}$ arylamino, (18) acyl selected from formyl, carboxyl, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5- or 6-membered heterocyclic carbonyl that contains, in addition to carbon atom, 1 to 4 hetero atoms selected from nitrogen atom, sulfur atom and oxygen atom, mono-$C_{1-6}$ alkyl-carbamoyl, di-$C_{1-6}$ alkyl-carbamoyl, $C_{6-14}$ aryl-carbamoyl, thiocarbamoyl, 5- or 6-membered heterocyclic carbamoyl that contains, in addition to carbon atom, 1 to 4 hetero atoms selected from nitrogen atom, sulfur atom and oxygen atom, $C_{1-6}$ alkylsulfonyl, $C_{6-14}$ arylsulfonyl, $C_{1-6}$ alkylsulfinyl and $C_{6-14}$ arylsulfinyl, (19) acylamino selected from formylamino, $C_{1-6}$ alkyl-carbonylamino, $C_{6-14}$ aryl-carbonylamino, $C_{1-6}$ alkoxy-carbonylamino, $C_{1-6}$ alkylsulfonylamino and $C_{6-14}$ arylsulfonylamino, (20) acyloxy selected from $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-14}$ aryl-carbamoyloxy and nicotinoyloxy, (21) 5- to 7-membered saturated-cyclic amino, which may have 1 to 3 substituents selected from $C_{1-6}$ alkyl, $C_{6-14}$ aryl, and a 5- to 10-membered aromatic heterocyclic group that contains, in addition to carbon atom, 1 to 4 hetero atoms selected from nitrogen atom, sulfur atom and oxygen atom, (22) a 5- to 10-membered aromatic heterocyclic group that contains, in addition to carbon atom, 1 to 4 hetero atoms selected from nitrogen atom, sulfur atom and oxygen atom, (23) sulfo, and (24) a $C_{6-14}$ aryloxy;

ring A is benzene ring, which respectively may have 1 to 5 substituents selected from (1) halogen, (2) $C_{1-3}$ alkylenedioxy, (3) nitro, (4) cyano, (5) $C_{1-6}$ alkyl that may be halogenated, (6) $C_{2-6}$ alkenyl that may be halogenated, (7) $C_{2-6}$ alkynyl that may be halogenated, (8) $C_{3-6}$ cycloalkyl that may be halogenated, (9) $C_{6-14}$ aryl, (10) $C_{1-6}$ alkoxy that may be halogenated, (11) $C_{1-6}$ alkylthio that may be halogenated or mercapto, (12) hydroxyl, (13) amino, (14) mono-$C_{1-6}$ alkylamino, (15) mono-$C_{6-14}$ arylamino, (16) di-$C_{1-6}$ alkylamino, (17) di-$C_{6-14}$ arylamino, (18) acyl selected from formyl, carboxyl, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5- or 6-membered heterocyclic carbonyl that contains, in addition to carbon atom, 1 to 4 hetero atoms selected from nitrogen atom, sulfur atom and oxygen atom, mono-$C_{1-6}$ alkyl-carbamoyl, di-$C_{1-6}$ alkyl-carbamoyl, $C_{6-14}$ aryl-carbamoyl, thiocarbamoyl, 5- or 6-membered, heterocyclic carbamoyl that contains, in addition to carbon atom, 1 to 4 hetero atoms selected from nitrogen atom, sulfur atom and oxygen atom, $C_{1-6}$ alkylsulfonyl, $C_{6-14}$ arylsulfonyl, $C_{1-6}$ alkylsulfinyl and $C_{6-14}$ arylsulfinyl, (19) acylamino selected from formylamino, $C_{1-6}$ alkylcarboxamido, $C_{6-14}$ arylcarboxamido, $C_{16}$ alkoxycarboxamido, $C_{1-6}$ alkylsulfonylamino and $C_{6-14}$ arylsulfonylamino, (20) acyloxy selected from $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-14}$ aryl-carbamoyloxy, and nicotinoyloxy, (21) 5- to 7-membered saturated-cyclic amino, which may have 1 to 3 substituents selected from $C_{1-6}$ alkyl, $C_{6-14}$ aryl and a 5- to 10-membered aromatic heterocyclic group that contains, in addition to carbon atom, 1 to 4 hetero atoms selected from nitrogen atom, sulfur atom and oxygen atom, (22) a 5- to 10-membered aromatic heterocyclic group that contains, in addition to carbon atom, 1 to 4 hetero atoms selected from nitrogen atom, sulfur atom and oxygen atom, (23) sulfo, and (24) a $C_{6-14}$ aryloxy;

ring B is a 5- to 7-membered nitrogen-containing heterocyclic ring that may be substituted with (i) halogen or (ii) a $C_{1-6}$ alkyl group, a $C_{2-6}$ alkenyl group, a $C_{2-6}$ alkynyl group, a $C_{3-6}$ cycloalkyl group, or a $C_{6-14}$ aryl group, which respectively may have 1 to 5 substituents selected from (1) halogen, (2) $C_{1-3}$ alkylenedioxy, (3) nitro, (4) cyano, (5) $C_{1-6}$ alkyl that may be halogenated, (6) $C_{2-6}$ alkenyl that may be halogenated, (7) $C_{2-6}$ alkynyl that may be halogenated, (8) $C_{3-6}$ cycloalkyl that may be halogenated, (9) $C_{6-14}$ aryl, (10) $C_{1-6}$ alkoxy that may be halogenated, (11) $C_{1-6}$ alkylthio that may be halogenated or mercapto, (12) hydroxyl, (13) amino, (14) mono-$C_{1-6}$ alkylamino, (15) mono-$C_{6-14}$ arylamino, (16) di-$C_{1-6}$ alkylamino, (17) di-$C_{6-14}$ arylamino, (18) acyl selected from formyl, carboxyl, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5- or 6-membered heterocyclic carbonyl that contains, in addition to carbon atom, 1 to 4 hetero atoms selected from nitrogen atom, sulfur atom and oxygen atom, mono-$C_{1-6}$ alkyl-carbamoyl, di-$C_{1-6}$ alkyl-carbamoyl, $C_{6-14}$ aryl-carbamoyl, thiocarbamoyl, 5- or 6-membered heterocyclic carbamoyl that contains, in addition to carbon atom, 1 to 4 hetero atoms selected from nitrogen atom, sulfur atom and oxygen atom, $C_{1-6}$ alkylsulfonyl, $C_{6-14}$ arylsulfonyl, $C_{1-6}$ alkylsulfinyl and $C_{6-14}$ arylsulfinyl, (19) acylamino selected from formylamino, $C_{1-6}$ alkyl-carboxamido, $C_{6-14}$ aryl-carboxamido, $C_{1-6}$ alkoxy-carboxamido, $C_{1-6}$ alkylsulfonylamino and $C_{6-14}$ arylsulfonylamino, (20) acyloxy selected from $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-14}$ aryl-carbamoyloxy, and nicotinoyloxy, (21) 5- to 7-membered saturated-cyclic amino, which may have 1 to 3 substituents selected from $C_{1-6}$ alkyl, $C_{6-14}$ aryl, and a 5- to 10-membered aromatic heterocyclic group that contains, in addition to carbon atom, 1 to 4 hetero atoms selected from nitrogen atom, sulfur atom and oxygen atom, (22) a 5- to 10-membered aromatic heterocyclic group that contains, in addition to carbon atom, 1 to 4 hetero atoms selected from nitrogen atom, sulfur atom and oxygen atom, (23) sulfo, and (24) a $C_{6-14}$ aryloxy; and ring C is benzene ring that may be substituted with a substituent selected from halogen, $C_{1-6}$ alkyl that may be halogenated, $C_{1-6}$ alkoxy that may be halogenated, and $C_{1-6}$ alkylthio that may be halogenated in addition to the group represented by the formula:

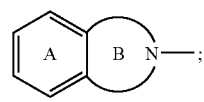

(Wa)

(ii) when W is Wb, $R^3$ is $C_{6-14}$ aryl, which respectively may have 1 to 5 substituents selected from (1) halogen, (2) $C_{1-3}$ alkylenedioxy, (3) nitro, (4) cyano, (5) $C_{1-6}$ alkyl that may be halogenated, (6) $C_{2-6}$ alkenyl that may be halogenated, (7) $C_{2-6}$ alkynyl that may be halogenated, (8) $C_{3-6}$ cycloalkyl that may be halogenated, (9) $C_{6-14}$ aryl, (10) $C_{1-6}$ alkoxy that may be halogenated, (11) $C_{1-6}$ alkylthio that may be halogenated or mercapto, (12) hydroxyl, (13) amino, (14) mono-$C_{1-6}$ alkylamino, (15) mono-$C_{6-14}$ arylamino, (16) di-$C_{1-6}$ alkylamino, (17) di-$C_{6-14}$ arylamino, (18) acyl selected from formyl, carboxyl, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5- or 6-membered heterocyclic carbonyl that contains, in addition to carbon atom, 1 to 4 hetero atoms selected from nitrogen atom, sulfur atom and oxygen atom, mono-$C_{1-6}$ alkyl-carbamoyl, di-$C_{1-6}$ alkyl-carbamoyl, $C_{6-14}$ aryl-carbamoyl, thiocarbamoyl, 5- or 6-membered heterocyclic carbamoyl that contains, in addition to carbon atom, 1 to 4 hetero atoms selected from nitrogen atom, sulfur atom and oxygen atom, $C_{1-6}$ alkylsulfonyl, $C_{6-14}$ arylsulfonyl, $C_{1-6}$ alkylsulfinyl and $C_{6-14}$ arylsulfinyl, (19) acylamino selected from formylamino, $C_{1-6}$ alkyl-carbonylamino, $C_{6-14}$ aryl-carbonylamino, $C_{1-6}$ alkoxy-carbonylamino, $C_{1-6}$ alkylsulfonylamino and $C_{6-14}$ arylsulfonylamino, (20) acyloxy selected from $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-14}$ aryl-carbamoyloxy and nicotinoyloxy, (21) 5- to 7-membered saturated-cyclic amino, which may have 1 to 3 substituents selected from $C_{1-6}$ alkyl, $C_{6-14}$ aryl and a 5- to 10-membered aromatic heterocyclic group that contains, in addition to carbon atom, 1 to 4 hetero atoms selected from nitrogen atom, sulfur atom and oxygen atom, (22) a 5- to 10-membered aromatic heterocyclic group that contains, in addition to carbon atom, 1 to 4 hetero atoms selected from nitrogen atom, sulfur atom and oxygen atom, (23) sulfo, and (24) a $C_{6-14}$ aryloxy;

$R^4$ is (i) a $C_{1-6}$ alkyl group, a $C_{2-6}$ alkenyl group, a $C_{2-6}$ alkynyl group, or a $C_{3-6}$ cycloalkyl group, which has 1 to 3 groups of a $C_{6-14}$ aryl group and a 5- to 14-membered, aromatic heterocyclic group that contains, in addition to carbon atom, 1 to 4 hetero atoms selected from nitrogen atom, sulfur atom and oxygen atom, which respectively may have 1 to 5 substituents selected from (1) halogen, (2) $C_{1-3}$ alkylenedioxy, (3) nitro, (4) cyano, (5) $C_{1-6}$ alkyl that may be halogenated, (6) $C_{2-6}$ alkenyl that may be halogenated, (7) $C_{2-6}$ alkynyl that may be halogenated, (8) $C_{3-6}$ cycloalkyl that may be halogenated, (9) $C_{6-14}$ aryl, (10) $C_{1-6}$ alkoxy that may be halogenated, (11) $C_{1-6}$ alkylthio that may be halogenated or mercapto, (12) hydroxyl, (13) amino, (14) mono-$C_{1-6}$ alkylamino, (15) mono-$C_{6-14}$ arylamino, (16) di-$C_{1-6}$ alkylamino, (17) di-$C_{6-14}$ arylamino, (18) acyl selected from formyl, carboxyl, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5- or 6-membered heterocyclic carbonyl that contains, in addition to carbon atom, 1 to 4 hetero atoms selected from nitrogen atom, sulfur atom and oxygen atom, mono-$C_{1-6}$ alkyl-carbamoyl, di-$C_{1-6}$ alkyl-carbamoyl, $C_{6-14}$ aryl-carbamoyl, thiocarbamoyl, 5- or 6-membered heterocyclic carbamoyl that contains, in addition to carbon atom, 1 to 4 hetero atoms selected from nitrogen atom, sulfur atom and oxygen atom, $C_{1-6}$ alkylsulfonyl, $C_{6-14}$ arylsulfonyl, $C_{1-6}$ alkylsulfinyl and $C_{6-14}$ arylsulfinyl, (19) acylamino selected from formylamino, $C_{1-6}$ alkyl-carbonylamino, $C_{6-14}$ aryl-carbonylamino, $C_{1-6}$ alkoxy-carbonylamino, $C_{1-6}$ alkylsulfonylamino and $C_{6-14}$ arylsulfonylamino, (20) acyloxy selected from $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-14}$ aryl-carbamoyloxy and nicotinoyloxy, (21) 5- to 7-membered saturated-cyclic amino, which may have 1 to 3 substituents selected from $C_{1-6}$ alkyl, $C_{6-14}$ aryl, and a 5- to 10-membered aromatic heterocyclic group that contains, in addition to carbon atom, 1 to 4 hetero atoms selected from nitrogen atom, sulfur atom and oxygen atom, (22) a 5- to 10-membered aromatic heterocyclic group that contains, in addition to carbon atom, 1 to 4 hetero atoms selected from nitrogen atom, sulfur atom and oxygen atom, (23) sulfo, and (24) a $C_{6-14}$ aryloxy, and further may have 1 to 5 substituents selected from (1) halogen, (2) $C_{1-3}$ alkylenedioxy, (3) nitro, (4) cyano, (5) $C_{1-6}$ alkyl that may be halogenated, (6) $C_{2-6}$ alkenyl that may be halogenated, (7) $C_{2-6}$ alkynyl that may be halogenated, (8) $C_{3-6}$ cycloalkyl that may be halogenated, (9) $C_{6-14}$ aryl, (10) $C_{1-6}$ alkoxy that may be halogenated, (11) $C_{1-6}$ alkylthio that may be halogenated or mercapto, (12) hydroxyl, (13) amino, (14) mono-$C_{1-6}$ alkylamino, (15) mono-$C_{6-14}$ arylamino, (16) di-$C_{1-6}$ alkylamino, (17) di-$C_{6-14}$ arylamino, (18) acyl selected from formyl, carboxyl, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5- or 6-membered heterocyclic carbonyl that contains, in addition to carbon atom, 1 to 4 hetero atoms selected from nitrogen atom, sulfur atom and oxygen atom, mono-$C_{1-6}$ alkyl-carbamoyl, di-$C_{1-6}$ alkyl-carbamoyl, $C_{6-14}$ aryl-carbamoyl, thiocarbamoyl, 5- or 6-membered heterocyclic carbamoyl that contains, in addition to carbon atom, 1 to 4 hetero atoms selected from nitrogen atom, sulfur atom and oxygen atom, $C_{1-6}$ alkylsulfonyl, $C_{6-14}$ arylsulfonyl, $C_{1-6}$ alkylsulfinyl, and $C_{6-14}$ arylsulfinyl, (19) acylamino selected from formylamino, $C_{1-6}$ alkyl-carbonylamino, $C_{6-14}$ aryl-carbonylamino, $C_{1-6}$ alkoxy-carbonylamino, $C_{1-6}$ alkylsulfonylamino and $C_{6-14}$ arylsulfonylamino, (20) acyloxy selected from $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-14}$ aryl-carbamoyloxy and nicotinoyloxy, (21) 5- to 7-membered saturated-cyclic amino which may have 1 to 3 substituents selected from $C_{1-6}$ alkyl, $C_{6-14}$ aryl and 5- to 10-membered aromatic heterocyclic group that contains, in addition to carbon atom, 1 to 4 hetero atoms selected from nitrogen atom, sulfur atom and oxygen atom, (22) a 5- to 10-membered, aromatic heterocyclic group that contains, in addition to carbon atom, 1 to 4 hetero atoms selected from nitrogen atom, sulfur atom and oxygen atom, (23) sulfo, and (24) a $C_{6-14}$ aryloxy, or (ii) an acyl group that is selected from formyl, carboxyl, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryl-oxycarbonyl, $C_{7-16}$ aralkyl-oxycarbonyl, 5- or 6-membered heterocyclic carbonyl that contains, in addition to carbon atom, 1 to 4 hetero atoms selected from nitrogen atom, sulfur atom, and oxygen atom, mono-$C_{1-6}$ alkyl-carbamoyl, di-$C_{1-6}$ alkyl-carbamoyl, $C_{6-14}$ aryl-carbamoyl, thiocarbamoyl, 5- or 6-membered heterocyclic carbamoyl that contains, in addition to carbon atom, 1 to 4 hetero atom selected from nitrogen atom, sulfur atom and oxygen atom, $C_{1-6}$ alkylsulfonyl, $C_{6-14}$ arylsulfonyl, $C_{1-6}$ alkylsulfinyl and $C_{6-14}$ arylsulfinyl, which has 1 to 3 groups of a $C_{6-14}$ aryl group and a 5- to 14-membered aromatic heterocyclic group that contains, in addition to the carbon atom, 1 to 4 hetero atoms selected from nitrogen atom, sulfur atom and oxygen atom, which respectively may have 1 to 5 substituents selected from (1) halogen, (2) $C_{1-3}$ alkylenedioxy, (3) nitro, (4) cyano, (5) $C_{1-6}$ alkyl that may be halogenated, (6) $C_{2-6}$ alkenyl that may be halogenated, (7) $C_{2-6}$ alkynyl that may be halogenated, (8) $C_{3-6}$ cycloalkyl that may be halogenated, (9) $C_{6-14}$ aryl, (10) $C_{1-6}$ alkoxy that may be halogenated, (11) $C_{1-6}$ alkylthio that may be halogenated or mercapto, (12) hydroxyl, (13) amino, (14) mono-$C_{1-6}$ alkylamino, (15) mono-$C_{6-14}$ arylamino, (16) di-$C_{1-6}$ alkylamino, (17) di-$C_{6-14}$ arylamino, (18) acyl selected from formyl, carboxyl, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5- or 6-membered heterocyclic carbonyl that contains, in addition to carbon atom, 1 to 4 hetero atoms selected from nitrogen atom, sulfur atom and oxygen atom, mono-$C_{1-6}$ alkyl-carbamoyl, di-$C_{1-6}$ alkyl-carbamoyl, $C_{6-14}$ aryl-carbamoyl, thiocarbamoyl, 5- or 6-membered heterocyclic carbamoyl that contains, in addition to carbon atom, 1 to 4 hetero atoms selected from nitrogen atom, sulfur atom and oxygen atom, $C_{1-6}$ alkylsulfonyl, $C_{6-14}$ arylsulfonyl, $C_{1-6}$ alkylsulfinyl and $C_{6-14}$ arylsulfinyl, (19) acylamino selected from formylamino, $C_{1-6}$ alkyl-carbonylamino, $C_{6-14}$ arylcarbonyl-amino, $C_{1-6}$ alkoxy-carbonylamino, $C_{1-6}$ alkylsulfonylamino and $C_{6-14}$ arylsulfonylamino, (20) acyloxy selected from $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-14}$ aryl-carbamoyloxy, and nicotinoyloxy, (21) 5- to 7-membered saturated-cyclic amino, which may have 1 to 3 substituents selected from $C_{1-6}$ alkyl, $C_{6-14}$ aryl, and a 5- to 10-membered, aromatic heterocyclic group that contains, in addition to carbon atom, 1 to 4 hetero atoms selected from nitrogen atom, sulfur atom and oxygen atom, (22) a 5- to 10-membered aromatic heterocyclic group that contains, in addition to carbon atom, 1 to 4 hetero atoms selected from nitrogen atom, sulfur atom and oxygen atom, (23) sulfo, and (24) $C_{6-14}$ aryloxy;

$R^5$ is (i) hydrogen atom, (ii) a $C_{1-6}$ alkyl group, or (iii) acyl selected from formyl, carboxyl, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5- or 6-membered heterocyclic carbonyl that contains, in addition to carbon atom, 1 to 4 hetero atoms selected from nitrogen atom, sulfur atom and oxygen atom, mono-$C_{1-6}$ alkyl-carbamoyl, di-$C_{1-6}$ alkyl-carbamoyl, $C_{6-14}$ aryl-carbamoyl, thiocarbamoyl, 5- or 6-membered heterocyclic carbamoyl that contains, in addition to carbon atom, 1 to 4 hetero atoms selected from nitrogen atom, sulfur atom and oxygen atom, $C_{1-6}$ alkylsulfonyl, $C_{6-14}$ arylsulfonyl, $C_{1-6}$ alkylsulfinyl and $C_{6-14}$ arylsulfinyl; and ring C is, in addition to a group represented by the formula —$NR^4(R^5)$, benzene ring, which may have 1 to 3 substituents selected from (1) halogen, (2) $C_{1-3}$ alkylenedioxy, (3) nitro, (4) cyano, (5) $C_{1-6}$ alkyl that may be halogenated, (6) $C_{2-6}$ alkenyl that may be halogenated, (7) $C_{2-6}$ alkynyl that may be halogenated, (8) $C_{3-6}$ cycloalkyl that may be halogenated, (9) $C_{6-14}$ aryl, (10) $C_{1-6}$ alkoxy that may be halogenated, (11) hydroxyl, (12) amino, (13) mono-$C_{1-6}$ alkylamino, (14) mono-$C_{6-14}$ arylamino, (15) di-$C_{1-6}$ alkylamino, (16) di-$C_{6-14}$ arylamino, (17) acyl selected from formyl, carboxyl, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5- or 6-membered heterocyclic carbonyl that contains, in addition to carbon atom, 1 to 4 hetero atoms selected from nitrogen atom, sulfur atom and oxygen atom, mono-$C_{1-6}$ alkyl-carbamoyl, di-$C_{1-6}$ alkyl-carbamoyl, $C_{6-14}$ aryl-carbamoyl, thiocarbamoyl, 5- or 6-membered heterocyclic carbamoyl that contains, in addition to carbon atom, 1 to 4 hetero atoms selected from nitrogen atom, sulfur atom and oxygen atom, $C_{1-6}$ alkylsulfonyl, $C_{6-14}$ arylsulfonyl, $C_{1-6}$ alkylsulfinyl, and $C_{6-14}$ arylsulfinyl, (18) acylamino selected from formylamino, $C_{1-6}$ alkyl-carboxamido, $C_{6-14}$ aryl-carboxamido, $C_{1-6}$ alkoxy-carboxamido, $C_{1-6}$ alkylsulfonylamino and $C_{6-14}$ arylsulfonylamino, (19) 5- to 7-membered saturated-cyclic amino, which may have 1 to 3 substituents selected from $C_{1-6}$ alkyl, $C_{6-14}$ aryl and a 5- to 10-membered aromatic heterocyclic group that contains, in addition to carbon atom, 1 to 4 hetero atoms selected from nitrogen atom, sulfur atom and oxygen atom, (20) a 5- to 10-membered aromatic heterocyclic group that contains, in addition to carbon atom, 1 to 4 hetero atoms selected from nitrogen atom, sulfur atom and oxygen atom, and (21) sulfo;

5. The compound according to the above 2, wherein $R^1$ and $R^2$ are the same or different and each is hydrogen atom or a $C_{1-6}$ alkyl group that may have substituents, or $R^1$ and $R^2$ may form, together with the adjacent carbon atom, a 3- to 8-membered heterocyclic ring that may be substituted;

6. The compound according to the above 2, wherein each of $R^1$ and $R^2$ is a $C_{1-6}$ alkyl group;

7. The compound according to the above 2, wherein $R^{3a}$ is a $C_{6-14}$ aryl group that may be substituted;

8. The compound according to the above 2, wherein $R^{3a}$ is phenyl group that may have $C_{1-6}$ alkyl or halogen;

9. The compound according to the above 2, wherein ring A is benzene ring that may be substituted selected from halogen, $C_{1-6}$ alkyl, $C_{1-6}$ alkoxy, and $C_{1-6}$ alkylenedioxy;

10. The compound according to the above 2, wherein ring B is a 5- to 7-membered nitrogen-containing heterocyclic ring that may be substituted with $C_{1-6}$ alkyl;

11. The compound according to the above 2, wherein ring $C^1$ is benzene ring that may be further substituted with $C_{1-6}$ alkyl or $C_{1-6}$ alkoxy;

12. The compound according to the above 2, wherein a group represented by the formula:

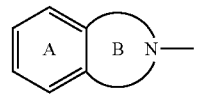

(wherein each symbol is as defined in the above 2) is a group represented by the formula:

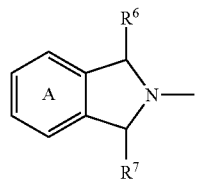

(wherein $R^6$ and $R^7$ are the same or different and each is hydrogen atom, halogen, or a hydrocarbon group that may be substituted and ring A is as defined in the above 2);

13. The compound according to the above 2, wherein a group represented by the formula:

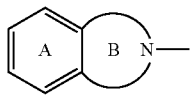

(wherein each symbol is as defined in the above 2) is a group represented by the formula:

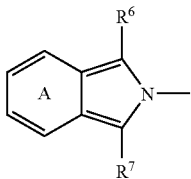

(wherein $R^6$ and $R^7$ are the same or different and each is hydrogen atom, halogen, or hydrocarbon group that may be substituted and ring A is as defined in the above 2);

14. The compound according to the above 12 or 13, wherein $R^6$ and $R^7$ are hydrogen atoms and ring A is benzene ring that may have 1 or 2 substituents selected from halogen, $C_{1-6}$ alkoxy, and $C_{1-6}$ alkylenedioxy;

15. The compound according to the above 2, wherein the substitution position on ring $C_1$ of a group represented by the formula:

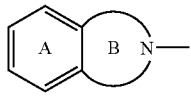

(wherein each symbol is as defined in the above 2) is 5-position on the benzofuran ring or the dihydrobenzofuran ring;

16. The compound according to the above 2, wherein each of $R^1$ and $R^2$ is a $C_{1-6}$ alkyl group, $R^{3a}$ is phenyl group that may have $C_{1-6}$ alkyl or halogen, ring A is benzene ring that may be substituted selected from halogen, $C_{1-6}$ alkyl, $C_{1-6}$ alkoxy and $C_{1-6}$ alkylenedioxy, ring B is a 5- to 7-membered nitrogen-containing heterocyclic ring that may be substituted with $C_{1-6}$ alkyl, ring $C^1$ is benzene ring that may be further substituted with $C_{1-6}$ alkyl or $C_{1-6}$ alkoxy, and a group represented by the formula:

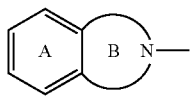

(wherein each symbol is as defined in the above 2) is a group represented by the formula:

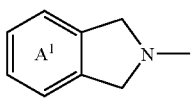

(wherein ring $A^1$ is benzene ring that may have 1 or 2 substituents selected from halogen, $C_{1-6}$ alkoxy and $C_{1-6}$ alkylenedioxy);

17. [1] 2-[2,2,4,6,7-pentamethyl-3-(4-methylphenyl)-2,3-dihydro-1-benzofuran-5-yl]isoindoline, [2] 5,6-dimethoxy-2-[2,2,4,6,7-pentamethyl-3-(4-methylphenyl)-2,3-dihydro-1-benzofuran-5-yl]isoindoline, [3] 5,6-dimethoxy-2-[3-(4-isopropylphenyl)-2,2,4,6,7-pentamethyl-2,3-dihydro-1-benzofuran-5-yl]isoindoline, [4] 6-[3-(4-isopropylphenyl)-2,2,4,6,7-pentamethyl-2,3-dihydro-1-benzofuran-5-yl]-6,7-dihydro-5H-[1,3]dioxolo[4,5-f]isoindole, [5] 6-[2,2,4,6,7-pentamethyl-3-(4-methylphenyl)-2,3-dihydro-1-benzofuran-5-yl]-6H-[1,3]dioxolo[4,5-f]isoindole, [6] 6-[2,2,4,6,7-pentamethyl-3-phenyl-2,3-dihydro-1-benzofuran-5-yl]-6,7-dihydro-5H-[1,3]dioxolo[4,5-f]isoindole, [7] (+)-5,6-dimethoxy-2-[2,2,4,6,7-pentamethyl-3-(4-methylphenyl)-2,3-dihydro-1-benzofuran-5-yl]isoindoline, or [8] (+)-5,6-dimethoxy-2-[2,2,4,6,7-pentamethyl-3-(4-methylphenyl)-2,3-dihydro-1-benzofuran-5-yl]isoindoline hydrochloride;

18. The compound according to the above 3, wherein ring A is benzene ring, which may have 1 to 3 substituents selected from halogen, $C_{1-3}$ alkylenedioxy, nitro, cyano, $C_{1-6}$ alkyl that may be halogenated, $C_{2-6}$ alkenyl that may be halogenated, $C_{2-6}$ alkynyl that may be halogenated, $C_{3-6}$ cycloalkyl that may be halogenated, $C_{6-14}$ aryl, $C_{1-6}$ alkoxy that may be halogenated, hydroxyl, amino, mono-$C_{1-6}$ alkylamino, mono-$C_{6-14}$ arylamino, di-$C_{1-6}$ alkylamino, di-$C_{6-14}$ arylamino, acyl, acylamino, 5- to 7-membered saturated-cyclic amino that may be substituted, a 5- to 10-membered aromatic heterocyclic group and sulfo;

19. The compound according to the above 3, wherein $R^1$ and $R^2$ are the same or different and each is (i) hydrogen atom, (ii) a $C_{1-6}$ alkyl group, a $C_{2-6}$ alkenyl group, a $C_{2-6}$ alkynyl group, a $C_{3-6}$ cycloalkyl group, or a $C_{6-14}$ aryl group, which respectively may have 1 to 5 substituents selected from (1) halogen, (2) $C_{1-3}$ alkylenedioxy, (3) nitro, (4) cyano, (5) $C_{1-6}$ alkyl that may be halogenated, (6) $C_{2-6}$ alkenyl that may be halogenated, (7) $C_{2-6}$ alkynyl that may be halogenated, (8) $C_{3-6}$ cycloalkyl that may be halogenated, (9) $C_{6-14}$ aryl, (10) $C_{1-6}$ alkoxy that may be halogenated, (11) $C_{1-6}$ alkylthio that may be halogenated or mercapto, (12) hydroxyl, (13) amino, (14) mono-$C_{1-6}$ alkylamino, (15) mono-$C_{6-14}$ arylamino, (16) di-$C_{1-6}$ alkylamino, (17) di-$C_{6-14}$ arylamino, (18) acyl selected from formyl, carboxyl, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{1-16}$ aralkyl-carbonyl, $C_{6-14}$ aryloxy-carbonyl, $C_{7-16}$ aralkyloxy-carbonyl, 5- or 6-membered heterocyclic carbonyl that contains, in addition to carbon atom, 1 to 4 hetero atoms selected from nitrogen atom, sulfur atom and oxygen atom, mono-$C_{1-6}$ alkyl-carbamoyl, di-$C_{1-6}$ alkyl-carbamoyl, $C_{6-14}$ aryl-carbamoyl, thiocarbamoyl, 5- or 6-membered heterocyclic carbamoyl that contains, in addition to carbon atom, 1 to 4 hetero atoms selected from nitrogen atom, sulfur atom and oxygen atom, $C_{1-6}$ alkylsulfonyl, $C_{6-14}$ arylsulfonyl, $C_{1-6}$ alkylsulfinyl and $C_{6-14}$ arylsulfinyl, (19) acylamino selected from formylamino, $C_{1-6}$ alkyl-carboxamido, $C_{6-14}$ aryl-carboxamido, $C_{1-6}$ alkoxy-carboxamido, $C_{1-6}$ alkylsulfonylamino and $C_{6-14}$ arylsulfonylamino, (20) acyloxy selected from $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-14}$ aryl-carbamoyloxy and nicotinoyloxy, (21) 5- to 7-membered saturated-cyclic amino, which may have 1 to 3 substituents selected from $C_{1-6}$ alkyl, $C_{6-14}$ aryl, and a 5- to 10-membered aromatic heterocyclic group that contains, in addition to carbon atom, 1 to 4 hetero atoms selected from nitrogen atom, sulfur atom and oxygen atom, (22) a 5- to 10-membered aromatic heterocyclic group that contains, in addition to carbon atom, 1 to 4 hetero atoms selected from nitrogen atom, sulfur atom and oxygen atom, (23) sulfo, and (24) a $C_{6-14}$ aryloxy, or (iii) a 5- to 14-membered heterocyclic group that contains, in addition to carbon atom, 1 to 4 hetero atoms selected from nitrogen atom, sulfur atom and oxygen atom, which respectively may have 1 to 5 substituents selected from (1) halogen, (2) $C_{1-3}$ alkylenedioxy, (3) nitro, (4) cyano, (5) $C_{1-6}$ alkyl that may be halogenated, (6) $C_{2-6}$ alkenyl that may be halogenated, (7) $C_{2-6}$ alkynyl that may be halogenated, (8) $C_{3-6}$ cycloalkyl that may be halogenated, (9) $C_{6-14}$ aryl, (10) $C_{1-6}$ alkoxy that may be halogenated, (11) $C_{1-6}$ alkylthio that may be halogenated or mercapto, (12) hydroxyl, (13) amino, (14) mono-$C_{1-6}$ alkylamino, (15) mono-$C_{6-14}$ arylamino, (16) di-$C_{1-6}$ alkylamino, (17) di-$C_{6-14}$ arylamino, (18) acyl selected from formyl, carboxyl, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5- or 6-membered heterocyclic carbonyl that contains, in addition to carbon atom, 1 to 4 hetero atoms selected from nitrogen atom, sulfur atom and oxygen atom, mono-$C_{1-6}$ alkyl-carbamoyl, di-$C_{1-6}$ alkyl-carbamoyl, $C_{6-14}$ aryl-carbamoyl, thiocarbamoyl, 5- or 6-membered, heterocyclic carbamoyl that contains, in addition to carbon atom, 1 to 4 hetero atoms selected from nitrogen atom, sulfur atom and oxygen atom, $C_{1-6}$ alkylsulfonyl, $C_{6-14}$ arylsulfonyl, $C_{1-6}$ alkylsulfinyl and $C_{6-14}$ arylsulfinyl, (19) acylamino selected from formylamino, $C_{1-6}$ alkyl-carbonylamino, $C_{6-14}$ aryl-carbonylamino, $C_{1-6}$ alkoxy-carbonylamino, $C_{1-6}$ alkylsulfonylamino and $C_{6-14}$ arylsulfonylamino, (20) acyloxy selected from $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-14}$ aryl-carbamoyloxy and nicotinoyloxy, (21) 5- to 7-membered saturated-cyclic amino, which may have 1 to 3 substituents selected from $C_{1-6}$ alkyl, $C_{6-14}$ aryl, and a 5- to 10-membered aromatic heterocyclic group that contains, in addition to carbon atom, 1 to 4 hetero atoms selected from nitrogen atom, sulfur atom and oxygen atom, (22) a 5- to 10-membered aromatic heterocyclic group that contains, in addition to carbon atom, 1 to 4 hetero atoms selected from nitrogen atom, sulfur atom and oxygen atom, (23) sulfo, and (24) a $C_{6-14}$ aryloxy, or (iv) $R^1$ and $R^2$ form, together with the adjacent carbon atom, $C_{3-8}$ cycloalkane or a 3- to 8-membered heterocyclic ring that contains, in addition to carbon atom, 1 to 4 hetero atoms selected from nitrogen atom, sulfur atom and oxygen atom, which respectively may have 1 to 5 substituents selected from (1) halogen, (2) $C_{1-3}$ alkylenedioxy, (3) nitro, (4) cyano, (5) $C_{1-6}$ alkyl that may be halogenated, (6) $C_{2-6}$ alkenyl that may be halogenated, (7) $C_{2-6}$ alkynyl that may be halogenated, (8) $C_{3-6}$ cycloalkyl that may be halogenated, (9) $C_{6-14}$ aryl, (10) $C_{1-6}$ alkoxy that may be halogenated, (11) $C_{1-6}$ alkylthio that may be halogenated or mercapto, (12) hydroxyl, (13) amino, (14) mono-$C_{1-6}$ alkylamino, (15) mono-$C_{6-14}$ arylamino, (16) di-$C_{1-6}$ alkylamino, (17) di-$C_{6-14}$ arylamino, (18) acyl selected from formyl, carboxyl, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5- or 6-membered heterocyclic carbonyl that contains, in addition to carbon atom, 1 to 4 hetero atoms selected from nitrogen atom, sulfur atom and oxygen atom, mono-$C_{1-6}$ alkyl-carbamoyl, di-$C_{1-6}$ alkyl-carbamoyl, thiocarbamoyl, $C_{6-14}$ aryl-carbamoyl, 5- or 6-membered heterocyclic carbamoyl that contains, in addition to carbon atom, 1 to 4 hetero atoms selected from nitrogen atom, sulfur atom and oxygen atom, $C_{1-6}$ alkylsulfonyl, $C_{6-14}$ arylsulfonyl, $C_{1-6}$ alkylsulfinyl and $C_{6-14}$ arylsulfinyl, (19) acylamino selected from formylamino, $C_{1-6}$ alkyl-carbonylamino, $C_{6-14}$ aryl-carbonylamino, $C_{1-6}$ alkoxy-carbonylamino, $C_{1-6}$ alkylsulfonylamino and $C_{6-14}$ arylsulfonylamino, (20) acyloxy selected from $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-14}$ aryl-carbamoyloxy and nicotinoyloxy, (21) 5- to 7-membered saturated-cyclic amino, which may have 1 to 3 substituents selected from $C_{1-6}$ alkyl, $C_{6-14}$ aryl, and a 5- to 10-membered aromatic heterocyclic group that contains, in addition to carbon atom, 1 to 4 hetero atoms selected from nitrogen atom, sulfur atom and oxygen atom, (22) a 5- to 10-membered aromatic heterocyclic group that contains, in addition to carbon atom, 1 to 4 hetero atoms selected from nitrogen atom, sulfur atom and oxygen atom, (23) sulfo, and (24) a $C_{6-14}$ aryloxy;

$R^3$ is $C_{6-14}$ aryl, which respectively may have 1 to 5 substituents selected from (1) halogen, (2) $C_{1-3}$ alkylenedioxy, (3) nitro, (4) cyano, (5) $C_{1-6}$ alkyl that may be halogenated, (6) $C_{2-6}$ alkenyl that may be halogenated, (7) $C_{2-6}$ alkynyl that may be halogenated, (8) $C_{3-6}$ cycloalkyl that may be halogenated, (9) $C_{6-14}$ aryl, (10) $C_{1-6}$ alkoxy that may be halogenated, (11) $C_{1-6}$ alkylthio that may be halogenated or mercapto, (12) hydroxyl, (13) amino, (14) mono-$C_{1-6}$ alkylamino, (15) mono-$C_{6-14}$ arylamino, (16) di-$C_{1-6}$ alkylamino, (17) di-$C_{6-14}$ arylamino, (18) acyl selected from formyl, carboxyl, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5- or 6-membered heterocyclic carbonyl that contains, in addition to carbon atom, 1 to 4 hetero atoms selected from nitrogen atom, sulfur atom and oxygen atom, mono-$C_{1-6}$ alkyl-carbamoyl, di-$C_{1-6}$ alkyl-carbamoyl, $C_{6-14}$ aryl-carbamoyl, thiocarbamoyl, 5- or 6-membered heterocyclic carbamoyl that contains, in addition to carbon atom, 1 to 4 hetero atoms selected from nitrogen atom, sulfur atom and oxygen atom, $C_{1-6}$ alkylsulfonyl, $C_{6-14}$ arylsulfonyl, $C_{1-6}$ alkylsulfinyl and $C_{6-14}$ arylsulfinyl, (19) acylamino selected from formylamino, $C_{1-6}$ alkyl-carbonylamino, $C_{6-14}$ aryl-carbonylamino, $C_{1-6}$ alkoxy-carbonylamino, $C_{1-6}$ alkylsulfonylamino and $C_{6-14}$ arylsulfonylamino, (20) acyloxy selected from $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-14}$ aryl-carbamoyloxy and nicotinoyloxy, (21) 5- to 7-membered saturated-cyclic amino, which may have 1 to 3 substituents selected from $C_{1-6}$ alkyl, $C_{6-14}$ aryl, and a 5- to 10-membered aromatic heterocyclic group that contains, in addition to carbon atom, 1 to 4 hetero atoms selected from nitrogen atom, sulfur atom and oxygen atom, (22) a 5- to 10-membered aromatic heterocyclic group that contains, in addition to carbon atom, 1 to 4 hetero atoms selected from nitrogen atom, sulfur atom and oxygen atom, (23) sulfo, and (24) $C_{6-14}$ aryloxy;

$R^4$ is (i) a $C_{1-6}$ alkyl group, a $C_{2-6}$ alkenyl group, a $C_{2-6}$ alkynyl group, or a $C_{3-6}$ cycloalkyl group, which have 1 to 3 groups of a $C_{6-14}$ aryl group and a 5- to 14-membered aromatic heterocyclic group that contains, in addition to carbon atom, 1 to 4 hetero atoms selected from nitrogen atom, sulfur atom and oxygen atom, which respectively may have 1 to 5 substituents selected from (1) halogen, (2) $C_{1-3}$ alkylenedioxy, (3) nitro, (4) cyano, (5) $C_{1-6}$ alkyl that may be halogenated, (6), $C_{2-6}$ alkenyl that may be halogenated, (7) $C_{2-6}$ alkynyl that may be halogenated, (8) $C_{3-6}$ cycloalkyl that may be halogenated, (9) $C_{6-14}$ aryl, (10) $C_{1-6}$ alkoxy that may be halogenated, (11) $C_{1-6}$ alkylthio that may be halogenated or mercapto, (12) hydroxyl, (13)

amino, (14) mono-$C_{1-6}$ alkylamino, (15) mono-$C_{6-14}$ arylamino, (16) di-$C_{1-6}$ alkylamino, (17) di-$C_{6-14}$ arylamino, (18) acyl selected from formyl, carboxyl, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5- or 6-membered heterocyclic carbonyl that contains, in addition to carbon atom, 1 to 4 hetero atoms selected from nitrogen atom, sulfur atom and oxygen atom, mono-$C_{1-6}$ alkyl-carbamoyl, di-$C_{1-6}$ alkyl-carbamoyl, $C_{6-14}$ aryl-carbamoyl, thiocarbamoyl, 5- or 6-membered heterocyclic carbamoyl that contains, in addition to carbon atom, 1 to 4 hetero atoms selected from nitrogen atom, sulfur atom and oxygen atom, $C_{1-6}$ alkylsulfonyl, $C_{6-14}$ arylsulfonyl, $C_{1-6}$ alkylsulfinyl and $C_{6-14}$ arylsulfinyl, (19) acylamino selected from formylamino, $C_{1-6}$ alkyl-carbonylamino, $C_{6-14}$ aryl-carbonylamino, $C_{1-6}$ alkoxy-carbonylamino, $C_{1-6}$ alkylsulfonylamino and $C_{6-14}$ arylsulfonylamino, (20) acyloxy selected from $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-14}$ aryl-carbamoyloxy and nicotinoyloxy, (21) 5- to 7-membered saturated-cyclic amino, which may have 1 to 3 substituents selected from $C_{1-6}$ alkyl, $C_{6-14}$ aryl, and a 5- to 10-membered aromatic heterocyclic group that contains, in addition to carbon atom, 1 to 4 hetero atoms selected from nitrogen atom, sulfur atom and oxygen atom, (22) a 5- to 10-membered aromatic heterocyclic group that contains, in addition to carbon atom, 1 to 4 hetero atoms selected from nitrogen atom, sulfur atom and oxygen atom, (23) sulfo, and (24) a $C_{6-14}$ aryloxy, and further may have 1 to 5 substituents selected from (1) halogen, (2) $C_{1-3}$ alkylenedioxy, (3) nitro, (4) cyano, (5) $C_{1-6}$ alkyl that may be halogenated, (6) $C_{2-6}$ alkenyl that may be halogenated, (7) $C_{2-6}$ alkynyl that may be halogenated, (8) $C_{3-6}$ cycloalkyl that may be halogenated, (9) $C_{6-14}$ aryl, (10) $C_{1-6}$ alkoxy that may be halogenated, (11) $C_{1-6}$ alkylthio that may be halogenated or mercapto, (12) hydroxyl, (13) amino, (14) mono-$C_{1-6}$ alkylamino, (15) mono-$C_{6-14}$ arylamino, (16) di-$C_{1-6}$ alkylamino, (17) di-$C_{6-14}$ arylamino, (18) acyl selected from formyl, carboxyl, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5- or 6-membered heterocyclic carbonyl that contains, in addition to carbon atom, 1 to 4 hetero atoms selected from nitrogen atom, sulfur atom and oxygen atom, mono-$C_{1-6}$ alkyl-carbamoyl, di-$C_{1-6}$ alkyl-carbamoyl, $C_{6-14}$ aryl-carbamoyl, thiocarbamoyl, 5- or 6-membered heterocyclic carbamoyl that contains, in addition to carbon atom, 1 to 4 hetero atoms selected from nitrogen atom, sulfur atom and oxygen atom, $C_{1-6}$ alkylsulfonyl, $C_{6-14}$ arylsulfonyl, $C_{1-6}$ alkylsulfinyl and $C_{6-14}$ arylsulfinyl, (19) acylamino selected from formylamino, $C_{1-6}$ alkyl-carbonylamino, $C_{6-14}$ aryl-carbonylamino, $C_{1-6}$ alkoxy-carbonylamino, $C_{1-6}$ alkylsulfonylamino and $C_{6-14}$ arylsulfonylamino (20) acyloxy selected from $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-14}$ aryl-carbamoyloxy and nicotinoyloxy, (21) 5- to 7-membered saturated-cyclic amino, which may have 1 to 3 substituents selected from $C_{1-6}$ alkyl, $C_{6-14}$ aryl, and a 5- to 10-membered aromatic heterocyclic group that contains, in addition to carbon atom, 1 to 4 hetero atoms selected from nitrogen atom, sulfur atom and oxygen atom, (22) a 5- to 10-membered aromatic heterocyclic group that contains, in addition to carbon atom, 1 to 4 hetero atoms selected from nitrogen atom, sulfur atom and oxygen atom, (23) sulfo, and (24) $C_{6-14}$ aryloxy, or (ii) an acyl group that is selected from formyl, carboxyl, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5- or 6-membered heterocyclic carbonyl that contains, in addition to carbon atom, 1 to 4 hetero atoms selected from nitrogen atom, sulfur atom and oxygen atom, mono-$C_{1-6}$ alkyl-carbamoyl, di-$C_{1-6}$ alkyl-carbamoyl, $C_{6-14}$ aryl-carbamoyl, thiocarbamoyl, 5- or 6-membered heterocyclic carbamoyl that contains, in addition to carbon atom, 1 to 4 hetero atoms selected from nitrogen atom, sulfur atom and oxygen atom, $C_{1-6}$ alkylsulfonyl, $C_{6-14}$ arylsulfonyl, $C_{1-6}$ alkylsulfinyl and $C_{6-14}$ arylsulfinyl, which have 1 to 3 groups of a $C_{6-14}$ aryl group and a 5- to 14-membered aromatic heterocyclic group that contains, in addition to carbon atom, 1 to 4 hetero atoms selected from nitrogen atom, sulfur atom and oxygen atom, which respectively may have 1 to 5 substituents selected from (1) halogen, (2) $C_{1-3}$ alkylenedioxy, (3) nitro, (4) cyano, (5) $C_{1-6}$ alkyl that may be halogenated, (6) $C_{2-6}$ alkenyl that may be halogenated, (7) $C_{2-6}$ alkynyl that may be halogenated, (8) $C_{3-6}$ cycloalkyl that may be halogenated, (9) $C_{6-14}$ aryl, (10) $C_{1-6}$ alkoxy that may be halogenated, (11) $C_{1-6}$ alkylthio that may be halogenated or mercapto, (12) hydroxyl, (13) amino, (14) mono-$C_{1-6}$ alkylamino, (15) mono-$C_{6-14}$ arylamino, (16) di-$C_{1-6}$ alkylamino, (17) di-$C_{6-14}$ arylamino, (18) acyl selected from formyl, carboxyl, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5- or 6-membered, heterocyclic carbonyl that contains, in addition to carbon atom, 1 to 4 hetero atoms selected from nitrogen atom, sulfur atom and oxygen atom, mono-$C_{1-6}$ alkyl-carbamoyl, di-$C_{1-6}$ alkyl-carbamoyl, $C_{6-14}$ aryl-carbamoyl, thiocarbamoyl, 5- or 6-membered heterocyclic carbamoyl that contains, in addition to carbon atom, 1 to 4 hetero atoms selected from nitrogen atom, sulfur atom and oxygen atom, $C_{1-6}$ alkylsulfonyl, $C_{6-14}$ arylsulfonyl, $C_{1-6}$ alkylsulfinyl and $C_{6-14}$ arylsulfinyl, (19) acylamino selected from formylamino, $C_{1-6}$ alkyl-carbonylamino, $C_{6-14}$ aryl-carbonylamino, $C_{1-6}$ alkoxy-carbonylamino, $C_{1-6}$ alkylsulfonylamino and $C_{6-14}$ arylsulfonylamino, (20) acyloxy selected from $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-14}$ aryl-carbamoyloxy and nicotinoyloxy, (21) 5- to 7-membered, saturated-cyclic amino, which may have 1 to 3 substituents selected from $C_{1-6}$ alkyl, $C_{6-14}$ aryl, and a 5- to 10-membered aromatic heterocyclic group that contains, in addition to carbon atom, 1 to 4 hetero atoms selected from nitrogen atom, sulfur atom and oxygen atom, (22) a 5- to 10-membered aromatic heterocyclic group that contains, in addition to carbon atom, 1 to 4 hetero atoms selected from nitrogen atom, sulfur atom and oxygen atom, (23) sulfo, and (24) $C_{6-14}$ aryloxy;

20. The compound according to the above 1, wherein $R^1$ and $R^2$ are the same or different and each is hydrogen atom or a $C_{1-6}$ alkyl group which may be substituted, or $R^1$ and $R^2$ form, together with the adjacent carbon atom, a 3- to 8-membered heterocyclic ring that may be substituted;

21. The compound according to the above 1, wherein each of $R^1$ and $R^2$ is hydrogen atom or a $C_{1-6}$ alkyl group;

22. The compound according to the above 1, wherein each of $R^1$ and $R^2$ is hydrogen atom or methyl group;

23. The compound according to the above 1, wherein $R^1$ and $R^2$ form, together with the adjacent carbon atom, a ring that is represented by

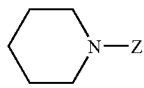

(wherein Z is hydrogen atom or a $C_{1-6}$ alkyl group);

24. The compound according to the above 1, wherein $R^3$ is phenyl group that may be substituted with halogen or $C_{1-6}$ alkyl;

25. The compound according to the above 1, wherein $R^3$ is phenyl group that may be substituted with fluorine, methyl or isopropyl;

26. The compound according to the above 1, wherein the substitution position on ring C of a group represented by the formula —$NR^4(R^5)$ is 5-position on the benzofuran ring or the dihydrobenzofuran ring;

27. The compound according to the above 1, wherein $R^4$ is (1) a $C_{1-6}$ alkyl group that is substituted with an aromatic group that may be substituted with halogen, $C_{1-6}$ alkoxy or $C_{1-3}$ alkylenedioxy, or (2) an acyl group, which contains an aromatic group that may be substituted with halogen, $C_{1-6}$ alkoxy or $C_{1-3}$ alkylenedioxy;

28. The compound according to the above 1, wherein $R^4$ is benzyl group or phenethyl group that may be substituted with fluorine, methoxy or methylenedioxy;

29. The compound according to the above 1, wherein $R^5$ is hydrogen atom, a $C_{1-6}$ alkyl group or a $C_{1-6}$ alkyl-carbonyl group;

30. The compound according the above 1, wherein $R^5$ is hydrogen atom or methyl group;

31. The compound according to the above 1, wherein ring C is benzene ring that may be further substituted with 1 to 3 $C_{1-6}$ alkyl groups;

32. The compound according to the above 1, wherein ring C is benzene ring that is further substituted with 3 methyl groups;

33. The compound according to the above 1, wherein $R^1$ and $R^2$ are the same or different and each is hydrogen atom or a $C_{1-6}$ alkyl group, or $R^1$ and $R^2$ form, together with the adjacent carbon atom, a piperidine ring that is substituted with $C_{1-6}$ alkyl;

$R^3$ is phenyl group that may be substituted with halogen or $C_{1-6}$ alkyl;

$R^4$ is (1) a $C_{1-6}$ alkyl group that is substituted with $C_{6-14}$ aryl, thienyl or pyridyl, which may be substituted with halogen, $C_{1-6}$ alkoxy or $C_{1-3}$ alkylenedioxy, or (2) a $C_{6-14}$ aryl-carbonyl group, a $C_{7-16}$ aralkyl-carbonyl group, a $C_{6-14}$ arylsulfonyl group, nicotinoyl group or thenoyl group, which may be substituted with halogen, $C_{1-6}$ alkoxy or $C_{1-3}$ alkylenedioxy;

$R^5$ is hydrogen atom, a $C_{1-6}$ alkyl group or a $C_{1-6}$ alkylcarbonyl group; and ring C is benzene ring that is further substituted with 1 to 3 $C_{1-6}$ alkyl groups;

34. The compound according to the above 1, wherein each of $R^1$ and $R^2$ is hydrogen atom or a $C_{1-3}$ alkyl group;

$R^3$ is a $C_{6-14}$ aryl group that may be substituted with a halogen atom or $C_{1-6}$ alkyl;

$R^4$ is a $C_{7-15}$ aralkyl group that may be substituted with a halogen atom, $C_{1-6}$ alkoxy or $C_{1-3}$ alkylenedioxy;

$R^5$ is hydrogen atom or a $C_{1-6}$ alkyl group;

----- is a single bond; and ring C is benzene ring that is further substituted with 3 $C_{1-6}$ alkyl groups;

35. The compound according to claim 1, wherein each of $R^1$ and $R^2$ is methyl group;

$R^3$ is phenyl group that may be substituted with fluorine, methyl or isopropyl;

$R^4$ is benzyl group or phenethyl group that may be substituted with fluorine, methoxy or methylenedioxy;

$R^5$ is hydrogen atom or methyl group;

----- is a single bond; and ring C is benzene ring that is further substituted with 3 methyl groups;

36. [1] N-(4-fluorobenzyl)-2,2,4,6,7-pentamethyl-3-phenyl-2,3-dihydro-1-benzofuran-5-amine, [2] N-benzyl-3-(4-isopropylphenyl)-2,2,4,6,7-pentamethyl-2,3-dihydro-1-benzofuran-5-amine, [3] 3-(4-isopropylphenyl)-N-(4-methoxybenzyl)-N,2,2,4,6,7-hexamethyl-2,3-dihydro-1-benzofuran-5-amine, [4] 3-(4-isopropylphenyl)-N-[2-(4-methoxyphenyl)ethyl]-2,2,4,6,7-pentamethyl-2,3-dihydro-1-benzofuran-5-amine, [5] N-(4-fluorobenzyl)-3-(4-isopropylphenyl)-2,2,4,6,7-pentamethyl-2,3-dihydro-1-benzofuran-5-amine, [6] N-(1,3-benzodioxol-5-ylmethyl)-3-(4-isopropylphenyl)-2,2,4,6,7-pentamethyl-2,3-dihydro-1-benzofuran-5-amine, [7] N-(4-fluorobenzyl)-3-(4-fluorophenyl)-2,2,4,6,7-pentamethyl-2,3-dihydro-1-benzofuran-5-amine, [8] N-(4-methoxybenzyl)-2,2,4,6,7-pentamethyl-3-(4-methylphenyl)-2,3-dihydro-1-benzofuran-5-amine, [9] N-(4-fluorobenzyl)-2,2,4,6,7-pentamethyl-3-(4-methylphenyl)-2,3-dihydro-1-benzofuran-5-amine, [10] 3-(4-isopropylphenyl)-N-(4-methoxybenzyl)-2,4,6,7-tetramethyl-1-benzofuran-5-amine, [11] N-(4-fluorobenzyl)-3-(4-isopropylphenyl)-2,4,6,7-tetramethyl-1-benzofuran-5-amine, [12] N-(4-fluorobenzyl)-3-(4-fluorophenyl)-2,4,6,7-tetramethyl-1-benzofuran-5-amine, [13] N-(4-fluorobenzyl)-3-(4-isopropylphenyl)-1',4,6,7-tetramethylspiro[benzofuran-2(3H),4'-piperidine]-5-amine, or [14] (+)-N-(4-fluorobenzyl)-3-(4-isopropylphenyl)-2,2,4,6,7-pentamethyl-2,3-dihydro-1-benzofuran-5-amine hydrochloride;

37. A prodrug of the compound according to the above 1;

38. A process for producing the compound according to the above 1 which comprises reacting a compound represented by the formula:

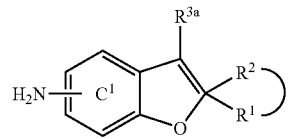

wherein each of the symbol is as defined in the above 2, or a salt thereof with a compound represented by the formula:

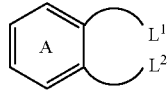

wherein each of L¹ and L² is a leaving group and ring A is as defined in the above 2, or a salt thereof, or reacting a compound represented by the formula:

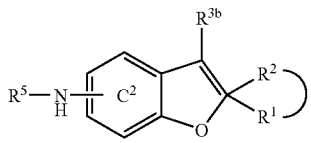

wherein each symbol is as defined in the above 3, or a salt thereof with a compound represented by the formula: R⁴-L (wherein L is a leaving group and R⁴ is as defined in the above 3);

39. A pharmaceutical composition which comprises a compound represented by the formula:

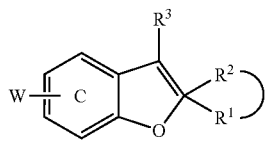

wherein R¹ and R² are the same or different and each is hydrogen atom, a hydrocarbon group that may be substituted or a heterocyclic group that may be substituted or R¹ and R² may form, together with the adjacent carbon, a 3- to 8-membered homocyclic or heterocyclic ring that may be subsituted,

----- is a single bond or a double bond,
W is
(i) a group represented by the formula:

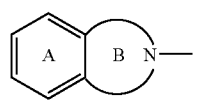

(Wa)

wherein ring A is benzene ring that may be substituted and ring B is a 5- to 7-membered nitrogen-containing heterocyclic ring, which may be substituted with a halogen or a hydrocarbon group that may be substituted, or (ii) a group represented by the formula:

(Wb)

wherein R⁴ is (1) an aliphatic hydrocarbon group which may be substituted with an aromatic group that may be substituted and, may further be substituted, or (2) an acyl group containing an aromatic group that may be substituted, R⁵ is hydrogen atom, a $C_{1-6}$ alkyl group, or an acyl group, when W is Wa, R³ is hydrogen atom, a hydrocarbon group that may be substituted or a heterocyclic group that may be substituted and ring C is benzene ring that may be substituted with, in addition to the group represented by Wa, a substituent selected from halogen, lower alkyl that may be halogenated, lower alkoxy that may be halogenated, and lower alkylthio that may be halogenated, when W is Wb, R³ is a $C_{6-14}$ aryl group that may be substituted and ring C is benzene ring that may be further substituted, in addition to the group represented by Wb, provided that, when

----- is a double bond, the partial structure:

or a salt thereof, or a prodrug thereof;

40. The composition according to the above 39 which is an agent for inhibiting neurodegeneration;

41. The composition according to the above 39 which is an agent for inhibiting cytotoxicity of β-amyloid;

42. The composition according to the above 39 which is an agent for exhibiting a neurotrophic factor-like activity;

43. The composition according to the above 39 which is a drug for preventing or treating neurodegenerative diseases;

44. The composition according to the above 39 which is a drug for preventing or treating Alzheimer's disease or Parkinson's disease.

45. A method for treating Alzheimer's disease or Parkinson's disease which comprises administrating an effective amount of the compound according to the above 1 or a prodrug thereof to a mammal;

46. Use of the compound according to the above 1 or a prodrug thereof for manufacturing an agent for treating Alzheimer's disease or Parkinson's disease;

47. An inhibitor of neurodegeneration which comprises a compound represented by the formula:

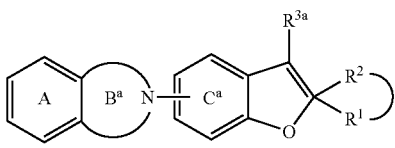

(Ia')

wherein R¹ and R² are the same or different and each is hydrogen atom, a hydrocarbon group that may be substituted or a heterocyclic group that may be substituted, or R¹ and R² may form, together with the adjacent carbon, a 3- to 8-membered homocylcic or heterocyclic ring that may be substituted, R$^{3a}$ is hydrogen atom, a hydrocarbon group that may be substituted or a heterocyclic group that may be substituted, ----- indicates a single bond or a double bond, ring A is benzene ring that may be substituted, ring B$^a$ is a 5- to 7-membered heterocyclic ring that may be substituted, ring C$^a$ is benzene ring which may be further substituted, in addition to the group represented by the formula:

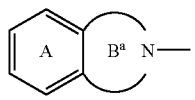

wherein each symbol is as defined above, or a salt thereof, or a prodrug thereof;

48. The inhibitor according to the above 47 which is an agent for inhibiting cytotoxicity of β-amyloid;

49. The inhibitor according to the above 47 which is an agent for exhibiting a neurotrophic factor-like activity;

50. The inhibitor according to the above 47 which is a drug for preventing or treating neurodegenerative diseases;

51. The inhibitor according to the above 47 which is a drug for preventing of treating Alzheimer's disease or Parkinson's disease;

52. A method for treating Alzheimer's disease or Parkinson's disease which comprises administrating an effective amount of the compound according the above 47 or a prodrug thereof to a mammal; and 53. Use of the compound according to the above 47 or a prodrug thereof for manufacturing an agent for treating Alzheimer's disease or Parkinson's disease.

BEST EMBODIMENT OF THE INVENTION

In the above-mentioned formulas,

----- indicates a single bond or a double bond.

In the above-mentioned formulas, R¹ and R² are the same or different and each is hydrogen atom, a hydrocarbon group that may be substituted or a heterocyclic group that may be substituted, or R¹ and R² may form, together with the adjacent carbon, a 3- to 8-membered, homocyclic or heterocyclic ring that may be substituted.

When

----- indicates a double bond in the above-mentioned formulas, R² is not present. In other words, in the above-mentioned formulas, (i) when

----- indicates a single bond, the partial structure: is

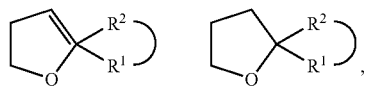

(ii) when

----- indicates a double bond, the partial structure: is

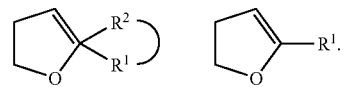

In the present specification, for convenience, sometimes, the above (i) and (ii) together are represented by the formula:

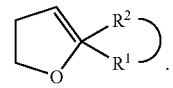

Examples of "a hydrocarbon group" of "a hydrocarbon group that may be substituted" indicated by R¹ or R² include a chain or cyclic hydrocarbon group (e.g., alkyl, alkenyl, alkynyl, cycloalkyl, aryl, etc.) or the like. Among them, a chain or cyclic hydrocarbon group having 1 to 16 carbon atoms is preferred.

Examples of "alkyl" include preferably $C_{1-6}$ alkyl (e.g., methyl, ethyl, propyl, isopropyl, butyl, isobutyl, sec-butyl, tert-butyl, pentyl, hexyl, etc.), etc.

Examples of "alkenyl" include preferably $C_{2-6}$ alkenyl (e.g., vinyl, allyl, isopropenyl, butenyl, isobutenyl, sec-butenyl, etc.), etc.

Examples of "alkynyl" include preferably $C_{2-6}$ alkynyl (e.g., ethynyl, propargyl, butynyl, 1-hexynyl, etc.), etc.

Examples of "cycloalkyl" include preferably $C_{3-6}$ cycloalkyl (e.g., cyclopropyl, cyclobutyl, cyclopentyl, cyclohexyl, etc.), etc.

Examples of "aryl" include preferably $C_{6-14}$ aryl (e.g., phenyl, 1-naphthyl, 2-naphthyl, biphenylyl, 2-anthryl, etc.), etc.

Examples of "substituent(s)" of "a hydrocarbon group that may be substituted" indicated by R¹ or R² include (1) halogen atom (e.g., fluorine, chlorine, bromine, iodine, etc.), (2) $C_{1-3}$ alkylenedioxy (e.g., methylenedioxy, ethylenedioxy, etc.), (3) nitro, (4) cyano, (5) $C_{1-6}$ alkyl that may be halogenated, (6) $C_{2-6}$ alkenyl that may be halogenated, (7) $C_{2-6}$ alkynyl that may be halogenated, (8) $C_{3-6}$ cycloalkyl that may be halogenated, (9) a $C_{6-14}$ aryl (e.g., phenyl, 1-naphthyl, 2-naphthyl, biphenylyl, 2-anthryl, etc.), (10) $C_{1-6}$ alkoxy that may be halogenated, (11) $C_{1-6}$ alkylthio that may be halogenated or mercapto, (12) hydroxyl, (13) amino, (14) mono-$C_{1-6}$ alkylamino (e.g., methylamino, ethylamino, etc.), (15) mono-$C_{6-14}$ arylamino (e.g., phenylamino, 1-naphthylamino, 2-naphthylamino, etc.), (16) di-$C_{1-6}$ alkylamino (e.g., dimethylamino, diethylamino, etc.), (17) di-$C_{6-14}$ arylamino (e.g., diphenylamino, etc.), (18) acyl, (19) acylamino, (20) acyloxy, (21) 5- to 7-membered saturated-cyclic amino that may be substituted, (22) 5- to 10-membered aromatic heterocyclic group (e.g., 2- or 3-thienyl, 2-, 3-, or 4-pyridyl, 2-, 3-, 4-, 5-, or 8-quinolyl, 1-, 3-, 4-, or 5-isoquinolyl, 1-, 2-, or 3-indolyl, 2-benzothiazolyl, 2-benzo[b]thienyl, benzo[b]furanyl, etc.), (23) sulfo, and (24) $C_{6-14}$ aryloxy (e.g., phenyloxy, 1-naphthyloxy, etc.), etc.

Said "hydrocarbon group" may have 1 to 5, preferably 1 to 3 substituents, for example, those as mentioned above, at any substitutable positions. When 2 or more substituents are present, each of them may be the same or different.

Examples of the above-mentioned "$C_{1-6}$ alkyl that may be halogenated" include $C_{1-6}$ alkyl (e.g., methyl, ethyl, propyl, isopropyl, butyl, isobutyl, sec-butyl, tert-butyl, pentyl, hexyl, etc.) that may have 1 to 5, preferably 1 to 3 halogen atoms (e.g., fluorine, chlorine, bromine, iodine, etc.) or the like. Specific examples include methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, or the like.

Examples of the above-mentioned "$C_{2-6}$ alkenyl that may be halogenated" include $C_{2-6}$ alkenyl (e.g., vinyl, allyl, isopropenyl, butenyl, isobutenyl, sec-butenyl, etc.) that may have 1 to 5, preferably 1 to 3 halogen atoms (e.g., fluorine, chlorine, bromine, iodine, etc.), or the like. Specific examples include vinyl, allyl, isopropenyl, butenyl, isobutenyl, sec-butenyl, 3,3,3-trifluoropropenyl, 4,4,4-trifluorobutenyl, or the like.

Examples of the above-mentioned "$C_{2-6}$ alkynyl that may be halogenated" include $C_{2-6}$ alkynyl (e.g., ethynyl, propargyl, butynyl, 1-hexynyl, etc.) that may have 1 to 5, preferably 1 to 3, halogen atoms (for example, fluorine, chlorine, bromine, iodine, and the like) or the like. Specific examples include ethinyl, propargyl, butinyl, 1-hexinyl, 3,3,3-trifluoro-1-propinyl, 4,4,4-trifluoro-1-butinyl, or the like.

Examples of the above-mentioned "$C_{3-6}$ cycloalkyl that may be halogenated" include $C_{3-6}$ cycloalkyl (e.g., cyclopropyl, cyclobutyl, cyclopentyl, cyclohexyl, etc.) that may have 1 to 5, preferably 1 to 3 halogen atoms (e.g., fluorine, chlorine, bromine, iodine, etc.), or the like. Specific examples include cyclopropyl, cyclobutyl, cyclopentyl, cyclohexyl, 4,4-dichlorocyclohexyl, 2,2,3,3, -tetraflourocyclopentyl, 4-chlorocyclohexyl, or the like.

Examples of the above-mentioned "$C_{1-6}$ alkoxy that may be halogenated" include $C_{1-6}$ alkoxy (e.g., methoxy, ethoxy, propoxy, isopropoxy, butoxy, isobutoxy, sec-butoxy, pentyloxy, hexyloxy, etc.) that may have 1 to 5, preferably 1 to 3 halogen atoms (e.g., fluorine, chlorine, bromine, iodine, etc.) or the like. Specific examples include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy, or the like.

Examples of the above-mentioned "$C_{1-6}$ alkylthio that may be halogenated" include $C_{1-6}$ alkylthio (e.g., methylthio, ethylthio, propylthio, isopropylthio, butylthio, sec-butylthio, tert-butylthio, etc.) that may have 1 to 5, preferably 1 to 3 halogen atoms (e.g., fluorine, chlorine, bromine, iodine, etc.) or the like. Specific examples include methylthio, difluoromethylthio, trifluoromethylthio, ethylthio, propylthio, isopropylthio, butylthio, 4,4,4-trifluorobutylthio, pentylthio, hexylthio, or the like.

Examples of the above-mentioned "acyl" include formyl, carboxyl, carbamoyl, $C_{1-6}$ alkylcarbonyl (e.g., acetyl, propionyl, etc.), $C_{3-6}$ cycloalkylcarbonyl (e.g., cyclopropylcarbonyl, cyclopentylcarbonyl, cyclohexylcarbonyl, etc.), $C_{1-6}$ alkoxycarbonyl (e.g., methoxycarbonyl, ethoxycarbonyl, propoxycarbonyl, tert-butoxycarbonyl, etc.), $C_{6-14}$ arylcarbonyl (e.g., benzoyl, 1-naphthoyl, 2-naphthoyl, etc.), $C_{7-16}$ aralkylcarbonyl (e.g., phenylacetyl, phenylpropionyl, etc.), $C_{6-14}$ aryloxycarbonyl (e.g., phenoxycarbonyl, etc.), $C_{7-16}$ aralkyloxycarbonyl (e.g., benzyloxycarbonyl, phenethyloxycarbonyl, etc.), 5- or 6-membered heterocyclic carbonyl (e.g., nicotinoyl, isonicotinoyl, 2-thenoyl, 3-thenoyl, 2-furoyl, 3-furoyl, morpholinocarbonyl, thiomorpholinocarbonyl, piperidinocarbonyl, 1-pyrrolidinylcarbonyl, etc.), mono-$C_{1-6}$ alkylcarbamoyl (e.g., methylcarbamoyl, ethylcarbamoyl, etc.), di-$C_{1-6}$ alkylcarbamoyl (e.g., dimethylcarbamoyl, diethylcarbamoyl, ethylmethylcarbamoyl, etc.), $C_{6-14}$ arylcarbamoyl (e.g., phenylcarbamoyl, 1-naphthylcarbamoyl, 2-naphthylcarbamoyl, etc.), thiocarbamoyl, 5- or 6-membered, heterocyclic carbamoyl (e.g., 2-pyridylcarbamoyl, 3-pyridylcarbamoyl, 4-pyridylcarbamoyl, 2-thienylcarbamoyl, 3-thienylcarbamoyl, etc.), $C_{1-6}$ alkylsulfonyl (e.g., methylsulfonyl, ethylsulfonyl, etc.), $C_{6-14}$ arylsulfonyl (e.g., phenylsulfonyl, 1-naphthylsulfonyl, 2-naphthylsulfonyl, etc.), $C_{1-6}$ alkylsulfinyl (e.g., methylsulfinyl, ethylsulfinyl, etc.), and $C_{6-14}$ arylsulfinyl (e.g., phenylsulfinyl, 1-naphthylsulfinyl, 2-naphthylsulfinyl, etc.), or the like.

Examples of the above-mentioned "acylamino" include formylamino, $C_{1-6}$ alkylcarbonylamino (e.g., acetylamino, etc.), $C_{6-14}$ arylcarbonylamino (e.g., phenylcarbonylamino, naphthylcarbonylamino, etc.), $C_{1-6}$ alkoxycarbonylamino (e.g., methoxycarbonylamino, ethoxycarbonylamino, propoxycarbonylamino, butoxycarbonylamino, etc.), $C_{1-6}$ alkylsulfonylamino (e.g., methylsulfonylamino, ethylsulfonylamino, etc.), and $C_{6-14}$ arylsulfonylamino (e.g., phenylsulfonylamino, 2-naphthylsulfonylamino, 1-naphthylsulfonylamino, etc.), or the like.

Examples of the above-mentioned "acyloxy" include $C_{1-6}$ alkylcarbonyloxy (e.g., acetoxy, propionyloxy, etc.), $C_{6-14}$ arylcarbonyloxy (e.g., benzoyloxy, naphthylcarbonyloxy, etc.), $C_{1-6}$ alkoxycarbonyloxy (e.g., methoxycarbonyloxy, ethoxycarbonyloxy, propoxycarbonyloxy, butoxycarbonyloxy, etc.), mono-$C_{1-6}$ alkylcarbamoyloxy (e.g., methylcarbamoyloxy, ethylcarbamoyloxy, etc.), di-$C_{1-6}$ alkylcarbamoyloxy (e.g., dimethylcarbamoyloxy, diethylcarbamoyloxy, etc.), $C_{6-14}$ arylcarbamoyloxy (e.g., phenylcarbamoyloxy, naphthylcarbamoyloxy, etc.), nicotinoyloxy, or the like.

Examples of "5- to 7-membered saturated cyclic amino" of the above-mentioned "5- to 7-membered saturated cyclic amino that may be substituted" include morpholino, thiomorpholino, piperazin-1-yl, piperidino, pyrrolidin-1-yl, or the like. Examples of the "substituent(s)" of said "5- to 7-membered saturated cyclic amino that may be substituted" include 1 to 3 substituents selected from $C_{1-6}$ alkyl (e.g., methyl, ethyl, propyl, isopropyl, butyl, isobutyl, sec-butyl, tert-butyl, pentyl, hexyl, etc.), $C_{6-14}$ aryl (e.g., phenyl, 1-naphthyl, 2-naphthyl, biphenylyl, 2-anthryl, etc.), a 5- to 10-membered aromatic, heterocyclic group (e.g., 2- or 3-thienyl, 2-, 3-, or 4-pyridyl, 2-, 3-, 4-, 5-, or 8-quinolyl, 1-, 3-, 4-, or 5-isoquinolyl, 1-, 2-, or 3-indolyl, 2-benzothiazolyl, 2-benzo[b]thienyl, benzo[b]furanyl, etc.), and the like.

Examples of "a heterocyclic group" of "a heterocyclic group that may be substituted" indicated by $R^1$ or $R^2$ include a 5- to 14-membered, heterocyclic group that contains, in addition to carbon atom, 1 to 4 hetero atoms selected from nitrogen atom, sulfur atom and oxygen atom (an aromatic heterocyclic group, or a saturated or unsaturated non-aromatic heterocyclic group) or the like.

Examples of said "aromatic heterocyclic group" include a 5- to 14-membered, preferably 5- to 10-membered aromatic heterocyclic group that contains, in addition to carbon atom, 1 or more (for example, 1 to 4) hetero atoms selected from nitrogen atom, sulfur atom and oxygen atom, or the like. Specific examples include a monovalent group formed by removing an optional hydrogen atom from an aromatic heterocyclic ring such as thiophene, benzothiophene, benzofuran, benzimidazole, benzoxazole, benzothiazole, benzisothiazole, naphtho[2,3-b]thiophene, furan, isoindolizine, xantholene, phenoxatine, pyrrole, imidazole, pyrazole, pyridine, pyrazine, pyrimidine, pyridazine, indole, isoindole, 1H-indazole, purine, 4H-quinolidine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, oxazole, isoxazole, furazane, phenoxazine, etc., or a ring formed by condensing the above ring (preferably a monocyclic ring) with 1 to plural (preferably, 1 or 2) aromatic rings (e.g., benzene ring, etc.), and the like.

Examples of "an aromatic heterocyclic group" include preferably a 5- to 10-membered aromatic heterocyclic group that may be condensed with a benzene ring. Specific examples include 2-, 3-, or 4-pyridyl, 2-, 3-, 4-, 5-, or 8-quinolyl, 1-, 3-, 4-, or 5-isoquinolyl, 1-, 2-, or 3-indolyl, 2-benzothiazolyl, 2-benzo[b]thienyl, benzo[b]furanyl, 2- or 3-thienyl, or the like. More preferred examples include 2- or 3-thienyl, 2-, 3-, or 4-pyridyl, 2- or 3-quinolyl, 1-isoquinolyl, 1- or 2-indolyl, 2-benzothiazolyl, and the like.

Examples of "a non-aromatic heterocyclic group" include a 3- to 8-membered (preferably, 5- or 6-membered), saturated or unsaturated (preferably, saturated), non-aromatic heterocyclic group (an aliphatic heterocyclic group) such as oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, or the like.

As for "substituent(s)" of "a heterocyclic group that may be substituted" indicated by $R^1$ or $R^2$, the same number and the "substituent(s)" as those of "a hydrocarbon group that may be substituted" indicated by $R^1$ or $R^2$ can be employed.

Examples of "a 3- to 8-membered homocyclic ring" of "a 3- to 8-membered homocyclic ring that may be substituted" formed by $R^1$ and $R^2$ include $C_{3-6}$ cycloalkane such as cyclopropane, cyclobutane, cyclopentane, cyclohexane, or the like.

Examples of "a 3- to 8-membered heterocyclic ring" of "a 3- to 8-membered heterocyclic ring that may be substituted" formed by $R^1$ and $R^2$ include a 3- to 8-membered heterocyclic group that contains, in addition to carbon atom, 1 to 4 hetero atoms selected from nitrogen atom, sulfur atom and oxygen atom, such as aziridine, azetidine, morpholine, thiomorpholine, piperazine, piperidine, pyrrolidine, hexamethyleneimine, heptamethyleneimine, hexahydropyrimidine, or the like.

As for "substituent(s)" of "a 3- to 8-membered homocyclic or heterocyclic ring that may be substituted" formed by $R^1$ and $R^2$, the same number and the same "substituents" as those of "a hydrocarbon group that may be substituted" indicated by $R^1$ or $R^2$ can be employed.

In the above-mentioned formulas, W indicates (i) a group represented by the formula:

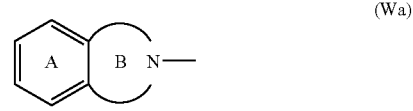

wherein ring A is benzene ring that may be substituted and ring B is a 5- to 7-membered nitrogen-containing heterocyclic ring, which may be substituted with a halogen or a hydrocarbon group that may be substituted, or (ii) a group represented by the formula:

wherein $R^4$ is (1) an aliphatic hydrocarbon group which may be substituted with an aromatic group that may be substituted and, may further be substituted, or (2) an acyl group containing an aromatic group that may be substituted, $R^5$ is hydrogen atom, a $C_{1-6}$ alkyl group, or an acyl group.

When W is Wa, in the above-mentioned formulas, $R^3$ is hydrogen atom, a hydrocarbon group that may be substituted or a heterocyclic group that may be substituted (hereinafter, sometimes, referred to as $R^{3a}$).

As for "a hydrocarbon group that may be substituted" and "a heterocyclic group that may be substituted" indicated by $R^3$, the same groups as the above-mentioned "hydrocarbon group that may be substituted" and "a heterocyclic group that may be substituted" indicated by $R^1$ or $R^2$ can be employed.

In the above-mentioned formulas, ring A indicates benzene ring that may be substituted.

The "substituent(s)" of the "benzene ring that may be substituted" indicated by ring A may have 1 to 4 (preferably 1 or 2) groups, which are the same as the above-mentioned "substituent(s)" of "a hydrocarbon group that may be substituted" indicated by $R^1$ or $R^2$, at substitutable positions. When the number of the substituents is 2 or more, the substituents may be the same or different.

In the above-mentioned formulas, ring B indicates a 5- to 7-membered nitrogen-containing heterocyclic ring which may be substituted with a halogen or a hydrocarbon group that may be substituted.

Examples of "a 5- to 7-membered, nitrogen-containing, heterocyclic ring" indicated by ring B include a 5- to 7-membered nitrogen-containing heterocyclic ring or the like such as pyrrole (e.g., 1H-pyrrole, etc.), dihydropyrrole (e.g., 2,5-dihydro-1H-pyrrole, etc.), dihydropyridine (e.g., 1,2-dihydropyridine, etc.), tetrahydropyridine (e.g., 1,2,3,4-tetrahyropyridine, etc.), azepine (e.g., 1H-azepine, etc.), dihydroazepine (e.g., 2,3-dihydro-1H-azepine, 2,5-dihydro-1H-azepine, 2,7-dihydro-1H-azepine, etc.), tetrahydroazepine (for example, 2,3,6,7-tetrahydro-1H-azepine, 2,3,4,7-tetrahydro-1H-azepine, etc.), or the like.

"A halogen" as "the substituent", which ring B may have, is exemplified by fluorine, chlorine, bromine, iodine, or the like.

As for "a hydrocarbon group that may be substituted", which ring B may have, the same group as the above-mentioned "hydrocarbon group that may be substituted" indicated by $R^1$ or $R^2$ can be employed.

Ring B may have 1 to 3 substituents as indicated above at substitutable positions. When the number of the substituents is 2 or more, the substituents may be the same or different.

Specific examples of a group represented by the formula:

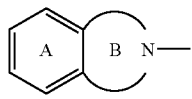

wherein each symbol is as defined above, include groups represented by formulas:

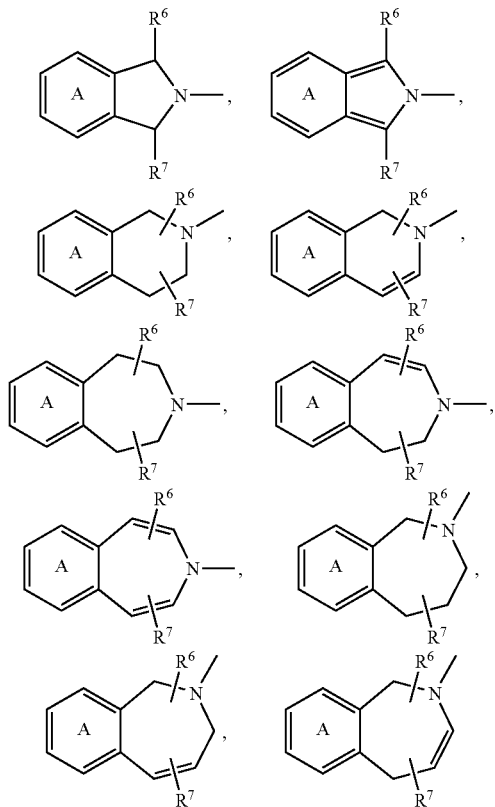

wherein $R^6$ and $R^7$ are the same or different and each is hydrogen atom, halogen, or a hydrocarbon group that be substituted, and ring A is as defined above, and the like.

Preferred are groups represented by

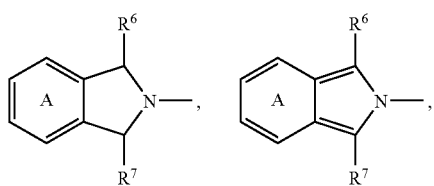

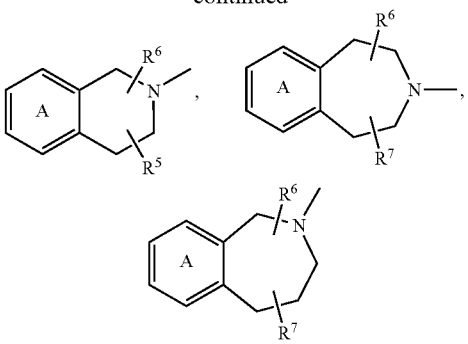

wherein each symbol is as defined above, and the like, and, more preferred are groups represented by

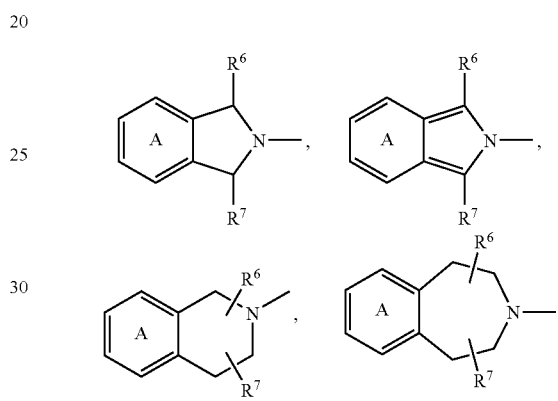

wherein each symbol is as defined above, and the like, among which, particularly preferably groups represented by

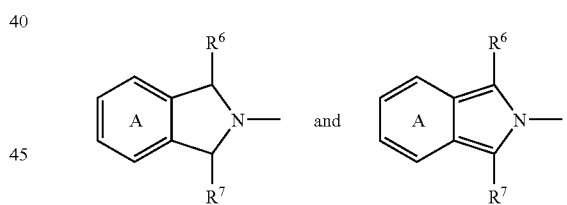

wherein each symbol is as defined above, and the like.

As for "halogen" or "a hydrocarbon group that may be substituted" indicated by $R^6$ and $R^7$, the same groups as "halogen" or "a hydrocarbon group that may be substituted" as the "substituents" of the above-mentioned ring B can be employed.

In the above-mentioned formulas, ring $B^a$ indicates a 5- to 7-membered nitrogen-containing heterocyclic ring that may be substituted.

As for "a 5- to 7-membered nitrogen-containing heterocyclic ring" indicated by ring $B^a$, the same ring as the "5- to 7-membered nitrogen-containing heterocyclic ring" indicated in the above-mentioned ring B can be employed.

As for "substituent(s)" of "a 5- to 7-membered nitrogen-containing, heterocyclic ring that may be substituted" indicated by ring $B^a$, in addition to "a halogen" and "a hydrocarbon group that may be substituted", which ring B may have, the same number and the same "substituent(s)" as those of the above-mentioned "hydrocarbon group that may be substituted" indicated by $R^1$ or $R^2$ can be employed. Also, oxo group and the like are employed as the substituent(s) of ring $B^a$.

When W is Wa, in the above-mentioned formula, ring C is benzene ring that may further be substituted with, in addition to the group represented by the formula:

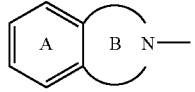

wherein each symbol is as defined above, a substituent selected from halogen, lower alkyl that may be halogenated, lower alkoxy that may be halogenated, and lower alkylthio that may be halogenated (hereinafter, sometimes, referred to as ring $C^1$).

Ring $C^1$ may have 1 to 3 (preferably, 1) substituents as indicated by formula

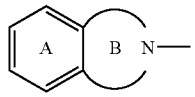

at substitutable positions. When the number of the substituents is 2 or more, the substituents may be the same or different.

"A halogen" as "the substituent", which ring $C^1$ may further have, is exemplified by fluorine, chlorine, bromine, iodine, or the like. "Lower alkyl that may be halogenated" is exemplified by $C_{1-6}$ alkyl (e.g., methyl, ethyl, propyl, isopropyl, butyl, isobutyl, sec-butyl, tert-butyl, pentyl, hexyl, etc.) that may have 1 to 5, preferably 1 to 3, halogen atoms (e.g., fluorine, chlorine, bromine, iodine, etc.), etc. Specific examples include methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, or the like. "Lower alkoxy that may be halogenated" is exemplified by $C_{1-6}$ alkoxy (e.g., methoxy, ethoxy, propoxy, isopropoxy, butoxy, isobutoxy, sec-butoxy, pentyloxy, hexyloxy, or the like) that may have 1 to 5, preferably 1 to 3, halogen atoms (e.g., fluorine, chlorine, bromine, iodine, etc.), or the like. Specific examples include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy, or the like. "Lower alkylthio that may be halogenated" is exemplified by $C_{1-6}$ alkylthio (e.g., methylthio, ethylthio, propylthio, isopropylthio, butylthio, sec-butylthio, tert-butylthio, etc.) that may have 1 to 5, preferably 1 to 3, halogen atoms (e.g., fluorine, chlorine, bromine, iodine, etc.), or the like. Specific examples include methylthio, difluoromethylthio, trifluoromethylthio, ethylthio, propylthio, isopropylthio, butylthio, 4,4,4-trifluorobutylthio, pentylthio, hexylthio, or the like.

Ring $C^1$ may have 1 to 3 (preferably, 3) substituents as indicated above at substitutable positions. When the number of the substituents is 2 or more, the substituents may be the same or different.

In the above-mentioned formula, ring $C^a$ is benzene ring that may further be substituted, in addition to a group represented by the formula:

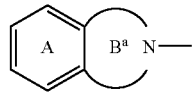

wherein each symbol is as defined above.

Ring $C^a$ may have 1 to 3 (preferably, 1) groups as indicated by the formula:

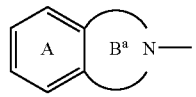

at substitutable positions. When the number of the substituents is 2 or more, the substituents may be the same or different.

As for "substituent(s)", which ring $C^a$ may further have, the same "substituents" as those of the above-mentioned "hydrocarbon group that may be substituted" indicated by $R^1$ or $R^2$ are employed. Also, "$C_{1-6}$ alkyl" as for "substituent(s)" of ring $C^a$ may be substituted with "a 4- to 8-membered lactone that may be substituted with hydroxyl or the like (e.g., 3-hydroxy-δ-valerolactone, etc.)". Ring $C^a$ may have 1 to 3 (preferably, 3) substituents as indicated above at substitutable positions. when the number of the substituents is 2 or more, the substituents may be the same or different.

When W indicates Wb, in the above-mentioned formulas, $R^3$ indicates a $C_{6-14}$ aryl group that may be substituted (hereinafter, sometimes, referred to as $R^{3b}$).

"$C_{6-14}$ aryl" of "a $C_{6-14}$ aryl group that may be substituted" indicated by $R^{3b}$ is exemplified by $C_{6-14}$ aryl such as phenyl, 1-naphthyl, 2-naphthyl, biphenylyl, anthryl, or the like.

As for "substituent(s)" of said "$C_{6-14}$ aryl group that may be substituted", the same number and the same "substituent(s)" as those of the above-mentioned "hydrocarbon group that may be substituted" indicated by $R^1$ or $R^2$ can be employed.

In the above-mentioned formulas, $R^4$ indicates (1) an aliphatic hydrocarbon group, which may be substituted with an aromatic group that may be substituted and, may further be substituted, or (2) an acyl group containing an aromatic group that may be substituted.

Examples of "an aromatic group" of "an aromatic group that may be substituted" as the substituent(s) of "an aliphatic hydrocarbon group, which may be substituted with an aromatic group that may be substituted and, may further be substituted" indicate by $R^4$ include an aromatic hydrocarbon group, an aromatic heterocyclic group, or the like.

Said "aromatic hydrocarbon group" as defined above is exemplified by a monocyclic or condensed polycyclic (bi- or tricyclic), aromatic, hydrocarbon group having 6 to 14 carbon atoms. Specific examples include $C_{6-14}$ aryl such as phenyl, 1-naphthyl, 2-naphthyl, biphenylyl, anthryl, or the like or the like, preferably a $C_{6-10}$ such as phenyl, 1-naphthyl, 2-naphthyl, or the like.

Said "aromatic heterocyclic group" is exemplified by a 5- to 14-membered, preferably 5- to 10-membered, aromatic heterocyclic group that contains, in addition to carbon atom, 1 or more (for example, 1 to 4) hetero atoms selected from nitrogen atom, sulfur atom and oxygen atom, or the like.

Specific examples include a monovalent group, which may be formed by removing an optional hydrogen atom from an aromatic heterocyclic ring such as thiophene, benzothiophene, benzofuran, benzimidazole, benzoxazole, benzothiazole, benzisothiazole, naphtho[2,3-b]thiophene, furan, isoindolizine, xantholene, phenoxatine, pyrrole, imidazole, pyrazole, pyridine, pyrazine, pyrimidine, pyridazine, indole, isoindole, 1H-indazole, purine, 4H-quinolidine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, oxazole, isoxazole, furazane, phenoxazine, or the like or a ring, which is formed by condensing these rings (preferably a monocyclic ring) with 1 to plural (preferably, 1 or 2) aromatic rings (for example, benzene ring, etc.), and so on.

"An aromatic heterocyclic group" is exemplified preferably by a 5- to 10-membered aromatic heterocyclic group that may be condensed with benzene ring. Specific examples include 2-, 3-, or 4-pyridyl, 2-, 3-, 4-, 5-, or 8-quinolyl, 1-, 3-, 4-, or 5-isoquinolyl, 1-, 2-, or 3-indolyl, 2-benzothiazolyl, 2-benzo[b]thienyl, benzo[b]furanyl, 2- or 3-thienyl, or the like. More preferable examples include 2- or 3-thienyl, 2-, 3-, or 4-pyridyl, 2- or 3-quinolyl, 1-isoquinolyl, 1- or 2-indolyl, 2-benzothiazolyl, and the like.

As for "substituent(s)" of said "aromatic group that may be substituted", the same number and the same "substituent(s)" as those of the above-mentioned "hydrocarbon group that may be substituted" indicated by $R^1$ or $R^2$ can be employed.

"An aliphatic hydrocarbon group" of "an aliphatic hydrocarbon group, which may be substituted with an aromatic group that may be substituted and, may further be substituted" indicate by $R^4$ is exemplified by alkyl, alkenyl, alkynyl, cycloalkyl, or the like. Among them, $C_{1-6}$ alkyl, $C_{2-10}$ alkenyl, $C_{2-10}$ alkynyl, $C_{3-10}$ cycloalkyl, and the like are preferred.

Preferred examples of "alkyl" include $C_{1-6}$ alkyl (e.g., methyl, ethyl, propyl, isopropyl, butyl, isobutyl, sec-butyl, tert-butyl, pentyl, hexyl, etc.) or the like.

Preferred examples of "alkenyl" include $C_{2-6}$ alkenyl (e.g., vinyl, allyl, isopropenyl, butenyl, isobutenyl, sec-butenyl, etc.) or the like.

Preferred examples of "alkynyl" include $C_{2-6}$ alkynyl (for example, ethynyl, propargyl, butynyl, 1-hexynyl, etc.) or the like.

Preferred examples of "cycloalkyl" include $C_{3-6}$ cycloalkyl (e.g., cyclopropyl, cyclobutyl, cyclopentyl, cyclohexyl, etc.) or the like.

Among them, $C_{1-6}$ alkyl is preferred.

Said "aliphatic hydrocarbon group" may have 1 to 3 "aromatic groups that may be substituted" at substitutable positions. When the number of the substituents is 2 or more, the substituents may be the same or different.

As for "substituent(s)", which said "aliphatic hydrocarbon group" may further have, the same number and the same "substituent(s)" as those of the above-mentioned "hydrocarbon group that may have substituents" indicated by $R^1$ or $R^2$ can be employed.

As for "an acyl group" of "an acyl group containing an aromatic group that may be substituted" indicated by $R^4$, the same group as "an acyl group" as "substituents" of the above-mentioned "hydrocarbon group that may have substituents" indicated by $R^1$ or $R^2$ can be employed.

As for "an aromatic group that may be substituted" of "an acyl group containing an aromatic group that may be substituted" indicated by $R^4$, the same group as "an aromatic group that may be substituted" of the above-mentioned "an aliphatic hydrocarbon group, which may be substituted with an aromatic group that may be substituted and, may further be substituted" indicate by $R^4$ can be employed.

Preferred specific examples of "an acyl group containing an aromatic group that may be substituted" indicated by $R^4$ include a $C_{6-14}$ arylcarbonyl (e.g., benzoyl, 1-naphthoyl, 2-naphthoyl, etc.), $C_{7-16}$ aralkylcarbonyl (e.g., phenylacetyl, phenylpropionyl, etc.), $C_{6-14}$ aryloxycarbonyl (e.g., phenoxycarbonyl, etc.), $C_{7-16}$ aralkyloxycarbonyl (e.g., benzyloxycarbonyl, phenethyloxycarbonyl, etc.), 5- or 6-membered heterocyclic carbonyl (e.g., nicotinoyl, isonicotinoyl, 2-thenoyl, 3-thenoyl, 2-furoyl, 3-furoyl, morpholinocarbonyl, thiomorpholinocarbonyl, piperidinocarbonyl, 1-pyrrolidinylcarbonyl, etc.), $C_{6-14}$ arylcarbamoyl (e.g., phenylcarbamoyl, 1-naphthylcarbamoyl, 2-naphthylcarbamoyl, etc.), 5- or 6-membered heterocyclic carbamoyl (e.g., 2-pyridylcarbamoyl, 3-pyridylcarbamoyl, 4-pyridylcarbamoyl, 2-thienylcarbamoyl, 3-thienylcarbamoyl, etc.), $C_{6-14}$ arylsulfonyl (e.g., phenylsulfonyl, 1-naphthylsulfonyl, 2-naphthylsulfonyl, etc.), $C_{6-14}$ arylsulfinyl (e.g., phenylsulfinyl, 1-naphthylsulfinyl, 2-naphthylsulfinyl, etc.), and the like.

In the above-mentioned formulas, $R^5$ is hydrogen atom, a $C_{1-6}$ alkyl group, or an acyl group.

Examples of "$C_{1-6}$ alkyl" indicated by $R^5$ include methyl, ethyl, propyl, isopropyl, butyl, isobutyl, sec-butyl, tert-butyl, pentyl, hexyl, or the like.

As for "an acyl group" indicated by $R^5$, the same group as "an acyl group" as "substituents" of the above-mentioned "hydrocarbon group that may be substituted" indicated by $R^1$ or $R^2$ can be employed.

When W is Wb, in the above-mentioned formulas, ring C is benzene ring that may be further substituted, in addition to the group represented by formula $-NR^4(R^5)$ (hereinafter, sometimes referred to as ring $C^2$).

Ring $C^2$ may have 1 to 3 groups represented by formula $-NR^4(R^5)$ at substitutable positions. When the number of the substituents is 2 or more, the substituents may be the same or different.

Examples of "substituent(s)", which ring $C^2$ may further have, in addition to the group represented by formula $-NR^4(R^5)$, include a halogen atom (for example, fluorine, chlorine, bromine, iodine, or the like), $C_{1-3}$ alkylenedioxy(for example, methylenedioxy, ethylenedioxy, or the like), nitro, cyano, $C_{1-6}$ alkyl that may be halogenated, $C_{2-6}$ alkenyl that may be halogenated, $C_{2-6}$ alkynyl that may be halogenated, $C_{3-6}$ cycloalkyl that may be halogenated, $C_{6-14}$ aryl (e.g., phenyl, 1-naphthyl, 2-naphthyl, biphenylyl, 2-anthryl, etc.), $C_{1-6}$ alkoxy that may be halogenated, hydroxyl, amino, mono-$C_{1-6}$ alkylamino(e.g., methylamino, ethylamino, etc.), mono-$C_{6-14}$ arylamino (e.g., phenylamino, 1-naphthylamino, 2-naphthylamino, etc.), di-$C_{1-6}$ alkylamino (e.g., dimethylamino, diethylamino, etc.), di-$C_{6-14}$ arylamino (e.g., diphenylamino, etc.), acyl, acylamino, 5- to 7-membered saturated-cyclic amino that may be substituted, a 5- to 10-membered aromatic heterocyclic group (e.g., 2- or 3-thienyl, 2-, 3-, or 4-pyridyl, 2-, 3-, 4-, 5-, or 8-quinolyl, 1-, 3-, 4-, or 5-isoquinolyl, 1-, 2-, or 3-indolyl, 2-benzothiazolyl, 2-benzo[b]thienyl, benzo[b]furanyl, etc.), sulfo, and the like.

Said "$C_{1-6}$ alkyl that may be halogenated", "$C_{2-6}$ alkenyl that may be halogenated", "$C_{2-6}$ alkynyl that may be halogenated", "$C_{3-6}$ cycloalkyl that may be halogenated", "$C_{1-6}$ alkoxy that may be halogenated", "acyl", "acylamino", and "5- to 7-membered saturated-cyclic amino that may be substituted" include, for example, the same groups as those described in detail as "substituents" of the above-mentioned "hydrocarbon group that may be substituted" indicated by $R^1$ or $R^2$.

Ring $C^2$ may have 1 to 3 of said groups at substitutable positions. When the number of the substituents is 2 or more, the substituents may be the same or different.

In this way, there are included in compounds (I) of the present invention compounds (Ia) represented by the formula:

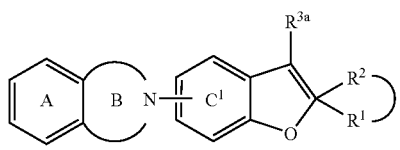

(Ia)

wherein each symbol is as defined above and compounds (Ib) represented by the formula:

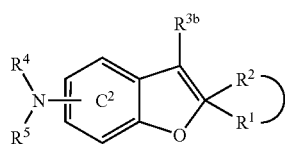

(Ib)

wherein each symbol is as defined above.

In the above-mentioned compounds (Ia), $R^1$ and $R^2$ are the same or different and, for example, each is preferably hydrogen atom or a $C_{1-6}$ alkyl group that may be substituted (particularly, a $C_{1-3}$ alkyl group such as methyl, etc.), or $R^1$ and $R^2$ form, together with the adjacent carbon atom, a 3- to 8-membered heterocyclic ring that may be substituted, or the like, among which each of $R^1$ and $R^2$ is a $C_{1-6}$ alkyl group, or the like is more preferred. Also, when ----indicates a double bond, $R^2$ is not present and, as for $R^1$, a $C_{1-6}$ alkyl group that may be substituted is preferred and, particularly, a $C_{1-3}$ alkyl group such as methyl or the like is preferred.

As for $R^{3a}$, for example, a $C_{6-14}$ aryl group that may be substituted or the like is preferred.

As for ring A, for example, benzene ring, which may be substituted with a substituent selected from halogen, $C_{1-6}$ alkyl, $C_{1-6}$ alkoxy, $C_{1-6}$ alkylenedioxy, etc. is preferred.

As for ring B, for example, a 5- to 7-membered nitrogen-containing heterocyclic ring, which may be substituted with a $C_{1-6}$ alkyl, or the like is preferred.

As for ring $C^1$, benzene ring, which may be further substituted with 1 to 3 $C_{1-6}$ alkyl groups or $C_{1-6}$ alkoxy groups, or the like is preferred.

As for a group represented by the formula:

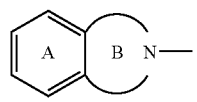

wherein each symbol is as defined above, a group represented by the formula:

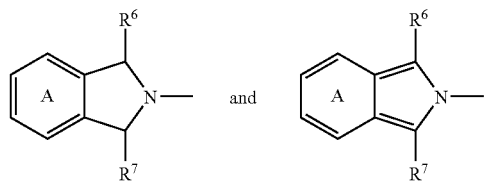

wherein each symbol is as defined above, or the like is preferred. Particularly, as for $R^6$ and $R^7$, hydrogen atom is preferred and, as for ring A, benzene ring, which may be further substituted with 1 to 2 substituents selected from halogen, $C_{1-6}$ alkoxy group and $C_{1-6}$ alkylenedioxy, is preferred.

The substitution position on ring $C^1$ in a group represented by the formula:

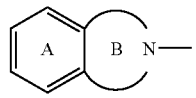

wherein each symbol is as defined in claim 1, is preferably 5-position on the benzofuran ring or the dihydrobenzofuran ring, or the like.

Also, as for compound (Ia'), compounds (Ia) or the like is preferred. As for ring $B^a$, for example, a 5- to 7-membered nitrogen-containing heterocyclic ring, which may be substituted with $C_{1-6}$ alkyl, or the like is preferred and, as for ring $C^a$, benzene ring, which may be further substituted with 1 to 3 $C_{1-6}$ alkyl groups or $C_{1-6}$ alkoxy groups, or the like is preferred.

Particularly, as for compound (Ia), that wherein each of $R^1$ and $R^2$ is a $C_{1-6}$ alkyl group (particularly, a $C_{1-3}$ alkyl group such as methyl, etc.), $R^{3a}$ is phenyl group that may have $C_{1-6}$ alkyl (particularly, $C_{1-3}$ alkyl such as methyl, ethyl, isopropyl, etc.) or a halogen atom (particularly, fluorine), ring A is benzene ring, which may have substituent(s) selected from halogen, $C_{1-6}$ alkyl (particularly, $C_{1-3}$ alkyl such as methyl, etc.), $C_{1-6}$ alkoxy (particularly, $C_{1-3}$ alkoxy such as methoxy, etc.), and $C_{1-6}$ alkylenedioxy (particularly, $C_{1-3}$ alkylenedioxy such as methylenedioxy, etc.), ring B is a 5- to 7-membered nitrogen-containing heterocyclic ring, which may be substituted with $C_{1-6}$ alkyl, and ring $C^1$ is benzene ring, which may be further substituted with 1 to 3 $C_{1-6}$ alkyl groups (particularly, $C_{1-3}$ alkyl groups such as methyl, etc.) or $C_{1-6}$ alkoxy groups (particularly, $C_{1-3}$ alkoxy groups such as methoxy, etc.), is preferred and, particularly, that wherein a group represented by the formula:

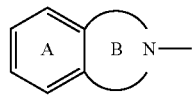

wherein each symbol is as defined above is a group represented by the formula:

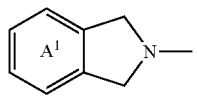

wherein ring $A^1$ is benzene ring, which may be substituted with 1 to 2 substituents selected from halogen, $C_{1-6}$ alkoxy, and $C_{1-6}$ alkylenedioxy, is preferred.

Also, when

----- indicates a double bond, $R^2$ is not present and, as for $R^1$, a $C_{1-6}$ alkyl group or the like that may be substituted is preferred and, particularly, a $C_{1-3}$ alkyl group such as methyl or the like is preferred. As for the other symbols, the same symbols as those described above are preferable, in particular, the compound wherein $R^{3a}$ is phenyl group that may have $C_{1-6}$ alkyl (particularly, $C_{1-3}$ alkyl such as methyl, ethyl, isopropyl, etc.), ring A is benzene ring, ring B is a 5- to 7-membered nitrogen-containing heterocyclic ring, and ring $C^1$ is benzene ring, which may be further substituted with 1 to 3 $C_{1-6}$ alkyl groups (particularly, $C_{1-3}$ alkyl groups such as methyl, etc.), are preferred and, particularly, the compound wherein a group represented by the formula:

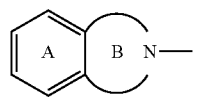

wherein each symbol is as defined above, is a group represented by the formula:

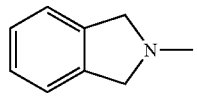

is preferred.

As for specific examples of compound (Ia), the compounds or salts thereof, which are produced in Example 1a to Example 22a described hereinafter, and the like are preferable, among which,

[1] 2-[2,2,4,6,7-pentamethyl-3-(4-methylphenyl)-2,3-dihydro-1-benzofuran-5-yl]isoindoline (Example 4a) or a salt thereof,

[2] 5,6-dimethoxy-2-[2,2,4,6,7-pentamethyl-3-(4-methylphenyl)-2,3-dihydro-1-benzofuran-5-yl]isoindoline (Example 6a) or a salt thereof,

[3] 5,6-dimethoxy-2-[3-(4-isopropylphenyl)-2,2,4,6,7-pentamethyl-2,3-dihydro-1-benzofuran-5-yl]isoindoline (Example 11a) or a salt thereof,

[4] 6-[3-(4-isopropylphenyl)-2,2,4,6,7-pentamethyl-2,3-dihydro-1-benzofuran-5-yl]-6,7-dihydro-5H-[1,3]dioxolo[4,5-f]isoindole (Example 12a) or a salt thereof,

[5] 6-[2,2,4,6,7-pentamethyl-3-(4-methylphenyl)-2,3-dihydro-1-benzofuran-5-yl]-6H-[1,3]dioxolo[4,5-f]isoindole (Example 14a) or a salt thereof,

[6] 6-[2,2,4,6,7-pentamethyl-3-phenyl-2,3-dihydro-1-benzofuran-5-yl]-6,7-dihydro-5H-[1,3]dioxolo[4,5-f]isoindole (Example 16a) or a salt thereof,

[7] (+)-5,6-dimethoxy-2-[2,2,4,6,7-pentamethyl-3-(4-methylphenyl)-2,3-dihydro-1-benzofuran-5-yl]isoindoline (Example 17a),

[8] (+)-5,6-dimethoxy-2-[2,2,4,6,7-pentamethyl-3-(4-methylphenyl)-2,3-dihydro-1-benzofuran-5-yl]isoindoline hydrochloride (Example 19a), or other salts thereof, and the like are preferable and, particularly,

[1] 5,6-dimethoxy-2-[2,2,4,6,7-pentamethyl-3-(4-methylphenyl)-2,3-dihydro-1-benzofuran-5-yl]isoindoline (Example 6a),

[2] 6-[3-(4-isopropylphenyl)-2,2,4,6,7-pentamethyl-2,3-dihydro-1-benzofuran-5-yl]-6,7-dihydro-5H-[1,3]dioxolo[4,5-f]isoindole (Example 12a),

[3] (+)-5,6-dimethoxy-2-[2,2,4,6,7-pentamethyl-3-(4-methylphenyl)-2,3-dihydro-1-benzofuran-5-yl]isoindoline (Example 17a),

[4] (+)-5,6-dimethoxy-2-[2,2,4,6,7-pentamethyl-3-(4-methylphenyl)-2,3-dihydro-1-benzofuran-5-yl]isoindoline hydrochloride (Example 19a), and the like are preferable.

In the above-mentioned compounds (Ib), $R^1$ and $R^2$ are the same or different and each is preferably exemplified by hydrogen atom or a $C_{1-6}$ alkyl group that may be substituted (particularly, a $C_{1-3}$ alkyl group such as methyl, etc.) or, $R^1$ and $R^2$ form, together with the adjacent carbon atom, a 3- to 8-membered heterocyclic ring that may be substituted (particularly, a 5- or 6-membered nitrogen-containing heterocyclic ring such as piperidine, etc.), or the like, and is more preferably exemplified by hydrogen atom or a $C_{1-6}$ alkyl group that may be substituted (particularly, a $C_{1-3}$ alkyl group such as methyl, etc.) or, $R^1$ and $R^2$ form, together with the adjacent carbon atom, a piperidine ring that is substituted with $C_{1-6}$ alkyl, or the like. Among them, more preferably, each of $R^1$ and $R^2$ is a $C_{1-6}$ alkyl group, in particular, each is methyl group.

As for $R^{3b}$, for example, phenyl group that may be substituted with halogen (particularly, fluorine) or $C_{1-6}$ alkyl (particularly, $C_{1-3}$ alkyl such as methyl, ethyl, isopropyl, etc.) or the like is preferred and phenyl group that may be substituted with fluorine, methyl, isopropyl or the like is more preferred.

As for $R^4$, (1) a $C_{1-6}$ alkyl group that may be substituted with an aromatic group (particularly, a $C_{6-14}$ aryl group such as phenyl or a 5- or 6-membered heterocyclic carbonyl that contains, in addition to carbon atom, 1 to 3 hetero atoms selected from nitrogen atom, sulfur atom and oxygen atom, such as, thienyl, pyridyl, etc.), which may be substituted with halogen, $C_{1-6}$ alkoxy, or $C_{1-3}$ alkylenedioxy, or (2) an acyl group that contains an aromatic group (particularly, a $C_{6-14}$ aryl group such as phenyl), which may be substituted with halogen, $C_{1-6}$ alkoxy, or $C_{1-3}$ alkylenedioxy, or the like is preferred. (1) A $C_{1-6}$ alkyl group (particularly, a $C_{1-3}$ alkyl group such as methyl) that may be substituted with $C_{6-14}$ aryl (particularly, phenyl), thienyl, or pyridyl, which may be substituted with halogen (particularly, fluorine or chlorine), $C_{1-6}$ alkoxy (particularly, a $C_{1-3}$ alkoxy group such as methoxy), or a $C_{1-3}$ alkylenedioxy (particularly, methylenedioxy), or (2) a $C_{6-14}$ arylcarbonyl group (particularly, phenylcarbonyl group), a $C_{7-16}$ aralkylcarbonyl group (particularly, benzylcarbonyl group), a $C_{6-14}$ arylsulfonyl group (particularly, phenylsulfonyl group), nicotinoyl group, or thenoyl group, which may be substituted with halogen (particularly, fluorine or chlorine), $C_{1-6}$ alkoxy (particularly, a $C_{1-3}$ alkoxy group such as methoxy), or $C_{1-3}$ alkylenedioxy (particularly, methylenedioxy), or the like is more preferred. Among them, benzyl group or phenethyl group, which may be substituted with fluorine, methoxy or methylenedioxy, or the like is particularly preferred.

As for $R^5$, for example, hydrogen atom, a $C_{1-6}$ alkyl group (particularly, a $C_{1-3}$ alkyl group such as methyl), or a $C_{1-6}$ alkylcarbonyl group (particularly, a $C_{1-3}$ alkylcarbonyl group such as acetyl), or the like is preferred, and hydrogen atom or methyl group, etc. is more preferred.

As for ring $C^2$, benzene ring that may be further substituted with 1 to 3 $C_{1-6}$ alkyl groups (particularly, a $C_{1-3}$ alkyl group such as methyl) or the like is preferred and benzene ring, which may be further substituted with 3 methyl groups, or the like is particularly preferred.

Particularly, as for compounds (Ib), the compound wherein $R^1$ and $R^2$ is the same or different and each is hydrogen atom or a $C_{1-6}$ alkyl group (particularly, a $C_{1-3}$ alkyl group such as methyl, etc.), or $R^1$ and $R^2$ form, together with the adjacent carbon atom, a piperidine ring that is substituted with $C_{1-6}$ alkyl (particularly, a $C_{1-3}$ alkyl group such as methyl, etc.);

$R^{3b}$ is phenyl group that may be substituted with halogen (particularly, fluorine) or $C_{1-6}$ alkyl (particularly, $C_{1-3}$ alkyl such as methyl, ethyl, isopropyl, etc.);

$R^4$ is (1) a $C_{1-6}$ alkyl group (particularly, a $C_{1-3}$ alkyl group such as methyl) that may be substituted with $C_{6-14}$ aryl (particularly phenyl), thienyl, or pyridyl, which may be substituted with halogen (particularly, fluorine or chlorine), $C_{1-6}$ alkoxy (particularly, a $C_{1-3}$ alkoxy group such as methoxy), or $C_{1-3}$ alkylenedioxy (particularly, methylenedioxy), or (2) a $C_{6-14}$ arylcarbonyl group (particularly phenylcarbonyl group), a $C_{7-16}$ aralkylcarbonyl group (particularly benzylcarbonyl group), a $C_{6-14}$ arylsulfonyl group (particularly phenylsulfonyl group), nicotinoyl group, or thenoyl group, which may be substituted with halogen (particularly, fluorine or chlorine), $C_{1-6}$ alkoxy (particularly, a $C_{1-3}$ alkoxy group such as methoxy), or $C_{1-3}$ alkylenedioxy (particularly, methylenedioxy);

$R^5$ is hydrogen atom, a $C_{1-6}$ alkyl group (particularly, a $C_{1-3}$ alkyl group such as methyl), or $C_{1-6}$ alkylcarbonyl (particularly, a $C_{1-3}$ alkylcarbonyl group such as acetyl); and ring $C^2$ is benzene ring that may be further substituted with 1 to 3 $C_{1-6}$ alkyl groups (particularly, a $C_{1-3}$ alkyl group such as methyl), and the like are preferred and the compound wherein each of $R^1$ and $R^2$ is methyl;

$R^{3b}$ is phenyl group that may be substituted with fluorine, methyl, or isopropyl;

$R^4$ is benzyl group or phenethyl group, which may be substituted with fluorine, methoxy, or methylenedioxy;

$R^5$ is hydrogen atom or methyl group;

----- is a single bond; and
ring $C^2$ is the benzene ring that is substituted with 3 methyl groups, and the like are particularly preferred.

Also, when

----- indicates a double bond, $R^2$ is not present and, as for $R^1$, a $C_{1-6}$ alkyl group that may be substituted is preferred and, particularly, a $C_{1-3}$ alkyl group such as methyl or the like is preferred. As for other symbols, the same symbols as those described above are preferred. In particular, the compound wherein $R^{3b}$ is phenyl group that may be substituted with halogen (particularly, fluorine) or $C_{1-6}$ alkyl (particularly, $C_{1-3}$ alkyl such as methyl, ethyl, isopropyl, etc.); $R^4$ is (1) a $C_{1-6}$ alkyl group (particularly, a $C_{1-3}$ alkyl group such as methyl) that may be substituted with $C_{6-14}$ aryl (particularly phenyl), which may be substituted with halogen (particularly, fluorine) or $C_{1-6}$ alkoxy (particularly, a $C_{1-3}$ alkoxy group such as methoxy), or (2) a $C_{6-14}$ arylcarbonyl group (particularly, phenylcarbonyl group) or a $C_{7-16}$ aralkylcarbonyl group (particularly, benzylcarbonyl group), which may be substituted with halogen (particularly, fluorine) or $C_{1-6}$ alkoxy (particularly, a $C_{1-3}$ alkoxy group such as methoxy); $R^5$ is hydrogen atom; and ring $C^2$ is benzene ring that may be further substituted with 1 to 3 $C_{1-6}$ alkyl groups (particularly, a $C_{1-3}$ alkyl group such as methyl) are preferred.

As for specific examples of compound (Ib), the compounds produced in Example 1b to Example 67b described hereinafter, and the like are preferable, among which,

[1] N-(4-fluorobenzyl)-2,2,4,6,7-pentamethyl-3-phenyl-2,3-dihydro-1-benzofuran-5-amine (Example 4b) or a salt thereof,

[2] N-benzyl-3-(4-isopropylphenyl)-2,2,4,6,7-pentamethyl-2,3-dihydro-1-benzofuran-5-amine (Example 6b) or a salt thereof,

[3] 3-(4-isopropylphenyl)-N-(4-methoxybenzyl)-N,2,2,4,6,7-hexamethyl-2,3-dihydro-1-benzofuran-5-amine (Example 9b) or a salt thereof,

[4] 3-(4-isopropylphenyl)-N-[2-(4-methoxyphenyl)ethyl]-2,2,4,6,7-pentamethyl-2,3-dihydro-1-benzofuran-5-amine (Example 11b) or a salt thereof,

[5] N-(4-fluorobenzyl)-3-(4-isopropylphenyl)-2,2,4,6,7-pentamethyl-2,3-dihydro-1-benzofuran-5-amine (Example 19b) or a salt thereof,

[6] N-(1,3-benzodioxol-5-ylmethyl)-3-(4-isopropylphenyl)-2,2,4,6,7-pentamethyl-2,3-dihydro-1-benzofuran-5-amine (Example 23b) or a salt thereof,

[7] N-(4-fluorobenzyl)-3-(4-fluorophenyl)-2,2,4,6,7-pentamethyl-2,3-dihydro-1-benzofuran-5-amine (Example 31b) or a salt thereof,

[8] N-(4-methoxybenzyl)-2,2,4,6,7-pentamethyl-3-(4-methylphenyl)-2,3-dihydro-1-benzofuran-5-amine (Example 33b) or a salt thereof,

[9] N-(4-fluorobenzyl)-2,2,4,6,7-pentamethyl-3-(4-methylphenyl)-2,3-dihydro-1-benzofuran-5-amine (Example 35b) or a salt thereof,

[10] 3-(4-isopropylphenyl)-N-(4-methoxybenzyl)-2,4,6,7-tetramethyl-1-benzofuran-5-amine (Example 45b) or a salt thereof,

[11] N-(4-fluorobenzyl)-3-(4-isopropylphenyl)-2,4,6,7-tetramethyl-1-benzofuran-5-amine (Example 47b) or a salt thereof,

[12] N-(4-fluorobenzyl)-3-(4-fluorophenyl)-2,4,6,7-tetramethyl-1-benzofuran-5-amine (Example 51b) or a salt thereof,

[13] N-(4-fluorobenzyl)-3-(4-isopropylphenyl)-1',4,6,7-tetramethylspiro[benzofuran-2(3H),4'-piperidine]-5-amine (Example 55b) or a salt thereof,

[14] (+)-N-(4-fluorobenzyl)-3-(4-isopropylphenyl)-2,2,4,6,7-pentamethyl-2,3-dihydro-1-benzofuran-5-amine, its hydrochloride (Example 61b), or other salts thereof, and the like are preferable and, particularly,

[1] N-(4-fluorobenzyl)-3-(4-isopropylphenyl)-2,2,4,6,7-pentamethyl-2,3-dihydro-1-benzofuran-5-amine (Example 19b) or a salt thereof,

[2] N-(4-fluorobenzyl)-3-(4-isopropylphenyl)-1',4,6,7-tetramethylspiro[benzofuran-2(3H),4'-piperidine]-5-amine (Example 55b) or a salt thereof,

[3] (+)-N-(4-fluorobenzyl)-3-(4-isopropylphenyl)-2,2,4,6,7-pentamethyl-2,3-dihydro-1-benzofuran-5-amine hydrochloride (Example 61b), and the like are preferable.

The salts of the above-mentioned compounds may be exemplified by a metal salt, ammonium salt and a salt with an organic base in the case of having an acidic group such as —COOH or the like and by salts with an inorganic acid, an organic acid, a basic or acidic amino acid, and the like as well as inner salts in the case of having a bsic group such as —NH$_2$ or the like. Preferred examples of a metal salt include alkali metal salts such as sodium salt, potassium salt, and the like; alkaline earth metal salts such as calcium salt, magnesium salt, barium salt, and the like; as well as aluminum salt, and so on. Preferred examples of a salt with an organic-base include salts with trimethylamine, triethylamine, pyridine, picoline, ethanolamine, diethanolamine, triethanolamine, dicyclohexylamine, N,N'-dibenzylethylenediamine, and the like. Preferable examples of a salt with an inorganic acid include salts with hydrochloric acid, hydrobromic acid, nitric acid, sulfuric acid, phosphoric acid, and the like. Preferred examples of a salt with an organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, and the like. Preferred examples of a salt with a basic amino acid include salts with arginine, lysine, ornithine, and the like and preferable examples of a salt with an acidic amino acid include salts with aspartic acid, glutamic acid, and the like.

Among them, pharmaceutically acceptable salts are preferable. The examples thereof include inorganic salts such as alkali metal salts (sodium salt, potassium salt, and the like), alkaline earth metal salts (calcium salt, magnesium salt, barium salt, and the like) as well as ammonium salt, and so on in the case of having an acidic functional group in the compound and, also, include inorganic salts such as hydrochloride, sulfate, phosphate, hydrobromide, and the like or organic salts such as acetate, maleate, fumarate, succinate, methanesulfonate, p-toluenesulfonate, citrate, tartarate, and so on in the case of having a basic functional group in the compound.

Next, processes for production of compound (Ia) and compound (Ia') of the present invention are illustrated.

Compound (Ia') can be produced according to the processes for production of compound (Ia) as well as per se known processes such as the processes described in WO 95/29907, JP 5-194466 A, U.S. Pat. Nos. 4,881,967, 4,212, 865, Tetrahedron Letters, Vol. 37, No. 51, pp. 9183-9186 (1996), and so on or modified processes thereof.

Compound (Ia) can be produced according to the following processes or modified processes thereof.

Each symbol in the compounds shown in the following reaction Schemes is as defined above. The compounds in the following reaction Schemes include the salts thereof and said salts are the same as those exemplified with respect to the salts of compound (Ia).

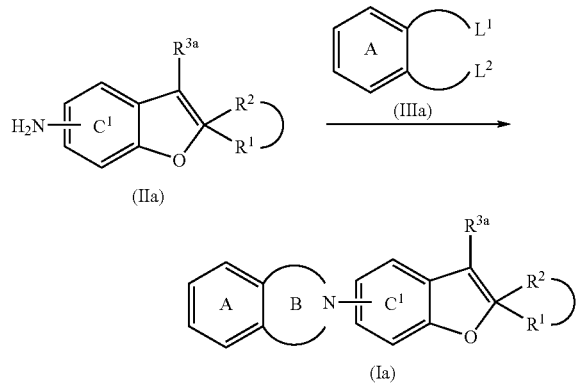

Compound (Ia) is produced by reacting compound (IIa) with compound (IIIa) represented by the formula:

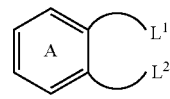

(wherein, each of $L^1$ and $L^2$ indicates a leaving group and ring A is defined above), if necessary, in the presence of a base.

As for "substituent(s) that may be had, in addition to —$NH_2$", by ring $C^1$ in compound (IIa), the same number and the same substituent(s) as those "substituents that may be further had", by ring $C^1$ in compound (Ia) is used.

"A leaving group" indicated by $L^1$ and $L^2$ is exemplified by hydroxyl, a halogen atom (for example, fluorine, chlorine, bromine, iodine, etc.), $C_{1-5}$ alkylsulfonyloxy, that may be halogenated (for example, methanesulfonyloxy, ethanesulfonyloxy, trichloromethanesulfonyloxy, etc.), $C_{6-10}$ arylsulfonyloxy that may be substitued, and the like. "$C_{6-10}$ arylsulfonyloxy that may be substitueted" is exemplified by $C_{6-10}$ arylsulfonyloxy (for example, phenylsulfonyloxy, naphthylsulfonyloxy, etc.) that may have 1 to 3 substituents, which are selected from $C_{1-6}$ alkyl (for example, methyl, ethyl, propyl, isopropyl, butyl, isobutyl, sec-butyl, tert-butyl, pentyl, hexyl, or the like), $C_{1-6}$ alkoxy (for example, methoxy, ethoxy, propoxy, isopropoxy, butoxy, isobutoxy, sec-butoxy, pentyloxy, hexyloxy, etc.), and nitro, and so on. Specific examples include benzenesulfonyloxy, m-nitrobenzenesulfonyloxy, p-toluenesulfonyloxy, and the like.

Compound (IIIa) is a compound that is capable of forming, together with the amino group substituted on ring $C^1$ of compound (IIa), a group represented by the formula:

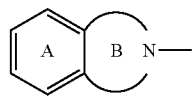

(wherein each symbol is as defined above), and, for example, there is used a compound represented by the formula:

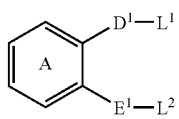

(wherein $D^1$ indicates a group represented by formula —$(CH_2)d^1$- ($d^1$ indicates an integer of 0 to 3), which may be substituted with a hydrocarbon group that may be have halogen or a substituent, $E^1$ indicates a group represented by formula —$(CH_2)e^1$- ($e^1$ indicates an integer of 0 to 3), which may be substituted with a hydrocarbon group that may have halogen or a substituent, the sum of $d^1$ and $e^1$ is an integer of 2 to 4, and each of $L^1$ and $L^2$ is as defined above) or the like.

As for said hydrocarbon group that may have halogen or a substituent, there is used the same group as the hydrocarbon group that may have halogen or a substituent, which is mentioned above as the substituent of a 5- to 7-membered nitrogen-containing heterocyclic ring indicated by ring B.

The amount of compound (IIIa) to be used is about 1.0 to about 5.0 moles, preferably about 1.0 to about 2.0 moles for 1 mole of compound (IIa).

Said "base" is exemplified by a basic salt such as sodium carbonate, potassium carbonate, cesium carbonate, sodium hydrogen carbonate, or the like, an aromatic amine such as pyridine, lutidine, or the like, a tertiary amine such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, or the like, an alkali metal hydride such as sodium hydride, potassium hydride, or the like, a metal amide such as sodium amide, lithium diisopropylamide, lithium hexamethyldisilazide, or the like, a metal alkoxide such as sodium methoxide, sodium ethoxide, potassium tert-butoxide, or the like, or the like.

The amount of the base to be used is about 1.0 to about 5.0 moles, preferably about 1.0 to about 3.0 moles for 1 mole of compound (IIa). Also, if desired, the reaction can also be carried out in the presence of a quaternary ammonium salt together with the base.

Said "quaternary ammonium salt" is exemplified by tetrabutylammonium iodide and the like.

The amount of the quaternary ammonium salt to be used is about 0.1 to about 2.0 moles, preferably about 0.5 to about 1.0 moles, for 1 mole of compound (IIa).

It is advantageous to carry out this reaction by using of a solvent inert to the reaction. Such a solvent, though being not particularly limited as far as the reaction proceeds, is preferably exemplified by alcohols such as methanol, ethanol, propanol, etc., ethers such as diethyl ether, tetrahydrofuran, dioxane, 1,2-dimethoxyethane, etc., a hydrocarbon such as benzene, toluene, cyclohexane, hexane, etc., amides such as N,N-dimethylformamide, N,N-dimethylacetamide, etc., halogenated hydrocarbons such as dichloromethane, chloroform, carbon tetrachloride, 1,2-dichloroethane, etc., nitriles such as acetonitrile, propionitrile, etc., sulfoxides such as dimethyl sulfoxide, etc., and a mixed solvent thereof, and the like.

The reaction time is usually about 30 minutes to about 48 hours, preferably for about 1 to about 24 hours. The reaction temperature is usually about −20 to about 200° C., preferably about 0 to about 150° C.

Alternatively, in place of the above-mentioned reaction, Mitsunobu reaction (Synthesis, 1981, pp. 1-27) can be employed.

Said reaction is carried out by reacting compound (IIa) with compound (IIIa), wherein each of $L^1$ and $L^2$ is OH, in the presence of azodicarboxylate (e.g., diethyl azodicarboxylate, etc.) and phosphine (e.g., triphenylphosphine, tributylphosphine, etc.).

The amount of the compound (IIIa) to be used, wherein each of $L^1$ and $L^2$ is OH, is about 1.0 to about 5.0 moles, preferably about 1.0 to about 2.0 moles, for 1 mole of compound (IIa).

The amount of each of said "azodicarboxylate" and "phosphine" to be used is respectively about 1.0 to about 5.0 moles, preferably about 1.0 to about 2.0 moles, for 1 mole of compound (IIa).

It is advantageous to carry out this reaction by using a solvent inert to the reaction. Such a solvent, though being not particularly limited as far as the reaction proceeds, is preferably exemplified by ethers such as diethyl ether, tetrahydrofuran, dioxane, 1,2-dimethoxyethane, and the like, hydrocarbons such as benzene, toluene, cyclohexane, hexane, and the like, amides such as N,N-dimethylformamide, N,N-dimethylacetamide, and the like, halogenated hydrocarbons such as dichloromethane, chloroform, carbon tetrachloride, 1,2-dichloroethane, and the like, nitriles such as acetonitrile, propionitrile, and the like, sulfoxides such as dimethyl sulfoxide and the like, or a mixed solvent thereof or the like.

The reaction time is usually about 5 minutes to about 48 hours, preferably for about 30 minutes to about 24 hours. The reaction temperature is usually about −20 to about 200° C., preferably about 0 to about 100° C.

Compound (IIa) can be produced according to per se known processes such as the processes described in JP 5-140142 A and so on or modified processes thereof.

In the case where compound (IIa) is a dihydrobenzofuran, the production is carried out according to the process described in the following reaction Scheme

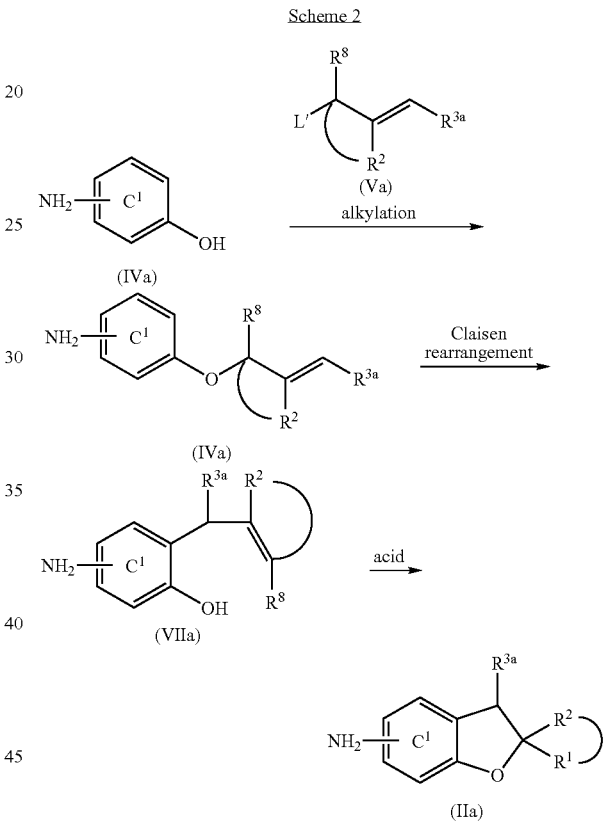

In the above formulas, L' indicates a leaving group and $R^8$ indicates hydrogen atom or a group, in which a methylene is removed from $R^1$.

"A leaving group" indicated by L' is exemplified by hydroxyl, a halogen atom (e.g., fluorine, chlorine, bromine, iodine, etc.), $C_{1-6}$ alkylsulfonyloxy (e.g., methanesulfonyloxy, ethanesulfonyloxy, etc.), $C_{6-10}$ arylsulfonyloxy that may be substituted, or the like.

"A $C_{6-10}$ arylsulfonyloxy that may be substituted" is exemplified by $C_{6-10}$ arylsulfonyloxy (for example, phenylsulfonyloxy, naphthylsulfonyloxy, etc.) that may have 1 to 3 substituents, which are selected from $C_{1-6}$ alkyl (e.g., methyl, ethyl, propyl, isopropyl, butyl, isobutyl, sec-butyl, tert-butyl, pentyl, hexyl, etc.), $C_{1-6}$ alkoxy (e.g., methoxy, ethoxy, propoxy, isopropoxy, butoxy, isobutoxy, sec-butoxy, pentyloxy, hexyloxy, etc.), and nitro, and so on. Specific examples include benzenesulfonyloxy, m-nitrobenzenesulfonyloxy, p-toluenesulfonyloxy, and the like.

Compound (IVa) and compound (Va) are easily commercially available or are produced according to per se known methods.

Compound (VIa) is produced by reacting a phenolate anion, which is formed by treatment of compound (IVa) with a base, with compound (Va) represented by formula $R^8$—CHL'-CHR$^2$=CHR$^{3a}$.

The amount of compound (Va) to be used is about 1.0 to about 5.0 moles, preferably about 1.0 to about 2.0 moles, for 1 mole of compound (IVa).

Said "base" is exemplified by an inorganic base such as an alkali metal hydroxide exemplified by sodium hydroxide, potassium hydroxide, or the like, an alkali metal alkoxide such as sodium methoxide, sodium ethoxide, potassium tert-butoxide, or the like, an alkali metal hydride such as sodium hydride, potassium hydride, or the like, a metal amide such as sodium amide, lithium diisopropylamide, lithium hexamethyldisilazide, or the like, a basic salt such as potassium hydrogen carbonate, sodium carbonate, potassium carbonate, sodium acetate, or the like, or the like. The amount of the base to be used is about 0.5 to about 5.0 moles, preferably about 1.0 to about 3.0 moles, for 1 mole of compound (IVa).

It is advantageous to carry out this reaction by using a solvent inert to the reaction. Such a solvent is preferably exemplified by alcohols such as methanol, ethanol, propanol, or the like, hydrocarbons such as cyclohexane, hexane, benzene, toluene, xylene, and the like, ethers such as tetrahydrofuran, dioxane, 1,2-dimethoxyethane, diethyl ether, diisopropyl ether, and the like, amides such as N,N-dimethylformamide, N,N-dimethylacetamide, hexamethylphosphoric triamide, and the like, sulfoxides such as dimethyl sulfoxide and the like, halogenated hydrocarbons such as dichloromethane, chloroform, carbon tetrachloride, 1,2-dichloroethane and the like, water, and a mixed solvent thereof and the like.

The reaction time is usually about 10 minutes to about 8 hours, preferably for about 30 minutes to about 3 hours. The reaction temperature is usually about 0 to about 120° C., preferably about 25 to about 100° C.

The product can be isolated from the reaction mixture by using a known isolation means and can be easily purified according to a usual separation means (e.g., recrystallization, distillation, chromatography, etc.).

Compound (VIIa) is produced by Claisen rearrangement of compound (VIa).

It is advantageous to carry out the present reaction without using a solvent or by using a solvent inert to the reaction. Such a solvent to be used, though being not particularly limited as far as the reaction proceeds, is exemplified by alcohols such as methanol, ethanol, propanol, and the like, hydrocarbons such as cyclohexane, hexane, benzene, toluene, xylene, mesitylene, and the like, organic acids such as formic acid, acetic acid, and the like, ethers such as tetrahydrofuran, dioxane, 1,2-dimethoxyethane, diethyl ether, diisopropyl ether, and the like, anilines such as N,N-dimethylaniline, N,N-diethylaniline, and the like, halogenated hydrocarbons such as dichloromethane, chloroform, carbon tetrachloride, 1,2-dichloroethane, and the like, and a mixed solvent thereof, and the like.

Also, if desired, this reaction may be carried out by using an acid catalyst. As for the acid catalyst, a Lewis acid such as aluminum chloride, boron trifluoride, or the like is used.

The amount of the acid catalyst to be used is, for instance, in the case of a Lewis acid, usually about 0.1 to about 20 moles, preferably about 0.1 to about 5.0 moles, for 1 mole of compound (VIa). The reaction time is usually about 30 minutes to about 24 hours, preferably for about 1 hour to about 6 hours. The reaction temperature is usually about −70 to about 300° C., preferably about 150 to about 250° C.

The product can be employed for the next reaction as the reaction mixture or a crude product, but the product can be isolated from the reaction mixture according to a conventional method and can be easily purified according to a usual separation means (e.g., recrystallization, distillation, chromatography, etc.).

Compound (IIa) can be produced by cyclization of compound (VIIa) with an acid catalyst.

The acid catalyst is exemplified by a mineral acid such as hydrochloric acid, hydrobromic acid, sulfuric acid, or the like, a sulfonic acid such as p-toluenesulfonic acid, camphorsulfonic acid, or the like, a Lewis acid such as aluminum chloride, boron trifluoride, or the like or the like.

The amount of the acid catalyst to be used is, for example, in the case of a mineral acid, usually about 1 to about 100 moles, preferably about 10 to about 50 moles, for 1 mole of compound (VIIa) and, for instance, in the case of a sulfonic acid, usually about 0.1 to about 20 moles, preferably about 0.1 to about 5 moles, for 1 mole of compound (VIIa).

It is advantageous to carry out this reaction without using any solvent or by using a solvent inert to the reaction. Such a solvent is not particularly limited as far as the reaction proceeds. For example, in the case where a mineral acid is used, the solvent is preferably exemplified by a mixed solvent of water and an organic solvent such as an alcohol such as methanol, ethanol, propanol, or the like, a saturated hydrocarbon such as cyclohexane, hexane, or the like, an aromatic hydrocarbon such as benzene, toluene, xylene, or the like, an ether such as tetrahydrofuran, dioxane, 1,2-dimethoxyethane, diethyl ether, diisopropyl ether, or the like, an amide such as N,N-dimethylformamide, N,N-dimethylacetamide, hexamethylphosphoric triamide, or the like, a sulfoxide such as dimethyl sulfoxide or the like, a halogenated hydrocarbon such as dichloromethane, chloroform, carbon tetrachloride, 1,2-dichloroethane, or the like or water.

The reaction time is usually about 30 minutes to about 24 hours, preferably for about 1 hour to about 6 hours. The reaction temperature is usually about −78 to about 200° C., preferably about −20 to about 150° C.

The product can be employed for the next reaction as the reaction mixture or a crude product, but the product can be isolated from the reaction mixture according to a conventional method and can be easily purified according to a usual separation means (e.g., recrystallization, distillation, chromatography, etc.).

Also, in the case where compound (IIa) is a benzofuran, the production is carried out according to the process described in the following reaction Scheme.

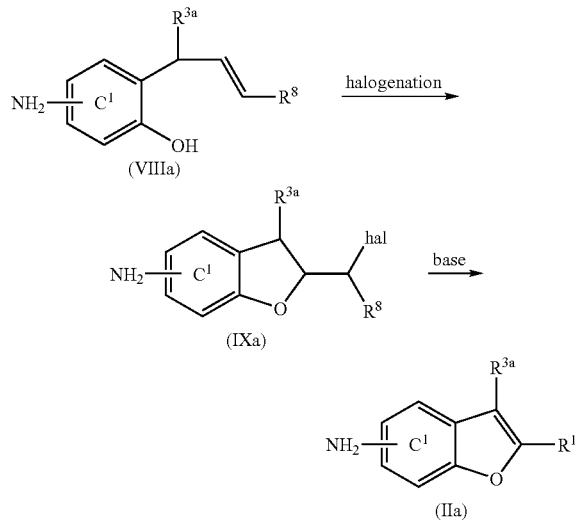

In the above formulas, hal indicates a halogen atom (for example, fluorine, chlorine, bromine, iodine, or the like).

Compound (IXa) is produced by reacting compound (VIIIa), which is synthesized according to the same manner as that for compound (VIIa), with a halogenating reagent.

Examples of "a halogenating reagent" include halogen atoms such as bromine, chlorine, iodine, or the like, imides such as N-bromosuccinimide or the like, halogen adducts such as benzyltrimethylammonium iodide chloride, benzyltrimethylammonium tribromide, or the like.

The amount of the halogenating reagent to be used is about 1.0 to about 5.0 moles, preferably about 1.0 to about 2.0 moles, for 1 mole of compound (VIIIa).

It is advantageous to carry out this reaction by using a solvent inert to the reaction. Such a solvent, though being not particularly limited as far as the reaction proceeds, is preferably exemplified by alcohols such as methanol, ethanol, propanol, and the like, hydrocarbons such as benzene, toluene, cyclohexane, hexane, and the like, amides such as N,N-dimethylformamide, N,N-dimethylacetamide, and the like, halogenated hydrocarbons such as dichloromethane, chloroform, carbon tetrachloride, 1,2-dichloroethane, and the like, nitrites such as acetonitrile, propionitrile, and the like, sulfoxides such as dimethyl sulfoxide and the like, organic acids such as acetic acid, propionic acid, and the like, nitroalkanes such as nitromethane, and the like, aromatic amines such as pyridine, lutidine, quinoline, and the like, and a mixed solvent thereof and the like.

If desired, this reaction is carried out in the presence of a base or a radical initiator or under irradiation with a light.

Said "base" is exemplified by a basic salt such as sodium carbonate, potassium carbonate, cesium carbonate, sodium hydrogen carbonate, sodium acetate, potassium acetate, or the like, an aromatic amine such as pyridine, lutidine, or the like, a tertiary amine such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, or the like, or the like. The amount of the base to be used is about 0.8 to about 10 moles for 1 mole of compound (VIIIa).

"A radical initiator" is exemplified by benzoyl peroxide, azobisisobutyronitrile, or the like.

The amount of the radical initiator to be used is about 0.01 to about 1.0 mole for 1 mole of compound (VIIIa).

In the case of irradiation with a light, a halogen lamp or the like can be used.

The reaction temperature is usually about −50 to about 150° C., preferably about 0 to about 100° C. The reaction time is usually about 5 minutes to about 24 hours, preferably for about 10 minutes to about 12 hours.

The product can be employed for the next reaction as the reaction mixture or a crude product, but the product can be isolated from the reaction mixture according to a conventional method and can be easily purified according to the usual separation means (e.g., recrystallization, distillation, chromatography, etc.).

Compound (IIa) is produced by treating compound (IXa) with a base.

Said "base" is exemplified by an inorganic salt such as a metal hydroxide such as sodium hydroxide, potassium hydroxide, or the like, an organic amine such as triethylamine, 1,8-diazabicyclo[5,4,0]-7-undecene, pyridine, or the like, a metal alkoxide such as sodium methoxide, sodium ethoxide, potassium tert-butoxide, or the like, an alkali metal hydride such as sodium hydride, potassium hydride, or the like, a metal amide such as sodium amide, lithium diisopropylamide, lithium hexamethyldisilazide, or the like, a basic salt such as potassium hydrogen carbonate, sodium carbonate, potassium carbonate, sodium acetate, or the like, or the like.

The amount of the base to be used is about 0.5 to about 10 moles, preferably about 1.0 to about 5.0 moles, for 1 mole of compound (IXa).

It is advantageous to carry out the present reaction by the use of a solvent inert to the reaction. Such a solvent is preferably exemplified by alcohols such as methanol, ethanol, propanol, and the like, hydrocarbons such as cyclohexane, hexane, benzene, toluene, xylene, and the like, ethers such as tetrahydrofuran, dioxane, 1,2-dimethoxyethane, diethyl ether, diisopropyl ether, and the like, amides such as N,N-dimethylformamide, N,N-dimethylacetamide, hexamethylphosphoric triamide, and the like, sulfoxides such as dimethyl sulfoxide and the like, halogenated hydrocarbons such as dichloromethane, chloroform, carbon tetrachloride, 1,2-dichloroethane, and the like, water, and a mixed solvent thereof and the like.

The reaction time is usually about 10 minutes to about 24 hours, preferably for about 30 minutes to about 12 hours. The reaction temperature is usually about 0 to about 120° C., preferably about 25 to about 100° C.

The product can be employed for the next reaction as the reaction mixture or a crude product, but the product can be isolated from the reaction mixture according to a conventional method and can be easily purified according to a usual separation means (e.g., recrystallization, distillation, chromatography, etc.).

Compound (IIIa) is easily commercially available or is produced according to the well-known methods.

Also, compound (Ia) is produced according to the process described in the following reaction Scheme 4.

Scheme 4

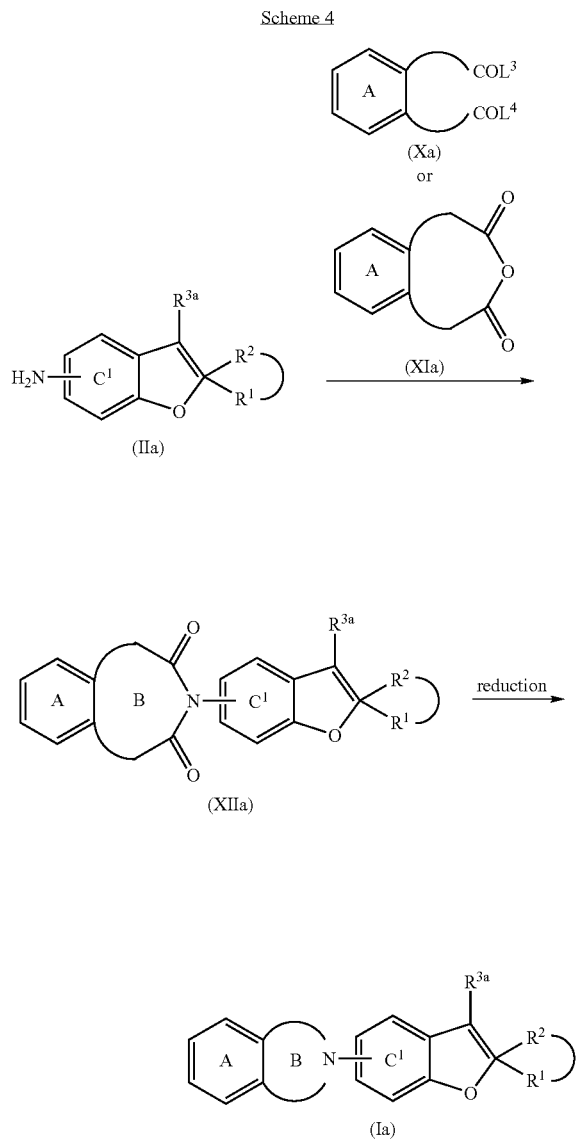

In the above formulas, each of $L^3$ and $L^4$ indicates a leaving group.

"A leaving group" indicated by $L^3$ and $L^4$ is exemplified by hydroxyl, a halogen atom (for example, fluorine, chlorine, bromine, iodine, or the like), $C_{1-6}$ alkylsulfonyloxy (for example, methanesulfonyloxy, ethanesulfonyloxy, or the like), $C_{6-10}$ arylsulfonyloxy that may have substituents, and the like.

"A $C_{6-10}$ arylsulfonyloxy that may have substituents" is exemplified by $C_{6-10}$ arylsulfonyloxy (for example, phenylsulfonyloxy, naphthylsulfonyloxy, or the like) that may have 1 to 3 substituents selected from $C_{1-6}$ alkyl (for example, methyl, ethyl, propyl, isopropyl, butyl, isobutyl, sec-butyl, tert-butyl, pentyl, hexyl, or the like), $C_{1-6}$ alkoxy (for example, methoxy, ethoxy, propoxy, isopropoxy, butoxy, isobutoxy, sec-butoxy, pentyloxy, hexyloxy, or the like), and nitro, and so on. Specific examples include benzenesulfonyloxy, m-nitrobenzenesulfonyloxy, p-toluenesulfonyloxy, and the like.

Compound (Xa) is a compound that is capable of forming, together with the amino group substituted on ring $C^1$ of compound (IIa), a group represented by the formula:

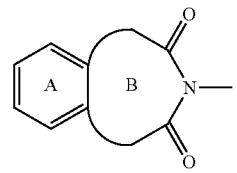

wherein each symbol is as defined above, and, for example, there is used a compound represented by the formula:

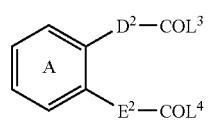

(wherein $D^2$ indicates a group represented by formula $—(CH_2)d^2—$ ($d^2$ is an integer of 0 to 2), which may be substituted with a hydrocarbon group that may have halogen or a substituent, $E^2$ indicates a group represented by formula $—(CH_2)e^2—$ ($e^2$ is an integer of 0 to 2), which may be substituted with a hydrocarbon group that may have halogen or substituent, the sum of $d^2$ and $e^2$ indicates an integer of 0 to 2, and each of $L^3$ and $L^4$ is as defined above), or the like.

As for said hydrocarbon group that may have halogen or a substituent, there is used the same group as the hydrocarbon group that may have a halogen or a substituent, which is mentioned above as the substituent of a 5- to 7-membered nitrogen-containing heterocyclic ring indicated by ring B.

Compound (Xa) and compound (XIa) are easily commercially available or are produced according to per se known methods.

Compound (XIIa) is obtained by reaction of compound (Xa) and compound (IIa), if necessary, in the presence of a base.

The amount of compound (Xa) to be used is about 1.0 to about 5.0 moles, preferably about 1.0 to about 2.0 moles, for 1 mole of compound (IIa).

Said "base" is exemplified by a basic salt such as sodium carbonate, potassium carbonate, cesium carbonate, sodium hydrogen carbonate, or the like, an aromatic amine such as pyridine, lutidine, or the like, a tertiary amine such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, or the like, an alkali metal hydride such as sodium hydride, potassium hydride, or the like, a metal amide such as sodium amide, lithium diisopropylamide, lithium hexamethyldisilazide, or the like, a metal alkoxide such as sodium methoxide, sodium ethoxide, potassium tert-butoxide, or the like, or the like. The amount of the base to be used is about 2.0 to about 5.0 moles, preferably about 2.0 to about 3.0 moles, for 1 mole of compound (IIa).

It is advantageous to carry out this reaction by using a solvent inert to the reaction. Such a solvent is preferably exemplified by alcohols such as methanol, ethanol, propanol, and the like, hydrocarbons such as cyclohexane, hexane, benzene, toluene, xylene, and the like, ethers such as tetrahydrofuran, dioxane, 1,2-dimethoxyethane, diethyl ether, diisopropyl ether, and the like, amides such as N,N-dimethylformamide, N,N-dimethylacetamide, hexamethylphosphoric triamide, and the like, sulfoxides such as dimethyl sulfoxide and the like, halogenated hydrocarbons such as dichloromethane, chloroform, carbon tetrachloride, 1,2-dichloroethane, and the like, and a mixed solvent thereof and the like.

The reaction time is usually about 10 minutes to about 8 hours, preferably for about 30 minutes to about 3 hours. The reaction temperature is usually about 0 to about 120° C., preferably about 25 to about 100° C.

The product can be employed for the next reaction as the reaction mixture or a crude product, but the product can be isolated from the reaction mixture according to a conventional method and can be easily purified according to a usual separation means (e.g., recrystallization, distillation, chromatography, etc.).

In place of the above-mentioned reaction, compound (IIa) and compound (Xa) can be reacted in the presence of an appropriate condensing agent.

The amount of compound (Xa) to be used is about 1.0 to about 5.0 moles, preferably about 1.0 to about 2.0 moles, for 1 mole of compound (IIa).

As for said "condensing agent", there is used, for example, an N,N'-dicarbodiimide such as N,N'-dicyclohexylcarbodiimide, 1-ethyl-3-(3-dimetylaminopropyl)carbodiimide (WSC) hydrochloride, or the like, an azolite such as N,N'-carbonyldiimidazole or the like, a dehydrating agent such as N-ethoxycarbonyl-2-ethoxy-1,2-dihydroquinoline, phosphorus oxychloride, acetic anhydride, or the like, a 2-halopyridinium salt such as 2-chloromethylpyridinium iodide, 2-fluoro-1-chloromethylpyridinium iodide, or the like, or the like.

The amount of the condensing agent to be used is about 1.0 to about 5.0 moles, preferably about 2.0 to about 3.0 moles, for 1 mole of compound (IIa).

Also, if desired, the reaction may be carried out in the presence of a base together with the condensing agent. Said "base" is exemplified by a basic salt such as potassium acetate, sodium acetate, or the like, 1-hydroxy-1H-benzotriazole (HOBT) monohydrate, or the like. The amount of the base to be used is about 1.0 to about 5.0 moles, preferably about 2.0 to about 3.0 moles, for 1 mole of compound (IIa).

It is advantageous to carry out this reaction by the use of a solvent inert to the reaction. Such a solvent is preferably exemplified by alcohols such as methanol, ethanol, propanol, and the like, hydrocarbons such as cyclohexane, hexane, benzene, toluene, xylene, and the like, ethers such as tetrahydrofuran, dioxane, 1,2-dimethoxyethane, diethyl ether, diisopropyl ether, and the like, amides such as N,N-dimethylformamide, N,N-dimethylacetamide, hexamethylphosphoric triamide, and the like, sulfoxides such as dimethyl sulfoxide and the like, halogenated hydrocarbons such as dichloromethane, chloroform, carbon tetrachloride, 1,2-dichloroethane, and the like, acid anhydrides such as acetic anhydride, and the like, and a mixed solvent thereof, and the like.

The reaction time is usually about 30 minutes to about 48 hours, preferably for about 30 minutes to about 24 hours. The reaction temperature is usually about 0 to about 120° C., preferably about 25 to about 100° C.

The product can be employed for the next reaction as the reaction mixture or a crude product, but the product can be isolated from the reaction mixture according to a conventional method and can be easily purified according to the usual separation means (e.g., recrystallization, distillation, chromatography, etc.).

Compound (XIIa) is synthesized also by a process comprising reacting compound (XIa) with compound (IIa), followed by, if desired, cyclization in the presence of a base.

The amount of compound (XIa) to be used is about 1.0 to about 5.0 moles, preferably about 1.0 to about 2.0 moles, for 1 mole of compound (IIa).

As for said "condensing agent", there is used, for example, an N,N'-dicarbodiimide such as N,N'-dicyclohexylcarbodiimide, 1-ethyl-3-(3-dimetylaminopropyl)carbodiimide (WSC) hydrochloride, or the like, an azolite such as N,N'-carbonyldiimidazole or the like, a dehydrating agent such as N-ethoxycarbonyl-2-ethoxy-1,2-dihydroquinoline, phosphorus oxychloride, acetic anhydride, or the like, a 2-halopyridinium salt such as 2-chloromethylpyridinium iodide, 2-fluoro-1-chloromethylpyridinium iodide, or the like, or the like.

The amount of the condensing agent to be used is respectively about 1.0 to about 5.0 moles, preferably about 1.0 to about 3.0 moles, for 1 mole of compound (IIa).

Also, if desired, the reaction may be carried out in the presence of a base together with the condensing agent. Said "base" is exemplified by a basic salt such as potassium acetate, sodium acetate, or the like, 1-hydroxy-1H-benzotriazole (HOBT) monohydrate, or the like. The amount of the base to be used is about 1.0 to about 5.0 moles, preferably about 1.0 to about 3.0 moles, for 1 mole of compound (IIa).

It is advantageous to carry out this reaction by using a solvent inert to the reaction. Such a solvent is preferably exemplified by alcohols such as methanol, ethanol, propanol, and the like, hydrocarbons such as cyclohexane, hexane, benzene, toluene, xylene, and the like, ethers such as tetrahydrofuran, dioxane, 1,2-dimethoxyethane, diethyl ether, diisopropyl ether, and the like, amides such as N,N-dimethylformamide, N,N-dimethylacetamide, hexamethylphosphoric triamide, and the like, sulfoxides such as dimethyl sulfoxide and the like, halogenated hydrocarbons such as dichloromethane, chloroform, carbon tetrachloride, 1,2-dichloroethane, and the like, acid anhydrides such as acetic anhydride, and the like, and a mixed solvent thereof, and the like.

The reaction time is usually about 30 minutes to about 48 hours, preferably for about 30 minutes to about 24 hours. The reaction temperature is usually about 0 to about 120° C., preferably about 25 to about 100° C.

The product can be employed for the next reaction as the reaction mixture or a crude product, but the product can be isolated from the reaction mixture according to a conventional method and can be easily purified according to the usual separation means (e.g., recrystallization, distillation, chromatography, etc.).

Compound (Ia) is produced by reduction of compound (XIIa) with a reducing agent.

As for said "reducing agent", for example, a metal hydride such as sodium borohydride, lithium aluminum hydride, or the like, a borane such as a borane-tetrahydrofuran complex, or the like.

The amount of the reducing agent to be used is respectively about 0.5 to about 10 moles, preferably about 1.0 to about 5.0 moles, for 1 mole of compound (XIIa).

Also, if desired, an acid catalyst may be added together with the reducing agent. As for said "acid catalyst", a Lewis acid such as boron trifluoride, aluminum chloride, or the like or the like is used. The amount of said "acid catalyst" to be used is respectively about 0.5 to about 10 moles, preferably about 1.0 to about 5.0 moles, for 1 mole of compound (XIIa).

It is advantageous to carry out this reaction without using any solvent or by using a solvent inert to the reaction. Such a solvent, though not particularly limited as far as the reaction proceeds, is preferably exemplified by alcohols such as methanol, ethanol, propanol, and the like, hydrocarbons such as cyclohexane, hexane, benzene, toluene, xylene, mesitylene, and the like, organic acids such as formic acid, acetic acid, and the like, ethers such as tetrahydrofuran, dioxane, 1,2-dimethoxyethane, diethyl ether, diisopropyl ether, and the like, anilines such as N,N-dimethylaniline, N,N-diethylaniline, and the like, halogenated hydrocarbons such as dichloromethane, chloroform, carbon tetrachloride, 1,2-dichloroethane, and the like, and a mixed solvent thereof, and the like.

The reaction time is usually about 10 minutes to about 24 hours, preferably for about 30 minutes to about 12 hours. The reaction temperature is usually about 0 to about 120° C., preferably about 25 to about 100° C.

The product can be employed for the next reaction as the reaction mixture or a crude product, but the product can be isolated from the reaction mixture according to a conventional method and can be easily purified according to a usual separation means (e.g., recrystallization, distillation, chromatography, and the like).

Also, in the case where compound (IIa) is a dihydrobenzofuran, the production is carried out according to the process described in the following reaction Scheme 5.

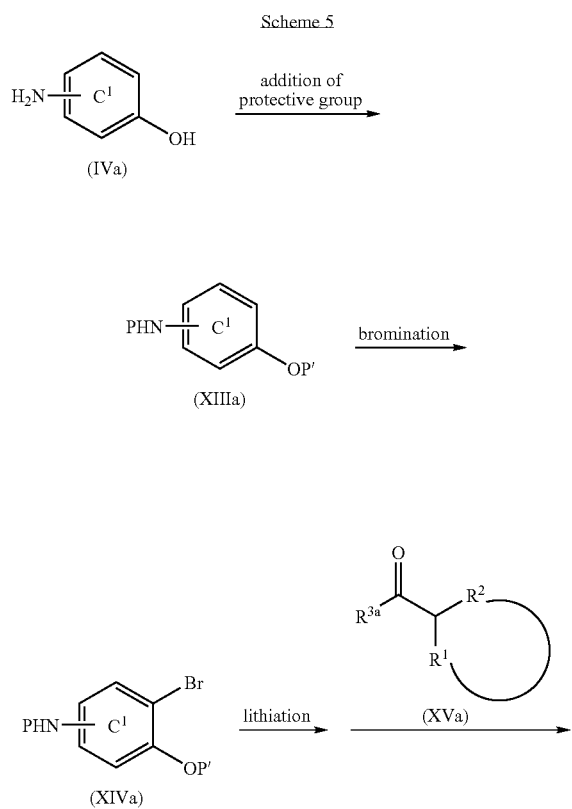

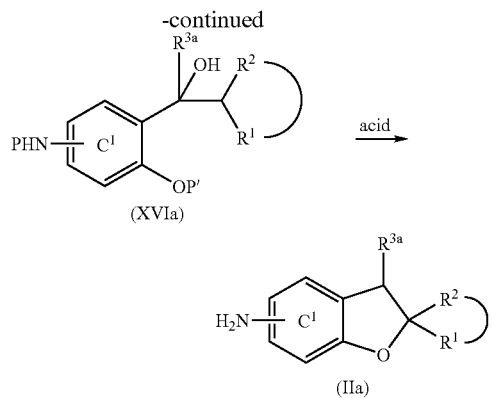

Compound (XIIIa) is produced by subjecting compound (IVa) to the addition reaction of a protective group that has been generally employed in the peptide chemistry, etc.

As for the protective group (P) for amino group, there is used, for example, formyl, or $C_{1-6}$ alkyl-carbonyl (for example, acetyl, propionyl, or the like), phenylcarbonyl, $C_{1-6}$ alkoxy-carbonyl (for example, methoxycarbonyl, ethoxycarbonyl, tert-butoxycarbonyl, or the like), phenyloxycarbonyl, $C_{7-10}$ aralkyloxy-carbonyl (for example, benzyloxycarbonyl or the like), trityl, phthaloyl, or the like, which respectively may be substituted. As for the substituent thereof, a halogen atom (for example, fluorine, chlorine, bromine, iodine, or the like), $C_{1-6}$ alkyl-carbonyl (for example, acetyl, propionyl, valeryl, or the like), nitro, or the like is used. The number of the substituents is 1 to 3.

As for the protective group (P') for hydroxyl group, there is used, for example, $C_{1-6}$ alkyl (for example, methyl, ethyl, propyl, isopropyl, butyl, tert-butyl, or the like), phenyl, $C_{7-11}$ aralkyl (for example, benzyl or the like), formyl, $C_{1-6}$ alkyl-carbonyl (for example, acetyl, propionyl, or the like), phenyloxycarbonyl, $C_{7-11}$ aralkyloxy-carbonyl (for example, benzyloxycarbonyl or the like), tetrahydropyranyl, tetrahydrofuranyl, silyl, or the like, which respectively may be substituted. As for the substituent thereof, for example, a halogen atom (for example, fluorine, chlorine, bromine, iodine, or the like), $C_{1-6}$ alkyl (for example, methyl, ethyl, tert-butyl, or the like), $C_{7-11}$ aralkyl (for example, benzyl or the like), $C_{6-10}$ aryl (for example, phenyl, naphthyl, or the like), nitro, or the like is used. The number of the substituents is 1 to 4.

Compound (XIVa) is produced by reaction of compound (XIIIa) and a brominating reagent.

As for "a brominating reagent", bromine, an imide such as N-bromosuccinimide or the like, a halogen adduct such as benzyltrimethylammonium tribromide, or the like or the like. The amount of the brominating reagent to be used is about 1.0 to about 5.0 moles, preferably about 1.0 to about 2.0 moles, for 1 mole of compound (XIIIa).

It is advantageous to carry out this reaction by using a solvent inert to the reaction. Such a solvent, though being not particularly limited as far as the reaction proceeds, is preferably exemplified by ethers such as diethyl ether, tetrahydrofuran, dioxane, 1,2-dimethoxyethane, and the like, alcohols such as methanol, ethanol, propanol, and the like, hydrocarbons such as benzene, toluene, cyclohexane, hexane, and the like, amides such as N,N-dimethylformamide, N,N-dimethylacetamide, and the like, halogenated hydrocarbons such as dichloromethane, chloroform, carbon tetrachloride, 1,2-dichloroethane, and the like, nitriles such as acetonitrile, propionitrile, and the like, sulfoxides such as dimethyl sulfoxide and the like, organic acids such as acetic acid, propionic acid, and the like, nitroalkanes such as nitromethane, and the like, aromatic amines such as pyridine, lutidine, quinoline, and the like, and a mixed solvent thereof and the like.

If desired, this reaction is carried out in the presence of a base or a Lewis acid or an iron.

Said "base" is exemplified by a basic salt such as sodium carbonate, potassium carbonate, cesium carbonate, sodium hydrogen carbonate, sodium acetate, potassium acetate, or the like, an aromatic amine such as pyridine, lutidine, or the like, a tertiary amine such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, or the like. The amount of the base to be used is about 0.8 to about 10 moles for 1 mole of compound (XIIIa).

As for "a Lewis acid", for example, ferric chloride, aluminum chloride, boron trifluoride, or the like is exemplified. The amount of the Lewis acid to be used is about 0.01 to about 1 mole for 1 mole of compound (XIIIa).

As for "an iron", the amount of the iron to be used is about 0.01 to about 1 mole for 1 mole of compound (XIIIa).

The reaction temperature is usually about −50 to about 150° C., preferably about 0 to about 100° C. The reaction time is usually about 5 minutes to about 24 hours, preferably for about 10 minutes to about 12 hours.

The product can be employed for the next reaction as the reaction mixture or a crude product, but the product can be isolated from the reaction mixture according to a conventional method and can be easily purified according to the usual separation means (e.g., recrystallization, distillation, chromatography, etc.).

Compound (XVIa) is produced by lithiation of compound (XIVa), followed by reaction with a ketone (XVa).

As for "a lithiating reagent", an alkyl lithium such as n-butyllithium is used. The amount of the lithiating reagent to be used is about 1.0 to about 5.0 moles, preferably about 1.0 to about 3.0 moles, for 1 mole of compound (XIVa).

It is advantageous to carry out this reaction by using a solvent inert to the reaction. Such a solvent, though being not particularly limited as far as the reaction proceeds, is preferably exemplified by ethers such as diethyl ether, tetrahydrofuran, dioxane, 1,2-dimethoxyethane, and the like, hydrocarbons such as benzene, toluene, cyclohexane, hexane, and the like, halogenated hydrocarbons such as dichloromethane, chloroform, carbon tetrachloride, 1,2-dichloroethane, and the like, and a mixed solvent thereof and the like.

The reaction temperature is usually about −78 to about 100° C., preferably about −78 to about 50° C. The reaction time is usually about 5 minutes to about 24 hours, preferably for about 10 minutes to about 3 hours.

The product can be employed for the next reaction as the reaction mixture or a crude product, but the product can be isolated from the reaction mixture according to a conventional method and can be easily purified according to the usual separation means (e.g., recrystallization, distillation, chromatography, etc.).

Compound (IIa) is produced by deprotection and cyclization of compound (XVIa) with an acid catalyst. As for the acid catalyst, there is used a mineral acid such as hydrochloric acid, hydrobromic acid, sulfuric acid, or the like, a sulfonic acid such as p-toluenesulfonic acid, camphorsulfonic acid, or the like, a Lewis acid such as aluminum chloride, boron trifluoride, or the like or the like. The amount of the acid catalyst to be used is, for instance, in the case of a mineral acid, usually about 1 to about 100 moles, preferably about 10 to about 50 moles, for 1 mole of compound (XVIa) and, for instance, in the case of a sulfonic acid, usually about 0.1 to about 20 moles, preferably about 0.1 to about 5 moles, for 1 mole of compound (XVIa).

It is advantageous to carry out this reaction without using any solvent or by using a solvent inert to the reaction. Such a solvent is not particularly limited as far as the reaction proceeds. For example, in the case where a mineral acid is used, the solvent is preferably exemplified by a mixed solvent of water and an organic solvent such as an alcohol such as methanol, ethanol, propanol, or the like, a saturated hydrocarbon such as cyclohexane, hexane, or the like, an aromatic hydrocarbon such as benzene, toluene, xylene, or the like, an ether such as tetrahydrofuran, dioxane, 1,2-dimethoxyethane, diethyl ether, diisopropyl ether, or the like, an amide such as N,N-dimethylformamide, N,N-dimethylacetamide, hexamethylphosphoric triamide, or the like, a sulfoxide such as dimethyl sulfoxide or the like, a halogenated hydrocarbon such as dichloromethane, chloroform, carbon tetrachloride, 1,2-dichloroethane, or the like or water.

The reaction time is usually about 30 minutes to about 24 hours, preferably for about 30 minutes to about 6 hours. The reaction temperature is usually about −78 to about 200° C., preferably about −20 to about 150° C.

The product can be employed for the next reaction as the reaction mixture or a crude product, but the product can be isolated from the reaction mixture according to a conventional method and can be easily purified according to the usual separation means (e.g., recrystallization, distillation, chromatography, etc.).

The starting compound for the above-mentioned compound (Ia) may form a salt, which, though not being particularly limited as far as the reaction is achieved, is exemplified by the same salt as that of the above-mentioned compound (Ia) may form, or the like.

The configurational isomers (E and Z forms) of compound (Ia) can be isolated and purified, at the moment when the isomerization occurs, according to a conventional separation means such as extraction, recrystallization, distillation, chromatography, and the like, thereby being able to isolate and purify the compound. Also, according to the methods described in Shin Jikken Kagaku Kouza (Text books on New Experimental Chemistry) 14 [Edited by Nihon Kagaku Kai (Chemical Society of Japan)], page 251 to page 253 and in Jikken Kagaku Kouza (Text books on Experimental Chemistry), 4th Edition, 19 [Edited by Nihon Kagaku Kai (Chemical Society of Japan)], page 273 to page 274, and modified methods thereof, the isomerization of the double bond is allowed to proceed by the use of heating, an acid catalyst, a transition-metal complex, a metal catalyst, a radical-species catalyst, irradiation with a light, a strong basic catalyst, or the like, thereby being able to obtain the corresponding pure isomers.

Compound (Ia) forms stereoisomers depending on a particular kind of a substituent. Both isomers, which present alone or as a mixture thereof, are included in the present invention.

Compound (Ia) and compound (Ia') may be in the form of hydrates or non-hydrates.

In each case, compound (Ia) can be synthesized, as desired further, by deprotection reaction, acylation reaction, alkylation reaction, hydrogenation reaction, oxidation reaction, reduction reaction, carbon-chain elongation reaction, and substituent-replacement reaction, each of which is carried out alone or in a combination of two or more of them.

In the case where the title compound is obtained in a free state according to the above-mentioned reaction, the compound may be converted into a salt according to a conventional method, or in the case where the compound is obtained as a salt, it can be converted into a free form or another salt according to a conventional method. The thus-obtained compound (Ia) can be isolated from the reaction mixture and purified according to a known means such as trans-solubilization, concentration, solvent extraction, fractional distillation, crystallization, recrystallization, chromatography, or the like.

In the case where compound (Ia) exists as configurational isomers, diastereomers, conformers, or the like, each of them can be isolated, as desired, by the above-mentioned separation and purification means. Also, in the case where compound (Ia) is in racemic forms, they can be separated into the d form and the l form by a conventional optical resolution means.

Also, in the case where a functional group such as amino group, hydroxyl group, carboxyl group or the like is present in each of the above-mentioned reactions, the reaction may be carried out after introduction of a protective group that is generally employed in the peptide chemistry or the like and the title compound can be obtained by removing the protective group, as needed, after the reaction.

As for the protective group, there is used, for example, formyl or a $C_{1-6}$ alkylcarbonyl (for example, acetyl, propionyl, or the like), phenylcarbonyl, a $C_{1-6}$ alkoxycarbonyl (for example, methoxycarbonyl, ethoxycarbonyl, or the like), phenoxycarbonyl, a $C_{7-10}$ aralkyloxycarbonyl (for example, benzyloxycarbonyl or the like), trityl, phthaloyl, or the like, which respectively may have substituents. As for the substituent thereof, a halogen atom (for example, fluorine, chlorine, bromine, iodine, or the like), a $C_{1-6}$ alkylcarbonyl (for example, acetyl, propionyl, valeryl, or the like), nitro, or the like is used. The number of the substituents is approximately 1 to 3.

Also, as for the method for removing the protective group, per se known methods or modified methods thereof are employed. For example, there is employed treatment with an acid, a base, a ultraviolet light, hydrazine, phenylhydrazine, sodium N-methyldithiocarbamate, tetrabutylammonium fluoride, palladium acetate or the like, or a reduction reaction.

Next, processes for production of compounds (Ib) of the present invention are illustrated.

Compounds (Ib) can be produced according to the following processes or modified processes thereof.

Scheme 6

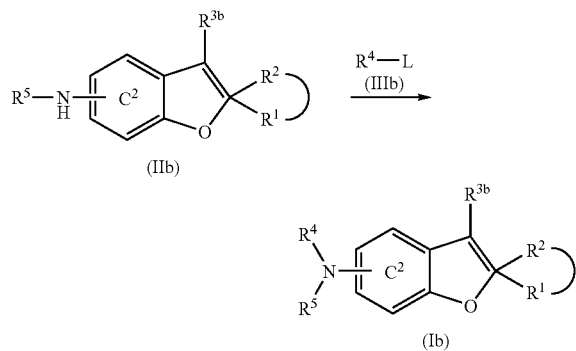

Compound (Ib) is produced by reaction of compound (IIb) and compound (IIIb) represented by formula $R^4$-L, wherein L indicates a leaving group and $R^4$ is as defined above.

"A leaving group" indicated by L is exemplified by hydroxyl, a halogen atom (for example, fluorine, chlorine, bromine, iodine, or the like), $C_{1-5}$ alkylsulfonyloxy that may be halogenated (for example, methanesulfonyloxy, ethanesulfonyloxy, trichloromethanesulfonyloxy, or the like), $C_{6-10}$ arylsulfonyloxy that may be substituted, or the like.

"A $C_{6-10}$ arylsulfonyloxy that may be substituted" is exemplified by $C_{6-10}$ arylsulfonyloxy (for example, phenylsulfonyloxy, naphthylsulfonyloxy, or the like) that may have 1 to 3 substituents selected from $C_{1-6}$ alkyl (for example, methyl, ethyl, propyl, isopropyl, butyl, isobutyl, sec-butyl, tert-butyl, pentyl, hexyl, or the like), $C_{1-6}$ alkoxy (for example, methoxy, ethoxy, propoxy, isopropoxy, butoxy, isobutoxy, sec-butoxy, pentyloxy, hexyloxy, or the like), and nitro, and so on. Specific examples include benzenesulfonyloxy, m-nitrobenzenesulfonyloxy, p-toluenesulfonyloxy, and the like.

(1) In the following are described the reaction conditions in the case where $R^4$ is "an acyl group containing an aromatic group that may be substituted".

The reaction of compound (IIb) and compound (IIIb) is carried out, if desired, in the presence of a base or an acid.

The amount of compound (IIIb) to be used is about 1.0 to about 5.0 moles, preferably about 1.0 to about 2.0 moles, for 1 mole of compound (IIb).

Said "base" is exemplified by a basic salt such as sodium carbonate, potassium carbonate, cesium carbonate, sodium hydrogen carbonate, or the like, an aromatic amine such as pyridine, lutidine, or the like, a tertiary amine such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, or the like, an alkali metal hydride such as sodium hydride, potassium hydride, or the like, a metal amide such as sodium amide, lithium diisopropylamide, lithium hexamethyldisilazide, or the like, a metal alkoxide such as sodium methoxide, sodium ethoxide, potassium tert-butoxide, or the like, or the like.

Said "acid" is exemplified by a sulfonic acid such as methanesulfonic acid, p-toluenesulfonic acid, camphorsulfonic acid, or the like, a Lewis acid such as zinc chloride, aluminum chloride, or the like, or the like.

The amount of said "base" to be used is about 0.1 to about 10 moles, preferably about 0.8 to about 2 moles, for 1 mole of compound (IIb).

The amount of said "acid" to be used is about 0.1 to about 10 moles, preferably about 0.8 to about 3 moles, for 1 mole of compound (IIb).

It is advantageous to carry out this reaction without using any solvent or by using a solvent inert to the reaction. Such a solvent, though being not particularly limited as far as the reaction proceeds, is preferably exemplified by a solvent such as an ether such as diethyl ether, tetrahydrofuran, dioxane, 1,2-dimethoxyethane, or the like, a hydrocarbon such as benzene, toluene, cyclohexane, hexane, or the like, an amide such as N,N-dimethylformamide, N,N-dimethylacetamide, or the like, a halogenated hydrocarbon such as dichloromethane, chloroform, carbon tetrachloride, 1,2-dichloroethane, or the like, a nitrile such as acetonitrile, propionitrile, or the like, a sulfoxide such as dimethyl sulfoxide or the like, a nitrogen-containing, aromatic amine such as pyridine, lutidine, quinoline, or the like, or a mixed solvent thereof or the like. The reaction temperature is usually about –20 to about 150° C., preferably about 0 to about 100° C. The reaction time is usually about 5 minutes to about 24 hours, preferably for about 10 minutes to about 5 hours.

In place of the above-mentioned reaction, compound (IIb) and compound (IIIb) can be reacted in the presence of an appropriate condensing agent.

The amount of compound (IIIb) to be used is about 1.0 to about 5.0 moles, preferably about 1.0 to about 2.0 moles, for 1 mole of compound (IIb).

As for a condensing agent, there is used, for example, an N,N'-dicarbodiimide such as N,N'-dicyclohexylcarbodiimide, 1-ethyl-3-(3-dimetylaminopropyl)carbodiimide (WSC) hydrochloride, or the like, an azolite such as N,N'-carbonyldiimidazole or the like, a dehydrating agent such as N-ethoxycarbonyl-2-ethoxy-1,2-dihydroquinoline, phosphorus oxychloride, or the like, a 2-halopyridinium salt such as 2-chloromethylpyridinium iodide, 2-fluoro-1-chloromethylpyridinium iodide, or the like, or the like.

The amount of the condensing agent to be used is about 1.0 to about 5.0 moles, preferably about 1.0 to about 2.0 moles, for 1 mole of compound (IIb).

It is advantageous to carry out this reaction by using a solvent inert to the reaction. Such a solvent, though being not particularly limited as far as the reaction proceeds, is preferably exemplified by a solvent such as an ether such as diethyl ether, tetrahydrofuran, dioxane, 1,2-dimethoxyethane, or the like, a hydrocarbon such as benzene, toluene, cyclohexane, hexane, or the like, an amide such as N,N-dimethylformamide, N,N-dimethylacetamide, or the like, a halogenated hydrocarbon such as dichloromethane, chloroform, carbon tetrachloride, 1,2-dichloroethane, or the like, a nitrile such as acetonitrile, propionitrile, or the like, a sulfoxide such as dimethyl sulfoxide or the like, or a mixed solvent thereof or the like.

The reaction time is usually about 5 minutes to about 48 hours, preferably for about 30 minutes to about 24 hours. The reaction temperature is usually about −20 to about 200° C., preferably about 0 to about 100° C.

(2) In the following are described the reaction conditions in the case where $R^4$ is "an aliphatic hydrocarbon group that may have an optionally substituted aromatic group, which may be further substituted".

The reaction of compound (IIb) and compound (IIIb) represented by $R^4$-L is carried out, if desired, in the presence of a base.

The amount of compound (IIIb) to be used is about 1.0 to about 5.0 moles, preferably about 1.0 to about 2.0 moles, for 1 mole of compound (IIb).

Said "base" is exemplified by a basic salt such as sodium carbonate, potassium carbonate, cesium carbonate, sodium hydrogen carbonate, or the like, an aromatic amine such as pyridine, lutidine, or the like, a tertiary amine such as triethylamine, tripropylamine, tributylamine, cyclohexyldimetylamine, 4-dimethylaminopyridine, N,N-dimethylaniline, N-methylpiperidine, N-methylpyrrolidine, N-methylmorpholine, or the like, an alkali metal hydride such as sodium hydride, potassium hydride, or the like, a metal amide such as sodium amide, lithium diisopropylamide, lithium hexamethyldisilazide, or the like, a metal alkoxide such as sodium methoxide, sodium ethoxide, potassium tert-butoxide, or the like, or the like.

The amount of the base to be used is about 1.0 to about 5.0 moles, preferably about 1.0 to about 2.0 moles, for 1mole of compound (IIb).

It is advantageous to carry out this reaction by the use of a solvent inert to the reaction. Such a solvent, though being not particularly limited as far as the reaction proceeds, is preferably exemplified by a solvent such as an alcohol such as methanol, ethanol, propanol, or the like, an ether such as diethyl ether, tetrahydrofuran, dioxane, 1,2-dimethoxyethane, or the like, a hydrocarbon such as benzene, toluene, cyclohexane, hexane, or the like, an amide such as N,N-dimethylformamide, N,N-dimethylacetamide, or the like, a halogenated hydrocarbon such as dichloromethane, chloroform, carbon tetrachloride, 1,2-dichloroethane, or the like, a nitrile such as acetonitrile, propionitrile, or the like, a sulfoxide such as dimethyl sulfoxide or the like, or a mixed solvent thereof or the like.

The reaction time is usually about 30 minutes to about 48 hours, preferably for about 1 hour to about 24 hours. The reaction temperature is usually about −20 to about 200° C., preferably about 0 to about 150° C.

In place of the above-mentioned reaction, compound (Ib) can also be synthesized by reductive amination.

Scheme 7

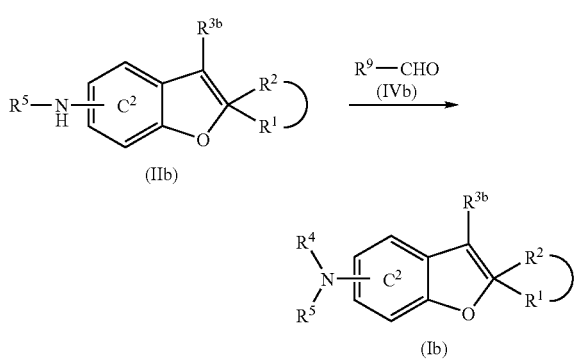

Compound (Ib) is produced by condensation of compound (IIb) and compound (IVb) represented by formula $R^9$—CHO ($R^9$ indicates a group where a methylene is removed from $R^4$.), followed by reduction with a reducing agent.

The amount of compound (IVb) to be used is about 1.0 to about 5.0 moles, preferably about 1.0 to about 2.0 moles, for 1 mole of compound (IIb).

As for said "reducing agent", for example, a metal hydride such as sodium borohydride, sodium cyanoborohydride, lithium aluminum hydride, or the like, a borane such as a borane-tetrahydrofuran complex or the like, a hydrosilane such as triethylsilane or the like, formic acid, or the like is used. Also, as desired, an acid catalyst may be added together with the reducing agent.

The acid catalyst is exemplified by a mineral acid such as hydrochloric acid, hydrobromic acid, sulfuric acid, or the like, a sulfonic acid such as methanesulfonic acid, p-toluenesulfonic acid, or the like, an organic acid such as acetic acid, propionic acid, trifluoroacetic acid, or the like, a Lewis acid such as zinc chloride, aluminum chloride, or the like, or the like.

The amount of said "reducing agent" to be used is about 0.25 to about 5.0 moles, preferably about 0.5 to about 2.0 moles, for 1 mole of compound (IIb).

The amount of the acid catalyst to be used is, for instance, in the case of a mineral acid, usually about 1 to about 100 moles, preferably about 1 to about 20 moles, for 1 mole of compound (IIb).

It is advantageous to carry out this reaction by using a solvent inert to the reaction. Such a solvent, though being not particularly limited as far as the reaction proceeds, is preferably exemplified by a solvent such as an alcohol such as methanol, ethanol, propanol, or the like, an ether such as diethyl ether, tetrahydrofuran, dioxane, 1,2-dimethoxyethane, or the like, a hydrocarbon such as benzene, toluene, cyclohexane, hexane, or the like, an amide such as N,N-dimethylformamide, N,N-dimethylacetamide, or the like, or a mixed solvent thereof or the like.

The reaction time is usually about 5 minutes to about 48 hours, preferably for about 30 minutes to about 24 hours. The reaction temperature is usually about −20 to about 200° C., preferably about 0 to about 100° C.

In said reaction, after condensation of compound (IIb) with compound (IVb), the reduction with a reducing agent is replaced by catalytic hydrogenation reaction in the presence of a variety of a catalyst under hydrogen atmosphere to carry out the production. The catalyst to be employed is exemplified by platinum oxide, platinum on activated carbon, palladium on activated carbon, nickel, copper-chrome oxide, rhodium, cobalt, ruthenium, or the like. The usage amount of the catalyst is about 5 to about 1000% by weight, preferably about 5 to about 1000% by weight, for compound (IIb).

It is advantageous to carry out the present reaction by the use of a solvent inert to the reaction. Such a solvent, though being not particularly limited as far as the reaction proceeds, is preferably exemplified by a solvent such as an alcohol such as methanol, ethanol, propanol, or the like, an ether such as diethyl ether, tetrahydrofuran, dioxane, 1,2-dimethoxyethane, or the like, a hydrocarbon such as benzene, toluene, cyclohexane, hexane, or the like, an amide such as N,N-dimethylformamide, N,N-dimethylacetamide, or the like, water, or the like, or a mixed solvent thereof or the like.

The reaction time is usually about 30 minutes to about 48 hours, preferably for about 30 minutes to about 24 hours. The reaction temperature is usually about 0 to about 120° C., preferably about 20 to about 80° C.

In place of the above-mentioned reaction, there can be employed a method to reduce the acylamide derivative that is synthesized in the above-mentioned (1).

As for the reducing agent, for example, a metal hydride such as sodium borohydride, lithium aluminum hydride, or the like, a borane such as a borane-tetrahydrofuran complex or the like, or the like is used.

Also, if desired, an acid catalyst may be added together with the reducing agent. The acid catalyst to be used is exemplified by a Lewis acid such as a trifluoroborane-diethyl ether complex, aluminum chloride, or the like, or the like.

The amount of said reducing agent to be used is respectively about 0.25 to about 10 moles, preferably about 0.5 to about 5 moles, for 1 mole of the acylamide derivative.

The amount of said Lewis acid to be used is respectively about 0.25 to about 10 moles, preferably about 0.5 to about 5 moles, for 1 mole of the acylamide derivative.

It is advantageous to carry out this reaction by using a solvent inert to the reaction. Such a solvent, though being not particularly limited as far as the reaction proceeds, is preferably exemplified by a solvent such as an alcohol such as methanol, ethanol, propanol, or the like, an ether such as diethyl ether, tetrahydrofuran, dioxane, 1,2-dimethoxyethane, or the like, a hydrocarbon such as benzene, toluene, cyclohexane, hexane, or the like, water or the like, or a mixed solvent thereof or the like.

The reaction time is usually about 30 minutes to about 24 hours, preferably for about 1 hour to about 16 hours. The reaction temperature is usually about 0 to about 150° C., preferably about 20 to about 100° C.

The product (1b) obtained as shown above can be isolated from the reaction mixture according to the known isolation means and can be easily purified according to the separation means such as recrystallization, distillation, chromatography, and the like.

Compound (IIb) can be produced, for example, according to the process described in JP 5-140142 A or a modified process thereof.

In the case where compound (IIb) is a dihydrobenzofuran (compound (IIb')), the production is carried out according to the method described in the following reaction Scheme.

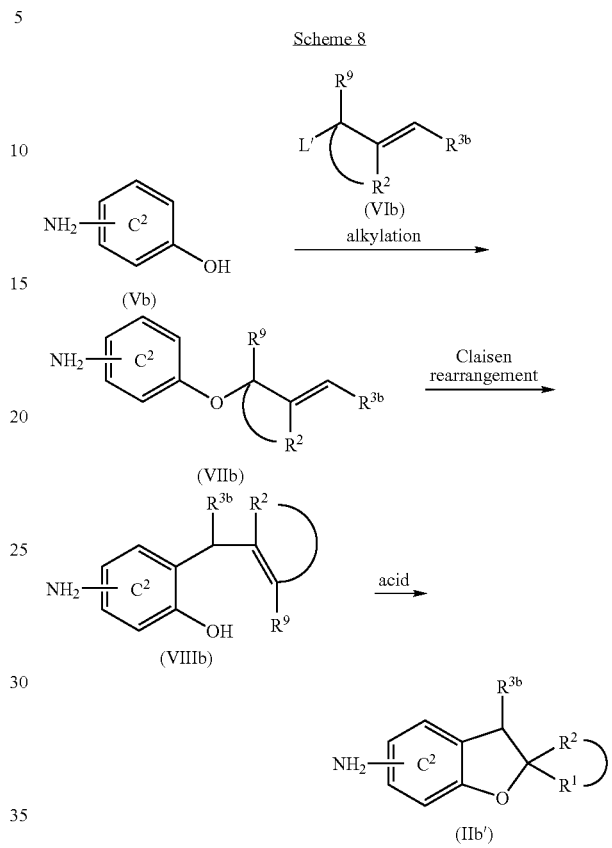

In the above formulas, L' indicates a leaving group and $R^9$ indicates the hydrogen atom or a group, in which a methylene is removed from $R^1$.

"A leaving group" indicated by L' is exemplified by hydroxyl, a halogen atom (for example, fluorine, chlorine, bromine, iodine, or the like), a $C_{1-6}$ alkylsulfonyloxy (for example, methylsulfonyloxy, ethylsulfonyloxy, or the like), a $C_{6-10}$ arylsulfonyloxy that may be substituted, or the like.

"A $C_{6-10}$ arylsulfonyloxy that may be substituted" is exemplified by a $C_{6-10}$ arylsulfonyloxy (for example, phenylsulfonyloxy, naphthylsulfonyloxy, or the like) that may have 1 to 3 substituents, which are selected from a $C_{1-6}$ alkyl (for example, methyl, ethyl, propyl, isopropyl, butyl, isobutyl, sec-butyl, tert-butyl, pentyl, hexyl, or the like), a $C_{1-6}$ alkoxy (for example, methoxy, ethoxy, propoxy, isopropoxy, butoxy, isobutoxy, sec-butoxy, pentyloxy, hexyloxy, or the like), and nitro, and so on, where specific examples include benzenesulfonyloxy, m-nitrobenzenesulfonyloxy, p-toluenesulfonyloxy, and the like.

Compound (Vb) and compound (VIb) are easily commercially available or are produced according to the well-known methods.

Compound (VIIb) is produced by reaction of a phenolate anion, which is formed by treatment of compound (Vb) with a base, and compound (VIb) represented by formula $R^9$—CHL'-$CHR^2$=$CHR^{3b}$.

The amount of compound (VIb) to be used is about 1.0 to about 5.0 moles, preferably about 1.0 to about 2.0 moles, for 1 mole of compound (Vb).

"A base" is exemplified by an inorganic base such as an alkali metal hydroxide exemplified by sodium hydroxide, potassium hydroxide, or the like, an alkali metal alkoxide such as sodium methoxide, sodium ethoxide, potassium tert-butoxide, or the like, an alkali metal hydride such as sodium hydride, potassium hydride, or the like, a metal amide such as sodium amide, lithium diisopropylamide, lithium hexamethyldisilazide, or the like, a basic salt such as potassium hydrogen carbonate, sodium carbonate, potassium carbonate, sodium acetate, or the like, or the like. The usage amount of the base is about 0.5 to about 5.0 moles, preferably about 1.0 to about 3.0 moles, for 1 mole of compound (Vb).

It is advantageous to carry out this reaction by using a solvent inert to the reaction. Such a solvent is preferably exemplified by an alcohol such as methanol, ethanol, propanol, or the like, a hydrocarbon such as cyclohexane, hexane, benzene, toluene, xylene, or the like, an ether such as tetrahydrofuran, dioxane, 1,2-dimethoxyethane, diethyl ether, diisopropyl ether, or the like, an amide such as N,N-dimethylformamide, N,N-dimethylacetamide, hexamethylphosphoric triamide, or the like, a sulfoxide such as dimethyl sulfoxide or the like, a halogenated hydrocarbon such as dichloromethane, chloroform, carbon tetrachloride, 1,2-dichloroethane, or the like, water, or a mixed solvent thereof or the like.

The reaction time is usually about 10 minutes to about 8 hours, preferably for about 30 minutes to about 3 hours. The reaction temperature is usually about 0 to about 120° C., preferably about 25 to about 100° C.

The product can be employed for the next reaction as the reaction mixture or a crude product, but the product can be isolated from the reaction mixture according to a conventional method and can be easily purified according to the usual separation means (e.g., recrystallization, distillation, chromatography, etc.).

Compound (VIIIb) is produced by the Claisen rearrangement reaction of compound (VIIb).

It is advantageous to carry out this reaction without using a solvent or by using a solvent inert to the reaction. Such a solvent to be used, though being not particularly limited as far as the reaction proceeds, is exemplified by an alcohol such as methanol, ethanol, propanol, or the like, a hydrocarbon such as cyclohexane, hexane, benzene, toluene, xylene, mesitylene, or the like, an organic acid such as formic acid, acetic acid, or the like, an ether such as tetrahydrofuran, dioxane, 1,2-dimethoxyethane, diethyl ether, diisopropyl ether, or the like, an aniline such as N,N-dimethylaniline, N,N-diethylaniline, or the like, a halogenated hydrocarbon such as dichloromethane, chloroform, carbon tetrachloride, 1,2-dichloroethane, or the like, or a mixed solvent thereof or the like.

Also, if desired, this reaction may be carried out by using an acid catalyst. As for the acid catalyst, for example, a Lewis acid such as aluminum chloride, boron trifluoride, or the like or the like is used. The usage amount of the acid catalyst is, for instance, in the case of a Lewis acid, usually about 0.1 to about 20 moles, preferably about 0.1 to about 5.0 moles, for 1 mole of compound (VIIb). The reaction time is usually about 30 minutes to about 24 hours, preferably for about 1 hour to about 6 hours. The reaction temperature is usually about −70 to about 300° C., preferably about 150 to about 250° C.

The product can be employed for the next reaction as the reaction mixture or a crude product, but the product can be isolated from the reaction mixture according to a conventional method and can be easily purified according to the usual separation means (e.g., recrystallization, distillation, chromatography, etc.).

Compound (IIb') is produced by cyclization of compound (VIIIb) with an acid catalyst. The acid catalyst is exemplified by a mineral acid such as hydrochloric acid, hydrobromic acid, sulfuric acid, or the like, a sulfonic acid such as p-toluenesulfonic acid, camphorsulfonic acid, or the like, a Lewis acid such as aluminum chloride, boron trifluoride, or the like or the like. The amount of the acid catalyst to be used is, for instance, in the case of a mineral acid, usually about 1 to about 100 moles, preferably about 10 to about 50 moles, for 1 mole of compound (VIIIb) and, for instance, in the case of a sulfonic acid, usually about 0.1 to about 20 moles, preferably about 0.1 to about 5 moles, for 1 mole of compound (VIIIb).

It is advantageous to carry out this reaction without using any solvent or by using a solvent inert to the reaction. Such a solvent is not particularly limited as far as the reaction proceeds. For instance, in the case where a mineral acid is used, the solvent is preferably exemplified by a mixed solvent of water and an organic solvent such as an alcohol such as methanol, ethanol, propanol, or the like, a saturated hydrocarbon such as cyclohexane, hexane, or the like, an aromatic hydrocarbon such as benzene, toluene, xylene, or the like, an ether such as tetrahydrofuran, dioxane, 1,2-dimethoxyethane, diethyl ether, diisopropyl ether, or the like, an amide such as N,N-dimethylformamide, N,N-dimethylacetamide, hexamethylphosphoric triamide, or the like, a sulfoxide such as dimethyl sulfoxide or the like, a halogenated hydrocarbon such as dichloromethane, chloroform, carbon tetrachloride, 1,2-dichloroethane, or the like or water.

The reaction time is usually about 30 minutes to about 24 hours, preferably for about 30 minutes to about 6 hours. The reaction temperature is usually about −78 to about 200° C., preferably about −20 to about 150° C.

The product can be employed for the next reaction as the reaction mixture or a crude product, but the product can be isolated from the reaction mixture according to a conventional method and can be easily purified according to the usual separation means (e.g., recrystallization, distillation, chromatography, etc.).

Also, in the case where compound (IIb) is a benzofuran (compound (IIb″)), the production is carried out according to the method described in the following reaction Scheme.

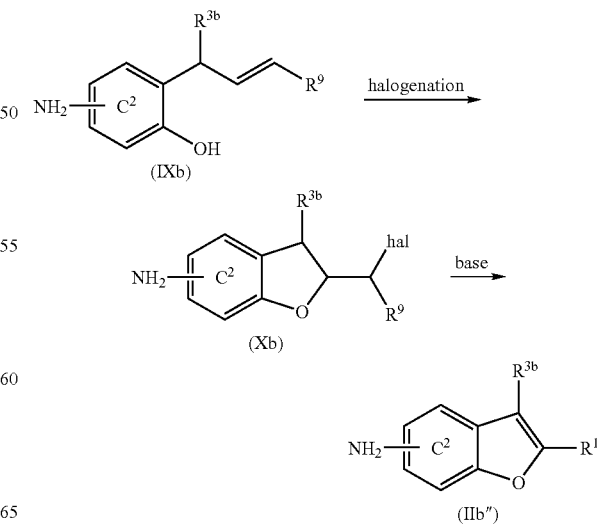

Scheme 9

In the above formulas, hal indicates a halogen atom (for example, fluorine, chlorine, bromine, iodine, or the like).

Compound (Xb) is produced by reaction of compound (IXb), which is synthesized in a manner similar to the case for compound (VIIIb), and a halogenating reagent.

As for "a halogenating reagent", for example, a halogen such as bromine, chlorine, iodine, or the like, an imide such as N-bromosuccinimide or the like, a halogen adduct such as benzyltrimethylammonium iodide chloride, benzyltrimethylammonium tribromide, or the like or the like. The usage amount of the halogenating reagent is about 1.0 to about 5.0 moles, preferably about 1.0 to about 2.0 moles, for 1 mole of compound (IXb).

It is advantageous to carry out this reaction by the use of a solvent inert to the reaction. Such a solvent, though being not particularly limited as far as the reaction proceeds, is preferably exemplified by an alcohol such as methanol, ethanol, propanol, or the like, a hydrocarbon such as benzene, toluene, cyclohexane, hexane, or the like, an amide such as N,N-dimethylformamide, N,N-dimethylacetamide, or the like, a halogenated hydrocarbon such as dichloromethane, chloroform, carbon tetrachloride, 1,2-dichloroethane, or the like, a nitrile such as acetonitrile, propionitrile, or the like, a sulfoxide such as dimethyl sulfoxide or the like, an organic acid such as acetic acid, propionic acid, or the like, a nitroalkane such as nitromethane, or the like, an aromatic amine such as pyridine, lutidine, quinoline, or the like, or a mixed solvent thereof or the like.

If desired, this reaction is carried out in the presence of a base or a radical initiator or under irradiation with a light.

"A base" is exemplified by a basic salt such as sodium carbonate, potassium carbonate, cesium carbonate, sodium hydrogen carbonate, sodium acetate, potassium acetate, or the like, an aromatic amine such as pyridine, lutidine, or the like, a tertiary amine such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, or the like, or the like. The usage amount of the base is about 0.8 to about 10 moles for 1 mole of compound (IXb).

"A radical initiator" is exemplified by benzoyl peroxide, azobisisobutyronitrile, or the like. The usage amount of the radical initiator is about 0.01 to about 1.0 mole for 1 mole of compound (IXb).

In the case of irradiation with a light, a halogen lamp or the like can be used.

The reaction temperature is usually about –50 to about 150° C., preferably about 0 to about 100° C. The reaction time is usually about 5 minutes to about 24 hours, preferably for about 10 minutes to about 12 hours.

The product can be employed for the next reaction as the reaction mixture or a crude product, but the product can be isolated from the reaction mixture according to a conventional method and can be easily purified according to the usual separation means (e.g., recrystallization, distillation, chromatography, etc.).

Compound (IIb″) is produced by treatment of compound (Xb) with a base.

"A base" is exemplified by an inorganic salt such as a metal hydroxide such as sodium hydroxide, potassium hydroxide, or the like, an organic amine such as triethylamine, 1.8-diazabicyclo[5,4,0]-7-undecene, pyridine, or the like, a metal alkoxide such as sodium methoxide, sodium ethoxide, potassium tert-butoxide, or the like, an alkali metal hydride such as sodium hydride, potassium hydride, or the like, a metal amide such as sodium amide, lithium diisopropylamide, lithium hexamethyldisilazide, or the like, a basic salt such as potassium hydrogen carbonate, sodium carbonate, potassium carbonate, sodium acetate, or the like, or the like.

The amount of the base to be used is about 0.5 to about 10 moles, preferably about 1.0 to about 5.0 moles, for 1 mole of compound (Xb).

It is advantageous to carry out this reaction by using a solvent inert to the reaction. Such a solvent is preferably exemplified by an alcohol such as methanol, ethanol, propanol, or the like, a hydrocarbon such as cyclohexane, hexane, benzene, toluene, xylene, or the like, an ether such as tetrahydrofuran, dioxane, 1,2-dimethoxyethane, diethyl ether, diisopropyl ether, or the like, an amide such as N,N-dimethylformamide, N,N-dimethylacetamide, hexamethylphosphoric triamide, or the like, a sulfoxide such as dimethyl sulfoxide or the like, a halogenated hydrocarbon such as dichloromethane, chloroform, carbon tetrachloride, 1,2-dichloroethane, or the like, water, or a mixed solvent thereof or the like.

The reaction time is usually about 10 minutes to about 24 hours, preferably for about 30 minutes to about 12 hours. The reaction temperature is usually about 0 to about 120° C., preferably about 25 to about 100° C.

The product can be employed for the next reaction as the reaction mixture or a crude product, but the product can be isolated from the reaction mixture according to a conventional method and can be easily purified according to the usual separation means (e.g., recrystallization, distillation, chromatography, etc.).

Also, in the case where compound (IIb) is a dihydrobenzofuran (compound (IIb′)), the production is carried out according to the method described in the following reaction Scheme.

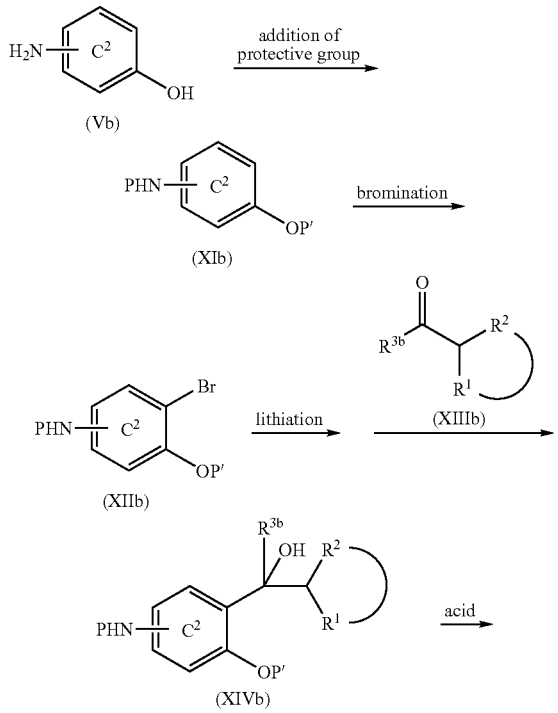

-continued

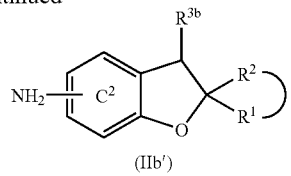

(IIb')

Compound (XIb) is produced by subjecting compound (Vb) to the addition reaction of a protective group that has been generally employed in the peptide chemistry.

As for the protective group (P) for amino group, there is used, for example, formyl or a $C_{1-6}$ alkyl-carbonyl (for example, acetyl, propionyl, or the like), phenylcarbonyl, a $C_{1-6}$ alkoxy-carbonyl (for example, methoxycarbonyl, ethoxycarbonyl, tert-butoxycarbonyl, or the like), phenyloxycarbonyl, a $C_{7-10}$ aralkyloxy-carbonyl (for example, benzyloxycarbonyl or the like), trityl, phthaloyl, or the like, which respectively may have substituents. As for the substituent thereof, a halogen atom (for example, fluorine, chlorine, bromine, iodine, or the like), a $C_{1-6}$ alkyl-carbonyl (for example, acetyl, propionyl, valeryl, or the like), nitro, or the like is used, where the number of the substituents is 1 to 3.

As for the protective group (P') for hydroxyl group, there is used, for example, a $C_{1-6}$ alkyl (for example, methyl, ethyl, propyl, isopropyl, butyl, tert-butyl, or the like), phenyl, a $C_{7-11}$ aralkyl (for example, benzyl or the like), formyl, a $C_{1-6}$ alkyl-carbonyl (for example, acetyl, propionyl, or the like), phenyloxycarbonyl, a $C_{7-11}$ aralkyloxy-carbonyl (for example, benzyloxycarbonyl or the like), tetrahydropyranyl, tetrahydrofuranyl, silyl, or the like, which respectively may have substituents. As for the substituent thereof, for example, a halogen atom (for example, fluorine, chlorine, bromine, iodine, or the like), a $C_{1-6}$ alkyl (for example, methyl, ethyl, tert-butyl, or the like), a $C_{7-11}$ aralkyl (for example, benzyl or the like), a $C_{6-10}$ aryl (for example, phenyl, naphthyl, or the like), nitro, or the like is used, where the number of the substituents is 1 to 4.

Compound (XIIb) is produced by reaction of compound (XIb) and a brominating reagent.

As for "a brominating reagent", bromine, an imide such as N-bromosuccinimide or the like, a halogen adduct such as benzyltrimethylammonium tribromide, or the like or the like. The usage amount of the brominating reagent is about 1.0 to about 5.0 moles, preferably about 1.0 to about 2.0 moles, for 1 mole of compound (XIb).

It is advantageous to carry out this reaction by the use of a solvent inert to the reaction. Such a solvent, though being not particularly limited as far as the reaction proceeds, is preferably exemplified by an ether such as diethyl ether, tetrahydrofuran, dioxane, 1,2-dimethoxyethane, or the like, an alcohol such as methanol, ethanol, propanol, or the like, a hydrocarbon such as benzene, toluene, cyclohexane, hexane, or the like, an amide such as N,N-dimethylformamide, N,N-dimethylacetamide, or the like, a halogenated hydrocarbon such as dichloromethane, chloroform, carbon tetrachloride, 1,2-dichloroethane, or the like, a nitrile such as acetonitrile, propionitrile, or the like, a sulfoxide such as dimethyl sulfoxide or the like, an organic acid such as acetic acid, propionic acid, or the like, a nitroalkane such as nitromethane, or the like, an aromatic amine such as pyridine, lutidine, quinoline, or the like, or a mixed solvent thereof or the like.

If desired, this reaction is carried out in the presence of a base or a Lewis acid or an iron.

"A base" is exemplified by a basic salt such as sodium carbonate, potassium carbonate, cesium carbonate, sodium hydrogen carbonate, sodium acetate, potassium acetate, or the like, an aromatic amine such as pyridine, lutidine, or the like, a tertiary amine such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, or the like, or the like. The usage amount of the base is about 0.8 to about 10 moles for 1 mole of compound (XIb).

As for "a Lewis acid", for example, ferric chloride, aluminum chloride, boron trifluoride, or the like is exemplified. The usage amount of the Lewis acid is about 0.01 to about 1 mole for 1 mole of compound (XIb).

As for "an iron", the usage amount of the iron is about 0.01 to about 1 mole for 1 mole of compound (XIb).

The reaction temperature is usually about −50 to about 150° C., preferably about 0 to about 100° C. The reaction time is usually about 5 minutes to about 24 hours, preferably for about 10 minutes to about 12 hours.

The product can be employed for the next reaction as the reaction mixture or a crude product, but the product can be isolated from the reaction mixture according to a conventional method and can be easily purified according to the usual separation means (e.g., recrystallization, distillation, chromatography, etc.).

Compound (XIVb) is produced by lithiation of compound (XIIb), followed by reaction with a ketone (XIIIb).

As for "a lithiating reagent", an alkyl lithium such as n-butyllithium is used. The usage amount of the lithiating reagent is about 1.0 to about 5.0 moles, preferably about 1.0 to about 3.0 moles, for 1 mole of compound (XIIb).

It is advantageous to carry out this reaction by using a solvent inert to the reaction. Such a solvent, though being not particularly limited as far as the reaction proceeds, is preferably exemplified by an ether such as diethyl ether, tetrahydrofuran, dioxane, 1,2-dimethoxyethane, or the like, a hydrocarbon such as benzene, toluene, cyclohexane, hexane, or the like, a halogenated hydrocarbon such as dichloromethane, chloroform, carbon tetrachloride, 1,2-dichloroethane, or the like, or a mixed solvent thereof or the like.

The reaction temperature is usually about −78 to about 100° C., preferably about −78 to about 50° C. The reaction time is usually about 5 minutes to about 24 hours, preferably for about 10 minutes to about 3 hours.

The product can be employed for the next reaction as the reaction mixture or a crude product, but the product can be isolated from the reaction mixture according to a conventional method and can be easily purified according to the usual separation means (e.g., recrystallization, distillation, chromatography, etc.).

Compound (IIb') is produced by deprotection and cyclization of compound (XIVb) with an acid catalyst. As for the acid catalyst, there is used a mineral cid such as hydrochloric acid, hydrobromic acid, sulfuric acid, or the like, a sulfonic acid such as p-toluenesulfonic acid, camphorsulfonic acid, or the like, a Lewis acid such as aluminum chloride, boron trifluoride, or the like or the like. The amount of the acid catalyst to be used is, for instance, in the case of a mineral acid, usually about 1 to about 100 moles, preferably about 10 to about 50 moles, for 1 mole of compound (XIVb) and, for instance, in the case of a sulfonic acid, usually about 0.1 to about 20 moles, preferably about 0.1 to about 5 moles, for 1 mole of compound (XIVb).

It is advantageous to carry out this reaction without using any solvent or by using a solvent inert to the reaction. Such a solvent is not particularly limited as far as the reaction proceeds. For example, in the case where a mineral acid is used, the solvent is preferably exemplified by a mixed solvent of water and an organic solvent such as an alcohol such as methanol, ethanol, propanol, or the like, a saturated hydrocarbon such as cyclohexane, hexane, or the like, an aromatic hydrocarbon such as benzene, toluene, xylene, or the like, an ether such as tetrahydrofuran, dioxane, 1,2-dimethoxyethane, diethyl ether, diisopropyl ether, or the like, an amide such as N,N-dimethylformamide, N,N-dimethylacetamide, hexamethylphosphoric triamide, or the like, a sulfoxide such as dimethyl sulfoxide or the like, a halogenated hydrocarbon such as dichloromethane, chloroform, carbon tetrachloride, 1,2-dichloroethane, or the like or water.

The reaction time is usually about 30 minutes to about 24 hours, preferably for about 30 minutes to about 6 hours. The reaction temperature is usually about −78 to about 200° C., preferably about −20 to about 150° C.

The product can be employed for the next reaction as the reaction mixture or a crude product, but the product can be isolated from the reaction mixture according to a conventional method and can be easily purified according to the usual separation means (e.g., recrystallization, distillation, chromatography, etc.).

Also, in the case where a functional group such as amino group, hydroxyl group, carboxyl group or the like exists in each of the above-mentioned reactions, the reaction may be carried out after introduction of a protective group that is generally employed in the peptide chemistry or the like and the title compound can be obtained by removing the protective group, as needed, after the reaction.

As for the protective group, there is used, for example, formyl or a $C_{1-6}$ alkyl-carbonyl (for example, acetyl, propionyl, or the like), phenylcarbonyl, a $C_{1-6}$ alkoxy-carbonyl (for example, methoxycarbonyl, ethoxycarbonyl, tert-butoxycarbonyl, or the like), phenoxycarbonyl, a $C_{7-10}$ aralkyloxy-carbonyl (for example, benzyloxycarbonyl or the like), trityl, phthaloyl, or the like, which respectively may have substituents. As for the substituent thereof, a halogen atom (for example, fluorine, chlorine, bromine, iodine, or the like), a $C_{1-6}$ alkyl-carbonyl (for example, acetyl, propionyl, valeryl, or the like), nitro, or the like is used, where the number of the substituents is approximately 1 to 3.

Also, as for the method for removing the protective group, the well-known methods or modified methods thereof are employed, where there is employed, for example, a method to treat with an acid, a base, a ultraviolet light, hydrazine, phenylhydrazine, sodium N-methyldithiocarbamate, tetrabutylammonium fluoride, palladium acetate, or the like or the reduction reaction.

The starting compound for the above-mentioned compound (Ib) may form a salt, which, though not being particularly limited as far as the reaction is achieved, is exemplified by a salt similar to the salt that the above-mentioned compound (Ib) may form, or the like.

The configurational isomers (E and Z forms) of compound (Ib) can be isolated and purified, at the moment when the isomerization occurs, according to the usual separation means such as extraction, recrystallization, distillation, chromatography, and the like, thereby being able to produce pure compounds. Also, according to the methods described in Shin Jikken Kagaku Kouza (Text books on New Experimental Chemistry) 14 [Edited by Nihon Kagaku Kai (Chemical Society of Japan)], page 251 to page 253 and in Jikken Kagaku Kouza (Text books on Experimental Chemistry), 4th Edition, 19 [Edited by Nihon Kagaku Kai (Chemical Society of Japan)], page 273 to page 274, and modified methods thereof, the isomerization of the double bond is allowed to proceed by the use of heating, an acid catalyst, a transition-metal complex, a metal catalyst, a radical-species catalyst, irradiation with a light, a strong basic catalyst, or the like, thereby being able to obtain the corresponding pure isomers.

Compound (Ib) forms stereoisomers depending on a particular kind of the substituent, but the isomers, which present as a single form or as a mixture, are included in the present prevention.

Compound (Ib) may be in the form of hydrates or non-hydrates.

In each case, compound (Ib) can be synthesized, as desired further, by deprotection reaction, acylation reaction, alkylation reaction, hydrogenation reaction, oxidation reaction, reduction reaction, carbon-chain elongation reaction, and substituent-replacement reaction, each of which is carried out singly or in a combination of two or more of them.

In the case where the title compound is obtained in a free state according to the above-mentioned reaction, the compound may be converted into a salt according to a conventional method, or in the case where the compound is obtained as a salt, it can be converted into a free form or another salt according to a conventional method. The thus-obtained compound (Ib) can be isolated from the reaction solution and purified according to the well-known means such as trans-solubilization, concentration, solvent extraction, fractional distillation, crystallization, recrystallization, chromatography, and the like.

In the case where compound (Ib) exists as configurational isomers, diastereomers, conformers, or the like, each of them can be isolated, as desired, by the above-mentioned separation and purification means. Also, in the case where compound (Ib) is in racemic forms, they can be separated into the d form and the l form by usual optical resolution means.

A prodrug of compound (Ia), (Ia'), or (Ib) of the present invention may be a compound that is converted into compound (Ia) or the like by a reaction with an enzyme, gastric acid, or the like under a physiological condition in the living body, namely, a compound that is converted into compound (Ia) or the like by an enzymatic oxidation, reduction, hydrolysis, or the like or a compound that is converted into compound (Ia) or its salt by hydrolysis with gastric acid or the like.

Examples of the prodrug of compound (Ia) or the like include a compound, where the amino group in compound (I) or the like is acylated, alkylated, or phosphorylated (for example, a compound or the like, where the amino group in compound (I) or the like is converted into eicosanoylamino, alanylamino, benzylaminocarbonylamino, (5-methyl-2-ox0-1,3-dioxolan-4-yl)methoxycarbonylamino, tetrahydrofuranylamino, pyrrolidylmethylamino, pivaloyloxymethylamino, or tert-butylamino); a compound, where the hydroxyl group in compound (Ia) or the like is acylated, alkylated, phosphorylated, or converted into the borate (for example, a compound or the like, where the hydroxyl group in compound (Ia) or the like is converted into acetyloxy, palmitoyloxy, propanoyloxy, pivaloyloxy, succinyloxy, fumaryloxy, alanyloxy, or dimethylaminomethylcarbonyloxy); a compound or the like, where the carboxyl group in compound (Ia) or the like is esterified or amidated (for example, a compound or the like, where the carboxyl group is subjected to ethyl esterification, phenyl esterification, carboxyoxymethyl esterification, dimethylaminomethyl esterification, pivaloyloxymethyl esterification, ethoxycarbonyloxyethyl esterification, phthalidyl esterification, (5-methyl-2-oxo-1,3-dioxolan-4-yl)methyl esterification, cyclohexyloxycarbonyl esterification, or conversion into the methyl amide), and so on. These compounds can be produced from compound (Ia) according to a well-known method.

Also, the prodrug of compound (Ia) or the like may be a compound that is converted into compound (Ia) or the like under a physiological condition as described in "Iyakuhin No Kaihatu (Development of Drugs)", Volume 7, Molecular Design, Hirokawa Shoten, published in 1990; page 163 to page 198.

Compound (Ia), (Ia'), or (Ib) or a salt thereof or a prodrug thereof (hereinafter, abbreviated as the compound of the present invention) possesses excellent pharmaceutical actions such as a neurotrophic factor-like action, an action to enhance the neurotrophic factor activity, an action to inhibit the nerve degeneration, an action to promote the neuroregeneration, an antioxidant action, an action to inhibit the nerve cell death by β-amyloid and the like and also possesses excellent properties such as a low toxicity, a small side effect, and the like, thereby being useful as pharmaceuticals.

The compound of the present invention acts as a neurotrophic factor-like substance, a substance to enhance the neurotrophic factor activity, a substance to inhibit the neurodegeneration or a substance to inhibit the β-amyloid toxicity for mammalian animals (for example, mouse, rat, hamster, rabbit, cat, dog, cattle, sheep, monkey, human, and the like), thereby inhibiting the nerve cell death and promoting the neuroregeneration. Also, the compound of the present invention possesses an action to activate the choline system (for examples, an action to enhance the activity of choline acetyltransferase and the like), thereby resulting in an increase of the content of acetylcholine, an activation of the neurological function, and the like.

Accordingly, the compound of the present invention is effective for the nerve degenerative diseases (for example, Alzheimer's disease, Parkinson's disease, amyotrophic lateral sclerosis (ALS), Hantington's disease, spinocerebellar degeneration and the like), psychoneurotic diseases (for example, schizophrenia and the like), the head injury, the spinal cord injury, the cerebrovascular accident, the cerebrovascular dementia, the peripheral neuropathies (for examples, diabetic neuropathy and the like), and the like), thereby being employed as prophylactic/therapeutic drugs for these diseases.

The compound of the present invention has a low toxicity and is capable of being safely administered orally or parenterally (for examples, topical, rectal, or intravenous administration, and the like) as it is or as a pharmaceutical composition, which is produced by compounding with a pharmaceutically permissible carrier according to the well-known means, such as a tablet (includes a sugar-coated tablet, a film-coated tablet, an intraoral disintegrating tablet, or the like), a powder, a granule, a capsule (includes a soft capsule), a liquid & solution, an injection, a suppository, a sustained-release formulation, a plaster, or the like.

The content of the compound of the present invention in the preparation of the present invention is about 0.01 to about 100% by weight of the total weight of the preparation.

Said dosage differs depending on the administration object, the administration route, the disease, and the like, whereas, for instance, in the case where an oral preparation is administered to an adult as a therapeutic drug for the Alzheimer's disease, the dosage as the active ingredient of the compound of the present invention is about 0.1 to about 20 mg/kg of body weight, preferably about 0.2 to about 10 mg/kg of body weight, more preferably about 0.5 to about 10 mg/kg of body weight, where the dosage can be administered with being divided in 1-3 times daily.

Furthermore, there may be used in combination with another active ingredient [for example, a choline esterase inhibitor (for example, Aricept (donepezil) or the like), a cerebral function activator (for example, idebenone, Vinpocetine, or the like), a therapeutic drug for the Parkinson's disease (for example, L-dopa, deprenyl, or the like), a therapeutic drug for the amyotrophic lateral sclerosis (for example, riluzole or the like), a neurotrophic factor, or the like]. For the combined usage, said another active ingredient and the compound of the present invention or a salt thereof may be compounded according to the well-known method and then formulated into one pharmaceutical composition (for example, a tablet, a powder, a granule, a capsule (includes a soft capsule), a liquid & solution, an injection, a suppository, a sustained-release formulation, or the like) or each of them may be subjected to a separate formulation, followed by a simultaneous or time-lapse administration to the same object.

The pharmaceutically acceptable carrier, which may be used for the production of the preparation of the present invention, is exemplified by a variety of organic or inorganic carrier substances, which have been conventionally employed as formulation materials, such as, for example, a bulking agent, a lubricant, a binding agent, and a disintegrator in solid formulations; a vehicle, a solubilizing agent, a suspending agent, an isotonicity agent, a buffering agent, and an analgesic in liquid formulations; and the like. Also, as needed, usual excipients such as a preservative, an antioxidant, a coloring agent, a sweetening agent, an absorbing agent, a wetting agent, and the like can be used.

The bulking agent is exemplified by lactose, white soft sugar, D-mannitol, starch, corn starch, crystalline cellulose, light anhydrous silicic acid, or the like.

The lubricant is exemplified by magnesium stearate, potassium stearate, talc, colloidal silica, or the like.

The binding agent is exemplified by crystalline cellulose, white soft sugar, D-mannitol, dextrin, hydroxypropyl cellulose, hydroxypropylmethyl cellulose, polyvinyl pyrrolidone, starch, sucrose, gelatin, methyl cellulose, sodium carboxymethyl cellulose, or the like.

The disintegrator is exemplified by starch, carboxymethyl cellulose, calcium carboxymethyl cellulose, croscarmellose sodium, sodium carboxymethyl starch, L-hydroxypropyl cellulose, or the like.

The vehicle is exemplified by water for injection, alcohol, propylene glycol, macrogol, sesame oil, corn oil, olive oil, and the like.

The solubilizing agent is exemplified by polyethylene glycol, propylene glycol, D-mannitol, benzyl benzoate, ethanol, trisamiomethane, cholesterol, triethanolamine, sodium carbonate, sodium citrate, or the like.

The suspending agent is exemplified by a surface active agent such as stearyltriethanolamine, sodium lauryl sulfate, laurylaminopropionic acid, lecithin, benzalkonium chloride, benzethonium chloride, glycerin monostearate, or the like; a hydrophilic, high molecular substance such as polyvinyl alcohol, polyvinyl pyrrolidone, sodium carboxymethyl cellulose, methyl cellulose, hydroxymethyl cellulose, hydroxyethyl cellulose, hydroxypropyl cellulose, or the like; etc.

The isotonicity agent is exemplified by glucose, D-sorbitol, sodium chloride, glycerin, D-mannitol, or the like.

The buffering agent is exemplified by a buffer solution of a phosphate, an acetate, a carbonate, a citrate, or the like.

The analgesic is exemplified by benzyl alcohol or the like.

The preservative is exemplified by a paraoxybenzoic acid ester, chlorobutanol, benzyl alcohol, phenethyl alcohol, dehydroacetic acid, sorbic acid, or the like.

The antioxidant is exemplified by a sulfite, ascorbic acid, α-tocopherol, or the like.

The present invention is further illustrate in detail by the following Reference Examples, Examples, Formulation Examples, and Experimental Examples, but these examples are merely examples, which are not intended to limit the present invention and may be varied without departing from the scope of the present invention.

"Room temperature" in the following Reference Examples and Examples usually indicates about 10 to about 35° C. Unless otherwise stated, % indicates the percent by weight.

Other symbols used in the present text indicate the following meanings.

s: singlet
d: doublet
dd: doublet of doublets
dt: doublet of triplets
t: triplet
q: quartet
septet: septet
m: multiplet
br: broad
J: coupling constant
Hz: hertz
$CDCl_3$: deuterated chloroform
DMSO-$d_6$: deuterated dimethyl sulfoxide
$^1$H-NMR: proton nuclear magnetic resonance
[Compounds (Ia)]

REFERENCE EXAMPLE 1a

Ethyl 3-(4-isopropylphenyl)-2-methyl-2-propenoate

To a suspension of sodium hydride (a 60% dispersion in liquid paraffin, 5.92 g, 148 mmol) in N,N-dimethylformamide (150 ml) was added at 0° C. triethyl 2-phosphonopropionate (35.0 g, 148 mmol) and the resulting mixture was stirred at the same temperature for 10 minutes. To the reaction solution was added 4-isopropylbenzaldehyde (20.0 g, 135 mmol) and the resulting mixture was stirred at room temperature for 30 minutes. Water was added into the reaction solution and the product was extracted twice with ethyl acetate. The combined extracts were washed with water, dried on magnesium sulfate, and then concentrated under reduced pressure to obtain 30.1 g (96% yield) of the oily title compound.

$^1$H-NMR ($CDCl_3$) δ: 1.26 (6H, d, J=7.0 Hz), 1.35 (3H, t, J=7.0 Hz), 2.13 (3H, s), 2.92 (1H, septet, J=7.0 Hz), 4.27 (2H, q, J=7.0 Hz), 7.21-7.38 (4H, m), 7.67 (1H, s).

REFERENCE EXAMPLE 2a

Ethyl 2-methyl-3-(4-methylphenyl)-2-propenoate

To a suspension of sodium hydride (a 60% dispersion in liquid paraffin, 15.0 g, 375 mmol) in N,N-dimethylformamide (160 ml) was added at 0° C. a solution of triethyl 2-phosphonopropionate (87.7 g, 368 mmol) in N,N-dimethylformamide (10 ml) and the resulting mixture was stirred at the same temperature for 1 hour. To the reaction solution was added 4-methylbenzaldehyde (43.3 g, 361 mmol) and the resulting mixture was stirred at room temperature for 1 hour. Water was added into the reaction solution and the product was extracted twice with ethyl acetate. The combined extracts were washed with water, dried on magnesium sulfate, and then concentrated under reduced pressure to obtain 66.7 g (91% yield) of the oily title compound.

$^1$H-NMR ($CDCl_3$) δ: 1.34 (3H, t, J=7.0 Hz), 2.12 (3H, d, J=1.4 Hz), 2.37 (3H, s), 4.26 (2H, q, J=7.0 Hz), 7.19 (2H, d, J=8.4 Hz), 7.31 (2H, d, J=8.4 Hz), 7.66 (1H, s).

REFERENCE EXAMPLE 3a

Ethyl 3-(4-fluorophenyl)-2-methyl-2-propenoate

By using 4-fluorobenzaldehyde, the title compound was synthesized according to Reference Example 1a. Yield: 97%. An oily substance.

$^1$H-NMR ($CDCl_3$) δ: 1.35 (3H, t, J=7.0 Hz), 2.10 (3H, d, J=1.2 Hz), 4.28 (2H, q, J=7.0 Hz), 7.08 (2H, t, J=8.8 Hz), 7.32-7.43 (2H, m), 7.65 (1H, s).

REFERENCE EXAMPLE 4a

Ethyl (E)-3-(4-isopropylphenyl)-2-propenoate

To a suspension of sodium hydride (a 60% dispersion in liquid paraffin, 10.4 g, 260 mmol) in N,N-dimethylformamide (200 ml) was added at 0° C. triethyl 2-phosphonoacetate (58.2 g, 236 mmol) and the resulting mixture was stirred at the same temperature for 10 minutes. To the reaction solution was added 4-isopropylbenzaldehyde (35.0 g, 260 mmol) and the resulting mixture was stirred at room temperature for 30 minutes. Water was added into the reaction solution and the product was extracted twice with ethyl acetate. The combined extracts were washed with water, dried on magnesium sulfate, and then concentrated under reduced pressure to obtain 47.5 g (92% yield) of the oily title compound.

$^1$H-NMR ($CDCl_3$) δ: 1.25 (6H, d, J=7.0 Hz), 1.33 (3H, t, J=7.0 Hz), 2.92 (1H, septet, J=7.0 Hz), 4.26 (2H, q, J=7.0 Hz), 6.40 (1H, d, J=15.8 Hz), 7.24 (2H, d, J=8.2 Hz), 7.46 (2H, d, J=8.2 Hz), 7.67 (1H, d, J=15.8 Hz).

REFERENCE EXAMPLE 5a

Ethyl (E)-3-(4-fluorophenyl)-2-propenoate

By using 4-fluorobenzaldehyde, the title compound was synthesized according to Reference Example 4a. Yield: 88%. An oily substance.

$^1$H-NMR ($CDCl_3$) δ: 1.34 (3H, t, J=7.0 Hz), 4.26 (2H, q, J=7.0 Hz), 6.31 (1H, d, J=15.8 Hz), 7.00-7.11 (2H, m), 7.43-7.58 (2H, m), 7.67 (1H, d, J=15.8 Hz).

REFERENCE EXAMPLE 6a 3-(4-Isopropylphenyl)-2-methyl-2-propen-1-ol

To a suspension of ethyl 3-(4-isopropylphenyl)-2-methyl-2-propenoate (9.00 g, 38.7 mmol) and cerium chloride (1.00 g, 4.06 mmol) in tetrahydrofuran (50 ml) was added in four portions at −40° C. over a period of 30 minutes lithium aluminum hydride (1.47 g, 38.7 mmol) and the resulting mixture was stirred at the same temperature for 30 minutes. Water was added into the reaction solution and the product was extracted twice with ethyl acetate. The combined extracts were washed with water, dried on magnesium sulfate, and then concentrated under reduced pressure. The residue was subjected to column chromatography on silica gel (hexane-ethyl acetate 8:1) to obtain 6.30 g (86% yield) of the oily title compound.

$^1$H-NMR ($CDCl_3$) δ: 1.25 (6H, d, J=7.0 Hz), 1.91 (3H, d, J=1.4 Hz), 2.90 (1H, septet, J=7.0 Hz), 4.17 (2H, d, J=0.8 Hz), 6.49 (1H, dd, J=2.6, 1.4 Hz), 7.15-7.25 (4H, m), 1H unidentified.

REFERENCE EXAMPLE 7a

2-Methyl-3-(4-methylphenyl)-2-propen-1-ol

To a suspension of ethyl 2-methyl-3-(4-methylphenyl)-2-propenoate (26.31 g, 128.8 mmol) and cerium chloride (10.32 g, 41.89 mmol) in tetrahydrofuran (120 ml) was added in four portions at −40° C. over a period of 30 minutes lithium aluminum hydride (4.89 g, 129 mmol) and the resulting mixture was stirred at the same temperature for 30 minutes. Water was added into the reaction solution and the product was extracted twice with ethyl acetate. The combined extracts were washed with water, dried on magnesium sulfate, and then concentrated under reduced pressure to obtain 8.87 g (42% yield) of the oily title compound.

$^1$H-NMR (CDCl$_3$) δ: 1.87 (3H, s), 2.32 (3H, s), 4.13 (2H,s), 6.46 (1H, s), 7.08-7.22 (4H, m), 1H unidentified.

REFERENCE EXAMPLE 8a 3-(4-Fluorophenyl)-2-methyl-2-propen-1-ol

By using ethyl 3-(4-fluorophenyl)-2-methyl-2-propenoate, the title compound was synthesized according to Reference Example 6a. Yield: 95%. An oily substance.

$^1$H-NMR (CDCl$_3$) δ: 1.98 (3H, d, J=1.6 Hz), 4.11 (2H, s), 6.58 (1H, s), 7.01 (2H, t, J=8.8 Hz), 7.18-7.28 (2H, m), 1H unidentified.

REFERENCE EXAMPLE 9a (E)-3-(4-Isopropylphenyl)-2-propen-1-ol

By using ethyl (E)-3-(4-isopropylphenyl)-2-propenoate, the title compound was synthesized according to Reference Example 6a. Yield: 65%. An oily substance.

$^1$H-NMR (CDCl$_3$) δ: 1.24 (6H, d, J=7.0 Hz), 2.79-3.00 (2H, m), 4.30 (2H, d, J=5.6 Hz), 6.35 (1H, dt, J=15.8, 5.6 Hz), 6.59 (1H, d, J=15.8 Hz), 7.10-7.39 (4H, m).

REFERENCE EXAMPLE 10a (E)-3-(4-Fluorophenyl)-2-propen-1-ol

By using ethyl (E)-3-(4-fluorophenyl)-2-propenoate, the title compound was synthesized according to Reference Example 6a. Yield: 84%. An oily substance.

$^1$H-NMR (CDCl$_3$) δ: 4.31 (2H, d, J=5.6 Hz), 6.28 (1H, dt, J=15.8, 5.6 Hz), 6.59 (1H, d, J=15.8 Hz), 6.90-7.40 (4H, m), 1H unidentified.

REFERENCE EXAMPLE 11a 1-(3-Bromo-2-methyl-1-propenyl)-4-isopropylbenzene

To a solution of 3-(4-isopropylphenyl)-2-methyl-2-propen-1-ol (6.30 g, 33.1 mmol) in isopropyl ether (50 ml) was added under ice cooling phosphorus tribromide (5.98 g, 22.1 mmol) and the resulting mixture was stirred at room temperature for 30 minutes. Water was added into the reaction solution and the product was extracted with isopropyl ether. The organic layer was washed with water and an aqueous saturated solution of sodium hydrogen carbonate, dried on magnesium sulfate, filtered, and then concentrated under reduced pressure to obtain 7.63 g (91% yield) of the oily title compound.

$^1$H-NMR (CDCl$_3$) δ: 1.25 (6H, d, J=7.0 Hz), 2.03 (3H, d, J=1.4 Hz), 2.90 (1H, septet, J=7.0 Hz), 4.15 (2H, d, J=0.8 Hz), 6.62 (1H, s), 7.14-7.26 (4H, m).

REFERENCE EXAMPLE 12a 1-(3-Bromo-2-methyl-1-propenyl)benzene

By using 2-methyl-3-phenyl-2-propen-1-ol, the title compound was synthesized according to Reference Example 11a. Yield: 89%. An oily substance.

$^1$H-NMR (CDCl$_3$) δ: 2.01 (3H, d, J=1.4 Hz), 4.13 (2H, d, J=0.8 Hz), 6.64 (1H, s), 7.19-7.44 (5H, m).

REFERENCE EXAMPLE 13a 1-(3-Bromo-2-methyl-1-propenyl)-4-methylbenzene

To a solution of 2-methyl-3-(4-methylphenyl)-2-propen-1-ol (11.40 g, 70.27 mmol) in isopropyl ether (100 ml) was added under ice cooling phosphorus tribromide (12.83 g, 47.38 mmol) and the resulting mixture was stirred at room temperature for 30 minutes. Water was added into the reaction solution and the product was extracted with isopropyl ether. The organic layer was washed with water and an aqueous saturated solution of sodium hydrogen carbonate, dried on magnesium sulfate, filtered, and then concentrated under reduced pressure to obtain 12.71 g (80% yield) of the oily title compound.

$^1$H-NMR (CDCl$_3$) δ: 2.01 (3H, s), 2.34 (3H, s), 4.13(2H, s), 6.60 (1H, s), 7.09-7.22 (4H, m).

REFERENCE EXAMPLE 14a 1-(3-Bromo-2-methyl-1-propenyl)-4-fluorobenzene

By using 3-(4-fluorophenyl)-2-methyl-2-propen-1-ol, the title compound was synthesized according to Reference Example 11a. Yield: 79%. An oily substance.

$^1$H-NMR (CDCl$_3$) δ: 1.87 (3H, s), 4.17 (2H, s), 6.48 (1H, s), 7.01 (2H, t, J=8.8 Hz), 7.18-7.27 (2H, m).

REFERENCE EXAMPLE 15a

1-[(E)-3-Bromo-1-propenyl]-4-isopropylbenzene

By using (E)-3-(4-isopropylphenyl)-2-propen-1-ol, the title compound was synthesized according to Reference Example 11a. Yield: 72%. An oily substance.

$^1$H-NMR (CDCl$_3$) δ: 1.24 (6H, d, J=7.0 Hz), 2.89 (1H, septet, J=7.0 Hz), 4.16 (2H, dd, J=7.8, 0.8 Hz), 6.35 (1H, dt, J=15.4, 7.8 Hz), 6.63 (1H, d, J=15.4 Hz), 7.14-7.35 (4H, m).

REFERENCE EXAMPLE 16a

1-[(E)-3-Bromo-1-propenyl]-4-fluorobenzene

By using (E)-3-(4-fluorophenyl)-2-propen-1-ol, the title compound was synthesized according to Reference Example 11a. Yield: 61%. An oily substance.

$^1$H-NMR (CDCl$_3$) δ: 4.15 (2H, d, J=7.6 Hz), 6.30 (1H, dt, J=15.4, 7.6 Hz), 6.61 (1H, d, J=15.4 Hz), 6.83-7.08 (2H, m), 7.31-7.45 (2H, m).

REFERENCE EXAMPLE 17a

N-[4-[[3-(4-Isopropylphenyl)-2-methyl-2-propenyl]oxy]-2,3,6-trimethylphenyl]formamide To a solution of N-(4-hydroxy-2,3,6-trimethylphenyl)formamide (3.00 g, 16.7 mmol) in N,N-dimethylformamide (30 ml) was added at 0° C. under a nitrogen atmosphere sodium hydride (a 60% dispersion in liquid paraffin, 0.74 g, 18.4 mmol) and the resulting mixture was stirred at the same temperature for 10 minutes. To the reaction solution was added 1-(3-bromo-2-methyl-1-propenyl)-4-isopropylbenzene (4.66 g, 18.4 mmol) and the resulting mixture was stirred at room temperature for 30 minutes. Water was added into the reaction solution and the product was extracted twice with ethyl acetate. The combined extracts were washed with water, dried on magnesium sulfate, and then concentrated under reduced pressure. The resulting residue was crystallized from ethyl acetate-hexane to obtain 3.70 g (63% yield) of the title compound. Melting point: 153-155° C.

$^1$H-NMR (CDCl$_3$) δ: 1.26 (6H, d, J=7.0 Hz), 2.00 (3H, s), 2.07-2.34 (9H, m), 2.91 (1H, septet, J=7.0 Hz), 4.54 (2H, d, J=5.4 Hz), 6.59-6.84 (3H, m), 7.17-7.36 (4H, m), 7.98 (0.5H, d, J=12.0 Hz), 8.41 (0.5H, s).

REFERENCE EXAMPLE 18a

N-[2,3,6-Trimethyl-4-[(2-methyl-3-phenyl-2-propenyl)oxy]phenyl]formamide

By using N-(4-hydroxy-2,3,6-trimethylphenyl)formamide and 1-(3-bromo-2-methyl-1-propenyl)benzene, the title compound was synthesized according to Reference Example 17a. Yield: 41%. Melting point: 152-154° C. (Ethyl acetate-hexane)

$^1$H-NMR (CDCl$_3$) δ: 1.98 (3H, d, J=1.6 Hz), 2.10-2.32 (9H, m), 4.54 (2H, d, J=5.2 Hz), 6.65 (1H, s), 6.67 (1H, s), 6.69-6.90 (1H, m), 7.11-7.41 (5H, m), 7.98 (0.5H, d, J=12.0 Hz), 8.41 (0.5H, d, J=1.4 Hz).

REFERENCE EXAMPLE 19a

N-[2,3,6-Trimethyl-4-[[2-methyl-3-(4-methylphenyl)-2-propenyl]oxy]phenyl]formamide To a solution of N-(4-hydroxy-2,3,6-trimethylphenyl)formamide (9.31 g, 52.0 mmol) in N,N-dimethylformamide (120 ml) was added at 0° C. under nitrogen atmosphere sodium hydride (a 60% dispersion in liquid paraffin, 2.11 g, 52.8 mmol) and the resulting mixture was stirred at the same temperature for 10 minutes. To the reaction solution was added a solution of 1-(3-bromo-2-methyl-1-propenyl)-4-methylbenzene (12.48 g, 55.44 mmol) in N,N-dimethylformamide (20 ml) and the resulting mixture was stirred at room temperature for 30 minutes. Water was added into the reaction solution and the product was extracted twice with ethyl acetate. The combined extracts were washed with water, dried on magnesium sulfate, and then concentrated under reduced pressure. The resulting residue was crystallized from ethyl acetate-isopropyl ether to obtain 7.34 g (44% yield) of the title compound. Melting point: 167-169° C.

$^1$H-NMR (CDCl$_3$) δ: 1.98 (3H, s), 2.07-2.38 (9H, m), 2.35 (3H, s), 4.53 (2H, d, J=6.6 Hz), 6.61 (1H, s), 6.66 (1H, d, J=2.4 Hz), 6.82-7.09 (1H, m), 7.11-7.31 (4H, m), 7.98 (0.5H, d, J=12.2 Hz), 8.38 (0.5H, s).

REFERENCE EXAMPLE 20a

N-[4-[[3-(4-Fluorophenyl)-2-methyl-2-propenyl]oxy]-2,3,6-trimethylphenyl]formamide By using N-(4-hydroxy-2,3,6-trimethylphenyl)formamide and 1-(3-bromo-2-methyl-1-propenyl)-4-fluorobenzene, the title compound was synthesized according to Reference Example 17a. Yield: 52%. Melting point: 164-165° C. (Ethyl acetate-hexane)

$^1$H-NMR (CDCl$_3$) δ: 1.96 (3H, s), 2.12-2.32 (9H, m), 4.53 (2H, d, J=5.2 Hz), 6.60 (1H, s), 6.66 (1H, s), 6.71-6.95 (1H, m), 7.04 (2H, t, J=8.8 Hz), 7.22-7.33 (2H, m), 8.04 (0.5H, d, J=12.0 Hz), 8.40 (0.5H, d, J=1.4 Hz).

REFERENCE EXAMPLE 21a

N-[4-[[(E)-3-(4-Isopropylphenyl)-2-propenyl]oxy]-2,3,6-trimethylphenyl]formamide By using N-(4-hydroxy-2,3,6-trimethylphenyl)formamide and 1-[(E)-3-bromo-1-propenyl]-4-isopropylbenzene, the title compound was synthesized according to Reference Example 17a. Yield: 59%. Melting point: 165-167° C. (Ethyl acetate-hexane)

$^1$H-NMR (CDCl$_3$) δ: 1.25 (6H, d, J=6.8 Hz), 2.13-2.27 (9H, m), 2.90 (1H, septet, J=6.8 Hz), 4.66 (2H, t, J=5.8 Hz), 6.37 (1H, dt, J=15.8, 5.8 Hz), 6.65-6.88 (3H, m), 7.16-7.26 (2H, m), 7.35 (2H, d, J=8.0 Hz), 7.98 (0.5H, d, J=12.0 Hz), 8.40 (0.5H, d, J=1.4 Hz).

REFERENCE EXAMPLE 22a

N-[2,3,6-Trimethyl-4-[[(E)-3-phenyl-2-propenyl]oxy]-phenyl]formamide

By using N-(4-hydroxy-2,3,6-trimethylphenyl)formamide and cinnamyl chloride, the title compound was synthesized according to Reference Example 17a. Yield: 44%. Melting point: 197-199° C. (Ethyl acetate-hexane)

$^1$H-NMR (CDCl$_3$) δ: 2.05-2.18 (9H, m), 4.62-4.72 (2H, m), 6.35-6.50 (1H, m), 6.62-7.00 (3H, m), 7.24-7.52 (5H, m), 8.00 (0.5H, d, J=12.0 Hz), 8.39 (0.5H, d, J=1.6 Hz).

REFERENCE EXAMPLE 23a

N-[4-[[(E)-3-(4-Fluorophenyl)-2-propenyl]oxy]-2,3,6-trimethylphenyl]formamide

By using N-(4-hydroxy-2,3,6-trimethylphenyl)formamide and 1-[(E)-3-bromo-1-propenyl]-4-fluorobenzene, the title compound was synthesized according to Reference Example 17a.

Yield: 52%. Melting point: 196-198° C. (Ethyl acetate-hexane)

$^1$H-NMR (CDCl$_3$) δ: 2.10-2.32 (9H, m), 4.67 (2H, t, J=5.0 Hz), 6.37(1H, dt, J=15.6, 5.0 Hz), 6.59-6.89 (3H, m), 6.92-7.09 (2H, m), 7.32-7.43 (2H, m), 7.99 (0.5H, d, J=12.0 Hz), 8.42 (0.5H, d, J=1.4 Hz).

REFERENCE EXAMPLE 24a

N-[4-Hydroxy-3-[1-(4-isopropylphenyl)-2-propenyl]-2,5,6-trimethylphenyl]formamide A solution of N-[4-[[(E)-3-(4-isopropylphenyl)-2-propenyl]oxy]-2,3,6-trimethylphenyl]formamide (5.80 g, 17.2 mmol) in N,N-dimethylaniline (50 ml) was stirred at 215° C. for 6 hours under an argon atmosphere. The reaction mixture was cooled down, then diluted with ethyl acetate, washed with 2 N hydrochloric acid and water, dried on magnesium sulfate, and then concentrated under reduced pressure. The residue was crystallized from ethyl acetate to obtain 3.50 g (60% yield) of the title compound. Melting point: 170-171° C.

$^1$H-NMR (CDCl$_3$) δ: 1.18-1.40 (6H, m), 2.11-2.27 (9H, m), 2.77-3.00 (1H, m), 5.00-5.22 (2H, m), 5.30-5.42 (1H, m), 6.30-6.85 (2H, m), 7.10-7.37 (5H, m), 7.97 (0.5H, d, J=12.2 Hz), 8.43 (0.5H, d, J=1.4 Hz).

REFERENCE EXAMPLE 25a

N-[4-Hydroxy-3-(1-phenyl-2-propenyl)-2,5,6-trimethylphenyl]formamide

By using N-[2,3,6-trimethyl-4-[[(E)-3-phenyl-2-propenyl]oxy]phenyl]formamide, the title compound was synthesized according to Reference Example 24a. Yield: 78%. Melting point: 144-145° C. (Ethyl acetate)

$^1$H-NMR (CDCl$_3$) δ: 2.08-2.27 (9H, m), 5.02-5.41 (3H, m), 6.32-6.52 (1H, m), 6.61-7.03 (2H, m), 7.18-7.42 (5H, m), 7.95 (0.5H, d, J=12.0 Hz), 8.42 (0.5H, d, J=1.8 Hz).

REFERENCE EXAMPLE 26a

N-[4-Hydroxy-3-[1-(4-fluorophenyl)-2-propenyl]-2,5,6-trimethylphenyl]formamide

By using N-[4-[[(E)-3-(4-fluorophenyl)-2-propenyl]oxy]-2,3,6-trimethylphenyl]formamide, the title compound was synthesized according to Reference Example 24a. Yield: 66%. Melting point: 168-170° C. (Ethyl acetate)

$^1$H-NMR (CDCl$_3$) δ: 2.10-2.29 (9H, m), 5.02-5.22 (1.5H, m), 5.33-5.50 (1.5H, m), 6.35-6.55 (1H, m), 6.72-7.08 (4H, m), 7.18-7.30 (2H, m), 7.96 (0.5H, d, J=12.2 Hz), 8.42 (0.5H, d, J=1.4 Hz).

REFERENCE EXAMPLE 27a 3-(4-Isopropylphenyl)-2,2,4,6,7-pentamethyl-2,3-dihydro-1-benzofuran-5-amine A solution of N-[4-[[3-(4-isopropylphenyl)-2-methyl-2-propenyl]oxy]-2,3,6-trimethylphenyl]formamide (3.70 g, 10.5 mmol) in N,N-dimethylaniline (20 ml) was heated at 215° C. for 6 hours under an argon atmosphere. The reaction mixture was cooled down, then diluted with ethyl acetate, washed with 2 N hydrochloric acid and water, dried on magnesium sulfate, and then concentrated under reduced pressure to obtain N-[4-hydroxy-3-[1-(4-isopropylphenyl)-2-methyl-2-propenyl]-2,5,6-trimethylphenyl]formamide as a crude product. A mixture of this compound (2.98 g, 8.47 mmol), concentrated hydrochloric acid (20 ml), and methanol (60 ml) was refluxed with heating for 2 hours under a nitrogen atmosphere. The solvent was concentrated under reduced pressure and the resulting residue was neutralized with an 8 N aqueous solution of sodium hydroxide. The product was extracted twice with ethyl acetate. The combined extracts were washed with water, dried on magnesium sulfate, and then concentrated under reduced pressure. The resulting residue was crystallized from isopropyl ether-hexane to obtain 2.23 g (66% yield) of the title compound. Melting point: 130-132° C.

$^1$H-NMR (CDCl$_3$) δ: 1.00 (3H, s), 1.21 (6H, d, J=6.6 Hz), 1.47 (3H, s), 1.78 (3H, s), 2.12 (3H, s), 2.19 (3H, s), 2.40-2.60 (3H, m), 4.08 (1H, s), 6.72-7.00 (2H, m), 7.07 (2H, d, J=8.0 Hz).

REFERENCE EXAMPLE 28a 2,2,4,6,7-Pentamethyl-3-phenyl-2,3-dihydro-1-benzofuran-5-amine By using N-[2,3,6-trimethyl-4-[(2-methyl-3-phenyl-2-propenyl)oxy]phenyl]formamide, the title compound was synthesized according to Reference Example 27a. Yield: 67%. Melting point: 129-131° C.

$^1$H-NMR (CDCl$_3$) δ: 1.00 (3H, s), 1.48 (3H, s), 1.77(3H, s), 2.13 (3H, s), 2.19 (3H, s), 3.20 (2H, br s), 4.12 (1H, s), 6.70-7.30 (5H, m).

REFERENCE EXAMPLE 29a 2,2,4,6,7-Pentamethyl-3-(4-methylphenyl)-2,3-dihydro-1-benzofuran-5-amine A solution of N-[2,3,6-trimethyl-4-[[2-methyl-3-(4-methylphenyl)-2-propenyl]oxy]phenyl]formamide (5.43 g, 16.8 mmol) in N,N-dimethylaniline (60 ml) was stirred at 210° C. for 6 hours under an argon atmosphere. The reaction mixture was cooled down, then diluted with ethyl acetate, washed with 2 N hydrochloric acid and water, dried on magnesium sulfate, and then concentrated under reduced pressure. A mixture of the resulting residue and a hydrochloric acid-methanol reagent (40 ml) was refluxed with heating for 2 hours under nitrogen atmosphere. The solvent was concentrated under reduced pressure and the resulting residue was neutralized with an 8 N aqueous solution of sodium hydroxide. The product was extracted twice with ethyl acetate. The combined extracts were washed with water, dried on magnesium sulfate, and then concentrated under reduced pressure. The resulting residue was crystallized from hexane to obtain 2.81 g (57% yield) of the title compound. Melting point: 114-115° C. (Petroleum ether)

$^1$H-NMR (CDCl$_3$) δ: 0.99 (3H, s), 1.47 (3H, s), 1.77 (3H, s), 2.12 (3H, s), 2.19 (3H, s), 2.30 (3H, s), 3.23 (2H, br s), 4.08 (1H, s), 6.60-7.23 (4H, m).

REFERENCE EXAMPLE 30a 3-(4-Fluorophenyl)-2,2,4,6,7-pentamethyl-2,3-dihydro-1-benzofuran-5-amine By using N-[4-[[3-(4-fluorophenyl)-2-methyl-2-propenyl]oxy]-2,3,6-trimethylphenyl]formamide, the title compound was synthesized according to Reference Example 27a. Yield: 78%. Melting point: 125-127° C. (Petroleum ether)

$^1$H-NMR (CDCl$_3$) δ: 0.99 (3H, s), 1.47 (3H, s), 1.77(3H, s), 2.12 (3H, s), 2.19 (3H, s), 3.10 (2H, br s), 4.09 (1H, s), 6.62-7.20 (4H, m).

REFERENCE EXAMPLE 31a 3-(4-Isopropylphenyl)-2,4,6,7-tetramethyl-1-benzofuran-5-amine hydrochloride To a suspension of N-[4-hydroxy-3-[1-(4-isopropylphenyl)-2-propenyl]-2,5,6-trimethylphenyl]formamide (3.50 g, 10.4 mmol) and calcium carbonate (1.35 g, 13.5 mmol) in a mixed solvent of tetrahydrofuran (15 ml) and methanol (15 ml) was gradually added benzyltrimethylammonium iodod- ichloride (3.90 g, 11.4 mmol). The reaction mixture was stirred at room temperature for 30 minutes. After filtration of the insoluble material, the solvent was concentrated under reduced pressure. Ethyl acetate and water were added to the residue. The organic layer was separated and the aqueous layer was extracted twice with ethyl acetate. The combined organic layers were successively washed with a 10% aqueous solution of sodium hydrosulfite, water, an aqueous saturated solution of sodium hydrogen carbonate, and an aqueous saturated solution of sodium chloride, dried on magnesium sulfate, and then concentrated under reduced pressure to obtain 4.08 g of N-[2-iodomethyl-3-(4-isopropylphenyl)-4,6,7-trimethyl-2,3-dihydro-1-benzofuran-5-yl]formamide. A solution of this compound (4.08 g, 8.81 mmol) and 1,8-diazabicyclo[5,4,0]-7-undecene (6.58 m, 44.0 mmol) in toluene (30 ml) was stirred at 100° C. for 3 hours under an argon atmosphere. Water was added into the reaction solution and the product was extracted twice with ethyl acetate. The combined extracts were washed with 2 N hydrochloric acid and water, dried on magnesium sulfate, and then concentrated under reduced pressure. The resulting residue was subjected to column chromatography on silica gel (hexane-ethyl acetate 20:1) to obtain 2.40 g of N-[3-(4-isopropylphenyl)-2,4,6,7-tetramethyl-1-benzofuran-5-yl]formamide. A mixture of this compound (2.40 g, 7.18 mmol), concentrated hydrochloric acid (20 ml) and methanol (60 ml) was refluxed with heating for 2 hours under a nitrogen atmosphere. The solvent was concentrated under reduced pressure and the resulting residue was neutralized with an 8 N aqueous solution of sodium hydroxide. The product was extracted twice with ethyl acetate. The combined extracts were washed with water, dried on magnesium sulfate, and then concentrated under reduced pressure to obtain 1.80 g of an oily free base. This free base (0.50 g, 1.63 mmol) was dissolved into a solution of hydrochloric acid in methanol and the solvent was concentrated under reduced pressure. The resulting residue was crystallized from methanol to obtain 0.41 g (41% yield) of the title compound. Melting point: 194-197° C.

$^1$H-NMR (CDCl$_3$) δ: 1.29 (6H, d, J=7.0 Hz), 2.30 (6H, s), 2.41 (3H, s), 2.60 (3H, s), 2.94 (1H, septet, J=7.0 Hz), 7.13-7.26 (4H, m), 10.1 (2H, br s), 1H unidentified.

REFERENCE EXAMPLE 32a 2,2,6,7-Tetramethyl-3-phenyl-1-benzofuran-5-amine hydrochloride By using N-[4-hydroxy-3-(1-phenyl-2-propenyl)-2,5,6-trimethylphenyl]formamide, the title compound was synthesized according to Reference Example 31a. Yield: 26%. Melting point: 189-192° C. (Ethanol-hexane)

$^1$H-NMR (CDCl$_3$) δ: 2.30 (6H, s), 2.42 (3H, s), 2.60(3H, s), 7.21-7.37 (5H, m), 10.2 (2H, br s), 1H unidentified.

REFERENCE EXAMPLE 33a 3-(4-Fluorophenyl)-2,4,6,7-tetramethyl-1-benzofuran-5-amine hydrochloride By using N-[4-hydroxy-3-[1-(4-fluorophenyl)-2-propenyl]-2,5,6-trimethylphenyl]formamide, the title compound was synthesized according to Reference Example 31a. Yield: 87%. Melting point: 208-210° C. (Ethanol)

$^1$H-NMR (CDCl$_3$) δ: 2.29 (6H, s), 2.42 (3H, s), 2.60(3H, s), 7.03-7.28 (4H, m), 10.2 (2H, br s), 1H unidentified.

REFERENCE EXAMPLE 34a 5,6-Dichloro-(2,2,4,6,7-pentamethyl-3-phenyl-2,3-dihydro-1-benzofuran-5-yl)-1H-isoindole-1,3(2H)-dione To a solution of 2,2,4,6,7-pentamethyl-3-phenyl-2,3-dihydro-1-benzofuran-5-amine (1.00 g, 3.56 mmol) in tetrahydrofuran (30 ml) was added under an argon atmosphere 4,5-dichlorophthalic anhydride (850.6 mg, 3.92 mmol) and the mixture was refluxed with heating for 13 hours. The reaction mixture was cooled down to room temperature and then 1-ethyl-3-(3-dimethylaminopropyl)carbodiimide (WSC) hydrochloride (760.0 mg, 3.96 mmol) and 1-hydroxy-1H-benzotriazole (HOBT) monohydrate (602.6 mg, 3.93 mmol) were added to the mixture. The resulting mixture was refluxed with heating for 3 hours and then cooled down to room temperature. Water and an 8 N aqueous solution of sodium hydroxide were added into the reaction mixture and the product was extracted twice with ethyl acetate. The combined extracts were washed with an aqueous, saturated solution of sodium hydrogen carbonate, dried on magnesium sulfate, filtered, and then concentrated under reduced pressure. The residue was crystallized from ethyl acetate to obtain 1.16 g (68% yield) of the title compound. Melting point: 178-181° C.

$^1$H-NMR (CDCl$_3$) δ: 1.02 (3H, s), 1.56 (3H, s), 1.61 (3H, s), 2.01 (3H, s), 2.20 (3H, s), 4.21 (1H, s), 6.8-7.4 (5H, m), 7.99 (1H, s), 8.03 (1H, s).

REFERENCE EXAMPLE 35a

2-[2,2,4,6,7-Pentamethyl-3-(4-methylphenyl)-2,3-dihydro-1-benzofuran-5-yl]-1H-isoindole-1,3(2H)-dione To a solution of phthalic anhydride (566.4 mg, 3.82 mmol) in tetrahydrofuran (5 ml) was added a solution of 2,2,4,6,7-pentamethyl-3-(4-methylphenyl)-2,3-dihydro-1-benzofuran-5-amine (987.3 mg, 3.38 mmol) in tetrahydrofuran (10 ml) and the resulting mixture was refluxed with heating for 11 hours. The reaction mixture was cooled down to room temperature and then concentrated under reduced pressure. Sodium acetate (314.6 mg, 3.84 mmol) and acetic anhydride (20 ml) were added into the residue and the resulting mixture was stirred at 90° C. for 2 hours. The reaction mixture was cooled down to room temperature and then an 8 N aqueous solution of sodium hydroxide was added into the mixture until it became basic. The product was extracted twice with ethyl acetate. The combined extracts were washed with an aqueous saturated solution of sodium hydrogen carbonate, dried on magnesium sulfate, filtered, and then concentrated under reduced pressure. The residue was crystallized from ethyl acetate to obtain 1.16 g (81% yield) of the title compound. Melting point: 222-224° C.

$^1$H-NMR (CDCl$_3$) δ: 1.03 (3H, s), 1.55 (3H, s), 1.64 (3H, s), 2.05 (3H, s), 2.20 (3H, s), 2.30 (3H, s), 4.19 (1H, s), 6.6-7.1 (4H, m), 7.76-7.82 (2H, m), 7.88-7.97 (2H, m).

REFERENCE EXAMPLE 36a 5,6-Dichloro-2-[2,2,4,6,7-pentamethyl-3-(4-methylphenyl)-2,3-dihydro-1-benzofuran-5-yl]-1H-isoindole-1,3(2H)-dione By using 2,2,4,6,7-pentamethyl-3-(4-methylphenyl)-2,3-dihydro-1-benzofuran-5-amine, the title compound was synthesized according to Reference Example 34a. Yield: 62%.

Melting point: 157-159° C. (Ethyl acetate)

¹H-NMR (CDCl₃) δ: 1.02 (3H, s), 1.54 (3H, s), 1.61 (3H, s), 2.01 (3H, s), 2.19 (3H, s), 2.30 (3H, s), 4.18 (1H, s), 6.8-7.1 (4H, m), 7.99 (1H, s), 8.03 (1H, s).

REFERENCE EXAMPLE 37a

2-[3-(4-Fluorophenyl)-2,2,4,6,7-pentamethyl-2,3-dihydro-1-benzofuran-5-yl]-1H-isoindole-1,3(2H)-dione By using 3-(4-fluorophenyl)-2,2,4,6,7-pentamethyl-2,3-dihydro-1-benzofuran-5-amine, the title compound was synthesized according to Reference Example 35a. Yield: 72%. Melting point: 209-211° C. (Ethyl acetate)

¹H-NMR (CDCl₃) δ: 1.02 (3H, s), 1.55 (3H, s), 1.61 (3H, s), 2.05 (3H, s), 2.20 (3H, s), 4.21 (1H, s), 6.9-7.1 (4H, m), 7.76-7.83 (2H, m), 7.90-7.97 (2H, m).

REFERENCE EXAMPLE 38a 5,6-Dichloro-2-[3-(4-fluorophenyl)-2,2,4,6,7-pentamethyl-2,3-dihydro-1-benzofuran-5-yl]-1H-isoindole-1,3(2H)-dione By using 3-(4-fluorophenyl)-2,2,4,6,7-pentamethyl-2,3-dihydro-1-benzofuran-5-amine, the title compound was synthesized according to Reference Example 34a. Yield: 62%. Melting point: 232-233° C. (Ethyl acetate)

¹H-NMR (CDCl₃) δ: 1.02 (3H, s), 1.54 (3H, s), 1.61 (3H, s), 2.01 (3H, s), 2.19 (3H, s), 4.19 (1H, s), 6.8-7.1 (4H, m), 8.00 (1H, s), 8.03 (1H, s).

REFERENCE EXAMPLE 39a

2-[3-(4-Isopropylphenyl)-2,2,4,6,7-pentamethyl-2,3-dihydro-1-benzofuran-5-yl]-1H-isoindole-1,3(2H)-dione By using 3-(4-isopropylphenyl)-2,2,4,6,7-pentamethyl-2,3-dihydro-1-benzofuran-5-amine, the title compound was synthesized according to Reference Example 35a. Yield: 97%. Melting point: 180-181° C. (Ethyl acetate-hexane)

¹H-NMR (CDCl₃) δ: 1.02 (3H, s), 1.21 (6H, d, J=7.0 Hz), 1.55 (3H, s), 1.64 (3H, s), 2.05 (3H, s), 2.20 (3H, s), 2.85 (1H, septet, J=7.0 Hz), 4.20 (1H, s), 6.7-7.2 (4H, m), 7.75-7.82 (2H, m), 7.87-7.97 (2H, m).

REFERENCE EXAMPLE 40a 5,6-Dichloro-2-[3-(4-isopropylphenyl)-2,2,4,6,7-pentamethyl-2,3-dihydro-1-benzofuran-5-yl]-1H-isoindole-1,3(2H)-dione By using 3-(4-isopropylphenyl)-2,2,4,6,7-pentamethyl-2,3-dihydro-1-benzofuran-5-amine, the title compound was synthesized according to Reference Example 34a. Yield: 31%. Melting point: 237-239° C. (Ethyl acetate)

¹H-NMR (CDCl₃) δ: 1.01 (3H, s), 1.21 (6H, d, J=6.6 Hz), 1.54 (3H, s), 1.62 (3H, s), 2.01 (3H, s), 2.19 (3H, s), 2.85 (1H, septet, J=6.6 Hz), 4.18 (1H, s), 6.8-7.2 (4H, m), 7.99 (1H, s), 8.03 (1H, s).

REFERENCE EXAMPLE 41a

2-[3-(4-Isopropylphenyl)-2,4,6,7-tetramethyl-1-benzofuran-5-yl]-1H-isoindole-1,3(2H)-dione By using 3-(4-isopropylphenyl)-2,4,6,7-tetramethyl-1-benzofuran-5-amine, the title compound was synthesized according to Reference Example 35a. Yield: 71%. Melting point: 232-234° C. (Ethyl acetate-hexane)

¹H-NMR (CDCl₃) δ: 1.27 (6H, d, J=7.0 Hz), 1.85 (3H, s), 2.14 (3H, s), 2.33 (3H, s), 2.48 (3H, s), 2.94 (1H, septet, J=7.0 Hz), 7.24 (4H, m), 7.72-7.83 (2H, m), 7.90-8.03 (2H, m).

REFERENCE EXAMPLE 42a

2-[2,2,4,6,7-Pentamethyl-2,3-dihydro-1-benzofuran-5-yl]-1H-isoindole-1,3(2H)-dione By using 2,2,4,6,7-pentamethyl-2,3-dihydro-1-benzofuran-5-amine, the title compound was synthesized according to Reference Example 34a. Yield: 77%. Melting point: 166-168° C. (Methanol)

¹H-NMR (CDCl₃) δ: 1.49 (6H, s), 1.95 (3H, s), 1.99 (3H, s), 2.12 (3H, s), 2.97 (2H, s), 7.66-7.83 (2H, m), 7.91-8.01 (2H, m).

REFERENCE EXAMPLE 43a

4-Methoxy-2,3,6-trimethylaniline

N-(4-Hydroxy-2,3,6-trimethylphenyl)formamide (30.0 g, 167 mmol) was dissolved into a mixed solvent of a 4 N aqueous solution of potassium hydroxide (100 ml) and methanol (300 ml) and dimethyl sulfate (42.0 g, 334 mmol) was added to the resulting solution at room temperature. The resulting mixture was refluxed with heating for 14 hours. After the reaction solution was cooled down, the crystals precipitated were collected by filtration to obtain N-(4-methoxy-2,3,6-trimethylphenyl)formamide as a crude product. To a suspension of this compound in methanol (200 ml) was added concentrated hydrochloric acid (50 ml) and the resulting mixture was refluxed with heating for 3 hours. The reaction mixture was cooled down and neutralized with an 8 N aqueous solution of sodium hydroxide. The product was extracted twice with ethyl acetate. The combined extracts were washed with a 10% aqueous solution of sodium hydrosulfite, dried on magnesium sulfate, and then concentrated under reduced pressure. The residue was crystallized from isopropyl ether to obtain 21.0 g (yield 76%) of the title compound. Melting point: 70-72° C.

¹H-NMR (CDCl₃) δ: 2.11 (3H, s), 2.16 (3H, s), 2.18 (3H, s), 3.16 (1H, br s), 3.74 (3H, s), 6.54 (1H, s).

REFERENCE EXAMPLE 44a

Tert-butyl 4-methoxy-2,3,6-trimethylphenylcarbamate

To a solution of 4-methoxy-2,3,6-trimethylaniline (21.0 g, 127 mmol) and triethylamine (21.0 ml, 152 mmol) in tetrahydrofuran (150 ml) was added at room temperature di-tert-butyl dicarbonate (32 ml, 140 mmol) and the resulting mixture was refluxed with heating for 14 hours. The solvent was concentrated under reduced pressure. Water was added into the residue and the product was extracted twice with ethyl acetate. The combined extracts were washed with 1 N hydrochloric acid and an aqueous saturated solution of sodium hydrogen carbonate, dried on magnesium sulfate, filtered, and then concentrated under reduced pressure. The residue was crystallized from ethyl acetate-hexane to obtain 25.2 g (75% yield) of the title compound. Melting point: 104-106° C.

$^1$H-NMR (CDCl$_3$) δ: 1.50 (9H, s), 2.12 (3H, s), 2.17 (3H, s), 2.24 (3H, s), 3.78 (3H, s), 5.81 (1H, br s), 6.58 (1H, s).

REFERENCE EXAMPLE 45a

Tert-butyl 3-bromo-4-methoxy-2,5,6-trimethylphenylcarbamate

To a solution of tert-butyl 4-methoxy-2,3,6-trimethylphenylcarbamate (12.7 g, 47.9 mmol) and sodium acetate (4.72 g, 57.5 mg) in acetic acid (50 ml) was added at room temperature bromine (8.42 g, 52.7 mmol) and the resulting mixture was stirred at the same temperature for 1 hour. Water (80 ml) was added into the reaction mixture and then the crystals precipitated were collected by filtration and dissolved into ethyl acetate. This solution was washed with an aqueous saturated solution of sodium hydrogen carbonate, dried on magnesium sulfate, filtered, and then concentrated under reduced pressure. The residue was crystallized from methanol to obtain 15.0 g (91% yield) of the title compound. Melting point: 159-161° C.

$^1$H-NMR (CDCl$_3$) δ: 1.50 (9H, s), 2.15 (3H, s), 2.24 (3H, s), 2.35 (3H, s), 3.74 (3H, s), 5.92 (1H, br s).

REFERENCE EXAMPLE 46a 2,2,4,6,7-Pentamethyl-3-(4-methylphenyl)-2,3-dihydro-1-benzofuran-5-amine To a solution of tert-butyl 3-bromo-4-methoxy-2,5,6-trimethylphenylcarbamate (27.8 g, 80.8 mmol) in tetrahydrofuran (150 ml) was added at −78° C. n-butyllithium (1.6 M, 110 ml, 176 mmol) and the reaction mixture was stirred at the same temperature for 20 minutes. To the reaction solution was added 2-methyl-1-(4-methylphenyl)propan-1-one (13.1 g, 80.7 mmol) and the resulting mixture was stirred at room temperature for 1 hour. Water (150 ml) was added into the reaction mixture and the product was extracted three times with ethyl acetate. The combined organic layers were washed with water, dried on magnesium sulfate, filtered, and then concentrated under reduced pressure to obtain 26.0 g of tert-butyl 3-[1-hydroxy-2-methyl-1-(4-methylphenyl)propyl]-4-methoxy-2,5,6-trimethylphenylcarbamate as a crude product. A mixture of this compound and 47% hydrobromic acid (100 ml) was refluxed with heating for 4 hours under an argon atmosphere. The reaction mixture was cooled down to room temperature and neutralized with an 8 N aqueous solution of sodium hydroxide. The product was extracted twice with ethyl acetate. The combined extracts were washed with an aqueous saturated solution of sodium hydrogen carbonate, dried on magnesium sulfate, filtered, and then concentrated under reduced pressure. The residue was crystallized from isopropyl ether-hexane to obtain 14.8 g (62% yield) of the title compound. Melting point: 114-115° C.

$^1$H-NMR (CDCl$_3$) δ: 0.99 (3H, s), 1.47 (3H, s), 1.78 (3H, s), 2.12 (3H, s), 2.17 (3H, s), 2.30 (3H, s), 2.80 (2H, br s), 4.08 (1H, s), 6.60-7.10 (4H, m).

REFERENCE EXAMPLE 47a (+)-2,2,4,6,7-Pentamethyl-3-(4-methylphenyl)-2,3-dihydro-1-benzofuran-5-amine 2,2,4,6,7-Pentamethyl-3-(4-methylphenyl)-2,3-dihydro-1-benzofuran-5-amine was subjected to high performance liquid chromatography (instrument: Waters semi-preparative separation system, column: CHIRALCEL OD (20 (i, d)×250 mm) manufactured by Daicel Chemical Industries, LTD.), mobile phase: hexane:isopropyl alcohol=95:5, flow rate: 5 ml/min, column temperature: 30° C., sample injection amount: 40 mg) to preparatively separate a fraction with a shorter retention time as the title compound. Melting point: 87-89° C. [α]D=+4.7° (c=0.495, methanol)

REFERENCE EXAMPLE 48a (−)-2,2,4,6,7-Pentamethyl-3-(4-methylphenyl)-2,3-dihydro-1-benzofuran-5-amine 2,2,4,6,7-Pentamethyl-3-(4-methylphenyl)-2,3-dihydro-1-benzofuran-5-amine was subjected to high performance liquid chromatography (instrument: Waters semi-preparative separation system, column: CHIRALCEL OD (20 (i, d)×250 mm) manufactured by Daicel Chemical Industries, LTD.), mobile phase: hexane:isopropyl alcohol=95:5, flow rate: 5 ml/min, column temperature: 30° C., sample injection amount: 40 mg) to preparatively separate a fraction with a longer retention time as the title compound. Melting point: 88-90° C. [α]D=−4.3° (c=0.499, methanol)

Example 1a 2-(2,2,4,6,7-Pentamethyl-3-phenyl-2,3-dihydro-1-benzofuran-5-yl)isoindoline A mixture of 2,2,4,6,7-pentamethyl-3-phenyl-2,3-dihydro-1-benzofuran-5-amine (1.00 g, 3.55 mmol), 1,2-bis(bromomethyl)benzene (1.03 g, 3.91 mmol), potassium carbonate (540 mg, 3.91 mmol), and N,N-dimethylformamide (20 ml) was stirred at room temperature for 1 hour. Water was added into the reaction mixture and the product was extracted twice with ethyl acetate. The combined organic layers were washed with water, dried on magnesium sulfate, filtered, and then concentrated under reduced pressure. The residue was subjected to column chromatography on silica gel (hexane-ethyl acetate 10:1) to obtain 208 mg (15% yield) of the title compound. Melting point: 164-166° C. (Ethyl acetate-hexane)

$^1$H-NMR (CDCl$_3$) δ: 1.02 (3H, s), 1.52 (3H, s), 1.76 (3H, s), 2.18 (3H, s), 4.13 (1H, s), 4.52 (4H, s), 6.70-7.41 (9H, m).

Example 2a 5,6-Dichloro-2-(2,2,4,6,7-pentamethyl-3-phenyl-2,3-dihydro-1-benzofuran-5-yl)isoindoline To a solution of aluminum chloride (1.01 g, 7.59 mmol) in tetrahydrofuran (30 ml) was added lithium aluminum hydride (276.5 mg, 7.29 mmol) and the resulting mixture was stirred for 10 minutes. To this mixture was added a solution of 5,6-dichloro-2-[2,2,4,6,7-pentamethyl-3-phenyl-2,3-dihydro-1-benzofuran-5-yl]-1H-isoindole-1,3(2H)-dione (907.4 mg, 1.89 mmol) in tetrahydrofuran (10 ml) and the resulting mixture was refluxed with heating for 2 hours. The reaction mixture was cooled down to room temperature and water was added into the mixture. The product was extracted twice with ethyl acetate. The combined extracts were washed with an aqueous saturated solution of sodium hydrogen carbonate, dried on magnesium sulfate, filtered, and then concentrated under reduced pressure. The residue was crystallized from ethyl acetate-hexane to obtain 153 mg (18% yield) of the title compound. Melting point: 194-196° C.

$^1$H-NMR (CDCl$_3$) δ: 1.02 (3H, s), 1.52 (3H, s), 1.74 (3H, s), 2.16 (6H, s), 4.12 (1H, s), 4.45 (4H, s), 6.8-7.4 (7H, m).

Example 3a 5,6-Dimethoxy-2-(2,2,4,6,7-pentamethyl-3-phenyl-2, 3-dihydro-1-benzofuran-5-yl)isoindoline To a solution of 2,2,4,6,7-pentamethyl-3-phenyl-2,3-dihydro-1-benzofuran-5-amine (1.00 g, 3.56 mmol) in tetrahydrofuran (30 ml) were added 1,2-bis(chloromethyl)-4,5-dimethoxybenzene (889.1 mg, 3.78 mmol), sodium carbonate (1.15 g, 10.85 mmol), and tetrabutylammonium iodide (701.4 mg, 1.90 mmol) and the mixture was refluxed with heating for 21 hours. The reaction mixture was cooled down to room temperature and then poured into ice water. The product was extracted twice with ethyl acetate. The combined extracts were washed with an aqueous saturated solution of sodium hydrogen carbonate, dried on magnesium sulfate, filtered, and then concentrated under reduced pressure. The residue was subjected to column chromatography on silica gel to obtain 403 mg (26% yield) of the title compound. Melting point: 154-157° C. (Ethyl acetate)

$^1$H-NMR (CDCl$_3$) δ: 1.02 (3H, s), 1.53 (3H, s), 1.76 (3H, s), 2.18 (6H, s), 3.87 (6H, s), 4.13 (1H, s), 4.46 (4H, s), 6.7-7.4 (7H, m).

Example 4a

2-[2,2,4,6,7-Pentamethyl-3-(4-methylphenyl)-2,3-dihydro-1-benzofuran-5-yl]isoindoline By using 2-[2,2,4,6,7-pentamethyl-3-(4-methylphenyl)-2, 3-dihydro-1-benzofuran-5-yl]-1H-isoindole-1,3(2H)-dione, the title compound was synthesized according to Example 2a. Yield: 46%. Melting point: 141-143° C. (Hexane)

$^1$H-NMR (CDCl$_3$) δ: 1.02 (3H, s), 1.51 (3H, s), 1.77 (3H, s), 2.17-2.18 (6H, s), 2.31 (3H, s), 4.10 (1H, s), 4.52 (4H, s), 6.8-7.1 (7H, m), 7.24 (4H, s).

Example 5a 5,6-Dichloro-2-[2,2,4,6,7-pentamethyl-3-(4-methylphenyl)-2,3-dihydro-1-benzofuran-5-yl]isoindoline By using 5,6-dichloro-2-[2,2,4,6,7-pentamethyl-3-(4-methylphenyl)-2,3-dihydro-1-benzofuran-5-yl]-1H-isoindole-1,3(2H)-dione, the title compound was synthesized according to Example 2a. Yield: 25%. Melting point: 201-203° C.

$^1$H-NMR (CDCl$_3$) δ: 1.01 (3H, s), 1.50 (3H, s), 1.74 (3H, s), 2.16 (6H, s), 2.31 (3H, s), 4.08 (1H, s), 4.45 (4H, s), 6.6-7.1 (4H, m), 7.31 (2H, s).

Example 6a 5,6-Dimethoxy-2-[2,2,4,6,7-pentamethyl-3-(4-methylphenyl)-2,3-dihydro-1-benzofuran-5-yl]isoindoline To a solution of 2,2,4,6,7-pentamethyl-3-(4-methylphenyl)-2,3-dihydro-1-benzofuran-5-amine (806.1 mg, 2.76 mmol) in tetrahydrofuran (30 ml) were added 1,2-bis(chloromethyl)-4,5-dimethoxybenzene (686.6 mg, 2.92 mmol), sodium carbonate (878.5 g, 8.29 mmol), and tetrabutylammonium iodide (543.6 mg, 1.47 mmol) and the mixture was refluxed with heating for 11 hours. The reaction mixture was cooled down to room temperature and then poured into ice water. The product was extracted twice with ethyl acetate. The combined extracts were washed with an aqueous saturated solution of sodium hydrogen carbonate, dried on magnesium sulfate, filtered, and then concentrated under reduced pressure. The residue was crystallized from ethyl acetate-hexane to obtain 199.6 mg (16% yield) of the title compound. Melting point: 156-159° C.

$^1$H-NMR (CDCl$_3$) δ: 1.02 (3H, s), 1.51 (3H, s), 1.76 (3H, s), 2.17 (6H, s), 2.31 (3H, s), 3.88 (6H, s), 4.10 (1H, s), 4.45 (4H, s), 6.7-7.2 (6H, m).

Example 7a

2-[3-(4-Fluorophenyl)-2,2,4,6,7-pentamethyl-2,3-dihydro-1-benzofuran-5-yl]isoindoline By using 2-[3-(4-fluorophenyl)-2,2,4,6,7-pentamethyl-2, 3-dihydro-1-benzofuran-5-yl]-1H-isoindole-1,3(2H)-dione, the title compound was synthesized according to Example 2a. Yield: 55%. Melting point: 204-205° C. (Ethyl acetate)

$^1$H-NMR (CDCl$_3$) δ: 1.02 (3H, s), 1.51 (3H, s), 1.76 qj(3H, s), 2.17 (3H, s), 2.18 (3H, s), 4.11 (1H, s), 4.52 (4H, s), 6.7-7.1 (4H, m), 7.25 (4H, s).

Example 8a 5,6-Dichloro-2-[3-(4-fluorophenyl)-2,2,4,6,7-pentamethyl-2,3-dihydro-1-benzofuran-5-yl]isoindoline By using 5,6-dichloro-2-[3-(4-fluorophenyl)-2,2,4,6,7-pentamethyl-2,3-dihydro-1-benzofuran-5-yl]-1H-isoindole-1,3(2H)-dione, the title compound was synthesized according to Example 2a. Yield: 25%. Melting point: 233-238° C. (Ethyl acetate)

$^1$H-NMR (CDCl$_3$) δ: 1.01 (3H, s), 1.50 (3H, s), 1.60 (3H, s), 1.74 (3H, s), 2.15 (3H, s), 4.09 (1H, s), 4.45 (4H, s), 6.8-7.1 (4H, m), 7.32 (2H, s).

Example 9a

2-[3-(4-Isopropylphenyl)-2,2,4,6,7-pentamethyl-2,3-dihydro-1-benzofuran-5-yl]isoindoline By using 2-[3-(4-isopropylphenyl)-2,2,4,6,7-pentamethyl-2,3-dihydro-1-benzofuran-5-yl]-1H-isoindole-1,3 (2H)-dione, the title compound was synthesized according to Example 2a. Yield: 57%. Melting point: 113-114° C. (Hexane)

$^1$H-NMR (CDCl$_3$) δ: 1.00 (3H, s), 1.22 (6H, d, J=7.0 Hz), 1.51 (3H, s), 1.77 (3H, s), 2.17 (3H, s), 2.18 (3H, s), 2.86 (1H, septet, J=7.0 Hz), 4.11 (1H, s), 4.53 (4H, s), 6.7-7.2 (4H, m), 7.24 (4H, s).

Example 10a 5,6-Dichloro-2-[3-(4-isopropylphenyl)-2,2,4,6,7-pentamethyl-2,3-dihydro-1-benzofuran-5-yl]isoindoline By using 5,6-dichloro-2-[3-(4-isopropylphenyl)-2,2,4,6, 7-pentamethyl-2,3-dihydro-1-benzofuran-5-yl]-1H-isoindole-1,3(2H)-dione, the title compound was synthesized according to Example 2a. Yield: 16%. Melting point: 148-150° C. (Hexane)

¹H-NMR (CDCl₃) δ: 1.01-1.06 (3H, s), 1.22 (6H, d, J=7.0 Hz), 1.50-1.54 (3H, m), 1.74-1.78 (3H, m), 2.16-2.20 (6H, m), 2.86 (1H, septet, J=7.0 Hz), 4.09-4.13 (1H, m), 4.46 (4H, s), 6.7-8.0 (6H, m).

Example 11a 5,6-Dimethoxy-2-[3-(4-isopropylphenyl)-2,2,4,6,7-pentamethyl-]-2,3-dihydro-1-benzofuran-5-yl]isoindoline By using 3-(4-isopropylphenyl)-2,2,4,6,7-pentamethyl-2,3-dihydro-1-benzofuran-5-amine, the title compound was synthesized according to Example 3a. Yield: 68%. Melting point: 153-155° C. (Isopropyl ether-hexane)

¹H-NMR (CDCl₃) δ: 1.01-1.05 (3H, s), 1.22 (6H, d, J=7.0 Hz), 1.48-1.55 (3H, m), 1.77-1.83 (3H, m), 2.17-2.19 (6H, m), 2.86 (1H, septet, J=7.0 Hz), 3.87-3.91 (7H, m), 4.10-4.14 (1H, m), 4.48 (3H, s), 6.77 (2H, s), 6.8-7.0 (2H, m), 7.07-7.11 (2H, m).

Example 12a

6-[3-(4-Isopropylphenyl)-2,2,4,6,7-pentamethyl-2,3-dihydro-1-benzofuran-5-yl]-6,7-dihydro-5H-[1,3]dioxolo[4,5-f]isoindole To a solution of 3-(4-isopropylphenyl)-2,2,4,6,7-pentamethyl-2,3-dihydro-1-benzofuran-5-amine (835.5 mg, 2.58 mmol) in tetrahydrofuran (20 ml) were added 5,6-bis(chloromethyl)-1,3-benzodioxazole (574.5 mg, 2.62 mmol), sodium carbonate (832.8 mg, 7.88 mmol), and tetrabutylammonium iodide (481.6 mg, 1.30 mmol) and the mixture was refluxed with heating for 23 hours. The reaction mixture was cooled down to room temperature and then poured into ice water. The product was extracted twice with ethyl acetate. The combined extracts were washed with an aqueous saturated solution of sodium hydrogen carbonate, dried on magnesium sulfate, filtered, and then concentrated under reduced pressure. The residue was crystallized from isopropyl ether to obtain 395.0 mg (33% yield) of the title compound. Melting point: 175-177° C.

¹H-NMR (CDCl₃) δ: 1.00 (3H, s), 1.22 (6H, d, J=7.0 Hz), 1.50 (3H, s), 1.76 (3H, s), 2.17 (6H, s), 2.86 (1H, septet, J=7.0 Hz), 4.10 (1H, s), 4.42 (4H, s), 5.94 (2H, s), 6.89 (2H, s), 6.80-7.11 (4H, m).

Example 13a

2-[3-(4-Isopropylphenyl)-2,4,6,7-tetramethyl-1-benzofuran-5-yl]isoindoline

By using 2-[3-(4-isopropylphenyl)-2,4,6,7-tetramethyl-1-benzofuran-5-yl]-1H-isoindole-1,3(2H)-dione, the title compound was synthesized according to Example 2a. Yield: 70%. Melting point: 126-129° C. (Ethanol)

¹H-NMR (CDCl₃) δ: 1.28 (6H, d, J=7.0 Hz), 1.97 (3H, s), 2.27 (3H, s), 2.31 (3H, s), 2.44 (3H, s), 2.95 (1H, septet, J=7.0 Hz), 4.57 (4H, s), 7.25 (8H, s).

Example 14a

6-[2,2,4,6,7-Pentamethyl-3-(4-methylphenyl)-2,3-dihydro-1-benzofuran-5-yl]-6H-[1,3]dioxolo[4,5-f]-isoindole To a solution of 2,2,4,6,7-pentamethyl-3-(4-methylphenyl)-2,3-dihydro-1-benzofuran-5-amine (799.8 mg, 2.73 mmol) in tetrahydrofuran (30 ml) were added 5,6-bis(chloromethyl)-1,3-benzodioxazole (603.8 mg, 2.76 mmol), sodium carbonate (877.8 mg, 8.28 mmol), and tetrabutylammonium iodide (506.8 mg, 1.37 mmol) and the mixture was refluxed with heating for 23 hours. The reaction mixture was cooled down to room temperature and then poured into ice water. The product was extracted twice with isopropyl ether. The combined extracts were washed with an aqueous saturated solution of sodium chloride, dried on magnesium sulfate, filtered, and then concentrated under reduced pressure. The residue was subjected to column chromatography on silica gel (hexane-ethyl acetate 10:1) to obtain 136.8 mg (11% yield) of the title compound. Melting point: 236-242° C. (Ethyl acetate)

¹H-NMR (CDCl₃) δ: 1.06 (3H, s), 1.47 (3H, s), 1.54 (3H, s), 1.82 (3H, s), 2.19 (3H, s), 2.31 (3H, s), 4.12 (1H, s), 5.85 (2H, s), 6.7-7.1 (8H, m).

Example 15a

2-[2,2,4,6,7-Pentamethyl-2,3-dihydro-1-benzofuran-5-yl]isoindoline

By using 2-[2,2,4,6,7-pentamethyl-2,3-dihydro-1-benzofuran-5-yl]-1H-isoindole-1,3(2H)-dione, the title compound was synthesized according to Example 2a. Yield: 84%. Melting point: 161-163° C. (Ethanol)

¹H-NMR (CDCl₃) δ: 1.48 (6H, s), 2.08 (3H, s), 2.11 (3H, s), 2.14 (3H, s), 2.93 (2H, s), 4.56 (4H, s), 7.27 (4H, s).

Example 16a 6-(2,2,4,6,7-Pentamethyl-3-phenyl-2,3-dihydro-1-benzofuran-5-yl)-6,7-dihydro-5H-[1,3]dioxolo[4,5-f]-isoindole To a solution of 2,2,4,6,7-pentamethyl-3-phenyl-2,3-dihydro-1-benzofuran-5-amine (1.00 g, 3.56 mmol) in tetrahydrofuran (30 ml) were added 5,6-bis(chloromethyl)-1,3-benzodioxazole (604 mg, 2.76 mmol), sodium carbonate (1.17 mg, 11.0 mmol), and tetrabutylammonium iodide (700 mg, 1.90 mmol) and the mixture was refluxed with heating for 15 hours. The reaction mixture was cooled down to room temperature and then poured into ice water. The product was extracted twice with ethyl acetate. The combined extracts were washed with an aqueous saturated solution of sodium chloride, dried on magnesium sulfate, filtered, and then concentrated under reduced pressure. The residue was subjected to column chromatography on silica gel (hexane-ethyl acetate 8:1) to obtain 853 mg (56% yield) of the title compound. Melting point: 245-248° C. (Ethyl acetate)

¹H-NMR (CDCl₃) δ: 1.01 (3H, s), 1.52 (3H, s), 1.76 (3H, s), 2.17 (6H, s), 4.12 (1H, s), 4.43 (4H, s), 5.94 (2H, s), 6.68 (2H, s), 6.8-7.3 (5H, m).

Example 17a (+)-5,6-Dimethoxy-2-[2,2,4,6,7-pentamethyl-3-(4-methylphenyl)-2,3-dihydro-1-benzofuran-5-yl]isoindoline To a solution of (+)-2,2,4,6,7-pentamethyl-3-(4-methylphenyl)-2,3-dihydro-1-benzofuran-5-amine (6.00 g, 20.3 mmol) in tetrahydrofuran (50 ml) was added under an argon atmosphere 4,5-dimethoxyphthalic anhydride (4.43 g, 21.3 mmol) and the mixture was refluxed with heating for 3 hours. The reaction mixture was cooled down to room temperature and then 1-ethyl-3-(3-dimethylaminopropyl)carbodiimide (WSC) hydrochloride (4.67 g, 24.4 mmol) and 1-hydroxy-1H-benzotriazole (HOBT) monohydrate (3.74 g, 24.4 mmol) were added to the mixture. The resulting mixture was refluxed with heating for 14 hours and then cooled down to room temperature. Water and an 8 N aqueous solution of sodium hydroxide were added into the reaction mixture and the product was extracted twice with ethyl acetate. The combined extracts were washed with an aqueous saturated solution of sodium hydrogen carbonate, dried on magnesium sulfate, filtered, and then concentrated under reduced pressure to obtain 8.40 g of (+)-5,6-dimethoxy-2-[2,2,4,6,7-pentamethyl-3-(4-methylphenyl)-2,3-dihydro-1-benzofuran-5-yl]-1H-isoindole-1,3(2H)-dione as a crude product. To a solution of aluminum chloride (13.6 g, 102 mmol) in tetrahydrofuran (60 ml) was added lithium aluminum hydride (3.87 g, 102 mmol) and the resulting mixture was stirred for 10 minutes. To this mixture was added a solution of the above-described crude product in tetrahydrofuran (30 ml) and the resulting mixture was refluxed with heating for 3 hours. The reaction mixture was cooled down to room temperature and water was added into the mixture. The product was extracted twice with ethyl acetate. The combined extracts were washed with a 1 N aqueous solution of sodium hydroxide, dried on magnesium sulfate, filtered, and then concentrated under reduced pressure. The residue was subjected to column chromatography (hexane-ethyl acetate 8:1) on silica gel to obtain 6.23 g (68% yield) of the title compound. Melting point: 157-159° C. $[\alpha]D=+62.3°$ (c=0.488, methanol)

$^1$H-NMR (CDCl$_3$) δ: 1.02 (3H, s), 1.51 (3H, s), 1.76 (3H, s), 2.17 (3H, s), 2.18 (3H, s), 2.31 (3H, s), 3.87 (6H, s), 4.10 (1H, s), 4.45 (4H, s), 6.70-7.15 (6H, m).

Example 18a (−)-5,6-Dimethoxy-2-[2,2,4,6,7-pentamethyl-3-(4-methylphenyl)-2,3-dihydro-1-benzofuran-5-yl]isoindoline By using (−)-2,2,4,6,7-pentamethyl-3-(4-methylphenyl)-2,3-dihydro-1-benzofuran-5-amine, the title compound was synthesized according to Example 17a. Yield: 34%. Melting point: 157-159° C. (Ethanol) $[\alpha]D=−61.5°$ (c=0.501, methanol)

$^1$H-NMR (CDCl$_3$) δ: 1.02 (3H, s), 1.51 (3H, s), 1.76 (3H, s), 2.17 (6H, s), 2.31 (3H, s), 3.88 (6H, s), 4.10 (1H, s), 4.45 (4H, s), 6.74-7.10 (6H, m).

Example 19a (+)-5,6-Dimethoxy-2-[2,2,4,6,7-pentamethyl-3-(4-methylphenyl)-2,3-dihydro-1-benzofuran-5-yl]isoindoline hydrochloride (+)-5,6-Dimethoxy-2-[2,2,4,6,7-pentamethyl-3-(4-methylphenyl)-2,3-dihydro-1-benzofuran-5-yl]isoindoline (296 mg, 0.65 mmol) was dissolved in ethyl acetate (5.0 ml) and then a 4 N solution of hydrogen chloride in ethyl acetate (0.38 ml) was added into this mixture. The solvent was removed under reduced pressure and the residue was crystallized from a mixed solution of ethyl acetate and diethyl ether (1:5). The crystals were collected by filtration and washed with a cold mixed solution of ethyl acetate and diethyl ether (1:5) to obtain 291 mg (87% yield) of the titled compound as a crystalline product. Melting point: 170-171° C. $[\alpha]D=+44.9°$ (c=0.495, chloroform)

$^1$H-NMR (CDCl$_3$) δ: 1.05 (3H, s), 1.49 (3H, s), 2.03 (3H, br), 2.18 (3H, s), 2.32 (3H, s), 2.45 (3H, br), 3.86 (6H, s), 4.06 (1H, s), 4.60 (2H, br), 5.70 (2H, br), 6.71 (2H, s), 6.80 (2H, br), 7.07 (2H, brd, J=6.0 Hz).

Example 20a (−)-5,6-Dimethoxy-2-[2,2,4,6,7-pentamethyl-3-(4-ethylphenyl)-2,3-dihydro-1-benzofuran-5-yl]isoindoline hydrochloride By using (−)-5,6-dimethoxy-2-[2,2,4,6,7-pentamethyl-3-(4-methylphenyl)-2,3-dihydro-1-benzofuran-5-yl]isoindoline, the title compound was synthesized according to Example 19a. Yield: 61%. Melting point: 173-175° C. $[\alpha]D=−44.4°$ (c=0.501, chloroform)

$^1$H-NMR (CDCl$_3$) δ: 1.05 (3H, s), 1.49 (3H, s), 2.05 (3H, br), 2.18 (3H, s), 2.31 (3H, s), 2.48 (3H, br), 3.86 (6H, s), 4.06 (1H, s), 4.55 (2H, br), 5.75 (2H, br), 6.71 (2H, s), 6.85 (2H, br), 7.07 (2H, brd, J=6.0 Hz).

Example 21a (+)-5,6-Dimethoxy-2-[2,2,4,6,7-pentamethyl-3-(4-methylphenyl)-2,3-dihydro-1-benzofuran-5-yl]isoindoline hydrobromide (+)-5,6-Dimethoxy-2-[2,2,4,6,7-pentamethyl-3-(4-methylphenyl)-2,3-dihydro-1-benzofuran-5-yl]isoindoline (150 mg, 0.327 mmol) was dissolved into a 25% solution of hydrogen bromide in acetic acid and the mixture was concentrated under reduced pressure. The residue was crystallized from methanol to obtain 92 mg (52% yield) of the title compound. Melting point: 174-177° C. $[\alpha]D=+40.2°$ (c=0.495, methanol)

$^1$H-NMR (CDCl$_3$) δ: 1.02 (3H, s), 1.51 (3H, s), 1.76 (3H, s), 2.17 (3H, s), 2.18 (3H, s), 2.31 (3H, s), 3.87 (6H, s), 4.10 (1H, s), 4.45 (4H, s), 6.70-7.15 (6H, m).

Example 22a

(−)-5,6-Dimethoxy-2-[2,2,4,6,7-pentamethyl-3-(4-methylphenyl)-2,3-dihydro-1-benzofuran-5-yl]isoindoline hydrobromide By using (−)-5,6-dimethoxy-2-[2,2,4,6,7-pentamethyl-3-(4-methylphenyl)-2,3-dihydro-1-benzofuran-5-yl]isoindoline, the title compound was synthesized according to Example 21a. Yield: 46%. Melting point: 171-174° C. $[\alpha]_D = -40.1°$ (c=0.498, methanol)

$^1$H-NMR (CDCl$_3$) δ: 1.02 (3H, s), 1.51 (3H, s), 1.76 (3H, s), 2.17 (6H, s), 2.31 (3H, s), 3.88 (6H, s), 4.10 (1H, s), 4.45 (4H, s), 6.74-7.10 (6H, m).

The chemical structures of the compounds obtained in the above-described Examples are shown below.

TABLE 1

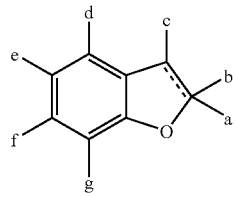

| example number | a | b | c | d | e | f | g |
|---|---|---|---|---|---|---|---|
| 1a | Me | Me | phenyl | Me | isoindoline | Me | Me | — |
| 2a | Me | Me | phenyl | Me | 5,6-dichloroisoindoline | Me | Me | — |
| 3a | Me | Me | phenyl | Me | 5,6-dimethoxyisoindoline | Me | Me | — |
| 4a | Me | Me | 4-methylphenyl | Me | isoindoline | Me | Me | — |
| 5a | Me | Me | 4-methylphenyl | Me | 5,6-dichloroisoindoline | Me | Me | — |
| 6a | Me | Me | 4-methylphenyl | Me | 5,6-dimethoxyisoindoline | Me | Me | — |
| 7a | Me | Me | 4-fluorophenyl | Me | isoindoline | Me | Me | — |
| 8a | Me | Me | 4-fluorophenyl | Me | 5,6-dichloroisoindoline | Me | Me | — |
| 9a | Me | Me | 4-isopropylphenyl | Me | isoindoline | Me | Me | — |

TABLE 1-continued

[Benzofuran core structure with positions a, b, c, d, e, f, g labeled]

| example number | a | b | c | d | e | f | g | ===== |
|---|---|---|---|---|---|---|---|---|
| 10a | Me | Me | -CH(Me)-C6H4-Me (p) | Me | 5,6-dichloro-N-methylisoindoline | Me | Me | — |
| 11a | Me | Me | -CH(Me)-C6H4-Me (p) | Me | 5,6-dimethoxy-N-methylisoindoline | Me | Me | — |
| 12a | Me | Me | -CH(Me)-C6H4-Me (p) | Me | methylenedioxy-N-methylisoindoline | Me | Me | — |

TABLE 2

[Benzofuran core structure with positions a, b, c, d, e, f, g labeled]

| example number | a | b | c | d | e | f | g | ===== | adduct |
|---|---|---|---|---|---|---|---|---|---|
| 13a | Me | — | -CH(Me)-C6H4-Me (p) | Me | N-methylisoindoline | Me | Me | = | |
| 14a | Me | Me | -C6H4-Me (p) | Me | methylenedioxy-N-methylisoindoline | Me | Me | — | |
| 15a | Me | Me | H | Me | N-methylisoindoline | Me | Me | — | |
| 16a | Me | Me | -C6H5 | Me | methylenedioxy-N-methylisoindoline | Me | Me | — | |
| 17a | Me | Me | -C6H4-Me (p)* | Me | 5,6-dimethoxy-N-methylisoindoline | Me | Me | — | |

TABLE 2-continued

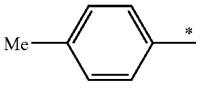

| example number | a | b | c | d | e | f | g | adduct |
|---|---|---|---|---|---|---|---|---|
| 18a | Me | Me | Me-⟨C6H4⟩-* | Me | MeO, MeO-isoindoline-N— | Me | Me | — |
| 19a | Me | Me | Me-⟨C6H4⟩-* | Me | MeO, MeO-isoindoline-N— | Me | Me | HCl |
| 20a | Me | Me | Me-⟨C6H4⟩-* | Me | MeO, MeO-isoindoline-N— | Me | Me | HCl |
| 21a | Me | Me | Me-⟨C6H4⟩-* | Me | MeO, MeO-isoindoline-N— | Me | Me | HBr |
| 22a | Me | Me | Me-⟨C6H4⟩-* | Me | MeO, MeO-isoindoline-N— | Me | Me | HBr |

Formulation Example 1a

| | |
|---|---|
| (1) The compound obtained in Example 14a | 50 mg |
| (2) Lactose | 34 mg |
| (3) Corn starch | 10.6 mg |
| (4) Corn starch (paste) | 5 mg |
| (5) Magnesium Stearate | 0.4 mg |
| (6) Calcium carboxymethyl cellulose | 20 mg |
| Total | 120 mg |

According to a conventional method, tablets were prepared by mixing the above-described substances, (1) to (6), and then subjecting the resulting mixture to a tablet compression process By using a tablet compression machine.

Experimental Example 1a

Cytoprotection in Human Neuroblastoma SK-N-SH Cells Against a PI-3-Kinase Inhibitor, LY-294002

(Materials for Experiments and Experimental Procedures)
a) Materials for Experiments Human neuroblastoma SK-N-SH cells were purchased from American Type Cell Culture (ATCC). DMEM/F-12 culture medium and potassium/magnesium-free phosphate buffer saline (PBS(−)) were purchased from Nikken Biomedical Co., Ltd., N2 additives and EDTA solution from GIBCO BRL Company, fetal bovine serum (FCS) and a mixed solution of penicillin (5000U/ml) and streptomycin (5 mg/ml) from BioWhittaker Inc., Alamarblue™ reagent from Wako Pure Chemical Industries Ltd., culture flasks from Falcon Company, collagen-coated 96-well multi-plates from Iwaki Glass Co., Ltd., and LY-294002 from Alexis Biochemicals, respectively. As for other reagents, commercially available guaranteed reagents were used.

b) Experimental Procedures (1) Cultivation of SK-N-SH Cells

By using DMEM/F-12 culture medium which contains 5% FCS, 0.5% N2, 10 mM HEPES, and a 1% mixed solution of penicillin (5000U/ml) and streptomycin (5 mg/ml), SK-N-SH cells were subcultured in a carbon dioxide incubator under a mixed gas atmosphere consisting of 10% carbon dioxide and 90% air. After being cultivated to a sub-confluent stage, the cells were detached by a PBS(−) solution containing 2.5 mM EDTA and seeded onto collagen-coated 96-well multi-plates in the proportion of $1.0 \times 10^4$ cells/100 μl/well. After cultivation for 24 hours, the cells thus prepared were used for the cytoprotection assay.

(2) Action to Protect the Nerve Cells from LY-294002-induced Cytotoxicity

There was removed 80 μl of the culture medium of SK-N-SH cells that was cultivated as described above on 96-wells, collagen-coated, multi-plates and thereto were added at the same time 40 μl each of LY-294002 of the final concentrations of 30 μM and each test compound the final concentrations of that was adjusted to be 1.0 μM, to initiate the cytotoxicity test. Hereupon, each test compound was used after adjusting the concentration to be 10 mM with dimethyl sulfoxide and LY-294002 was used after adjusting the concentration to be 100 mM with dimethyl sulfoxide, each of which was diluted prior to its use in the test.

(3) Evaluation of the Survival Activity of Cells

The survival activity of nerve cells that were still living one day after initiation of the cytotoxicity test was determined by the activity of the cells to reduce the Alamarblue™ reagent as an index. There was removed 20 μl of the culture medium and 20 μl of Alamarblue™ reagent was added. The amount of Alamarblue™ reagent reduced by the cells over the period of 4 hours was calorimetrically determined (measurement wave length: 570 nm; reference wave length: 600 nm) By using a plate reader (WAKO SPECTRAMAX 250 Microplate Reader). Cytoprotection activity was calculated according to the following equation.

Cytoprotection activity of each compound=$(A-B)/(C-B) \times 100$ (%)

A: The survival activity of the group consisting of a test compound and LY-294002 added
B: The survival activity of the group consisting of LY-294002 added
C: The survival activity of the control group (Results)

The cytoprotection activity of each compound was obtained By using at least 4 wells for every dose of a test compound. The results are shown below.

TABLE 3

| Compound of Example | Cytoprotection Activity (%) |
|---|---|
| 6a | 28.2 |
| 14a | 26.6 |

These results reveal that, like neurotrophic factors, compounds (Ia) and compounds (Ia') possess cytoprotection against the cytotoxicity by LY-294002, which is a PI-3 kinase inhibitor and causes nerve degeneration, thereby suppressing the nerve degeneration.

[Compounds (Ib)]

REFERENCE EXAMPLE 1b

Ethyl 3-(4-isopropylphenyl)-2-methyl-2-propenoate

To a suspension of sodium hydride (a 60% dispersion in liquid paraffin, 5.92 g, 148 mmol) in N,N-dimethylformamide (150 ml) was added at 0° C. triethyl 2-phosphonopropionate (35.0 g, 148 mmol) and the resulting mixture was stirred at the same temperature for 10 minutes. To the reaction solution was added 4-isopropylbenzaldehyde (20.0 g, 135 mmol) and the resulting mixture was stirred at room temperature for 30 minutes. Water was added into the reaction solution and the product was extracted twice with ethyl acetate. The combined extracts were washed with water, dried on magnesium sulfate, and then concentrated under reduced pressure to obtain 30.1 g (96% yield) of the oily title compound.

$^1$H-NMR (CDCl$_3$) δ: 1.26 (6H, d, J=7.0 Hz), 1.35 (3H, t, J=7.0 Hz), 2.13 (3H, s), 2.92 (1H, septet, J=7.0 Hz), 4.27 (2H, q, J=7.0 Hz), 7.21-7.38 (4H, m), 7.67 (1H, s).

REFERENCE EXAMPLE 2b

Ethyl 2-methyl-3-(4-methylphenyl)-2-propenoate

By using 4-methylbenzaldehyde, the title compound was synthesized according to Reference Example 1b. Yield: 94%. An oily substance.

$^1$H-NMR (CDCl$_3$) δ: 1.34 (3H, t, J=7.0 Hz), 2.12 (3H, d, J=1.4 Hz), 2.37 (3H, s), 4.26 (2H, q, J=7.0 Hz), 7.19 (2H, d, J=8.4 Hz), 7.31 (2H, d, J=8.4 Hz), 7.66 (1H, s).

REFERENCE EXAMPLE 3b

Ethyl 3-(4-fluorophenyl)-2-methyl-2-propenoate

By using 4-fluorobenzaldehyde, the title compound was synthesized according to Reference Example 1b. Yield: 97%. An oily substance.

$^1$H-NMR (CDCl$_3$) δ: 1.35 (3H, t, J=7.0 Hz), 2.10 (3H, d, J=1.2 Hz), 4.28 (2H, q, J=7.0 Hz), 7.08 (2H, t, J=8.8 Hz), 7.32-7.43 (2H, m), 7.65 (1H, s).

REFERENCE EXAMPLE 4b

Ethyl (E)-3-(4-isopropylphenyl)-2-propenoate

To a suspension of sodium hydride (a 60% dispersion in liquid paraffin, 10.4 g, 260 mmol) in N,N-dimethylformamide (200 ml) was added at 0° C. triethyl phosphonoacetate (58.2 g, 236 mmol) and the resulting mixture was stirred at the same temperature for 10 minutes. To the reaction mixture was added 4-isopropylbenzaldehyde (35.0 g, 260 mmol) and the resulting mixture was stirred at room temperature for 30 minutes. Water was added into the reaction mixture and the product was extracted twice with ethyl acetate. The combined extracts were washed with water, dried on magnesium sulfate, and then concentrated under reduced pressure to obtain 47.5 g (92% yield) of the oily title compound.

$^1$H-NMR (CDCl$_3$) δ: 1.25 (6H, d, J=7.0 Hz), 1.33 (3H, t, J=7.0 Hz), 2.92 (1H, septet, J=7.0 Hz), 4.26 (2H, q, J=7.0 Hz), 6.40 (1H, d, J=15.8 Hz), 7.24 (2H, d, J=8.2 Hz), 7.46 (2H, d, J=8.2 Hz), 7.67 (1H, d, J=15.8 Hz).

REFERENCE EXAMPLE 5b

Ethyl (E)-3-(4-fluorophenyl)-2-propenoate

By using 4-fluorobenzaldehyde, the title compound was synthesized according to Reference Example 4b. Yield: 88%. An oily substance.

$^1$H-NMR (CDCl$_3$) δ: 1.34 (3H, t, J=7.0 Hz), 4.26 (2H, q, J=7.0 Hz), 6.31 (1H, d, J=15.8 Hz), 7.00-7.11 (2H, m), 7.43-7.58 (2H, m), 7.67 (1H, d, J=15.8 Hz).

REFERENCE EXAMPLE 6b 3-(4-Isopropylphenyl)-2-methyl-2-propen-1-ol

To a suspension of ethyl 3-(4-isopropylphenyl)-2-methyl-2-propenoate (9.00 g, 38.7 mmol) and cerium chloride (1.00 g, 4.06 mmol) in tetrahydrofuran (50 ml) was added in four portions at −40° C. for 30 minutes lithium aluminum hydride (1.47 g, 38.7 mmol) and the resulting mixture was stirred at the same temperature for 30 minutes. Water was added into the reaction mixture and the product was extracted twice with ethyl acetate. The combined extracts were washed with water, dried on magnesium sulfate, and then concentrated under reduced pressure. The residue was subjected to column chromatography on silica gel (hexane-ethyl acetate 8:1) to obtain 6.30 g (86% yield) of the oily title compound.

$^1$H-NMR (CDCl$_3$) δ: 1.25 (6H, d, J=7.0 Hz), 1.91 (3H, d, J=1.4 Hz), 2.90 (1H, septet, J=7.0 Hz), 4.17 (2H, d, J=0.8 Hz), 6.49 (1H, dd, J=2.6, 1.4 Hz), 7.15-7.25 (4H, m), 1H unidentified.

REFERENCE EXAMPLE 7b

2-Methyl-3-(4-methylphenyl)-2-propen-1-ol

By using 2-methyl-3-(4-methylphenyl)-2-propenoate, the title compound was synthesized according to Reference Example 6b. Yield: 98%. An oily substance.

$^1$H-NMR (CDCl$_3$) δ: 1.87 (3H, s), 2.32 (3H, s), 4.13 (2H, s), 6.46 (1H, s), 7.08-7.22 (4H, m), 1H unidentified.

REFERENCE EXAMPLE 8b 3-(4-Fluorophenyl)-2-methyl-2-propen-1-ol

By using ethyl 3-(4-fluorophenyl)-2-methyl-2-propenoate, the title compound was synthesized according to Reference Example 6b. Yield: 95%. An oily substance.

$^1$H-NMR (CDCl$_3$) δ: 1.98 (3H, d, J=1.6 Hz), 4.11 (2H, s), 6.58 (1H, s), 7.01 (2H, t, J=8.8 Hz), 7.18-7.28 (2H, m), 1H unidentified.

REFERENCE EXAMPLE 9b (E)-3-(4-Isopropylphenyl)-2-propen-1-ol

To a suspension of ethyl (E)-3-(4-isopropylphenyl)-2-propenoate (20.0 g, 91.6 mmol) in tetrahydrofuran (200 ml) was added in four portions at −40° C. for 30 minutes lithium aluminum hydride (2.61 g, 68.7 mmol) and the resulting mixture was stirred at the same temperature for 30 minutes. Water was added into the reaction solution and the product was extracted twice with ethyl acetate. The combined extracts were washed with water, dried on magnesium sulfate, and then concentrated under reduced pressure. The residue was subjected to column chromatography on silica gel (hexane-ethyl acetate 8:1) to obtain 10.5 g (65% yield) of the oily title compound.

$^1$H-NMR (CDCl$_3$) δ: 1.24 (6H, d, J=7.0 Hz), 2.79-3.00 (2H, m), 4.30 (2H, d, J=5.6 Hz), 6.35 (1H, dt, J=15.8, 5.6 Hz), 6.59 (1H, d, J=15.8 Hz), 7.10-7.39 (4H, m).

REFERENCE EXAMPLE 10b (E)-3-(4-Fluorophenyl)-2-propen-1-ol

By using ethyl (E)-3-(4-fluorophenyl)-2-propenoate, the title compound was synthesized according to Reference Example 6b. Yield: 84%. An oily substance.

$^1$H NMR (CDCl$_3$) δ: 4.31 (2H, d, J=5.6 Hz), 6.28 (1H, dt, J=15.8, 5.6 Hz), 6.59 (1H, d, J=15.8 Hz), 6.90-7.40 (4H, m), 1H unidentified.

REFERENCE EXAMPLE 11b 1-(3-Bromo-2-methyl-1-propenyl)-4-isopropylbenzene

To a solution of 3-(4-isopropylphenyl)-2-methyl-2-propen-1-ol (6.30 g, 33.1 mmol) in isopropyl ether (50 ml) was added under ice cooling phosphorus tribromide (5.98 g, 22.1 mmol) and the resulting mixture was stirred at room temperature for 30 minutes. Water was added into the reaction mixture and the product was extracted with isopropyl ether. The organic layer was washed with water and an aqueous saturated solution of sodium hydrogen carbonate, dried on magnesium sulfate, filtered, and then concentrated under reduced pressure to obtain 7.63 g (91% yield) of the oily title compound.

$^1$H-NMR (CDCl$_3$) δ: 1.25 (6H, d, J=7.0 Hz), 2.03 (3H, d, J=1.4 Hz), 2.90 (1H, septet, J=7.0 Hz), 4.15 (2H, d, J=0.8 Hz), 6.62 (1H, s), 7.14-7.26 (4H, m).

REFERENCE EXAMPLE 12b 1-(3-Bromo-2-methyl-1-propenyl)-benzene

By using 2-methyl-3-phenyl-2-propen-1-ol, the title compound was synthesized according to Reference Example 11b. Yield: 89%. An oily substance.

$^1$H-NMR (CDCl$_3$) δ: 2.01 (3H, d, J=1.4 Hz), 4.13 (2H, d, J=0.8 Hz), 6.64 (1H, s), 7.19-7.44 (5H, m).

REFERENCE EXAMPLE 13b 1-(3-Bromo-2-methyl-1-propenyl)-4-methylbenzene

By using 2-methyl-3-(4-methylphenyl)-2-propen-1-ol, the title compound was synthesized according to Reference Example 11b. Yield: 77%. An oily substance.

$^1$H-NMR (CDCl$_3$) δ: 2.01 (3H, s), 2.34 (3H, s), 4.13 (2H, s), 6.60 (1H, s), 7.09-7.22 (4H, m).

REFERENCE EXAMPLE 14b 1-(3-Bromo-2-methyl-1-propenyl)-4-fluorobenzene

By using 3-(4-fluorophenyl)-2-methyl-2-propen-1-ol, the title compound was synthesized according to Reference Example 11b. Yield: 79%. An oily substance.

$^1$H-NMR (CDCl$_3$) δ: 1.87 (3H, s), 4.17 (2H, s), 6.48 (1H, s), 7.01 (2H, t, J=8.8 Hz), 7.18-7.27 (2H, m).

REFERENCE EXAMPLE 15b

1-[(E)-3-Bromo-1-propenyl]-4-isopropylbenzene

To a solution of (E)-3-(4-isopropylphenyl)-2-propen-1-ol (10.5 g, 59.6 mmol) in isopropyl ether (100 ml) was added under ice cooling phosphorus tribromide (10.7 g, 39.7 mmol) and the resulting mixture was stirred at room temperature for 30 minutes. Water was added into the reaction solution and the product was extracted with isopropyl ether. The organic layer was washed with water and an aqueous saturated solution of sodium hydrogen carbonate, dried on magnesium sulfate, filtered, and then concentrated under reduced pressure to obtain 10.2 g (72% yield) of the oily title compound.

$^1$H-NMR (CDCl$_3$) δ: 1.24 (6H, d, J=7.0 Hz), 2.89 (1H, septet, J=7.0 Hz), 4.16 (2H, dd, J=7.8, 0.8 Hz), 6.35 (1H, dt, J=15.4, 7.8 Hz), 6.63 (1H, d, J=15.4 Hz), 7.14-7.35 (4H, m).

REFERENCE EXAMPLE 16b

1-[(E)-3-Bromo-1-propenyl]-4-fluorobenzene

By using (E)-3-(4-fluorophenyl)-2-propen-1-ol, the title compound was synthesized according to Reference Example 11b. Yield: 61%. An oily substance.

¹H-NMR (CDCl₃) δ: 4.15 (2H, d, J=7.6 Hz), 6.30 (1H, dt, J=15.4, 7.6 Hz), 6.61 (1H, d, J=15.4 Hz), 6.83-7.08 (2H, m), 7.31-7.45 (2H, m).

REFERENCE EXAMPLE 17b

N-[4-[[3-(4-Isopropylphenyl)-2-methyl-2-propenyl]oxy]-2,3,6-trimethylphenyl]formamide To a solution of N-(4-hydroxy-2,3,6-trimethylphenyl)formamide (3.00 g, 16.7 mmol) in N,N-dimethylformamide (30 ml) was added at 0° C. under a nitrogen atmosphere sodium hydride (a 60% dispersion in liquid paraffin, 0.74 g, 18.4 mmol) and the resulting mixture was stirred at the same temperature for 10 minutes. To the reaction solution was added 1-(3-bromo-2-methyl-1-propenyl)-4-isopropylbenzene (4.66 g, 18.4 mmol) and the resulting mixture was stirred at room temperature for 30 minutes. Water was added into the reaction solution and the product was extracted twice with ethyl acetate. The combined extracts were washed with water, dried on magnesium sulfate, and then concentrated under reduced pressure. The resulting residue was crystallized from ethyl acetate-hexane to obtain 3.70 g (63% yield) of the title compound. Melting point: 153-155° C.
¹H-NMR (CDCl₃) δ: 1.26 (6H, d, J=7.0 Hz), 2.00 (3H, s), 2.07-2.34 (9H, m), 2.91 (1H, septet, J=7.0 Hz), 4.54 (2H, q, J=7.0 Hz), 6.59-6.84 (3H, m), 7.17-7.36 (4H, m), 7.98 (0.5H, d, J=12.0 Hz), 8.41 (0.5H, s).

REFERENCE EXAMPLE 18b

N-[2,3,6-Trimethyl-4-[(2-methyl-3-phenyl-2-propenyl)oxy]phenyl]formamide

By using N-(4-hydroxy-2,3,6-trimethylphenyl)formamide and 1-(3-bromo-2-methyl-1-propenyl)benzene, the title compound was synthesized according to Reference Example 17b. Yield: 41%. Melting point: 152-154° C. (Ethyl acetate-hexane)
¹H-NMR (CDCl₃) δ: 1.98 (3H, d, J=1.60 Hz), 2.10-2.32 (9H, m), 4.54 (2H, d, J=5.2 Hz), 6.65 (1H, s), 6.67 (1H, s), 6.69-6.90 (1H, m), 7.11-7.41 (5H, m), 7.98 (0.5H, d, J=12.0 Hz), 8.41 (0.5H, d, J=1.4 Hz).

REFERENCE EXAMPLE 19b

N-[2,3,6-Trimethyl-4-[[2-methyl-3-(4-methylphenyl)-2-propenyl]oxy]phenyl]formamide By using N-(4-hydroxy-2,3,6-trimethylphenyl)formamide and 1-(3-bromo-2-methyl-1-propenyl)-4-methylbenzene, the title compound was synthesized according to Reference Example 17b. Yield: 57%. Melting point: 167-169° C. (Ethyl acetate-hexane)
¹H-NMR (CDCl₃) δ: 1.98 (3H, s), 2.07-2.38 (9H, m), 2.35 (3H, s), 4.53 (2H, d, J=6.6 Hz), 6.61 (1H, s), 6.66 (1H, d, J=2.4 Hz), 6.82-7.09 (1H, m), 7.11-7.31 (4H, m), 7.98 (0.5H, d, J=12.2 Hz), 8.38 (0.5H, s).

REFERENCE EXAMPLE 20b

N-[4-[[3-(4-Fluorophenyl)-2-methyl-2-propenyl]oxy]-2,3,6-trimethylphenyl]formamide By using N-(4-hydroxy-2,3,6-trimethylphenyl)formamide and 1-(3-bromo-2-methyl-1-propenyl)-4-fluorobenzene, the title compound was synthesized according to Reference Example 17b. Yield: 52%. Melting point: 164-165° C. (Ethyl acetate-hexane)
¹H-NMR (CDCl₃) δ: 1.96 (3H, s), 2.12-2.32 (9H, m), 4.53 (2H, d, J=5.2 Hz), 6.60 (1H, s), 6.66 (1H, s), 6.71-6.95 (1H, m), 7.04 (2H, t, J=8.8 Hz), 7.22-7.33 (2H, m), 8.04 (0.5H, d, J=12.0 Hz), 8.40 (0.5H, d, J=1.4 Hz).

REFERENCE EXAMPLE 21b

N-[4-[[(E)-3-(4-Isopropylphenyl)-2-propenyl]oxy]-2,3,6-trimethylphenyl]formamide To a solution of N-(4-hydroxy-2,3,6-trimethylphenyl)formamide (5.20 g, 29.0 mmol) in N,N-dimethylformamide (30 ml) was added at 0° C. under a nitrogen atmosphere sodium hydride (a 60% dispersion in liquid paraffin, 1.39 g, 34.8 mmol) and the resulting mixture was stirred at the same temperature for 10 minutes. To the reaction solution was added 1-[(E)-3-bromo-1-propenyl]-4-isopropylbenzene (9.00 g, 37.7 mmol) and the resulting mixture was stirred at room temperature for 30 minutes. Water was added into the reaction solution and the product was extracted twice with ethyl acetate. The combined extracts were washed with water, dried on magnesium sulfate, and then concentrated under reduced pressure. The resulting residue was crystallized from ethyl acetate-hexane to obtain 5.80 g (59% yield) of the title compound. Melting point: 165-167° C.
¹H-NMR (CDCl₃) δ: 1.25 (6H, d, J=6.8 Hz), 2.13-2.27 (9H, m), 2.90 (1H, septet, J=6.8 Hz), 4.66 (2H, t, J=5.8 Hz), 6.37 (1H, dt, J=15.8, 5.8 Hz), 6.65-6.88 (3H, m), 7.16-7.26 (2H, m), 7.35 (2H, d, J=8.0 Hz), 7.98 (0.5H, d, J=12.0 Hz), 8.40 (0.5H, d, J=1.4 Hz).

REFERENCE EXAMPLE 22b

N-[2,3,6-Trimethyl-4-[[(E)-3-phenyl-2-propenyl]oxy]-phenyl]formamide

By using N-(4-hydroxy-2,3,6-trimethylphenyl)formamide and cinnamyl chloride, the title compound was synthesized according to Reference Example 17b. Yield: 44%. Melting point: 197-199° C. (Ethyl acetate-hexane)
¹H-NMR (CDCl₃) δ: 2.05-2.18 (9H, m), 4.62-4.72 (2H, m), 6.35-6.50 (1H, m), 6.62-7.00 (3H, m), 7.24-7.52 (5H, m), 8.00 (0.5H, d, J=12.0 Hz), 8.39 (0.5H, d, J=1.6 Hz).

REFERENCE EXAMPLE 23b

N-[4-[[(E)-3-(4-Fluorophenyl)-2-propenyl]oxy]-2,3,6-trimethylphenyl]formamide

By using N-(4-hydroxy-2,3,6-trimethylphenyl)formamide and 1-[(E)-3-bromo-1-propenyl]-4-fluorobenzene, the title compound was synthesized according to Reference Example 17b. Yield: 52%. Melting point: 196-198° C. (Ethyl acetate-hexane)
¹H-NMR (CDCl₃) δ: 2.10-2.32 (9H, m), 4.67 (2H, t, J=5.0 Hz), 6.37(1H, dt, J=15.6, 5.0 Hz), 6.59-6.89 (3H, m), 6.92-7.09 (2H, m), 7.32-7.43 (2H, m), 7.99 (0.5H, d, J=12.0 Hz), 8.42 (0.5H, d, J=1.4 Hz).

REFERENCE EXAMPLE 24b

N-[4-Hydroxy-3-[1-(4-isopropylphenyl)-2-propenyl]-2,5,6-trimethylphenyl]formamide A solution of N-[4-[[(E)-3-(4-isopropylphenyl)-2-propenyl]oxy]-2,3,6-trimethylphenyl]formamide (5.80 g, 17.2 mmol) in N,N-dimethylaniline (50 ml) was stirred at 215° C. for 6 hours under argon atmosphere. The reaction mixture was cooled down, diluted with ethyl acetate, washed with 2 N hydrochloric acid and water, dried on magnesium sulfate, and then concentrated under reduced pressure. The residue was crystallized from ethyl acetate to obtain 3.50 g (60% yield) of the title compound. Melting point: 170-171° C.
$^1$H-NMR (CDCl$_3$) δ: 1.18-1.40 (6H, m), 2.11-2.27 (9H, m), 2.77-3.00 (1H, m), 5.00-5.22 (2H, m), 5.30-5.42 (1H, m), 6.30-6.85 (2H, m), 7.10-7.37 (5H, m), 7.97 (0.5H, d, J=12.2 Hz), 8.43 (0.5H, d, J=1.4 Hz).

REFERENCE EXAMPLE 25b

N-[4-Hydroxy-3-[1-phenyl-2-propenyl]-2,5,6-trimethylphenyl]formamide

By using N-[2,3,6-trimethyl-4-[[(E)-3-phenyl-2-propenyl]oxy]phenyl]formamide, the title compound was synthesized according to Reference Example 24b. Yield: 78%. Melting point: 144-145° C. (Ethyl acetate)
$^1$H-NMR (CDCl$_3$) δ: 2.08-2.27 (9H, m), 5.02-5.41 (3H, m), 6.32-6.52 (1H, m), 6.61-7.03 (2H, m), 7.18-7.42 (5H, m), 7.95 (0.5H, d, J=12.0 Hz), 8.42 (0.5H, d, J=1.8 Hz).

REFERENCE EXAMPLE 26b

N-[4-Hydroxy-3-[1-(4-fluorophenyl)-2-propenyl]-2,5,6-trimethylphenyl]formamide

By using N-[4-[[(E)-3-(4-fluorophenyl)-2-propenyl]oxy]-2,3,6-trimethylphenyl]formamide, the title compound was synthesized according to Reference Example 24b. Yield: 66%. Melting point: 168-170° C. (Ethyl acetate)
$^1$H-NMR (CDCl$_3$) δ: 2.10-2.29 (9H, m), 5.02-5.22 (1.5H, m), 5.33-5.50 (1.5H, m), 6.35-6.55 (1H, m), 6.72-7.08 (4H, m), 7.18-7.30 (2H, m), 7.96 (0.5H, d, J=12.2 Hz), 8.42 (0.5H, d, J=1.4 Hz).

REFERENCE EXAMPLE 27b 3-(4-Isopropylphenyl)-2,2,4,6,7-pentamethyl-2,3-dihydro-1-benzofuran-5-amine A solution of N-[4-[[3-(4-isopropylphenyl)-2-methyl-2-propenyl]oxy]-2,3,6-trimethylphenyl]formamide (3.70 g, 10.5 mmol) in N,N-dimethylaniline (20 ml) was stirred at 215° C. for 6 hours under an argon atmosphere. The reaction mixture was cooled down, then diluted with ethyl acetate, washed with 2 N hydrochloric acid and water, dried on magnesium sulfate, and then concentrated under reduced pressure to obtain N-[4-hydroxy-3-[1-(4-isopropylphenyl)-2-methyl-2-propenyl]-2,5,6-trimethylphenyl]formamide as a crude product. A mixture of this compound (2.98 g, 8.47 mmol), concentrated hydrochloric acid (20 ml), and methanol (60 ml) was refluxed with heating for 2 hours under a nitrogen atmosphere. The solvent was concentrated under reduced pressure and the resulting residue was neutralized with an 8 N aqueous solution of sodium hydroxide. The product was extracted twice with ethyl acetate. The combined extracts were washed with water, dried on magnesium sulfate, and then concentrated under reduced pressure. The resulting residue was crystallized from isopropyl ether-hexane to obtain 2.23 g (66% yield) of the title compound. Melting point: 130-132° C.
$^1$H-NMR (CDCl$_3$) δ: 1.00 (3H, s), 1.21 (6H, d, J=6.6 Hz), 1.47 (3H, s), 1.78 (3H, s), 2.12 (3H, s), 2.19 (3H, s), 2.40-2.60 (3H, m), 4.08 (1H, s), 6.72-7.00 (2H, m), 7.07 (2H, d, J=8.0 Hz).

REFERENCE EXAMPLE 28b 2,2,4,6,7-Pentamethyl-3-phenyl-2,3-dihydro-1-benzofuran-5-amine By using N-[2,3,6-trimethyl-4-[(2-methyl-3-phenyl-2-propenyl)oxy]phenyl]formamide, the title compound was synthesized according to Reference Example 27b. Yield: 67%. Melting point: 129-131° C. (Petroleum ether)
$^1$H-NMR (CDCl$_3$) δ: 1.00 (3H, s), 1.48 (3H, s), 1.77(3H, s), 2.13 (3H, s), 2.19 (3H, s), 3.20 (2H, br s), 4.12 (1H, s), 6.70-7.30 (5H, m).

REFERENCE EXAMPLE 29b 2,2,4,6,7-Pentamethyl-3-(4-methylphenyl)-2,3-dihydro-1-benzofuran-5-amine By using N-[2,3,6-trimethyl-4-[[2-methyl-3-(4-methylphenyl)-2-propenyl]oxy]phenyl]formamide, the title compound was synthesized according to Reference Example 27b. Yield: 62%. Melting point: 114-115° C. (Petroleum ether)
$^1$H-NMR (CDCl$_3$) δ: 0.99 (3H, s), 1.47 (3H, s), 1.77 (3H, s), 2.12 (3H, s), 2.19 (3H, s), 2.30 (3H, s), 3.23 (2H, br s), 4.08 (1H, s), 6.60-7.23 (4H, m).

REFERENCE EXAMPLE 30b 3-(4-Fluorophenyl)-2,2,4,6,7-pentamethyl-2,3-dihydro-1-benzofuran-5-amine By using N-[4-[[3-(4-fluorophenyl)-2-methyl-2-propenyl]oxy]-2,3,6-trimethylphenyl]formamide, the title compound was synthesized according to Reference Example 27b. Yield: 78%. Melting point: 125-127° C. (Petroleum ether)
$^1$H-NMR (CDCl$_3$) δ: 0.99 (3H, s), 1.47 (3H, s), 1.77(3H, s), 2.12 (3H, s), 2.19 (3H, s), 3.10 (2H, br s), 4.09 (1H, s), 6.62-7.20 (4H, m).

REFERENCE EXAMPLE 31b 3-(4-Isopropylphenyl)-2,4,6,7-tetramethyl-1-benzofuran-5-amine hydrochloride To a suspension of N-[4-hydroxy-3-[1-(4-isopropylphenyl)-2-propenyl]-2,5,6-trimethylphenyl]formamide (3.50 g, 10.4 mmol) and calcium carbonate (1.35 g, 13.5 mmol) in a mixed solvent of tetrahydrofuran (15 ml) and methanol (15 ml) was gradually added benzyltrimethylammonium iododichloride (3.90 g, 11.4 mmol). The reaction solution was stirred at room temperature for 30 minutes. After filtration of the insoluble substances, the solvent was concentrated under reduced pressure. Ethyl acetate and water were added to the residue. The organic layer was separated and the aqueous layer was extracted twice with ethyl acetate. The combined organic layers were successively washed with a 10% aqueous solution of sodium hydrosulfite, water, an aqueous, saturated solution of sodium hydrogen carbonate, and an aqueous, saturated solution of sodium chloride, dried on magnesium sulfate, and then concentrated under reduced pressure to obtain 4.08 g of N-[2-iodomethyl-3-(4-isopropylphenyl)-4,6,7-trimethyl-2,3-dihydro-1-benzofuran-5-yl]formamide. A solution of this compound (4.08 g, 8.81 mmol) and 1,8-diazabicyclo[5,4,0]-7-undecene (6.58 m, 44.0 mmol) in toluene (30 ml) was stirred at 100° C. for 3 hours under an argon atmosphere. Water was added into the reaction solution and the product was extracted twice with ethyl acetate. The combined extracts were washed with 2 N hydrochloric acid and water, dried on magnesium sulfate, and then concentrated under reduced pressure. The residue was subjected to column chromatography on silica gel (hexane-ethyl acetate 20:1) to obtain 2.40 g of N-[3-(4-isopropylphenyl)-2,4,6,7-tetramethyl-1-benzofuran-5-yl]formamide. A mixture of this compound (2.40 g, 7.18 mmol), concentrated hydrochloric acid (20 ml), and methanol (60 ml) was refluxed with heating for 2 hours under a nitrogen atmosphere. The solvent was concentrated under reduced pressure and the resulting residue was neutralized with an 8 N aqueous solution of sodium hydroxide. The product was extracted twice with ethyl acetate. The combined extracts were washed with water, dried on magnesium sulfate, and then concentrated under reduced pressure to obtain 1.80 g of an oily free base. The free base (0.50 g, 1.63 mmol) was dissolved into a solution of hydrochloric acid in methanol and the solvent was concentrated under reduced pressure. The resulting residue was crystallized from methanol to obtain 0.41 g (yield 41%) of the title compound.

$^1$H-NMR (CDCl$_3$) δ: 1.29 (6H, d, J=7.0 Hz), 2.30 (6H, s), 2.41 (3H, s), 2.60 (3H, s), 2.94 (1H, septet, J=7.0 Hz), 7.13-7.26 (4H, m), 10.1 (2H, br s), 1H unidentified.

REFERENCE EXAMPLE 32b 2,2,6,7-Tetramethyl-3-phenyl-1-benzofuran-5-amine hydrochloride By using N-[4-hydroxy-3-(1-phenyl-2-propenyl)-2,5,6-trimethylphenyl]formamide, the title compound was synthesized according to Reference Example 31b. Yield: 26%. Melting point: 189-192° C. (Ethanol-hexane)

$^1$H-NMR (CDCl$_3$) δ: 2.30 (6H, s), 2.42 (3H, s), 2.60(3H, s), 7.21-7.37 (5H, m), 10.2 (2H, br s), 1H unidentified.

REFERENCE EXAMPLE 33b 3-(4-Fluorophenyl)-2,4,6,7-tetramethyl-1-benzofuran-5-amine hydrochloride By using N-[4-hydroxy-3-[1-(4-fluorophenyl)-2-propenyl]-2,5,6-trimethylphenyl]formamide, the title compound was synthesized according to Reference Example 31b. Yield: 87%. Melting point: 208-210° C. (Ethanol)

$^1$H-NMR (CDCl$_3$) δ: 2.29 (6H, s), 2.42 (3H, s), 2.60(3H, s), 7.03-7.28 (4H, m), 10.2 (2H, br s), 1H unidentified.

REFERENCE EXAMPLE 34b (1-Benzyl-4-piperidyl)(4-isopropylphenyl)(3,4,6-trimethyl-2-methoxyphenyl)methanol To a solution of 2-methoxy-3,4,6-trimethylbromobenzene (15.48 g, 67.56 mmol) in tetrahydrofuran (200 ml), which was kept at −78° C., was added dropwise under an argon atmosphere a solution of n-butyllithium in hexane (1.59 mol/l, 42 ml, 66.78 mmol) and the mixture was stirred for 30 minutes. To this mixture was added dropwise a solution of 1-benzyl-4-(4-isopropylbenzoyl)piperidine (19.81 g, 61.63 mmol) in tetrahydrofuran (50 ml) and the resulting mixture was stirred at room temperature for 30 minutes. Water was added to the reaction mixture and the product was extracted with ethyl acetate. The extracts were washed with an aqueous saturated solution of sodium chloride, dried on magnesium sulfate, filtered, and then concentrated under reduced pressure. The residue was crystallized from ethyl acetate-hexane to obtain 23.01 g (79% yield) of the title compound. Melting point: 154-156° C.

$^1$H-NMR (CDCl$_3$) δ: 1.18 (6H, d, J=7.0 Hz), 1.40-1.47 (2H, m), 1.85-1.96 (4H, m), 2.07 (3H, s), 2.17 (3H, s), 2.26 (1H, m), 2.39 (3H, s), 2.57-2.94 (6H, m), 3.48 (2H, s), 6.18 (1H, br), 6.72 (1H, s), 7.08-7.12 (2H, d, J=8.0 Hz), 7.12-7.34 (7H, m).

REFERENCE EXAMPLE 35b

1'-Benzyl-3-(4-isopropylphenyl)-4,6,7-trimethylspiro[benzofuran-2(3H),4'-piperidine]

To a solution of (1-benzyl-4-piperidyl)(4-isopropylphenyl) (3,4,6-trimethyl-2-methoxyphenyl)methanol (5.61 g, 11.89 mmol) in acetic acid (40 ml) was added a 47% hydrobromic acid (50 ml) and the resulting mixture was refluxed with heating for 13 hours. The reaction mixture was cooled down to room temperature and then an 8 N aqueous solution of sodium hydroxide was added into the mixture until it became basic. The product was extracted with ethyl acetate. The extracts were washed with an aqueous saturated solution of sodium chloride, dried on magnesium sulfate, filtered, and then concentrated under reduced pressure. The residue was crystallized from hexane to obtain 4.44 g (76% yield) of the title compound. Melting point: 125-128° C.

$^1$H-NMR (CDCl$_3$) δ: 1.20 (6H, d, J=6.8 Hz), 1.36-1.40 (2H, m), 1.72-1.95 (5H, m), 2.17 (3H, s), 2.23 (3H, s), 2.29-2.91 (5H, m), 3.52 (2H, s), 4.04 (1H, s), 6.48 (1H, m), 6.6-7.2 (4H, m), 7.22-7.32 (5H, m).

REFERENCE EXAMPLE 36b 3-(4-Isopropylphenyl)-4,6,7-trimethylspiro[benzofuran-2(3H), 4'-piperidine]hydrochloride To a solution of 1'-benzyl-3-(4-isopropylphenyl)-4,6,7-trimethylspiro[benzofuran-2(3H),4'-piperidine] (10.26 g, 23.34 mmol) in tetrahydrofuran (100 ml) was added α-chloroethyl chloroformate (3.76 g, 26.60 mmol) and the resulting mixture was refluxed with heating for 1 hour. The reaction mixture was cooled down to room temperature and concentrated under reduced pressure. Methanol (80 ml) was added into the resulting residue and the mixture was refluxed for 1 hour. The reaction mixture was cooled down to room temperature and concentrated under reduced pressure. The residue was crystallized from ethanol to obtain 7.32 g (81% yield) of the title compound. Melting point: >260° C. (decomposed).

$^1$H-NMR (DMSO-d$_6$) δ: 1.17 (6H, d, J=7.0 Hz), 1.29-1.67 (2H, m), 1.77 (3H, s), 1.95-2.05 (2H, m), 2.11 (3H, s), 2.18 (3H, s), 2.78-3.28 (5H, m), 4.31 (1H, s), 6.50 (1H, s), 6.6-7.2 (4H, m), 2H unidentified.

REFERENCE EXAMPLE 37b 3-(4-Isopropylphenyl)-1',4,6,7-tetramethylspiro[benzofuran-2(3H),4'-piperidine]

To a suspension of 3-(4-isopropylphenyl)-4,6,7-trimethylspiro[benzofuran-2(3H),4'-piperidine]hydrochloride (389.6 mg, 1.01 mmol) in acetonitrile (5 ml) was added 37% formalin (2.0 ml) and the mixture was cooled to 0° C. Sodium cyanoborohydride (101.8 mg, 1.62 mmol) was added into this mixture and the mixture was stirred at room temperature for 1 hour. The reaction mixture was concentrated under reduced pressure and an aqueous saturated solution of sodium hydrogen carbonate was added to the residue. The product was extracted twice with ethyl acetate. The combined extracts were washed with water, dried on magnesium sulfate, filtered, and then concentrated under reduced pressure. The residue was subjected to column chromatography (on Chromatorex NHDM1020 (trade name, manufactured by Fuji Silysia Chemical Ltd.); hexane-ethyl acetate 10:1) to obtain 145.0 mg (40% yield) of the title compound. Melting point: 63-64° C. (Petroleum ether)

$^1$H-NMR (CDCl$_3$) δ: 1.21 (6H, d, J=7.0 Hz), 1.34-1.41 (2H, m), 1.84 (3H, s), 1.87-1.97 (2H, m), 2.04 (3H, s), 2.17 (3H, s), 2.30 (3H, s), 2.32-2.69 (4H, m), 2.85 (1H, septet, J=7.0 Hz), 4.05 (1H, s), 6.48 (1H, s), 6.6-7.2 (4H, m).

REFERENCE EXAMPLE 38b 3-(4-Isopropylphenyl)-1',4,6,7-tetramethylspiro[benzofuran-2(3H),4'-piperidine]-5-amine A solution of nitrosyl tetrafluoroborate (470.7 mg, 4.03 mmol) in acetonitrile (40 ml) was cooled to 0° C. To the solution was added a solution of 3-(4-isopropylphenyl)-1',4,6,7-tetramethylspiro[benzofuran-2(3H),4'-piperidine] (479.1 mg, 1.32 mmol) in acetonitrile (10 ml) and the mixture was stirred for 20 minutes. The reaction mixture was poured into ice water and basified with an 8 N aqueous solution of sodium hydroxide. The product was extracted twice with ethyl acetate. The combined extracts were washed with an aqueous saturated solution of sodium hydrogen carbonate, dried on magnesium sulfate, filtered, and then concentrated under reduced pressure. The residue was dissolved into ethanol (20 ml) and palladium-carbon (59.9 mg) was added into the solution, then the mixture was stirred at 60° C. for 18 hours under a hydrogen atmosphere. The reaction mixture was cooled down to room temperature, filtered to remove insoluble materials, and then concentrated under reduced pressure. The residue was subjected to column chromatography (on Chromatorex NHDM1020 (trade name, manufactured by Fuji Silysia Chemical Ltd.); hexane-ethyl acetate 3:1) to obtain 402.0 mg (83% yield) of the title compound. Melting point: 123-124° C. (Hexane)

$^1$H-NMR (CDCl$_3$) δ: 1.10-1.38 (8H, m), 1.69-2.04 (5H, m), 2.12 (3H, s), 2.22 (3H, m), 2.25-2.51 (7H, m), 2.84 (1H, septet, J=6.6 Hz), 3.23 (2H, br), 4.05 (1H, s), 6.6-7.1 (4H, m).

REFERENCE EXAMPLE 39b

4-Methoxy-2,3,6-trimethylaniline

N-(4-Hydroxy-2,3,6-trimethylphenyl)formamide (30.0 g, 167 mmol) was dissolved into a mixed solvent comprising of a 4 N aqueous solution of potassium hydroxide (100 ml) and methanol (300 ml) and then dimethyl sulfate (42.0 g, 334 mmol) was added into the resulting solution. The mixture was refluxed with heating for 14 hours. The reaction mixture was cooled down and the crystals precipitated were collected by filtration to obtain N-(4-methoxy-2,3,6-trimethylphenyl)formamide as a crude product. To a suspension of this compound in methanol (200 ml) was added concentrated hydrochloric acid (50 ml) and the mixture was refluxed with heating for 3 hours. The reaction mixture was cooled down to room temperature and then neutralized with an 8 N aqueous solution of sodium hydroxide. The product was extracted twice with ethyl acetate. The combined extracts were washed with a 10% aqueous solution of sodium hydrosulfite, dried on magnesium sulfate, and then concentrated under reduced pressure. The residue was crystallized from isopropyl ether to obtain 21.0 g (76% yield) of the title compound. Melting point: 70-72° C.

$^1$H-NMR (CDCl$_3$) δ: 2.11 (3H, s), 2.16 (3H, s), 2.18 (3H, s), 3.16 (1H, br s), 3.74 (3H, s), 6.54 (1H, s).

REFERENCE EXAMPLE 40b

Tert-butyl 4-methoxy-2,3,6-trimethylphenylcarbamate

To a solution of 4-methoxy-2,3,6-trimethylaniline (21.0 g, 127 mmol) and triethylamine (21.0 ml, 152 mmol) in tetrahydrofuran (150 ml) was added at room temperature di-tert-butyl dicarbonate (32 ml, 140 mmol) and the resulting mixture was refluxed with heating for 14 hours. The solvent was concentrated under reduced pressure. Water was added into the residue and the product was extracted twice with ethyl acetate. The combined organic layers were washed with 1N hydrochloric acid and an aqueous saturated solution of sodium hydrogen carbonate, dried on magnesium sulfate, filtered, and then concentrated under reduced pressure. The residue was crystallized from ethyl acetate-hexane to obtain 25.2 g (75% yield) of the title compound. Melting point: 104-106° C.

$^1$H-NMR (CDCl$_3$) δ: 1.50 (9H, s), 2.12 (3H, s), 2.17 (3H, s), 2.24 (3H, s), 3.78 (3H, s), 5.81 (1H, br s), 6.58 (1H, s).

REFERENCE EXAMPLE 41b

Tert-butyl 3-bromo-4-methoxy-2,5,6-trimethylphenylcarbamate

To a solution of tert-butyl 4-methoxy-2,3,6-trimethylphenylcarbamate (12.7 g, 47.9 mmol) and sodium acetate (4.72 g, 57.5 mg) in acetic acid (50 ml) was added at room temperature bromine (8.42 g, 52.7 mmol) and the resulting mixture was stirred at the same temperature for 1 hour. Water (80 ml) was added into the reaction mixture. The crystals precipitated were collected by filtration and dissolved into ethyl acetate. The solution was washed with an aqueous saturated solution of sodium hydrogen carbonate, dried on magnesium sulfate, filtered, and then concentrated under reduced pressure. The residue was crystallized from methanol to obtain 15.0 g (91% yield) of the title compound. Melting point: 159-161° C.

$^1$H-NMR (CDCl$_3$) δ: 1.50 (9H, s), 2.15 (3H, s), 2.24 (3H, s), 2.35 (3H, s), 3.74 (3H, s), 5.92 (1H, br s).

REFERENCE EXAMPLE 42b 2,2,4,6,7-Pentamethyl-3-(4-methylphenyl)-2,3-dihydro-1-benzofuran-5-amine To a solution of tert-butyl 3-bromo-4-methoxy-2,5,6-trimethylphenylcarbamate (27.8 g, 80.8 mmol) in tetrahydrofuran (150 ml) was added at −78° C. n-butyllithium (1.6 M, 110 ml, 176 mmol) and the reaction mixture was stirred at the same temperature for 20 minutes. To the reaction solution was added 2-methyl-1-(4-methylphenyl)propan-1-one (13.1 g, 80.7 mmol) and stirred at room temperature for 1 hour. Water (150 ml) was added to the reaction mixture and the product was extracted three times with ethyl acetate. The combined organic layers were washed with water, dried on magnesium sulfate, filtered, and then concentrated under reduced pressure to obtain 26.0 g of tert-butyl 3-[1-hydroxy-2-methyl-1-(4-methylphenyl)propyl]-4-methoxy-2,5,6-trimethylphenyl-carbamate as a crude product. A mixture of this compound and 47% hydrobromic acid (100 ml) was refluxed with heating for 4 hours under argon atmosphere. The reaction mixture was cooled down to room temperature and neutralized with an 8 N aqueous solution of sodium hydroxide. The product was extracted twice with ethyl acetate. The combined extracts were washed with an aqueous, saturated solution of sodium hydrogen carbonate, dried on magnesium sulfate, and then concentrated under reduced pressure. The residue was crystallized from isopropyl ether-hexane to obtain 14.8 g (62% yield) of the title compound. Melting point: 114-115° C.

$^1$H-NMR (CDCl$_3$) δ: 0.99 (3H, s), 1.47 (3H, s), 1.78 (3H, s), 2.12 (3H, s), 2.17 (3H, s), 2.30 (3H, s), 2.80 (2H, br s), 4.08 (1H, s), 6.60-7.10 (4H, m).

REFERENCE EXAMPLE 43b (+)-3-(4-Isopropylphenyl)-2,2,4,6,7-pentamethyl-2,3-dihydro-1-benzofuran-5-amine 3-(4-Isopropylphenyl)-2,2,4,6,7-pentamethyl-2,3-dihydro-1-benzofuran-5-amine was subjected to high performance liquid chromatography (instrument: Waters semi-preparative separation system, column: CHIRALCEL OD (20 (i, d)×250 mm) manufactured by Daicel Chemical Industries, LTD.), mobile phase:hexane:isopropyl alcohol=98:2, flow rate: 6 ml/min, column temperature: 30° C., sample injection amount: 40 mg) to preparatively separate a fraction with a shorter retention time as the title compound. Melting point: 72-75° C. [α]D=+2.8° (c=0.500, methanol)

REFERENCE EXAMPLE 44b (−)-3-(4-Isopropylphenyl)-2,2,4,6,7-pentamethyl-2,3-dihydro-1-benzofuran-5-amine 3-(4-Isopropylphenyl)-2,2,4,6,7-pentamethyl-2,3-dihydro-1-benzofuran-5-amine was subjected to high performance liquid chromatography (instrument: Waters semi-preparative separation system, column: CHIRALCEL OD (20 (i, d)×250 mm) manufactured by Daicel Chemical Industries, LTD.), mobile phase: hexane:isopropyl alcohol=98:2, flow rate: 6 ml/min, column temperature: 30° C., sample injection amount: 40 mg) to preparatively separate a fraction with a shorter retention time as the title compound. Melting point: 74-76° C. [α]D=−3.3° (c=0.506, methanol)

Example 1b

4-Methoxy-N-(2,2,4,6,7-pentamethyl-3-phenyl-2,3-dihydro-1-benzofuran-5-yl)benzamide To a solution of 2,2,4,6,7-pentamethyl-3-phenyl-2,3-dihydro-1-benzofuran-5-amine (1.60 g, 5.69 mmol) and 4-methoxybenzoyl chloride (1.16 g, 6.82 mmol) in chloroform (20 ml) was added triethylamine (0.87 ml, 6.26 mmol) and the mixture was stirred at room temperature for 30 minutes. The solvent was removed under reduced pressure. Water (30 ml) was added into the residue and the product was extracted twice with ethyl acetate. The combined organic layers were washed with 1N hydrochloric acid and an aqueous, saturated solution of sodium hydrogen carbonate, dried on magnesium sulfate, filtered, and then concentrated under reduced pressure. The residue was crystallized from methanol to obtain 1.70 g (72% yield) of the title compound. Melting point: 190-192° C.

$^1$H-NMR (CDCl$_3$) δ: 1.03 (3H, s), 1.53 (3H, s), 1.80 (3H, s), 2.19 (6H, s), 3.86 (3H, s), 4.16 (1H, s), 6.80-7.36 (8H, m), 7.86 (2H, d, J=8.8 Hz).

Example 2b

N-(4-Methoxybenzyl)-2,2,4,6,7-pentamethyl-3-phenyl-2,3-dihydro-1-benzofuran-5-amine To a suspension of aluminum chloride (2.25 g, 16.9 mmol) in tetrahydrofuran (20 ml) was gradually added under ice cooling lithium aluminum hydride (640 mg, 16.9 mmol) and the resulting mixture was stirred at the same temperature for 10 minutes. To this mixture was added 4-Methoxy-N-(2,2,4,6,7-pentamethyl-3-phenyl-2,3-dihydro-1-benzofuran-5-yl)benzamide (1.40 g, 3.37 mmol) and the mixture was refluxed with heating for 3 hours. The reaction mixture was poured into ice water and neutralized with an 8 N aqueous solution of sodium hydroxide. The product was extracted twice with ethyl acetate. The combined organic layers were washed with water, dried on magnesium sulfate, filtered, and then concentrated under reduced pressure. The residue was crystallized from methanol to obtain 0.80 g (59% yield) of the title compound. Melting point: 113-115° C.

$^1$H-NMR (CDCl$_3$) δ: 1.01 (3H, s), 1.50 (3H, s), 1.78 (3H, s), 1.98 (1H, br s), 2.18 (3H, s), 2.27 (3H, s), 3.79 (3H, s), 3.85 (2H, s), 4.11 (1H, s), 6.80-7.31 (9H, m).

Example 3b

4-Fluoro-N-(2,2,4,6,7-pentamethyl-3-phenyl-2,3-dihydro-1-benzofuran-5-yl)benzamide By using 2,2,4,6,7-pentamethyl-3-phenyl-2,3-dihydro-1-benzofuran-5-amine and 4-fluorobenzoyl chloride, the title compound was synthesized according to Example 1b. Yield: 92%. Melting point: 156-158° C. (Ethyl acetate)

$^1$H-NMR (CDCl$_3$) δ: 1.03 (3H, s), 1.53 (3H, s), 1.80 (3H, s), 2.19 (3H, s), 2.20 (3H, s), 4.17 (1H, s), 6.62-7.35 (8H, m), 7.85-7.94 (2H, m).

Example 4b

N-(4-Fluorobenzyl)-2,2,4,6,7-pentamethyl-3-phenyl-2,3-dihydro-1-benzofuran-5-amine By using 4-fluoro-N-(2,2,4,6,7-pentamethyl-3-phenyl-2,3-dihydro-1-benzofuran-5-yl)benzamide, the title compound was synthesized according to Example 2b. Yield: 60%. Melting point: 93-95° C. (Methanol)

$^1$H-NMR (CDCl$_3$) δ: 1.01 (3H, s), 1.52 (3H, s), 1.76 (3H, s), 2.18 (3H, s), 2.26 (3H, s), 2.61 (1H, br s), 3.88 (2H, s), 4.11 (1H, s), 6.62-7.40 (9H, m).

Example 5b

N-[3-(4-Isopropylphenyl)-2,2,4,6,7-pentamethyl-2,3-dihydro-1-benzofuran-5-yl]benzamide By using 3-(4-isopropylphenyl)-2,2,4,6,7-pentamethyl-2,3-dihydro-1-benzofuran-5-amine and benzoyl chloride, the title compound was synthesized according to Example 1b. Yield: 90%. Melting point: 218-220° C. (Ethyl acetate-hexane)

$^1$H-NMR (CDCl$_3$) δ: 1.03 (3H, s), 1.21 (6H, d, J=7.0 Hz), 1.52 (3H, s), 1.82 (3H, s), 2.19 (6H, s), 2.85 (1H, septet, J=7.0 Hz), 4.14 (1H, s), 6.70-7.13 (4H, m), 7.30 (1H, br s), 7.42-7.61 (3H, m), 7.85-7.92 (2H, m).

Example 6b

N-Benzyl-3-(4-isopropylphenyl)-2,2,4,6,7-pentamethyl-2,3-dihydro-1-benzofuran-5-amine hydrochloride To a suspension of aluminum chloride (1.18 g, 8.89 mmol) in tetrahydrofuran (20 ml) was gradually added under ice cooling lithium aluminum hydride (337 mg, 8.89 mmol) and the resulting mixture was stirred at the same temperature for 10 minutes. To this mixture was added N-[3-(4-isopropylphenyl)-2,2,4,6,7-pentamethyl-2,3-dihydro-1-benzofuran-5-yl]benzamide (0.76 g, 1.78 mmol) and the mixture was refluxed with heating for 3 hours. The reaction mixture was poured into ice water and neutralized with an 8 N aqueous solution of sodium hydroxide. The product was extracted twice with ethyl acetate. The combined organic layers were washed with water, dried on magnesium sulfate, filtered, and then concentrated under reduced pressure to obtain 0.52 g of an oily free base. The free base (0.52 g, 1.26 mmol) was dissolved into a solution of hydrochloric acid in methanol and then solvent was concentrated under reduced pressure. The resulting residue was crystallized from methanol to obtain 0.47 g (59% yield) of the title compound. Melting point: 186-188° C.

$^1$H-NMR (DMSO-d$_6$) δ: 0.94 (3H, s), 1.20 (6H, d, J=6.6 Hz), 1.41 (3H, s), 1.62 (3H, s), 2.10 (3H, s), 2.26 (3H, s), 2.86 (1H, septet, J=6.6 Hz), 4.14 (1H, s), 4.23-4.58 (2H, s), 6.40-7.42 (9H, m), 10.4 (2H, br s).

Example 7b

N-[3-(4-Isopropylphenyl)-2,2,4,6,7-pentamethyl-2,3-dihydro-1-benzofuran-5-yl]-4-methoxybenzamide By using 3-(4-isopropylphenyl)-2,2,4,6,7-pentamethyl-2,3-dihydro-1-benzofuran-5-amine and 4-methoxybenzoyl chloride, the title compound was synthesized according to Example 1b. Yield: 42%. Melting point: 202-205° C. (Ethyl acetate-hexane)

$^1$H-NMR (CDCl$_3$) δ: 1.02 (3H, s), 1.21 (6H, d, J=6.8 Hz), 1.49 (3H, s), 1.80 (3H, s), 2.18 (6H, s), 2.85 (1H, septet, J=6.8 Hz), 3.86 (3H, s), 4.13 (1H, s), 6.62-7.19 (6H, m), 7.23 (1H, s), 7.85 (2H, d, J=9.2 Hz).

Example 8b 3-(4-Isopropylphenyl)-N-(4-methoxybenzyl)-2,2,4,6,7-pentamethyl-2,3-dihydro-1-benzofuran-5-amine By using N-[3-(4-isopropylphenyl)-2,2,4,6,7-pentamethyl-2,3-dihydro-1-benzofuran-5-yl]-4-methoxybenzamide, the title compound was synthesized according to Example 2b. Yield: 80%. Melting point: 95-96° C. (Hexane)

$^1$H-NMR (CDCl$_3$) δ: 1.00 (3H, s), 1.22 (6H, d, J=6.8 Hz), 1.49 (3H, s), 1.6-1.7 (1H, br), 1.79 (3H, s), 2.81 (3H, s), 2.27 (3H, s), 2.86 (1H, septet, J=6.8 Hz), 3.80 (3H, s), 3.86 (2H, s), 4.09 (1H, s), 6.81-6.88 (4H, m), 7.06-7.11 (2H, m), 7.24-7.28 (2H, m).

Example 9b 3-(4-Isopropylphenyl)-N-(4-methoxybenzyl)-N,2,2,4,6,7-hexamethyl-2,3-dihydro-1-benzofuran-5-amine Sodium hydride (a 60% dispersion in liquid paraffin, 598.8 mg, 14.97 mmol) was washed twice with hexane and then suspended to N,N-dimethylformamide (10 ml). To this suspension was gradually added a solution of 3-(4-isopropylphenyl)-N-(4-methoxybenzyl)-2,2,4,6,7-pentamethyl-2,3-dihydro-1-benzofuran-5-amine (998.9 mg, 2.25 mmol) in N,N-dimethylformamide (30 ml) and the reaction mixture was stirred at 60° C. for 30 minutes. To this mixture was added methyl iodide (2.19 g, 15.45 mmol) and the mixture was stirred at the same temperature for 30 minutes. The reaction solution was cooled down to room temperature and water was added to the solution. The product was extracted with ethyl acetate. The extracts were dried on magnesium sulfate, filtered, and concentrated under reduced pressure. The residue was subjected to column chromatography on silica gel (hexane-ethyl acetate 10:1) to obtain the title compound (69% yield) as an oily mixture of rotamers.

$^1$H-NMR (CDCl$_3$) δ: 0.97-1.00 (3H, s), 1.20-1.25 (6H, m), 1.50 (3H, m), 1.83-1.88 (3H, m), 2.14-2.16 (3H, m), 2.27-2.28 (3H, m), 2.59-2.67 (3H, m), 2.80-2.94 (1H, m), 3.79-3.80 (3H, m), 4.03-4.06 (2H, m), 4.08-4.10 (1H, m), 6.78-6.87 (4H, m), 7.06-7.30 (4H, m).

Example 10b

N-[3-(4-Isopropylphenyl)-2,2,4,6,7-pentamethyl-2,3-dihydro-1-benzofuran-5-yl]-4-methoxyphenylacetamide By using 3-(4-isopropylphenyl)-2,2,4,6,7-pentamethyl-2,3-dihydro-1-benzofuran-5-amine and 4-methoxyphenylacetyl chloride, the title compound was synthesized according to Example 1b. Yield: 74%. Melting point: 171-173° C. (Methanol)

$^1$H-NMR (CDCl$_3$) δ: 0.98 (3H, s), 1.20 (6H, d, J=6.6 Hz), 1.46 (3H, s), 1.64 (3H, s), 2.03 (3H, s), 2.12 (3H, s), 2.84 (1H, septet, J=6.6 Hz), 3.68 (2H, s), 3.80 (3H, s), 4.06 (1H, s), 6.45 (1H, br), 6.6-6.9 (2H, m), 6.89 (2H, d, J=8.6 Hz), 7.05 (2H, d, J=8.0 Hz), 7.26 (d, 2H, J=8.6 Hz).

Example 11b 3-(4-Isopropylphenyl)-N-[2-(4-methoxyphenyl)ethyl]-2,2,4,6,7-pentamethyl-2,3-dihydro-1-benzofuran-5-amine By using N-[3-(4-isopropylphenyl)-2,2,4,6,7-pentamethyl-2,3-dihydro-1-benzofuran-5-yl]-4-methoxyphenylacetamide, the title compound was synthesized according to Example 2b. Yield: 66%. Melting point: 63-65° C. (Hexane)

$^1$H-NMR (CDCl$_3$) δ: 0.98 (3H, s), 1.21 (6H, d, J=6.8 Hz), 1.46 (3H, s), 1.68 (3H, s), 1.8-1.9 (1H, br), 2.12 (3H, s), 2.14 (3H, s), 2.76-3.04 (5H, m), 3.78 (3H, s), 4.05 (1H, s), 6.6-7.0 (4H, m), 7.04-7.08 (4H, m), 7.12-7.19 (2H, m).

Example 12b 3-(4-Isopropylphenyl)-N-[2-(4-methoxyphenyl)ethyl]-N,2,2,4,6,7-hexamethyl-2,3-dihydro-1-benzofuran-5-amine By using 3-(4-isopropylphenyl)-N-[2-(4-methoxyphenyl)ethyl]-2,2,4,6,7-pentamethyl-2,3-dihydro-1-benzofuran-5-amine, the title compound was synthesized according to Example 9b. Yield: 85%. An oily substance.

$^1$H-NMR (CDCl$_3$) δ: 0.99 (3H, s), 1.20-1.24 (6H, m), 1.48-1.50 (3H, m), 1.77 (3H, s), 2.14-2.17 (6H, m), 2.58-2.89 (6H, m), 3.1-3.2 (2H, m), 3.76-3.77 (3H, m), 4.06-4.09 (1H, m), 6.74-6.90 (4H, m), 7.00-7.04 (4H, m).

Example 13b

N-[3-(4-Isopropylphenyl)-2,2,4,6,7-pentamethyl-2,3-dihydro-1-benzofuran-5-yl]-N-[2-(4-methoxyphenyl)ethyl]acetamide Sodium hydride (a 60% dispersion in liquid paraffin, 232.1 mg, 5.80 mmol) was washed twice with hexane and then suspended to N,N-dimethylformamide (25 ml). To this suspension was added under an argon atmosphere 3-(4-isopropylphenyl)-N-[2-(4-methoxyphenyl)ethyl]-2,2,4,6,7-pentamethyl-2,3-dihydro-1-benzofuran-5-amine (537.9 mg, 1.18 mmol) and the reaction mixture was stirred at 60° C. for 20 minutes. Then, acetyl chloride (0.5 ml, 7.03 mmol) was added into the reaction mixture and stirred at the same temperature for 1 hour. After the reaction solution was cooled down to room temperature, an aqueous saturated solution of sodium hydrogen carbonate was added to the reaction mixture and the product was extracted twice with ethyl acetate. The combined extracts were washed with water, dried on magnesium sulfate, filtered, and concentrated under reduced pressure. The residue was subjected to column chromatography on silica gel (hexane-ethyl acetate 3:1) to obtain the rotamer 1 (Rf=0.38; hexane-ethyl acetate 3:1) of the title compound (46% yield). Melting point: 134-136° C. (Ethyl acetate-hexane)

$^1$H-NMR (CDCl$_3$) δ: 1.03 (3H, s), 1.22 (6H, d, J=7.0 Hz), 1.54 (3H, s), 1.66 (3H, s), 1.72 (3H, s), 2.12 (3H, s), 2.18 (3H, s), 2.77-2.89 (3H, m), 3.59-3.70 (2H, m), 3.77 (3H, s), 4.11 (1H, s), 6.77-7.13 (8H, m).

Example 14b

N-[3-(4-Isopropylphenyl)-2,2,4,6,7-pentamethyl-2,3-dihydro-1-benzofuran-5-yl]-N-[2-(4-methoxyphenyl)ethyl]acetamide The residue treated in the same manner as described in the Example 13b was subjected to column chromatography on silica gel (hexane-ethyl acetate 3:1) to obtain the rotamer 2 (Rf=0.25; hexane-ethyl acetate 3:1) of the title compound (36% yield). Amorphous.

$^1$H-NMR (CDCl$_3$) δ: 1.03 (3H, s), 1.23 (6H, d, J=6.8 Hz), 1.53 (3H, s), 1.73 (3H, s), 1.75 (3H, s), 2.12 (3H, s), 2.18 (3H, s), 2.67-2.75 (2H, m), 2.80-2.94 (1H, septet, J=6.8 Hz), 3.57-3.74 (2H, s), 3.77 (3H, s), 4.14 (1H, S), 6.77-7.13 (8H, m).

Example 15b

N-[3-(4-Isopropylphenyl)-2,2,4,6,7-pentamethyl-2,3-dihydro-1-benzofuran-5-yl]-3-(4-methoxyphenyl)propionamide By using 3-(4-isopropylphenyl)-2,2,4,6,7-pentamethyl-2,3-dihydro-1-benzofuran-5-amine and 3-(4-methoxyphenyl)propionyl chloride, the title compound was synthesized according to Example 1b. Yield: 72%. Melting point: 188-191° C. (Ethyl acetate-hexane).

$^1$H-NMR (CDCl$_3$) δ: 0.99-1.01 (3H, m), 1.19-1.26 (6H, m), 1.48 (3H, s), 1.64-1.68 (3H, m), 1.99 (3H, s), 2.05-2.13 (5H, m), 2.65-3.04 (3H, m), 3.72-3.77 (3H, m), 4.08 (1H, s), 6.47-7.19 (9H, m).

Example 16b 3-(4-Isopropylphenyl)-N-[3-(4-methoxyphenyl)propyl]-2,2,4,6,7-pentamethyl-2,3-dihydro-1-benzofuran-5-amine By using N-[3-(4-isopropylphenyl)-2,2,4,6,7-pentamethyl-2,3-dihydro-1-benzofuran-5-yl]-3-(4-methoxyphenyl)propionamide, the title compound was synthesized according to Example 2b. Yield: 99%. Melting point: 62-65° C. (Pentane)

$^1$H-NMR (CDCl$_3$) δ: 0.99 (3H, s), 1.21 (6H, d, J=6.6 Hz), 1.48 (3H, s), 1.78-1.88 (6H, s), 2.15 (3H, s), 2.20 (3H, s), 2.65 (2H, t, J=7.6 Hz), 2.76 (3H, m), 3.78 (3H, s), 4.08 (1H, s), 6.6-6.8 (4H, m), 7.05-7.12 (4H, m).

Example 17b

N-[3-(4-Isopropylphenyl)-2,2,4,6,7-pentamethyl-2,3-dihydro-1-benzofuran-5-yl]-4-methoxybenzenesulfonamide To a solution of 3-(4-isopropylphenyl)-2,2,4,6,7-pentamethyl-2,3-dihydro-1-benzofuran-5-amine (0.35 g, 1.08 mmol) and 4-methoxybenzenesulfonyl chloride (0.25 g, 1.19 mmol) in chloroform (5 ml) was added triethylamine (0.16 ml, 1.19 mmol) and the mixture was stirred at room temperature for 14 hours. The solvent was concentrated under reduced pressure. Water (20 ml) was added into the residue and the product was extracted twice with ethyl acetate. The combined organic layers were washed with 1N hydrochloric acid and an aqueous saturated solution of sodium hydrogen carbonate, dried on magnesium sulfate, filtered, and then concentrated under reduced pressure. The residue was crystallized from ethyl acetate-hexane to obtain 0.18 g (34% yield) of the title compound. Melting point: 206-208° C.

$^1$H-NMR (CDCl$_3$) δ: 0.99 (3H, s), 1.23 (6H, d, J=6.8 Hz), 1.40 (3H, s), 1.47 (3H, s), 2.10 (3H, s), 2.13 (3H, s), 2.87 (1H, septet, J=6.8 Hz), 3.80 (3H, s), 3.90 (1H, s), 5.79 (1H, s), 6.70-7.15 (4H, m), 7.09 (2H, d, J=8.4 Hz), 7.57 (2H, d, J=8.8 Hz).

Example 18b

4-Fluoro-N-[3-(4-isopropylphenyl)-2,2,4,6,7-pentamethyl-2,3-dihydro-1-benzofuran-5-yl]benzamide By using 3-(4-isopropylphenyl)-2,2,4,6,7-pentamethyl-2,3-dihydro-1-benzofuran-5-amine and 4-fluorobenzoyl chloride, the title compound was synthesized according to Example 1b. Yield: 65%. Amorphous.

¹H-NMR (CDCl₃) δ: 1.02 (3H, s), 1.21 (6H, d, J=6.8 Hz), 1.41 (3H, s), 1.80 (3H, s), 2.17 (3H, s), 2.19 (3H, s), 2.85 (1H, septet, J=6.8 Hz), 4.13 (1H, s), 6.60-7.31 (7H, m), 7.89 (2H, dd, J=8.8, 5.2 Hz).

Example 19b

N-(4-Fluorobenzyl)-3-(4-isopropylphenyl)-2,2,4,6,7-pentamethyl-2,3-dihydro-1-benzofuran-5-amine hydrochloride To a suspension of aluminum chloride (1.20 g, 9.00 mmol) in tetrahydrofuran (25 ml) was gradually added under ice cooling lithium aluminum hydride (340 mg, 9.00 mmol) and the resulting mixture was stirred at the same temperature for 10 minutes. To this mixture was added 4-fluoro-N-[3-(4-isopropylphenyl)-2,2,4,6,7-pentamethyl-2,3-dihydro-1-benzofuran-5-yl]benzamide (0.83 g, 1.86 mmol) and the mixture was refluxed with heating for 3 hours. The reaction mixture was poured into ice water and neutralized with an 8 N aqueous solution of sodium hydroxide. The product was extracted twice with ethyl acetate. The combined organic layers were washed with water, dried on magnesium sulfate, filtered, and then concentrated under reduced pressure to obtain 0.51 g of an oily free base. The free base (0.51 g, 1.18 mmol) was dissolved into a solution of hydrochloric acid in methanol and then solvent was concentrated under reduced pressure. The resulting residue was crystallized from methanol to obtain 0.49 g (56% yield) of the title compound. Melting point: 201-204° C.

¹H-NMR (DMSO-d₆) δ: 0.92 (3H, s), 1.19 (6H, d, J=7.0 Hz), 1.40 (3H, s), 1.54 (3H, s), 2.10 (3H, s), 2.31 (3H, s), 2.85 (1H, septet, J=6.8 Hz), 4.13 (1H, s), 4.29 (1H, d, J=12.8 Hz), 4.43 (1H, d, J=12.8 Hz), 6.20-7.40 (8H, m), 10.4 (2H, br s).

Example 20b

4-Chloro-N-[3-(4-isopropylphenyl)-2,2,4,6,7-pentamethyl-2,3-dihydro-1-benzofuran-5-yl]benzamide By using 3-(4-isopropylphenyl)-2,2,4,6,7-pentamethyl-2,3-dihydro-1-benzofuran-5-amine and 4-chlorobenzoyl chloride, the title compound was synthesized according to Example 1b. Yield: 71%. Melting point: 201-203° C. (Ethyl acetate-hexane)

¹H-NMR (CDCl₃) δ: 1.02 (3H, s), 1.21 (6H, d, J=7.0 Hz), 1.51 (3H, s), 1.80 (3H, s), 2.17 (3H, s), 2.19 (3H, s), 2.85 (1H, septet, J=6.8 Hz), 4.13 (1H, s), 6.62-7.31 (4H, m), 7.24 (1H, br s), 7.44 (2H, d, J=8.8 Hz), 7.82 (2H, d, J=8.8 Hz).

Example 21b

N-(4-Chlorobenzyl)-3-(4-isopropylphenyl)-2,2,4,6,7-pentamethyl-2,3-dihydro-1-benzofuran-5-amine By using 4-chloro-N-[3-(4-isopropylphenyl)-2,2,4,6,7-pentamethyl-2,3-dihydro-1-benzofuran-5-yl]benzamide, the title compound was synthesized according to Example 2b. Yield: 37%. Melting point: 93-94° C. (Methanol)

¹H-NMR (CDCl₃) δ: 1.00 (3H, s), 1.22 (6H, d, J=7.0 Hz), 1.49 (3H, s), 1.58 (1H, br s), 1.74 (3H, s), 2.18 (3H, s), 2.25 (3H, s), 2.86 (1H, septet, J=6.8 Hz), 3.89 (2H, s), 4.07 (1H, s), 6.63-7.12 (4H, m), 7.25 (4H, s).

Example 22b

N-[3-(4-Isopropylphenyl)-2,2,4,6,7-pentamethyl-2,3-dihydro-1-benzofuran-5-yl]-1,3-benzodioxol-5-carboxamide By using 3-(4-isopropylphenyl)-2,2,4,6,7-pentamethyl-2,3-dihydro-1-benzofuran-5-amine and 1,3-benzodioxol-5-carbonyl chloride, the title compound was synthesized according to Example 1b. Yield: 67%. Melting point: 165-167° C. (Ethyl ether-hexane)

¹H-NMR (CDCl₃) δ: 1.02 (3H, s), 1.21 (6H, d, J=7.0 Hz), 1.51 (3H, s), 1.80 (3H, s), 2.17 (3H, s), 2.18 (3H, s), 2.85 (1H, septet, J=7.0 Hz), 4.13 (1H, s), 6.03 (2H, s), 6.63-7.13 (5H, m), 7.17 (1H, br s), 7.35-7.45 (2H, m).

Example 23b

N-(1,3-Benzodioxol-5-ylmethyl)-3-(4-isopropylphenyl)-2,2,4,6,7-pentamethyl-2,3-dihydro-1-benzofuran-5-amine To a suspension of aluminum chloride (847 mg, 6.35 mmol) in tetrahydrofuran (10 ml) was gradually added under ice cooling lithium aluminum hydride (240 mg, 6.35 mmol) and the resulting mixture was stirred at the same temperature for 10 minutes. To this mixture was added N-[3-(4-isopropylphenyl)-2,2,4,6,7-pentamethyl-2,3-dihydro-1-benzofuran-5-yl]-1,3-benzodioxol-5-carboxamide (0.60 g, 1.27 mmol) and the mixture was refluxed with heating for 3 hours. The reaction mixture was poured into ice water and neutralized with an 8 N aqueous solution of sodium hydroxide. The product was extracted twice with ethyl acetate. The combined organic layers were washed with water, dried on magnesium sulfate, filtered, and then concentrated under reduced pressure. The residue was crystallized from methanol to obtain 0.23 g (40% yield) of the title compound. Melting point: 100-102° C.

¹H-NMR (CDCl₃) δ: 1.00 (3H, s), 1.22 (6H, d, J=7.0 Hz), 1.49 (3H, s), 1.80 (3H, s), 1.86 (1H, br s), 2.17 (3H, s), 2.26 (3H, s), 2.86 (1H, septet, J=7.0 Hz), 3.82 (2H, s), 4.08 (1H, s), 5.93 (2H, s), 6.62-7.00 (5H, m), 7.08 (2H, d, J=8.0 Hz).

Example 24b

N-[3-(4-Isopropylphenyl)-2,2,4,6,7-pentamethyl-2,3-dihydro-1-benzofuran-5-yl]-2-thiophenecarboxamide By using 3-(4-isopropylphenyl)-2,2,4,6,7-pentamethyl-2,3-dihydro-1-benzofuran-5-amine and 2-thiophenecarbonyl chloride, the title compound was synthesized according to Example 1b. Yield: 66%. Melting point: 222-224° C. (Ethyl acetate-hexane)

¹H-NMR (CDCl₃) δ: 1.02 (3H, s), 1.21 (6H, d, J=7.0 Hz), 1.51 (3H, s), 1.82 (3H, s), 2.19 (3H, s), 2.85 (1H, septet, J=7.0 Hz), 4.13 (1H, s), 6.70-7.20 (6H, m), 7.50 (1H, dd, J=4.8, 1.2 Hz), 7.63 (1H, dd, J=3.6, 1.2 Hz).

Example 25b 3-(4-Isopropylphenyl)-2,2,4,6,7-pentamethyl-N-(2-thienylmethyl)-2,3-dihydro-1-benzofuran-5-amine By using N-[3-(4-isopropylphenyl)-2,2,4,6,7-pentamethyl-2,3-dihydro-1-benzofuran-5-yl]-2-thiophenecarboxamide, the title compound was synthesized according to Example 2b. Yield: 61%. Melting point: 101-103° C. (Methanol)

¹H-NMR (CDCl₃) δ: 1.00 (3H, s), 1.22 (6H, d, J=7.0 Hz), 1.49 (3H, s), 1.80 (3H, s), 3.00-2.40 (7H, s), 2.86 (1H, septet, J=7.0 Hz), 4.08 (1H, s), 4.11 (2H, s), 6.71-7.30 (7H, m).

Example 26b

N-[3-4-(Isopropylphenyl)-2,2,4,6,7-pentamethyl-2,3-dihydro-1-benzofuran-5-yl]nicotinamide To a solution of 3-(4-isopropylphenyl)-2,2,4,6,7-pentamethyl-2,3-dihydro-1-benzofuran-5-amine (0.85 g, 2.63 mmol) and nicotinoyl chloride hydrochloride (516 mg, 2.90 mmol) in chloroform (15 ml) was added triethylamine (0.80 ml, 5.80 mmol) and the mixture was stirred at room temperature for 30 minutes. The solvent was concentrated under reduced pressure. Water (30 ml) was added into the residue and the product was extracted twice with ethyl acetate. The combined organic layers were washed with an aqueous saturated solution of sodium hydrogen carbonate, dried on magnesium sulfate, filtered, and then concentrated under reduced pressure. The residue was subjected to column chromatography (hexane-ethyl acetate 5:1) on silica gel to obtain 0.72 g (61% yield) of the title compound. Melting point: 214-216° C. (Ethyl ether-hexane)

¹H-NMR (CDCl₃) δ: 1.03 (3H, s), 1.21 (6H, d, J=7.0 Hz), 1.52 (3H, s), 1.82 (3H, s), 2.19 (6H, s), 2.86 (1H, septet, J=7.0 Hz), 4.14 (1H, s), 6.70-7.13 (4H, m), 7.31 (1H, br s), 7.44 (1H, dd, J=7.8, 4.8 Hz), 8.23 (1H, dt, J=8.0, 2.2 Hz), 8.74-8.79 (1H, m), 9.12 (1H, br s).

Example 27b

N-[3-(4-Isopropylphenyl)-2,2,4,6,7-pentamethyl-2,3-dihydro-1-benzofuran-5-yl]isonicotinamide hydrochloride To a solution of 3-(4-isopropylphenyl)-2,2,4,6,7-pentamethyl-2,3-dihydro-1-benzofuran-5-amine (0.85 g, 2.63 mmol) and isonicotinoyl chloride hydrochloride (516 mg, 2.90 mmol) in chloroform (15 ml) was added triethylamine (0.80 ml, 5.80 mmol) and the mixture was stirred at room temperature for 30 minutes. The solvent was concentrated under reduced pressure. Water (30 ml) was added into the residue and the product was extracted twice with ethyl acetate. The combined organic layers were washed with an aqueous saturated solution of sodium hydrogen carbonate, dried on magnesium sulfate, filtered, and then concentrated under reduced pressure. The residue was subjected to column chromatography (hexane-ethyl acetate 5:1) on silica gel to obtain 0.90 g of an oily free base. The free base (0.90 g, 2.10 mmol) was dissolved into a solution of hydrochloric acid in methanol and the solvent was concentrated under reduced pressure to obtain 0.47 g (64% yield) of the amorphous title compound.

¹H-NMR (CDCl₃) δ: 0.99 (3H, s), 1.19 (6H, d, J=6.8 Hz), 1.49 (3H, s), 1.80 (3H, s), 2.14 (6H, s), 2.83 (1H, septet, J=6.8 Hz), 4.13 (1H, s), 6.70-7.19 (5H, m), 8.20-9.20 (4H, m), 9.79 (1H, br s).

Example 28b

N-[3-(4-Fluorophenyl)-2,2,4,6,7-pentamethyl-2,3-dihydro-1-benzofuran-5-yl]-4-methoxybenzamide By using 3-(4-fluorophenyl)-2,2,4,6,7-pentamethyl-2,3-dihydro-1-benzofuran-5-amine and 4-methoxybenzoyl chloride, the title compound was synthesized according to Example 1b. Yield: 79%. Melting point: 191-194° C. (Ethyl acetate-hexane)

¹H-NMR (CDCl₃) δ: 1.02 (3H, s), 1.51 (3H, s), 1.79 (3H, s), 2.17 (3H, s), 2.20 (3H, s), 3.86 (3H, s), 4.14 (1H, s), 6.60-7.21 (7H, m), 7.85 (2H, d, J=8.8 Hz).

Example 29b 3-(4-Fluorophenyl)-N-(4-methoxybenzyl)-2,2,4,6,7-pentamethyl-2,3-dihydro-1-benzofuran-5-amine By using N-[3-(4-fluorophenyl)-2,2,4,6,7-pentamethyl-2,3-dihydro-1-benzofuran-5-yl]-4-methoxybenzamide, the title compound was synthesized according to Example 2b. Yield: 52%. Melting point: 114-115° C. (Methanol)

¹H-NMR (CDCl₃) δ: 1.00 (3H, s), 1.49 (3H, s), 1.76 (3H, s), 2.18 (3H, s), 2.27 (3H, s), 2.80 (1H, br s), 3.79 (3H, s), 3.85 (2H, s), 4.08 (1H, s), 6.71-7.03 (6H, m), 7.20-7.27 (2H, m).

Example 30b

4-Fluoro-N-[3-(4-fluorophenyl)-2,2,4,6,7-pentamethyl-2,3-dihydro-1-benzofuran-5-yl]benzamide By using 3-(4-fluorophenyl)-2,2,4,6,7-pentamethyl-2,3-dihydro-1-benzofuran-5-amine and 4-fluorobenzoyl chloride, the title compound was synthesized according to Example 1b. Yield: 75%. Melting point: 140-142° C. (Ethyl acetate-hexane)

¹H-NMR (CDCl₃) δ: 1.02 (3H, s), 1.52 (3H, s), 1.80 (3H, s), 2.19 (6H, s), 4.14 (1H, s), 6.75-7.25 (7H, m), 7.85-7.94 (2H, m).

Example 31b

N-(4-Fluorobenzyl)-3-(4-fluorophenyl)-2,2,4,6,7-pentamethyl-2,3-dihydro-1-benzofuran-5-amine By using 4-fluoro-N-[3-(4-fluorophenyl)-2,2,4,6,7-pentamethyl-2,3-dihydro-1-benzofuran-5-yl]benzamide, the title compound was synthesized according to Example 2b. Yield: 66%. Melting point: 118-120° C. (Ethanol)

¹H-NMR (CDCl₃) δ: 1.00 (3H, s), 1.49 (3H, s), 1.77 (3H, s), 2.18 (3H, s), 2.26 (3H, s), 2.92 (1H, br s), 3.88 (2H, s), 4.08 (1H, s), 6.50-7.21 (6H, m), 7.24-7.41 (2H, m).

Example 32b

4-Methoxy-N-[2,2,4,6,7-pentamethyl-3-(4-methylphenyl)-2,3-dihydro-1-benzofuran-5-yl]benzamide By using 2,2,4,6,7-pentamethyl-3-(4-methylphenyl)-2,3-dihydro-1-benzofuran-5-amine and 4-methoxybenzoyl chloride, the title compound was synthesized according to Example 1b. Yield: 86%. Melting point: 161-163° C. (Ethyl acetate-hexane)

¹H-NMR (CDCl₃) δ: 1.03 (3H, s), 1.51 (3H, s), 1.79 (3H, s), 2.18 (6H, s), 2.30 (3H, s), 3.86 (3H, s), 4.12 (1H, s), 6.58-7.11 (6H, m), 7.20 (1H, br s), 7.85 (2H, d, J=8.8 Hz).

Example 33b

N-(4-Methoxybenzyl)-2,2,4,6,7-pentamethyl-3-(4-methylphenyl)-2,3-dihydro-1-benzofuran-5-amine By using 4-methoxy-N-[2,2,4,6,7-pentamethyl-3-(4-methylphenyl)-2,3-dihydro-1-benzofuran-5-yl]benzamide, the title compound was synthesized according to Example 2b. Yield: 58%. Melting point: 97-98° C. (Ethanol)

$^1$H-NMR (CDCl$_3$) δ: 1.00 (3H, s), 1.49 (3H, s), 1.78 (3H, s), 2.18 (3H, s), 2.26 (3H, s), 2.31(3H, s), 2.60(1H, br s), 3.79 (3H, s), 3.85 (2H, s), 4.08 (1H, s), 6.58-7.38 (8H, m).

Example 34b

4-Fluoro-N-[2,2,4,6,7-pentamethyl-3-(4-methylphenyl)-2,3-dihydro-1-benzofuran-5-yl]benzamide By using 2,2,4,6,7-pentamethyl-3-(4-methylphenyl)-2,3-dihydro-1-benzofuran-5-amine and 4-fluorobenzoyl chloride, the title compound was synthesized according to Example 1b. Yield: 43%. Melting point: 148-120° C. (Ethyl acetate-hexane)

$^1$H-NMR (CDCl$_3$) δ: 1.03 (3H, s), 1.52 (3H, s), 1.80 (3H, s), 2.19 (6H, s), 2.30 (3H, s), 4.13 (1H, s), 6.60-7.20 (7H, m), 7.85-7.94 (2H, m).

Example 35b

N-(4-Fluorobenzyl)-2,2,4,6,7-pentamethyl-3-(4-methylphenyl)-2,3-dihydro-1-benzofuran-5-amine By using 4-fluoro-N-[2,2,4,6,7-pentamethyl-3-(4-methylphenyl)-2,3-dihydro-1-benzofuran-5-yl]benzamide, the title compound was synthesized according to Example 2b. Yield: 39%. Melting point: 92-94° C. (Methanol)

$^1$H-NMR (CDCl$_3$) δ: 1.01 (3H, s), 1.49 (3H, s), 1.77 (3H, s), 2.18 (3H, s), 2.25 (3H, s), 2.31 (3H, s), 2.82 (1H, br s), 3.87 (2H, s), 4.07 (1H, s), 6.60-7.32 (8H, m).

Example 36b

Methyl 4-[[3-(4-isopropylphenyl)-2,2,4,6,7-pentamethyl-2,3-dihydro-1-benzofuran-5-ylamino]carbonyl]benzoate By using 3-(4-isopropylphenyl)-2,2,4,6,7-pentamethyl-2,3-dihydro-1-benzofuran-5-amine and 4-methoxycarbonylbenzoyl chloride, the title compound was synthesized according to Example 1b. Yield: 92%. Melting point: 220-223° C. (Methanol).

$^1$H-NMR (CDCl$_3$) δ: 1.03 (3H, s), 1.21 (6H, d, J=7.0 Hz), 1.52 (3H, s), 1.82 (3H, s), 2.19 (6H, s), 2.85 (1H, septet, J=7.0 Hz), 3.95 (3H, S), 4.14 (1H, s), 6.88 (2H, br s), 7.07-7.11 (2H, m), 7.30 (1H, s), 7.92-7.96 (2H, m), 8.11-8.16 (2H, m).

Example 37b

4-[[3-(4-Isopropylphenyl)-2,2,4,6,7-pentamethyl-2,3-dihydro-1-benzofuran-5-ylamino]carbonyl]benzoic acid To a solution of methyl 4-[[3-(4-isopropylphenyl)-2,2,4,6,7-pentamethyl-2,3-dihydro-1-benzofuran-5-ylamino]carbonyl]benzoate (341.7 mg, 0.70 mmol) in a mixed solvent of tetrahydrofuran (10 ml) and methanol (2.5 ml) was added a 1 N aqueous solution of sodium hydroxide (0.75 ml, 0.75 mmol) and the resulting mixture was stirred at room temperature for 3 hours. The reaction mixture was concentrated under reduced pressure and 1N hydrochloric acid was added into the residue. The product was extracted twice with ethyl acetate. The combined extracts were dried on magnesium sulfate, filtered, and concentrated under reduced pressure. The residue was crystallized from ethyl acetate-hexane to obtain the title compound (60% yield). Melting point: 258-261° C.

$^1$H-NMR (DMSO-d$_6$) δ: 0.97 (3H, s), 1.17 (6H, d, J=7.0 Hz), 1.47 (3H, s), 1.71 (3H, s), 2.07 (3H, s), 2.13 (3H, s), 2.84 (1H, septet, J=7.0 Hz), 4.24 (1H, s), 6.90 (2H, br s), 7.15 (2H, d, J=7.6 Hz), 8.04 (4H, s), 9.47 (1H, s), 1H unidentified.

Example 38b 5-(4-Methoxybenzylamino)-2,4,6,7-tetramethyl-3-phenyl-1-benzofuran hydrochloride To a solution of 2,4,6,7-tetramethyl-3-phenyl-1-benzofuran-5-amine (0.50 g, 1.88 mmol) and 4-methoxybenzaldehyde (282 mg, 2.07 mmol) in methanol (15 ml) was added sodium cyanoborohydride (130 mg, 2.07 mmol) and the resulting mixture was stirred at room temperature for 1 hour. The reaction mixture was concentrated under reduced pressure and the residue was neutralized with a 1 N aqueous solution of sodium hydroxide. The product was extracted twice with ethyl acetate. The combined organic layers were washed with water, dried on magnesium sulfate, filtered, and concentrated under reduced pressure to obtain 0.37 g of an oily free base. The free base (0.37 g, 0.96 mmol) was dissolved into a hydrochloric acid-methanol mixed solution and the solvent was concentrated under reduced pressure. The resulting residue was crystallized from methanol to obtain 0.21 g (27% yield) of the title compound. Melting point: 200-203° C.

$^1$H-NMR (CDCl$_3$) δ: 1.97 (3H, s), 2.30 (3H, s), 2.34 (3H, s), 2.37 (3H, s), 3.73 (3H, s), 4.53 (3H, s), 6.69 (2H, d, J=8.4 Hz), 7.11-7.25 (4H, m), 7.32-7.37 (3H, m), 1H unidentified.

Example 39b

4-Fluoro-N-(2,4,6,7-tetramethyl-3-phenyl-1-benzofuran-5-yl)benzamide

By using 2,4,6,7-tetramethyl-3-phenyl-1-benzofuran-5-amine and 4-fluorobenzoyl chloride, the title compound was synthesized according to Example 1b. Yield: 80%. Melting point: 242-245° C. (Ethyl acetate-hexane).

$^1$H-NMR (CDCl$_3$) δ: 1.96 (3H, s), 2.25 (3H, s), 2.32 (3H, s), 2.45 (3H, s), 7.04-7.14 (2H, m), 7.24-7.50 (6H, m), 7.84-7.93 (2H, m).

Example 40b

N-(4-Fluorobenzyl)-2,4,6,7-tetramethyl-3-phenyl-1-benzofuran-5-amine

By using 4-fluoro-N-(2,4,6,7-tetramethyl-3-phenyl-1-benzofuran-5-yl)benzamide, the title compound was synthesized according to Example 2b. Yield: 56%. Melting point: 135-136° C. (Methanol).

$^1$H-NMR (CDCl$_3$) δ: 2.00 (3H, s), 2.30 (3H, s), 2.35 (3H, s), 2.45 (3H, s), 3.08 (1H, br s), 3.92 (2H, s), 6.95-7.06 (2H, m), 7.28-7.47 (7H, m).

Example 41b

N-[3-(4-Isopropylphenyl)-2,4,6,7-tetramethyl-1-benzofuran-5-yl]benzamide

By using 3-(4-isopropylphenyl)-2,4,6,7-tetramethyl-1-benzofuran-5-amine and benzoyl chloride, the title compound was synthesized according to Example 1b. Yield: 91%. Melting point: 225-227° C. (Ethyl acetate)

$^1$H-NMR (CDCl$_3$) δ: 1.29 (6H, d, J=7.0 Hz), 2.01 (3H, s), 2.30 (3H, s), 2.33 (3H, s), 2.47 (3H, s), 2.95 (1H, septet, J=7.0 Hz), 7.25 (4H, s), 7.39 (1H, br s), 7.41-7.62 (3H, m), 7.88-7.97 (2H, m).

Example 42b

N-Benzyl-3-(4-isopropylphenyl)-2,4,6,7-tetramethyl-1-benzofuran-5-amine

By using N-[3-(4-isopropylphenyl)-2,4,6,7-tetramethyl-1-benzofuran-5-yl]benzamide, the title compound was synthesized according to Example 2b. Yield: 55%. Melting point: 94-95° C. (Ethanol).

$^1$H-NMR (CDCl$_3$) δ: 1.31 (6H, d, J=7.0 Hz), 1.95 (1H, br s), 2.04 (3H, s), 2.31 (3H, S), 2.37 (3H, s), 2.45 (3H, s), 2.97 (1H, septet, J=7.0 Hz), 3.96 (2H, s), 7.23-7.44 (9H, m).

Example 43b

N-[3-(4-Isopropylphenyl)-2,4,6,7-tetramethyl-1-benzofuran-5-yl]-4-methoxybenzamide By using 3-(4-isopropylphenyl)-2,4,6,7-tetramethyl-1-benzofuran-5-amine and 4-methoxybenzoyl chloride, the title compound was synthesized according to Example 1b. Yield: 49%. Amorphous.

$^1$H-NMR (CDCl$_3$) δ: 1.29 (6H, d, J=7.0 Hz), 1.99 (3H, S), 2.28 (3H, s), 2.32 (3H, s), 2.46 (3H, s), 2.95 (1H, septet, J=7.0 Hz), 3.86 (3H, s), 6.95 (2H, d, J=8.8 Hz), 7.24 (4H, s), 7.33 (1H, br s), 7.88 (2H, d, J=8.8 Hz).

Example 44b

N-[3-(4-Isopropylphenyl)-2,4,6,7-tetramethyl-1-benzofuran-5-yl]-4-methoxyphenylacetamide By using 3-(4-isopropylphenyl)-2,4,6,7-tetramethyl-1-benzofuran-5-amine and 4-methoxyphenylacetyl chloride, the title compound was synthesized according to Example 1b. Yield: 42%. Melting point: 202-204° C. (Methanol)

$^1$H-NMR (CDCl$_3$) δ: 1.30 (6H, d, J=7.0 Hz), 1.84 (3H, s), 2.13 (3H, s), 2.28 (3H, s), 2.40 (3H, s), 2.95 (1H, septet, J=7.0 Hz), 3.72 (2H, s), 3.81 (3H, s), 6.58 (1H, br s), 6.92 (2H, d, J=8.8 Hz), 7.20-7.33 (6H, m).

Example 45b 3-(4-Isopropylphenyl)-N-(4-methoxybenzyl)-2,4,6,7-tetramethyl-1-benzofuran-5-amine hydrochloride By using [N-[3-(4-isopropylphenyl)-2,4,6,7-tetramethyl-1-benzofuran-5-yl]]-4-methoxyphenylacetamide, the title compound was synthesized according to Example 6b. Yield: 87%. Amorphous.

$^1$H-NMR (CDCl$_3$) δ: 1.28 (6H, d, J=7.0 Hz), 2.00 (3H, S), 2.30 (3H, s), 2.32 (3H, s), 2.35 (3H, s), 2.94 (1H, septet, J=7.0 Hz), 3.72 (3H, s), 4.53 (2H, s), 6.68-6.72 (4H, m), 7.07-7.25 (4H, m), 10.9 (1H, br s), 1H unidentified.

Example 46b

4-Fluoro-N-[3-(4-isopropylphenyl)-2,4,6,7-tetramethyl-1-benzofuran-5-yl]benzamide By using 3-(4-isopropylphenyl)-2,4,6,7-tetramethyl-1-benzofuran-5-amine and 4-fluorobenzoyl chloride, the title compound was synthesized according to Example 1b. Yield: 72%. Melting point: 242-245° C. (Ethyl acetate-hexane).

$^1$H-NMR (CDCl$_3$) δ: 1.28 (6H, d, J=7.0 Hz), 1.98 (3H, s), 2.26 (3H, s), 2.33 (3H, s), 2.45 (3H, s), 2.95 (1H, septet, J=7.0 Hz), 7.06-7.17 (2H, m), 7.24 (4H, s), 7.39 (1H, br s), 7.86-7.95 (2H, m).

Example 47b

N-(4-Fluorobenzyl)-3-(4-isopropylphenyl)-2,4,6,7-tetramethyl-1-benzofuran-5-amine To a suspension of aluminum chloride (807 mg, 6.05 mmol) in tetrahydrofuran (10 ml) was gradually added under ice cooling lithium aluminum hydride (230 mg, 6.05 mmol) and the resulting mixture was stirred at the same temperature for 10 minutes. To this mixture was added 4-fluoro-N-[3-(4-isopropylphenyl)-2,4,6,7-tetramethyl-1-benzofuran-5-yl]benzamide (0.52 g, 1.21 mmol) and the mixture was refluxed with heating for 3 hours. The reaction mixture was poured into ice water and neutralized with an 8 N aqueous solution of sodium hydroxide. The product was extracted twice with ethyl acetate. The combined organic layers were washed with water, dried on magnesium sulfate, filtered, and then concentrated under reduced pressure. The residue was crystallized from ethanol to obtain 0.27 g (54% yield) of the title compound. Melting point: 95-97° C.

$^1$H-NMR (CDCl$_3$) δ: 1.30 (6H, d, J=7.0 Hz), 1.98 (1H, br s), 2.02 (3H, s), 2.31 (3H, s), 2.34 (3H, s), 2.45 (3H, s), 2.96 (1H, septet, J=7.0 Hz), 3.92 (2H, s), 6.95-7.06 (2H, m), 7.24-7.40 (6H, m).

Example 48b

N-[3-(4-Fluorophenyl)-2,4,6,7-tetramethyl-1-benzofuran-5-yl]-4-methoxybenzamide

By using 3-(4-fluorophenyl)-2,4,6,7-tetramethyl-1-benzofuran-5-amine and 4-methoxybenzoyl chloride, the title compound was synthesized according to Example 1b. Yield: 75%. Melting point: 225-227° C. (Ethyl acetate).

$^1$H-NMR (CDCl$_3$) δ: 1.96 (3H, s), 2.27 (3H, s), 2.30 (3H, s), 2.45 (3H, s), 3.86 (3H, s), 6.95 (2H, d, J=8.8 Hz), 7.03-7.13 (2H, m), 7.24-7.36 (3H, m), 7.88 (2H, d, J=8.8 Hz).

Example 49b

N-(4-Methoxybenzyl)-3-(4-fluorophenyl)-2,4,6,7-tetramethyl-1-benzofuran-5-amine

By using N-[3-(4-fluorophenyl)-2,4,6,7-tetramethyl-1-benzofuran-5-yl]-4-methoxybenzamide, the title compound was synthesized according to Example 2b. Yield: 75%. Melting point: 100-102° C. (Ethanol).

$^1$H-NMR (CDCl$_3$) δ: 2.01 (3H, s), 2.20-2.60 (10H, m), 3.81 (3H, s), 3.89 (2H, s), 6.87 (2H, d, J=8.8 Hz), 7.05-7.16 (2H, s), 7.23-7.34 (4H, m).

Example 50b

4-Fluoro-N-[3-(4-fluorophenyl)-2,4,6,7-tetramethyl-1-benzofuran-5-yl]benzamide

By using 3-(4-fluorophenyl)-2,4,6,7-tetramethyl-1-benzofuran-5-amine and 4-fluorobenzoyl chloride, the title compound was synthesized according to Example 1b. Yield: 75%. Melting point: 232-234° C. (Ethyl acetate-hexane).

$^1$H-NMR (CDCl$_3$) δ: 1.97 (3H, s), 2.28 (3H, s), 2.31 (3H, s), 2.46 (3H, s), 7.03-7.37 (7H, m), 7.86-7.98 (2H, m).

Example 51b

N-(4-Fluorobenzyl)-3-(4-fluorophenyl)-2,4,6,7-tetramethyl-1-benzofuran-5-amine

By using 4-fluoro-N-[3-(4-fluorophenyl)-2,4,6,7-tetramethyl-1-benzofuran-5-yl]benzamide, the title compound was synthesized according to Example 2b. Yield: 66%. Melting point: 107-109° C. (Ethanol).

$^1$H-NMR (CDCl$_3$) δ: 1.87 (1H, br s), 1.99 (3H, s), 2.28 (3H, s), 2.34 (3H, s), 2.45 (3H, s), 3.92 (2H, s), 6.94-7.13 (4H, m), 7.20-7.43 (4H, m).

Example 52b

N-[3-(4-Isopropylphenyl)-1',4,6,7-tetramethylspiro[benzofuran-2(3H),4'-piperidine]-5-yl]-4-methoxybenzamide

By using 3-(4-isopropylphenyl)-1',4,6,7-tetramethylspiro[benzofuran-2(3H),4'-piperidine]-5-amine, the title compound was synthesized according to Example 1b. Yield: 40%. Melting point: 277-278° C. (Ethanol-isopropyl ether).

$^1$H-NMR (CDCl$_3$) δ: 1.20 (6H, d, J=7.0 Hz), 1.35-1.45 (2H, m), 1.81 (3H, s), 2.18-2.91 (16H, m), 3.86 (3H, s), 4.09 (1H, s), 6.6-7.1 (6H, m), 7.19 (1H, br), 7.83-7.88 (2H, m).

Example 53b

3-(4-Isopropylphenyl)-N-(methoxybenzyl)-1',4,6,7-tetramethylspiro[benzofuran-2(3H),4'-piperidine]-5-amine

By using N-[3-(4-isopropylphenyl)-1',4,6,7-tetramethylspiro[benzofuran-2(3H),4'-piperidine]-5-yl]-4-methoxybenzamide, the title compound was synthesized according to Example 2b. Yield: 59%. Amorphous.

$^1$H-NMR (CDCl$_3$) δ: 1.21 (6H, d, J=7.0 Hz), 1.3-1.4 (2H, m), 1.79 (3H, s), 1.8-2.0 (3H, m), 2.21 (3H, s), 2.27 (3H, s), 2.31 (3H, s), 2.4-2.7 (4H, m), 2.85 (1H, septet, J=7.0 Hz), 3.79 (3H, s), 3.85 (2H, s), 4.05 (1H, s), 6.6-7.1 (6H, m), 7.23-7.27 (2H, m).

Example 54b

4-Fluoro-N-[3-(4-isopropylphenyl)-1',4,6,7-tetramethylspiro[benzofuran-2(3H),4'-piperidine]-5-yl]benzamide

By using 3-(4-isopropylphenyl)-1',4,6,7-tetramethylspiro[benzofuran-2(3H),4'-piperidine]-5-amine and 4-fluorobenzoyl chloride, the title compound was synthesized according to Example 1b. Yield: 38%. Melting point: 271-272° C. (Methanol-isopropyl ether).

$^1$H-NMR (CDCl$_3$) δ: 1.20 (6H, d, J=7.0 Hz), 1.30-1.40 (2H, m), 1.81 (3H, s), 2.02-2.12 (2H, m), 2.18 (3H, s), 2.22 (3H, s), 2.30 (3H, s), 2.37-2.71 (4H, m), 2.85 (1H, septet, J=7.0 Hz), 4.10 (1H, s), 6.6-7.2 (6H, m), 7.24 (1H, br), 7.86-7.93 (2H, m).

Example 55b

N-(4-Fluorobenzyl)-3-(4-isopropylphenyl)-1',4,6,7-tetramethylspiro[benzofuran-2(3H),4'-piperidine]-5-amine

By using 4-fluoro-N-[3-(4-isopropylphenyl)-1',4,6,7-tetramethylspiro[benzofuran-2(3H),4'-piperidine]-5-yl]benzamide, the title compound was synthesized according to Example 2b. Yield: 83%. Amorphous.

$^1$H-NMR (CDCl$_3$) δ: 1.21 (6H, d, J=7.0 Hz), 1.34-1.42 (2H, m), 1.75 (3H, s), 1.80-2.05 (3H, m), 2.21 (3H, s), 2.26 (3H, s), 2.31 (3H, s), 2.35-2.72 (4H, m), 2.85 (1H, septet, J=7.0 Hz), 3.87 (2H, s), 4.04 (1H, s), 6.5-7.1 (6H, m), 7.23-7.30 (2H, m).

Example 56b

4-Chloro-N-[3-(4-isopropylphenyl)-1',4,6,7-tetramethylspiro[benzofuran-2(3H),4'-piperidine]-5-yl]benzamide

By using 3-(4-isopropylphenyl)-1',4,6,7-tetramethylspiro[benzofuran-2(3H),4'-piperidine]-5-amine and 4-chlorobenzoyl chloride, the title compound was synthesized according to Example 1b. Yield: 58%. Melting point: 293-295° C. (Methanol).

$^1$H-NMR (CDCl$_3$) δ: 1.09 (6H, d, J=7.0 Hz), 1.3-1.4 (2H, m), 1.7-2.7 (18H, m), 2.84 (1H, septet, J=7.0 Hz), 4.09 (1H, s), 6.6-7.1 (4H, m), 7.33 (1H, br), 7.40-7.44 (2H, m), 7.79-7.83 (2H, m).

Example 57b

N-(4-Chlorobenzyl)-3-(4-isopropylphenyl)-1',4,6,7-tetramethylspiro[benzofuran-2(3H),4'-piperidine]-5-amine

By using 4-chloro-N-[3-(4-isopropylphenyl)-1',4,6,7-tetramethylspiro[benzofuran-2(3H),4'-piperidine]-5-yl]benzamide, the title compound was synthesized according to Example 2b. Yield: 96%. Amorphous.

$^1$H-NMR (CDCl$_3$) δ: 1.22 (6H, d, J=7.0 Hz), 1.3-1.4 (2H, m), 1.74 (3H, s), 1.8-2.1 (3H, m), 2.21 (3H, s), 2.25 (3H, s), 2.30 (3H, s), 2.34-2.69 (4H, m), 2.86 (1H, septet, J=7.0 Hz), 3.83 (2H, s), 4.04 (1H, s), 6.6-7.1 (4H, m), 7.24 (4H, s).

Example 58b

N-[3-(4-Isopropylphenyl)-2,2,4,6,7-pentamethyl-2,3-dihydro-1-benzofuran-5-yl]-3,4-dimethoxybenzamide

By using 3-(4-isopropylphenyl)-2,2,4,6,7-pentamethyl-2,3-dihydro-1-benzofuran-5-amine and 3,4-dimethoxybenzoyl chloride, the title compound was synthesized according to Example 1b. Yield: 71%. Melting point: 171-173° C. (Ethyl acetate-hexane).

$^1$H-NMR (CDCl$_3$) δ: 1.03 (3H, s), 1.21 (6H, d, J=7.0 Hz), 1.52 (3H, s), 1.82 (3H, s), 2.19 (6H, s), 2.85 (1H, septet, J=7.0 Hz), 3.938 (3H, s), 3.943 (3H, s), 4.13 (1H, s), 6.80-7.00 (3H, m), 7.09 (2H, d, J=7.6 Hz), 7.22 (1H, br s), 7.42 (1H, dd, J=8.4, 2.2 Hz), 7.52 (1H, d, J=2.2 Hz).

Example 59b

N-(3,4-Dimethoxybenzyl)-3-(4-isopropylphenyl)-2,2,4,6,7-pentamethyl-2,3-dihydro-1-benzofuran-]-5-amine hydrochloride By using N-[3-(4-isopropylphenyl)-2,2,4,6,7-pentamethyl-2,3-dihydro-1-benzofuran-]-5-yl]-3,4-dimethoxybenzamide, the title compound was synthesized according to Example 6b. Yield: 76%. Melting point: 181-184° C. (Ethanol-hexane).

$^1$H-NMR (DMSO-$d_6$) δ: 0.92 (3H, s), 1.19 (6H, d, J=7.0 Hz), 1.42 (3H, s), 1.69 (3H, s), 2.10 (3H, s), 2.22 (3H, s), 2.85 (1H, septet, J=7.0 Hz), 3.66 (3H, s), 3.75 (3H, s), 4.17 (1H, s), 4.20-4.42 (2H, m), 6.40-6.90 (5H, m), 7.13 (2H, d, J=7.4 Hz), 10.0 (1H, br s), 1H unidentified.

Example 60b (+)-4-Fluoro-N-[3-(4-isopropylphenyl)-2,2,4,6,7-pentamethyl-2,3-dihydro-1-benzofuran-5-yl]benzamide By using (+)-3-(4-isopropylphenyl)-2,2,4,6,7-pentamethyl-2,3-dihydro-1-benzofuran-5-amine and 4-fluorobenzoyl chloride, the title compound was synthesized according to Example 1b. Yield: 91%. Melting point: 251-253° C. (Ethyl acetate-hexane) [α]D=+74.4° (c=0.501, methanol).

$^1$H-NMR (CDCl$_3$) δ: 1.01 (3H, s), 1.19 (6H, d, J=6.8 Hz), 1.50 (3H, s), 1.78 (3H, s), 2.15 (3H, s), 2.17 (3H, s), 2.83 (1H, septet, J=6.8 Hz), 4.12 (1H, s), 6.60-7.40 (7H, m), 7.80-7.91 (2H, m).

Example 61b (+)-N-(4-Fluorobenzyl)-3-(4-isopropylphenyl)-2,2,4,6,7-pentamethyl-2,3-dihydro-1-benzofuran-5-amine hydrochloride To a suspension of aluminum chloride (0.67 g, 5.05 mmol) in tetrahydrofuran (15 ml) was gradually added under ice cooling lithium aluminum hydride (190 mg, 5.05 mmol) and the resulting mixture was stirred at the same temperature for 10 minutes. To this mixture was added (+)-4-fluoro-N-[3-(4-isopropylphenyl)-2,2,4,6,7-pentamethyl-2,3-dihydro-1-benzofuran-5-yl]benzamide (0.45 g, 1.01 mmol) and the mixture was refluxed with heating for 3 hours. The reaction mixture was poured into ice water and neutralized with an 8 N aqueous solution of sodium hydroxide. The product was extracted twice with ethyl acetate. The combined organic layers were washed with water, dried on magnesium sulfate, filtered, and then concentrated under reduced pressure to obtain 0.29 g of an oily free base. The free base (0.29 g, 0.67 mmol) was dissolved into a mixed solution of hydrochloric acid and methanol and solvent was concentrated under reduced pressure. The resulting residue was crystallized from methanol to obtain 0.27 g (56% yield) of the title compound. Melting point: 158-160° C. [α]D=+70.7° (c=0.461, methanol).

$^1$H-NMR (DMSO-$d_6$) δ: 0.93 (3H, s), 1.20 (6H, d, J=6.6 Hz), 1.41 (3H, s), 1.55 (3H, s), 2.11 (3H, S), 2.31 (3H, s), 2.85 (1H, septet, J=6.6 Hz), 4.13 (1H, s), 4.31 (1H, d, J=12.8 Hz), 4.45 (1H, d, J=12.8 Hz), 7.02-7.29 (8H, m), 10.3 (1H, br s), 10.8 (1H, br. s).

Example 62b (−)-4-Fluoro-N-[3-(4-isopropylphenyl)-2,2,4,6,7-pentamethyl-2,3-dihydro-1-benzofuran-5-yl]benzamide By using (−)-3-(4-isopropylphenyl)-2,2,4,6,7-pentamethyl-2,3-dihydro-1-benzofuran-5-amine and 4-fluorobenzoyl chloride, the title compound was synthesized according to Example 1b. Yield: 91%. Melting point: 253-254° C. [α]D=−77.4° (c=0.500, methanol).

$^1$H-NMR (CDCl$_3$) δ: 1.03 (3H, s), 1.21 (6H, d, J=7.0 Hz), 1.51 (3H, s), 1.81 (3H, s), 2.18 (6H, s), 2.85 (1H, septet, J=7.0 Hz), 4.13 (1H, s), 6.8-7.4 (7H, m), 7.86-7.93 (2H, m).

Example 63b (−)-N-(4-Fluorobenzyl)-3-(4-isopropylphenyl)-2,2,4,6,7-pentamethyl-2,3-dihydro-1-benzofuran-5-amine hydrochloride To a suspension of aluminum chloride (351 mg, 2.63 mmol) in tetrahydrofuran (35 ml) was gradually added under ice cooling lithium aluminum hydride (101 mg, 2.67 mmol) and the resulting mixture was stirred at the same temperature for 10 minutes. To this mixture was added (−)-4-fluoro-N-[3-(4-isopropylphenyl)-2,2,4,6,7-pentamethyl-2,3-dihydro-1-benzofuran-5-yl]benzamide (528 mg, 1.19 mmol) and the mixture was refluxed with heating for 2 hours. The reaction mixture was poured into ice water and neutralized with an 8 N aqueous solution of sodium hydroxide. The product was extracted twice with ethyl acetate. The combined organic layers were washed with water, dried on magnesium sulfate, filtered, and then concentrated under reduced pressure to obtain 502 mg of an oily free base. The free base (502 mg, 1.17 mmol) was dissolved into a mixed solution of hydrochloric acid and methanol and the solvent was concentrated under reduced pressure. The resulting residue was crystallized from methanol to obtain 115 mg (21% yield) of the title compound. Melting point: 148-151° C. [α]D=−70.5° (c=0.503, methanol).

$^1$H-NMR (DMSO-$d_6$) δ: 0.92 (3H, s), 1.19 (6H, d, J=6.8 Hz), 1.41 (3H, s), 1.54 (3H, s), 2.11 (3H, s), 2.32 (3H, s), 2.85 (1H, septet, J=6.8 Hz), 4.16 (1H, s), 4.29-4.45 (2H, m), 6.6-7.4 (8H, m), 10.2-10.6 (2H, m).

Example 64b 3,4-Dimethoxy-N-[2,2,4,6,7-pentamethyl-3-(4-methylphenyl)-2,3-dihydro-1-benzofuran-5-yl]benzamide By using 2,2,4,6,7-pentamethyl-3-(4-methylphenyl)-2,3-dihydro-1-benzofuran-5-amine and 3,4-dimethoxybenzoyl chloride, the title compound was synthesized according to Example 1b. Yield: 90%. Melting point: 169-171° C. (Ethyl acetate-hexane).

$^1$H-NMR (CDCl$_3$) δ: 1.03 (3H, s), 1.51 (3H, s), 1.80 (3H, s), 2.19 (6H, s), 2.29 (3H, s), 3.92 (6H, s), 4.13 (1H, s), 6.60-7.20 (5H, m), 7.29 (1H, br s), 7.42 (1H, dd, J=8.2, J=2.0 Hz), 7.51 (1H, d, J=2.0 Hz).

Example 65b

N-(3,4-Dimethoxybenzyl)-2,2,4,6,7-pentamethyl-3-(4-methylphenyl)-2,3-dihydro-1-benzofuran-5-amine hydrochloride

By using 3,4-dimethoxy-N-[2,2,4,6,7-pentamethyl-3-(4-methylphenyl)-2,3-dihydro-1-benzofuran-5-yl]benzamide, the title compound was synthesized according to Example 6b. Yield: 68%. Melting point: 195-198° C. (Ethanol-hexane).

$^1$H-NMR (DMSO-$d_6$) δ: 0.93 (3H, s), 1.41 (3H, s), 1.65 (3H, s), 2.10 (3H, s), 2.23 (3H, s), 2.27 (3H, s), 3.66 (3H, s), 3.73 (3H, s), 4.16 (1H, s), 4.23 (1H, d, J=12.4 Hz), 4.35 (1H, d, J=12.4 Hz), 6.40-6.82 (5H, m), 7.08 (2H, d, J=7.0 Hz), 10.2 (1H, br s), 1H unidentified.

Example 66b

N-[2,2,4,6,7-Pentamethyl-3-(4-methylphenyl)-2,3-dihydro-1-benzofuran-5-yl]-1,3-benzodioxol-5-carboxamide

By using 2,2,4,6,7-pentamethyl-3-(4-methylphenyl)-2,3-dihydro-1-benzofuran-5-amine and 1,3-benzodioxol-5-carbonyl chloride, the title compound was synthesized according to Example 1b. Yield: 65%. Melting point: 164-165° C. (Ethyl acetate-hexane).

$^1$H-NMR (CDCl$_3$) δ: 1.03 (3H, s), 1.51 (3H, s), 1.79 (3H, s), 2.17 (3H, s), 2.18 (3H, s), 2.30 (3H, s), 4.12 (1H, s), 6.03 (2H, s), 6.62-7.12 (5H, m), 7.16 (1H, br s), 7.34-7.45 (2H, m).

Example 67b

N-(1,3-Benzodioxol-5-ylmethyl)-2,2,4,6,7-pentamethyl-3-(4-methylphenyl)-2,3-dihydro-1-benzofuran-5-amine hydrochloride

By using N-[2,2,4,6,7-pentamethyl-3-(4-methylphenyl)-2,3-dihydro-1-benzofuran-5-yl]-1,3-benzodioxol-5-carboxamide, the title compound was synthesized according to Example 6b. Yield: 62%. Melting point: 147-149° C. (Ethanol-hexane).

$^1$H-NMR (CDCl$_3$) δ: 0.95 (3H, s), 1.42 (3H, s), 1.72 (3H, s), 2.10 (3H, s), 2.25 (3H, s), 2.27 (3H, s), 4.17 (1H, s), 4.28 (1H, s), 5.97 (1H, s), 6.01 (1H, s), 6.40-7.18 (8H, m), 10.2 (1H, br s).

The chemical structures of the compounds obtained in the above-described Examples are shown below.

TABLE 4

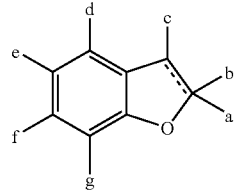

| example number | a | b | c | d | e | f | g | |
|---|---|---|---|---|---|---|---|---|
| 1b | Me | Me | phenyl | Me | H$_3$CO—C$_6$H$_4$—C(O)NH— | Me | Me | — |
| 2b | Me | Me | phenyl | Me | H$_3$CO—C$_6$H$_4$—CH$_2$NH— | Me | Me | — |
| 3b | Me | Me | phenyl | Me | F—C$_6$H$_4$—C(O)NH— | Me | Me | — |
| 4b | Me | Me | phenyl | Me | F—C$_6$H$_4$—CH$_2$NH— | Me | Me | — |
| 5b | Me | Me | Me$_2$CH—C$_6$H$_4$— | Me | C$_6$H$_5$—C(O)NH— | Me | Me | — |
| 6b | Me | Me | Me$_2$CH—C$_6$H$_4$— | Me | C$_6$H$_5$—CH$_2$NH— | Me | Me | — |

TABLE 4-continued
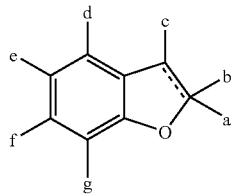
| example number | a | b | c | d | e | f | g | ---- |
|---|---|---|---|---|---|---|---|---|
| 7b | Me | Me | 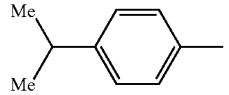 | Me | 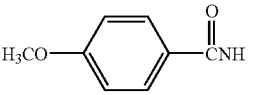 | Me | Me | — |
| 8b | Me | Me | 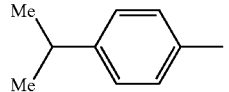 | Me | 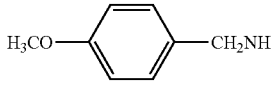 | Me | Me | — |
| 9b | Me | Me | 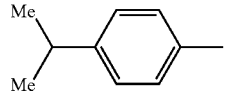 | Me | 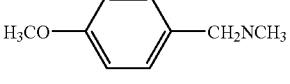 | Me | Me | — |
| 10b | Me | Me | 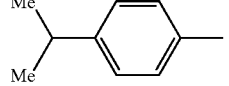 | Me | 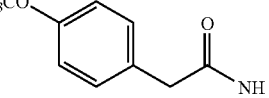 | Me | Me | — |
| 11b | Me | Me | 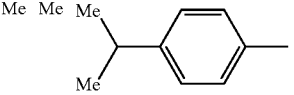 | Me | 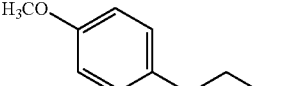 | Me | Me | — |
| 12b | Me | Me | 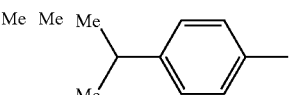 | Me | 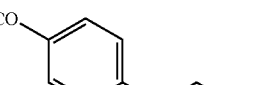 | Me | Me | — |
| 13b | Me | Me | 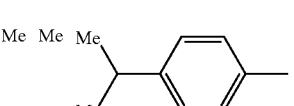 | Me | 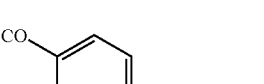 | Me | Me | — |
| 14b | Me | Me | 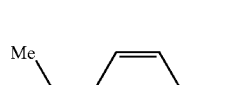 | Me | 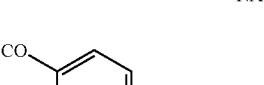 | Me | Me | — |
| 15b | Me | Me | 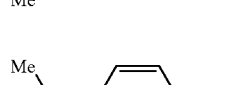 | Me |  | Me | Me | — |
| 16b | Me | Me | 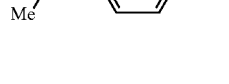 | Me | 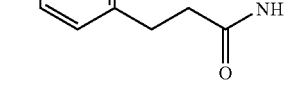 | Me | Me | — |

TABLE 4-continued

[Benzofuran core structure with positions labeled a, b, c, d, e, f, g]

| example number | a | b | c | d | e | f | g | ==== |
|---|---|---|---|---|---|---|---|---|
| 17b | Me | Me | -CH(Me)-C6H4-Me (para) | Me | 4-H3CO-C6H4-SO2NH- | Me | Me | — |

TABLE 5

[Benzofuran core structure with positions labeled a, b, c, d, e, f, g]

| example number | a | b | c | d | e | f | g | ==== |
|---|---|---|---|---|---|---|---|---|
| 18b | Me | Me | -CH(Me)-C6H4- | Me | 4-F-C6H4-C(O)NH- | Me | Me | — |
| 19b | Me | Me | -CH(Me)-C6H4- | Me | 4-F-C6H4-CH2NH- | Me | Me | — |
| 20b | Me | Me | -CH(Me)-C6H4- | Me | 4-Cl-C6H4-C(O)NH- | Me | Me | — |
| 21b | Me | Me | -CH(Me)-C6H4- | Me | 4-Cl-C6H4-CH2NH- | Me | Me | — |
| 22b | Me | Me | -CH(Me)-C6H4- | Me | 1,3-benzodioxol-5-yl-C(O)NH- | Me | Me | — |
| 23b | Me | Me | -CH(Me)-C6H4- | Me | 1,3-benzodioxol-5-yl-CH2NH- | Me | Me | — |
| 24b | Me | Me | -CH(Me)-C6H4- | Me | thiophen-2-yl-C(O)NH- | Me | Me | — |

TABLE 5-continued
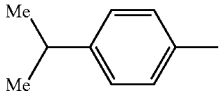
| example number | a | b | c | d | e | f | g | ===== |
|---|---|---|---|---|---|---|---|---|
| 25b | Me | Me | 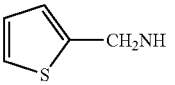 | Me |  | Me | Me | — |
| 26b | Me | Me | 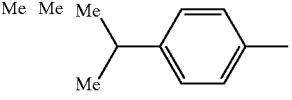 | Me | 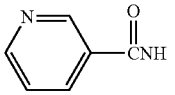 | Me | Me | — |
| 27b | Me | Me |  | Me | 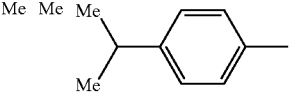 | Me | Me | — |
| 28b | Me | Me | 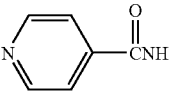 | Me |  | Me | Me | — |
| 29b | Me | Me | 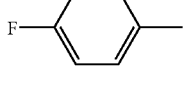 | Me | 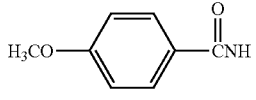 | Me | Me | — |
| 30b | Me | Me |  | Me | 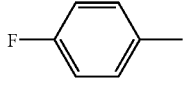 | Me | Me | — |
| 31b | Me | Me | 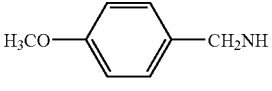 | Me |  | Me | Me | — |
| 32b | Me | Me | 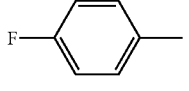 | Me | 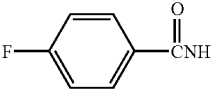 | Me | Me | — |
| 33b | Me | Me |  | Me | 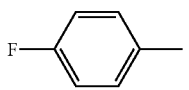 | Me | Me | — |
| 34b | Me | Me | 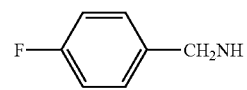 | Me |  | Me | Me | — |

TABLE 6

| example number | a | b | c | d | e | f | g | ---- |
|---|---|---|---|---|---|---|---|---|
| 35b | Me | Me | 4-Me-C6H4- | Me | 4-F-C6H4-CH2NH- | Me | Me | — |
| 36b | Me | Me | 4-(iPr)-C6H4- | Me | 4-(H3COOC)-C6H4-C(O)NH- | Me | Me | — |
| 37b | Me | Me | 4-(iPr)-C6H4- | Me | 4-(HOOC)-C6H4-C(O)NH- | Me | Me | — |
| 38b | Me | — | C6H5- | Me | 4-(H3CO)-C6H4-CH2NH- | Me | Me | = |
| 39b | Me | — | C6H5- | Me | 4-F-C6H4-C(O)NH- | Me | Me | = |
| 40b | Me | — | C6H5- | Me | 4-F-C6H4-CH2NH- | Me | Me | = |
| 41b | Me | — | 4-(iPr)-C6H4- | Me | C6H5-C(O)NH- | Me | Me | = |
| 42b | Me | — | 4-(iPr)-C6H4- | Me | C6H5-CH2NH- | Me | Me | = |
| 43b | Me | — | 4-(iPr)-C6H4- | Me | 4-(H3CO)-C6H4-C(O)NH- | Me | Me | = |
| 44b | Me | — | 4-(iPr)-C6H4- | Me | 4-(H3CO)-C6H4-CH2-C(O)NH- | Me | Me | = |
| 45b | Me | — | 4-(iPr)-C6H4- | Me | 4-(H3CO)-C6H4-CH2NH- | Me | Me | = |
| 46b | Me | — | 4-(iPr)-C6H4- | Me | 4-F-C6H4-C(O)NH- | Me | Me | = |

TABLE 6-continued
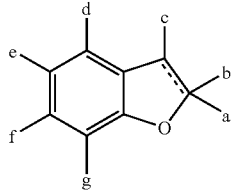
| example number | a | b | c | d | e | f | g | ═ |
|---|---|---|---|---|---|---|---|---|
| 47b | Me | — | 4-(1-methyl-1-methylethyl)phenyl (Me-C(Me)-C6H4-) | Me | 4-F-C6H4-CH2NH | Me | Me | = |
| 48b | Me | — | 4-F-C6H4- | Me | 4-H3CO-C6H4-C(O)NH | Me | Me | = |
| 49b | Me | — | 4-F-C6H4- | Me | 4-H3CO-C6H4-CH2NH | Me | Me | = |
| 50b | Me | — | 4-F-C6H4- | Me | 4-F-C6H4-C(O)NH | Me | Me | = |
| 51b | Me | — | 4-F-C6H4- | Me | 4-F-C6H4-CH2NH | Me | Me | = |
TABLE 7
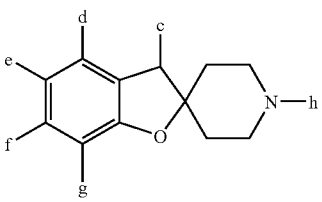
| example number | c | d | e | f | g | h |
|---|---|---|---|---|---|---|
| 52b | 4-(C(Me)2)-C6H4- | Me | 4-H3CO-C6H4-C(O)NH | Me | Me | Me |
| 53b | 4-(C(Me)2)-C6H4- | Me | 4-H3CO-C6H4-CH2NH | Me | Me | Me |
| 54b | 4-(C(Me)2)-C6H4- | Me | 4-F-C6H4-C(O)NH | Me | Me | Me |
| 55b | 4-(C(Me)2)-C6H4- | Me | 4-F-C6H4-CH2NH | Me | Me | Me |

TABLE 7-continued

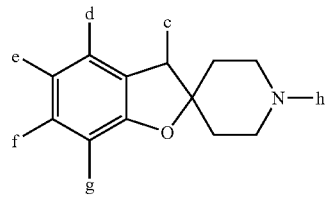

| example number | c | d | e | f | g | h |
|---|---|---|---|---|---|---|
| 56b | Me-CH(Me)-C6H4-(p-Me) | Me | 4-Cl-C6H4-C(O)NH | Me | Me | Me |
| 57b | Me-CH(Me)-C6H4-(p-Me) | Me | 4-Cl-C6H4-CH2NH | Me | Me | Me |

TABLE 8

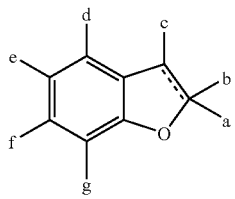

| example number | a | b | c | d | e | f | g | optical rotatory power |
|---|---|---|---|---|---|---|---|---|
| 58b | Me | Me | Me-CH(Me)-C6H4-(p-Me) | Me | 3,4-(H3CO)2-C6H3-C(O)NH | Me | Me | — |
| 59b | Me | Me | Me-CH(Me)-C6H4-(p-Me) | Me | 3,4-(H3CO)2-C6H3-CH2NH | Me | Me | — |
| 60b | Me | Me | Me-CH(Me)-C6H4-(p-*) | Me | 4-F-C6H4-C(O)NH | Me | Me | — + |
| 61b | Me | Me | Me-CH(Me)-C6H4-(p-*) | Me | 4-F-C6H4-CH2NH | Me | Me | — + |
| 62b | Me | Me | Me-CH(Me)-C6H4-(p-*) | Me | 4-F-C6H4-C(O)NH | Me | Me | — − |
| 63b | Me | Me | Me-CH(Me)-C6H4-(p-*) | Me | 4-F-C6H4-CH2NH | Me | Me | — − |

TABLE 8-continued

[Structure: 2,2-disubstituted benzofuran with positions a,b on C2; c on C3; d,e,f,g on benzene ring positions 4,5,6,7]

| example number | a | b | c | d | e | f | g | optical rotatory power |
|---|---|---|---|---|---|---|---|---|
| 64b | Me | Me | Me-C6H4- (p-tolyl) | Me | 3,4-dimethoxybenzamide (H3CO, H3CO—C6H3—C(O)NH—) | Me | Me | — |
| 65b | Me | Me | Me-C6H4- (p-tolyl) | Me | 3,4-dimethoxybenzylamine (H3CO, H3CO—C6H3—CH2NH—) | Me | Me | — |
| 66b | Me | Me | Me-C6H4- (p-tolyl) | Me | 1,3-benzodioxol-5-yl-C(O)NH— | Me | Me | — |
| 67b | Me | Me | Me-C6H4- (p-tolyl) | Me | 1,3-benzodioxol-5-yl-CH2NH— | Me | Me | — |

Formulation Example 1b

| | |
|---|---|
| (1) The compound obtained in Example 19b | 50 mg |
| (2) Lactose | 34 mg |
| (3) Corn starch | 10.6 mg |
| (4) Corn starch (paste) | 5 mg |
| (5) Magnesium Stearate | 0.4 mg |
| (6) Calcium carboxymethyl cellulose | 20 mg |
| Total | 120 mg |

According to the usual methods, tablets were prepared by mixing the above-described substances (1) to (6), and then subjecting the resulting mixture to a tablet compression process By using a tablet compression machine.

Experimental Example 1b

Cytoprotection in Human Neuroblastoma SK-N-SH Cells Against a PI-3-Kinase Inhibitor, LY-294002

(Materials for Experiments and Experimental Procedures)
a) Materials for Experiments Human neuroblastoma SK-N-SH cells were purchased from American Type Cell Culture (ATCC). DMEM/F-12 culture medium and potassium/magnesium-free phosphate buffer saline (PBS(−)) were purchased from Nikken Biomedical Co., Ltd., N2 additives and EDTA solution from GIBCO BRL Company, fetal bovine serum (FCS) and a mixed solution of penicillin (5000U/ml) and streptomycin (5 mg/ml) from BioWhittaker Inc., Alamarblue™ reagent from Wako Pure Chemical Industries Ltd., culture flasks from Falcon Company, collagen-coated 96-well multi-plates from Iwaki Glass Co., Ltd., and LY-294002 from Alexis Biochemicals, respectively. As for other reagents, commercially available guaranteed reagents were used.

b) Experimental Procedures
(1) Cultivation of SK-N-SH Cells

By using DMEM/F-12 culture medium which contains 5% FCS, 0.5% N2, 10 mM HEPES, and a 1% mixed solution of penicillin (5000U/ml) and streptomycin (5 mg/ml), SK-N-SH cells were subcultured in a carbon dioxide incubator under a mixed gas atmosphere consisting of 10% carbon dioxide and 90% air. After being cultivated to a sub-confluent stage, the cells were detached by a PBS(−) solution containing 2.5 mM EDTA and seeded onto collagen-coated 96-well multi-plates in the proportion of $1.0 \times 10^4$ cells/100 μl/well. After cultivation for 24 hours, the cells thus prepared were used for the cytoprotection assay.

(2) An Action to Protect the Nerve Cells from LY-294002-induced Cytotoxicity

There was removed 80 μl of the culture medium of SK-N-SH cells that was cultivated as described above on 96-wells, collagen-coated, multi-plates and thereto were added at the same time 40 μl each of LY-294002 of the final concentrations of 30 μM and each test compound the final concentrations of that was adjusted to be 1.0 μM, to initiate the cytotoxicity assay. Hereupon, each test compound was used after adjusting the concentration to be 10 mM with dimethyl sulfoxide and LY-294002 was used after adjusting the concentration to be 100 mM with dimethyl sulfoxide, each of which was diluted prior to its use in the test.

(3) Evaluation of the Survival Activity of Cells

The survival activity of nerve cells that were still living one day after initiation of the cytotoxicity test was determined by the activity of the cells to reduce the Alamarblue™ reagent as an index. There was removed 20 μl of the culture medium and 20 μl of Alamarblue™ reagent was added. The amount of Alamarblue™ reagent reduced by the cells over the period of 4 hours was calorimetrically determined (measurement wave length: 570 nm; reference wave length: 600 nm) By using a plate reader (WAKO SPECTRAMAX 250 Microplate Reader). Cytoprotection activity was calculated according to the following equation.

Cytoprotection activity of each compound=$(A-B)/(C-B) \times 100$ (%)

A: The survival activity of the group consisting of a test compound and LY-294002 added
B: The survival activity of the group consisting of LY-294002 added
C: The survival activity of the control group (Results)

The cytoprotection activity of each compound was obtained By using at least 4 wells for every dose of a test compound. The results are shown below.

TABLE 9

| Compound of Example | Cytoprotection Activity (%) |
| --- | --- |
| 20b | 12.6 |
| 22b | 12.8 |
| 24b | 16.4 |
| 45b | 20.6 |
| 52b | 16.4 |

These results reveal that, like neurotrophic factors, compounds (Ib) possess cytoprotection against the cytotoxicity by LY-294002, which is a PI-3 kinase inhibitor and causes nerve degeneration, thereby suppressing the nerve degeneration.

INDUSTRIAL UTILITY

Compounds (Ia), (Ia'), and (Ib) of the present invention or salts or prodrugs thereof possess an excellent action to inhibit the nerve degeneration and the like as well as an excellent brain penetrability and are low in the toxicity, thereby being useful as prophylactic/therapeutic drugs for nerve degenerative diseases and the like.

What is claimed is:

1. A compound represented by the formula:

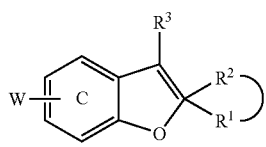

wherein $R^1$ and $R^2$ are the same or different and each is hydrogen atom, a hydrocarbon group that may be substituted or a heterocyclic group that may be substituted, or $R^1$ and $R^2$ may form, together with the adjacent carbon atom, a 3- to 8-membered homocyclic or heterocyclic ring that may be substituted; ----is a single bond or a double bond;

W is (i) a group represented by the formula:

wherein $R^4$ is (1) an aliphatic hydrocarbon group which is substituted with an aromatic group that may be substituted and, said, may further be substituted or (2) an acyl group containing an aromatic group that may be substituted; $R^5$ is hydrogen atom, a $C_{1-6}$ alkyl group, or an acyl group and, $R^3$ is a $C_{6-14}$ aryl group that may be substituted and ring C is benzene ring that may further be substituted, in addition to the group represented by Wb, or a salt thereof.

2. The compound according to claim 1, wherein $R^1$ and $R^2$ are the same or different and each is (i) hydrogen atom, (ii) a $C_{1-6}$ alkyl group, a $C_{2-6}$ alkenyl group, a $C_{2-6}$ alkynyl group, a $C_{3-6}$ cycloalkyl group, or a $C_{6-14}$ aryl group, which respectively may have 1 to 5 substituents selected from (1) halogen, (2) $C_{1-3}$ alkylenedioxy, (3) nitro, (4) cyano, (5) $C_{1-6}$ alkyl that may be halogenated, (6) $C_{2-6}$ alkenyl that may be halogenated, (7) $C_{2-6}$ alkynyl that may be halogenated, (8) $C_{3-6}$ cycloalkyl that may be halogenated, (9) $C_{6-14}$ aryl, (10) $C_{1-6}$ alkoxy that may be halogenated, (11) $C_{1-6}$ alkylthio that may be halogenated or mercapto, (12) hydroxyl, (13) amino, (14) mono-$C_{1-6}$ alkylamino, (15) mono-$C_{6-14}$ arylamino, (16) di-$C_{1-6}$ alkylamino, (17) di-$C_{6-14}$ arylamino, (18) acyl selected from formyl, carboxyl, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5- or 6-membered heterocyclic carbonyl containing, in addition to carbon atom, 1 to 4 hetero atoms selected from nitrogen atom, sulfur atom and oxygen atom, mono-$C_{1-6}$ alkyl-carbamoyl, di-$C_{1-6}$ alkyl-carbamoyl, $C_{6-14}$ aryl-carbamoyl, thiocarbamoyl, 5- or 6-membered heterocyclic carbamoyl containing, in addition to carbon atom(s), 1 to 4 hetero atoms selected from nitrogen atom, sulfur atom and oxygen atom, $C_{1-6}$ alkylsulfonyl, $C_{6-14}$ arylsulfonyl, $C_{1-6}$ alkylsulfinyl, and $C_{6-14}$ arylsulfinyl, (19) acylamino selected from formylamino, $C_{1-6}$ alkyl-carboxamido, $C_{6-14}$ aryl-carboxamido, $C_{1-6}$ alkoxy-carboxamido, $C_{1-6}$ alkylsulfonylamino, and $C_{6-14}$ arylsulfonylamino, (20) acyloxy selected from $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-14}$ aryl-carbamoyloxy and nicotinoyloxy, (21) 5- to 7-membered saturated cyclic amino, which may have 1 to 3 substituents selected from $C_{1-6}$ alkyl, $C_{6-14}$ aryl, and 5- to 10-membered aromatic heterocyclic group containing, in addition to carbon atom(s), 1 to 4 hetero atoms selected from nitrogen atom, sulfur atom and oxygen atom, (22) 5- to 10-membered aromatic heterocyclic group containing, in addition to carbon atom(s), 1 to 4 hetero atoms selected from nitrogen atom, sulfur atom and oxygen atom, (23) sulfo, and (24) $C_{6-14}$ aryloxy, or (iii) 5- to 14-membered heterocyclic group containing, in addition to carbon atom, 1 to 4 hetero atoms selected from nitrogen atom, sulfur atom and oxygen atom, which respectively may have 1 to 5 substituents selected from (1) halogen, (2) $C_{1-3}$ alkylenedioxy, (3) nitro, (4) cyano, (5) $C_{1-6}$ alkyl that may be halogenated, (6) $C_{2-6}$ alkenyl that may be halogenated, (7) $C_{2-6}$ alkynyl that may be halogenated, (8) $C_{3-6}$ cycloalkyl that may be halogenated, (9) $C_{6-14}$ aryl, (10) $C_{1-6}$ alkoxy that may be halogenated, (11) $C_{1-6}$ alkylthio that may be halogenated or mercapto, (12) hydroxyl, (13) amino, (14) mono-$C_{1-6}$ alkylamino, (15) mono-$C_{6-14}$ arylamino, (16) di-$C_{1-6}$ alkylamino, (17) di-$C_{6-14}$ arylamino, (18) acyl selected from formyl, carboxyl, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5- or 6-membered heterocyclic carbonyl containing, in addition to carbon atom(s), 1 to 4 hetero atoms selected from nitrogen atom, sulfur atom and oxygen atom, mono-$C_{1-6}$ alkyl-carbamoyl, di-$C_{1-6}$ alkyl-carbamoyl, $C_{6-14}$ aryl-carbamoyl, thiocarbamoyl, 5- or 6-membered heterocyclic carbamoyl containing, in addition to carbon atom(s), 1 to 4 hetero atoms selected from nitrogen atom, sulfur atom and oxygen atom, $C_{1-6}$ alkylsulfonyl, $C_{6-14}$ arylsulfonyl, $C_{1-6}$ alkylsulfinyl and $C_{6-14}$ arylsulfinyl, (19) acylamino selected from formylamino, $C_{1-6}$ alkyl-carbonylamino, $C_{6-14}$ aryl-carbonylamino, $C_{1-6}$ alkoxy-carbonylamino, $C_{1-6}$ alkylsulfonylamino and $C_{6-14}$ arylsulfonylamino, (20) acyloxy selected from $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-14}$ aryl-carbamoyloxy and nicotinoyloxy, (21) 5- to 7-membered saturated cyclic amino, which may have 1 to 3 substituents selected from $C_{1-6}$ alkyl, $C_{6-14}$ aryl and 5- to 10-membered aromatic heterocyclic group containing, in addition to carbon atom(s), 1 to 4 hetero atoms selected from nitrogen atom, sulfur atom and oxygen atom, (22) 5- to 10-membered aromatic heterocyclic group containing, in addition to carbon atom(s), 1 to 4 hetero atoms selected from nitrogen atom, sulfur atom and oxygen atom, (23) sulfo, and (24) a $C_{6-14}$ aryloxy, $R^3$ is $C_{6-14}$ aryl, which respectively may have 1 to 5 substituents selected from (1) halogen, (2) $C_{1-3}$ alkylenedioxy, (3) nitro, (4) cyano, (5) $C_{1-6}$ alkyl that may be halogenated, (6) $C_{2-6}$ alkenyl that may be halogenated, (7) $C_{2-6}$ alkynyl that may be halogenated, (8) $C_{3-6}$ cycloalkyl that may be halogenated, (9) $C_{6-14}$ aryl, (10) $C_{1-6}$ alkoxy that may be halogenated, (11) $C_{1-6}$ alkylthio that may be halogenated or mercapto, (12) hydroxyl, (13) amino, (14) mono-$C_{1-6}$ alkylamino, (15) mono-$C_{6-14}$ arylamino, (16) di-$C_{1-6}$ alkylamino, (17) di-$C_{6-14}$ arylamino, (18) acyl selected from formyl, carboxyl, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5- or 6-membered heterocyclic carbonyl containing, in addition to carbon atom, 1 to 4 hetero atoms selected from nitrogen atom, sulfur atom, and oxygen atom, mono-$C_{1-6}$ alkyl-carbamoyl, di-$C_{1-6}$ alkyl-carbamoyl, $C_{6-14}$ aryl-carbamoyl, thiocarbamoyl, 5- or 6-membered heterocyclic carbamoyl that contains, in addition to carbon atom, 1 to 4 hetero atoms selected from nitrogen atom, sulfur atom and oxygen atom, $C_{1-6}$ alkylsulfonyl, $C_{6-14}$ arylsulfonyl, $C_{1-6}$ alkylsulfinyl, and $C_{6-14}$ arylsulfinyl, (19) acylamino selected from formylamino, $C_{1-6}$ alkyl-carbonylamino, $C_{6-14}$ aryl-carbonylamino, $C_{1-6}$ alkoxy-carbonylamino, $C_{1-6}$ alkylsulfonylamino, and $C_{6-14}$ arylsulfonylamino, (20) acyloxy selected from $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-14}$ aryl-carbamoyloxy and nicotinoyloxy, (21) 5- to 7-membered saturated-cyclic amino, which may have 1 to 3 substituents selected from a $C_{1-6}$ alkyl, $C_{6-14}$ aryl, and a 5- to 10-membered aromatic heterocyclic group containing, in addition to carbon atom, 1 to 4 hetero atoms selected from nitrogen atom, sulfur atom and oxygen atom, (22) a 5- to 10-membered aromatic heterocyclic group that containing, in addition to carbon atom, 1 to 4 hetero atoms selected from nitrogen atom, sulfur atom and oxygen atom, (23) sulfo, and (24) $C_{6-14}$ aryloxy;

$R^4$ is (i) a $C_{1-6}$ alkyl group, a $C_{2-6}$ alkenyl group, a $C_{2-6}$ alkynyl group, or a $C_{3-6}$ cycloalkyl group, which has 1 to 3 group of a $C_{6-14}$ aryl group and a 5- to 14-membered, aromatic heterocyclic group that contains, in addition to carbon atom, 1 to 4 hetero atoms selected from nitrogen atom, sulfur atom and oxygen atom, which respectively may have 1 to 5 substituents selected from (1) halogen, (2) $C_{1-3}$ alkylenedioxy, (3) nitro, (4) cyano, (5) $C_{1-6}$ alkyl that may be halogenated, (6) $C_{2-6}$ alkenyl that may be halogenated, (7) $C_{2-6}$ alkynyl that may be halogenated, (8) $C_{3-6}$ cycloalkyl that may be halogenated, (9) $C_{6-14}$ aryl, (10) $C_{1-6}$ alkoxy that may be halogenated, (11) $C_{1-6}$ alkylthio that may be halogenated or mercapto, (12) hydroxyl, (13) amino, (14) mono-$C_{1-6}$ alkylamino, (15) mono-$C_{6-14}$ arylamino, (16) di-$C_{1-6}$ alkylamino, (17) di-$C_{6-14}$ arylamino, (18) acyl selected from formyl, carboxyl, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5- or 6-membered heterocyclic carbonyl that contains, in addition to carbon atom, 1 to 4 hetero atoms selected from nitrogen atom, sulfur atom and oxygen atom, mono-$C_{1-6}$ alkyl-carbamoyl, di-$C_{1-6}$ alkyl-carbamoyl, $C_{6-14}$ aryl-carbamoyl, thiocarbamoyl, 5- or 6-membered heterocyclic carbamoyl that contains, in addition to carbon atom, 1 to 4 hetero atoms selected from nitrogen atom, sulfur atom and oxygen atom, $C_{1-6}$ alkylsulfonyl, $C_{6-14}$ arylsulfonyl, $C_{1-6}$ alkylsulfinyl and $C_{6-14}$ arylsulfinyl, (19) acylamino selected from formylamino, $C_{1-6}$ alkyl-carbonylamido, $C_{6-14}$ aryl-carbonylamido, $C_{1-6}$ alkoxy-carbonylamido, $C_{1-6}$ alkylsulfonylamino and $C_{6-14}$ arylsulfonylamino, (20) acyloxy selected from $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, a di-$C_{1-6}$ alkyl-carbamoyloxy, $C_{6-14}$ aryl-carbamoyloxy and nicotinoyloxy, (21) 5- to 7-membered saturated-cyclic amino, which may have 1 to 3 substituents selected from $C_{1-6}$ alkyl, $C_{6-14}$ aryl, and a 5- to 10-membered aromatic heterocyclic group that contains, in addition to carbon atom, 1 to 4 hetero atoms selected from nitrogen atom, sulfur atom and oxygen atom, (22) a 5- to 10-membered aromatic heterocyclic group that contains, in addition to carbon atom, 1 to 4 hetero atoms selected from nitrogen atom, sulfur atom and oxygen atom, (23) sulfo, and (24) a $C_{6-14}$ aryloxy, and further may have 1 to 5 substituents selected from (1) halogen, (2) $C_{1-3}$ alkylenedioxy, (3) nitro, (4) cyano, (5) $C_{1-6}$ alkyl that may be halogenated, (6) $C_{2-6}$ alkenyl that may be halogenated, (7) $C_{2-6}$ alkynyl that may be halogenated, (8) $C_{3-6}$ cycloalkyl that may be halogenated, (9) $C_{6-14}$ aryl, (10) $C_{1-6}$ alkoxy that may be halogenated, (11) $C_{1-6}$ alkylthio that may be halogenated or mercapto, (12) hydroxyl, (13) amino, (14) mono-$C_{1-6}$ alkylamino, (15) mono-$C_{6-14}$ arylamino, (16) di-$C_{1-6}$ alkylamino, (17) di-$C_{6-14}$ arylamino, (18) acyl selected from formyl, carboxyl, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxycarbonyl, $C_{7-16}$ aralkyloxy-carbonyl, 5- or 6-membered heterocyclic carbonyl that contains, in addition to carbon atom, 1 to 4 hetero atoms selected from nitrogen atom, sulfur atom and oxygen atom, mono-$C_{1-6}$ alkyl-carbamoyl, di-$C_{1-6}$ alkyl-carbamoyl, $C_{6-14}$ aryl-carbamoyl, thiocarbamoyl, 5- or 6-membered heterocyclic carbamoyl that contains, in addition to carbon atom, 1 to 4 hetero atoms selected from nitrogen atom, sulfur atom and oxygen atom, $C_{1-6}$ alkylsulfonyl, $C_{6-14}$ arylsulfonyl, $C_{1-6}$ alkylsulfinyl and $C_{6-14}$ arylsulfinyl, (19) acylamino selected from formylamino, $C_{1-6}$ alkyl-carbonylamino, $C_{6-14}$ aryl-carbonylamino, $C_{1-6}$ alkoxy-carbonylamino, $C_{1-6}$ alkylsulfonylamino and $C_{6-14}$ arylsulfonylamino, (20) acyloxy selected from $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-14}$ aryl-carbamoyloxy and nicotinoyloxy, (21) 5- to 7-membered saturated-cyclic amino, which may have 1 to 3 substituents selected from $C_{1-6}$ alkyl, $C_{6-14}$ aryl, and 5- to 10-membered aromatic heterocyclic group that contains, in addition to carbon atom, 1 to 4 hetero atoms selected from nitrogen atom, sulfur atom and oxygen atom, (22) a 5- to 10-membered, aromatic heterocyclic group that contains, in addition to carbon atom, 1 to 4 hetero atoms selected from nitrogen atom, sulfur atom and oxygen atom, (23) sulfo, and (24) a $C_{6-14}$ aryloxy, or (ii) an acyl group that is selected from formyl, carboxyl, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryl-oxycarbonyl, $C_{7-16}$ aralkyl-oxycarbonyl, 5- or 6-membered heterocyclic carbonyl that contains, in addition to carbon atom, 1 to 4 hetero atoms selected from nitrogen atom, sulfur atom, and oxygen atom, mono-$C_{1-6}$ alkyl-carbamoyl, di-$C_{1-6}$ alkyl-carbamoyl, $C_{6-14}$ aryl-carbamoyl, thiocarbamoyl, 5- or 6-membered heterocyclic carbamoyl that contains, in addition to carbon atom, 1 to 4 hetero atom selected from nitrogen atom, sulfur atom and oxygen atom, $C_{1-6}$ alkylsulfonyl, $C_{6-14}$ arylsulfonyl, $C_{1-6}$ alkylsulfinyl and $C_{6-14}$ arylsulfinyl, which has 1 to 3 groups of a $C_{6-14}$ aryl group and a 5- to 14-membered aromatic heterocyclic group that contains, in addition to the carbon atom, 1 to 4 hetero atoms selected from nitrogen atom, sulfur atom and oxygen atom, which respectively may have 1 to 5 substituents selected from (1) halogen, (2) $C_{1-3}$ alkylenedioxy, (3) nitro, (4) cyano, (5) $C_{1-6}$ alkyl that may be halogenated, (6) $C_{2-6}$ alkenyl that may be halogenated, (7) $C_{2-6}$ alkynyl that may be halogenated, (8) $C_{3-6}$ cycloalkyl that may be halogenated, (9) $C_{6-14}$ aryl, (10) $C_{1-6}$ alkoxy that may be halogenated, (11) $C_{1-6}$ alkylthio that may be halogenated or mercapto, (12) hydroxyl, (13) amino, (14) mono-$C_{1-6}$ alkylamino, (15) mono-$C_{6-14}$ arylamino, (16) di-$C_{1-6}$ alkylamino, (17) di-$C_{6-14}$ arylamino, (18) acyl selected from formyl, carboxyl, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5- or 6-membered heterocyclic carbonyl that contains, in addition to carbon atom, 1 to 4 hetero atoms selected from nitrogen atom, sulfur atom and oxygen atom, mono-$C_{1-6}$ alkyl-carbamoyl, di-$C_{1-6}$ alkyl-carbamoyl, $C_{6-14}$ aryl-carbamoyl, thiocarbamoyl, 5- or 6-membered heterocyclic carbamoyl that contains, in addition to carbon atom, 1 to 4 hetero atoms selected from nitrogen atom, sulfur atom and oxygen atom, $C_{1-6}$ alkylsulfonyl, $C_{6-14}$ arylsulfonyl, $C_{1-6}$ alkylsulfinyl and $C_{6-14}$ arylsulfinyl, (19) acylamino selected from formylamino, $C_{1-6}$ alkyl-carbonylamino, $C_{6-14}$ arylcarbonylamino, $C_{1-6}$ alkoxy-carbonylamino, $C_{1-6}$ alkylsulfonylamino and $C_{6-14}$ arylsulfonylamino, (20) acyloxy selected from $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-14}$ aryl-carbamoyloxy, and nicotinoyloxy, (21) 5- to 7-membered, saturated-cyclic amino, which may have 1 to 3 substituents selected from $C_{1-6}$ alkyl, $C_{6-14}$ aryl, and a 5- to 10-membered, aromatic heterocyclic group that contains, in addition to carbon atom, 1 to 4 hetero atoms selected from nitrogen atom, sulfur atom and oxygen atom, (22) a 5- to 10-membered aromatic heterocyclic group that contains, in addition to carbon atom, 1 to 4 hetero atoms selected from nitrogen atom, sulfur atom and oxygen atom, (23) sulfo, and (24) $C_{6-14}$ aryloxy;

$R^5$ is (i) hydrogen atom, (ii) a $C_{1-6}$ alkyl group, or (iii) acyl selected from formyl, carboxyl, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5- or 6-membered heterocyclic carbonyl that contains, in addition to carbon atom, 1 to 4 hetero atoms selected from nitrogen atom, sulfur atom and oxygen atom, mono-$C_{1-6}$ alkyl-carbamoyl, di-$C_{1-6}$ alkyl-carbamoyl, $C_{6-14}$ aryl-carbamoyl, thiocarbamoyl, 5- or 6-membered heterocyclic carbamoyl that contains, in addition to carbon atom, 1 to 4 hetero atoms selected from nitrogen atom, sulfur atom and oxygen atom, $C_{1-6}$ alkylsulfonyl, $C_{6-14}$ arylsulfonyl, $C_{1-6}$ alkylsulfinyl and $C_{6-14}$ arylsulfinyl; and ring C is, in addition to a group represented by the formula —$NR^4(R^5)$, benzene ring, which may have 1 to 3 substituents selected from (1) halogen, (2) $C_{1-3}$ alkylenedioxy, (3) nitro, (4) cyano, (5) $C_{1-6}$ alkyl that may be halogenated, (6) $C_{2-6}$ alkenyl that may be halogenated, (7) $C_{2-6}$ alkynyl that may be halogenated, (8) $C_{3-6}$ cycloalkyl that may be halogenated, (9) $C_{6-14}$ aryl, (10) $C_{1-6}$ alkoxy that may be halogenated, (11) hydroxyl, (12) amino, (13) mono-$C_{1-6}$ alkylamino, (14) mono-$C_{6-14}$ arylamino, (15) di-$C_{1-6}$ alkylamino, (16) di-$C_{6-14}$ arylamino, (17) acyl selected from formyl, carboxyl, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5- or 6-membered heterocyclic carbonyl that contains, in addition to carbon atom, 1 to 4 hetero atoms selected from nitrogen atom, sulfur atom and oxygen atom, mono-$C_{1-6}$ alkyl-carbamoyl, di-$C_{1-6}$ alkyl-carbamoyl, $C_{6-14}$ aryl-carbamoyl, thiocarbamoyl, 5- or 6-membered heterocyclic carbamoyl that contains, in addition to carbon atom, 1 to 4 hetero atoms selected from nitrogen atom, sulfur atom and oxygen atom, $C_{1-6}$ alkylsulfonyl, $C_{6-14}$ arylsulfonyl, $C_{1-6}$ alkylsulfinyl, and $C_{6-14}$ arylsulfinyl, (18) acylamino selected from formylamino, $C_{1-6}$ alkyl-carboxamido, $C_{6-14}$ aryl-carboxamido, $C_{1-6}$ alkoxy-carboxamido, $C_{1-6}$ alkylsulfonylamino and $C_{6-14}$ arylsulfonylamino, (19) 5- to 7-membered saturated-cyclic amino, which may have 1 to 3 substituents selected from $C_{1-6}$ alkyl, $C_{6-14}$ aryl and a 5- to 10-membered aromatic heterocyclic group that contains, in addition to carbon atom, 1 to 4 hetero atoms selected from nitrogen atom, sulfur atom and oxygen atom, (20) a 5- to 10-membered aromatic heterocyclic group that contains, in addition to carbon atom, 1 to 4 hetero atoms selected from nitrogen atom, sulfur atom and oxygen atom, and (21) sulfo.

3. The compound according to claim 1, wherein $R^1$ and $R^2$ are the same or different and each is (i) hydrogen atom, (ii) a $C_{1-6}$ alkyl group, a $C_{2-6}$ alkenyl group, a $C_{2-6}$ alkynyl group, a $C_{3-6}$ cycloalkyl group, or a $C_{6-14}$ aryl group, which respectively may have 1 to 5 substituents selected from (1) halogen, (2) $C_{1-3}$ alkylenedioxy, (3) nitro, (4) cyano, (5) $C_{1-6}$ alkyl that may be halogenated, (6) $C_{2-6}$ alkenyl that may be halogenated, (7) $C_{2-6}$ alkynyl that may be halogenated, (8) $C_{3-6}$ cycloalkyl that may be halogenated, (9) $C_{6-14}$ aryl, (10) $C_{1-6}$ alkoxy that may be halogenated, (11) $C_{1-6}$ alkylthio that may be halogenated or mercapto, (12) hydroxyl, (13) amino, (14) mono-$C_{1-6}$ alkylamino, (15) mono-$C_{6-14}$ arylamino, (16) di-$C_{1-6}$ alkylamino, (17) di-$C_{6-14}$ arylamino, (18) acyl selected from formyl, carboxyl, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5- or 6-membered heterocyclic carbonyl that contains, in addition to carbon atom, 1 to 4 hetero atoms selected from nitrogen atom, sulfur atom and oxygen atom, mono-$C_{1-6}$ alkyl-carbamoyl, di-$C_{1-6}$ alkyl-carbamoyl, $C_{6-14}$ aryl-carbamoyl, thiocarbamoyl, 5- or 6-membered heterocyclic carbamoyl that contains, in addition to carbon atom, 1 to 4 hetero atoms selected from nitrogen atom, sulfur atom and oxygen atom, $C_{1-6}$ alkylsulfonyl, $C_{6-14}$ arylsulfonyl, $C_{1-6}$ alkylsulfinyl and $C_{6-14}$ arylsulfinyl, (19) acylamino selected from formylamino, $C_{1-6}$ alkyl-carboxamido, $C_{6-14}$ aryl-carboxamido, $C_{1-6}$ alkoxy-carboxamido, $C_{1-6}$ alkylsulfonylamino and $C_{6-14}$ arylsulfonylamino, (20) acyloxy selected from $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-14}$ aryl-carbamoyloxy and nicotinoyloxy, (21) 5- to 7-membered saturated-cyclic amino, which may have 1 to 3 substituents selected from $C_{1-6}$ alkyl, $C_{6-14}$ aryl, and a 5- to 10-membered aromatic heterocyclic group that contains, in addition to carbon atom, 1 to 4 hetero atoms selected from nitrogen atom, sulfur atom and oxygen atom, (22) a 5- to 10-membered aromatic heterocyclic group that contains, in addition to carbon atom, 1 to 4 hetero atoms selected from nitrogen atom, sulfur atom and oxygen atom, (23) sulfo, and (24) a $C_{6-14}$ aryloxy, or (iii) a 5- to 14-membered heterocyclic group that contains, in addition to carbon atom, 1 to 4 hetero atoms selected from nitrogen atom, sulfur atom and oxygen atom, which respectively may have 1 to 5 substituents selected from (1) halogen, (2) $C_{1-3}$ alkylenedioxy, (3) nitro, (4) cyano, (5) $C_{1-6}$ alkyl that may be halogenated, (6) $C_{2-6}$ alkenyl that may be halogenated, (7) $C_{2-6}$ alkynyl that may be halogenated, (8) $C_{3-6}$ cycloalkyl that may be halogenated, (9) $C_{6-14}$ aryl, (10) $C_{1-6}$ alkoxy that may be halogenated, (11) $C_{1-6}$ alkylthio that may be halogenated or mercapto, (12) hydroxyl, (13) amino, (14) mono-$C_{1-6}$ alkylamino, (15) mono-$C_{6-14}$ arylamino, (16) di-$C_{1-6}$ alkylamino, (17) di-$C_{6-14}$ arylamino, (18) acyl selected from formyl, carboxyl, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5- or 6-membered heterocyclic carbonyl that contains, in addition to carbon atom, 1 to 4 hetero atoms selected from nitrogen atom, sulfur atom and oxygen atom, mono-$C_{1-6}$ alkyl-carbamoyl, di-$C_{1-6}$ alkyl-carbamoyl, $C_{6-14}$ aryl-carbamoyl, thiocarbamoyl, 5- or 6-membered, heterocyclic carbamoyl that contains, in addition to carbon atom, 1 to 4 hetero atoms selected from nitrogen atom, sulfur atom and oxygen atom, $C_{1-6}$ alkylsulfonyl, $C_{6-14}$ arylsulfonyl, $C_{1-6}$ alkylsulfinyl and $C_{6-14}$ arylsulfinyl, (19) acylamino selected from formylamino, $C_{1-6}$ alkyl-carbonylamino, $C_{6-14}$ aryl-carbonylamino, $C_{1-6}$ alkoxy-carbonylamino, $C_{1-6}$ alkylsulfonylamino and $C_{6-14}$ arylsulfonylamino, (20) acyloxy selected from $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-14}$ aryl-carbamoyloxy and nicotinoyloxy, (21) 5- to 7-membered saturated-cyclic amino, which may have 1 to 3 substituents selected from $C_{1-6}$ alkyl, $C_{6-14}$ aryl, and a 5- to 10-membered aromatic heterocyclic group that contains, in addition to carbon atom, 1 to 4 hetero atoms selected from nitrogen atom, sulfur atom and oxygen atom, (22) a 5- to 10-membered aromatic heterocyclic group that contains, in addition to carbon atom, 1 to 4 hetero atoms selected from nitrogen atom, sulfur atom and oxygen atom, (23) sulfo, and (24) a $C_{6-14}$ aryloxy, or (iv) $R^1$ and $R^2$ form, together with the adjacent carbon atom, $C_{3-8}$ cycloalkane or a 3- to 8-membered heterocyclic ring that contains, in addition to carbon atom, 1 to 4 hetero atoms selected from nitrogen atom, sulfur atom and oxygen atom, which respectively may have 1 to 5 substituents selected from (1) halogen, (2) $C_{1-3}$ alkylenedioxy, (3) nitro, (4) cyano, (5) $C_{1-6}$ alkyl that may be halogenated, (6) $C_{2-6}$ alkenyl that may be halogenated, (7) $C_{2-6}$ alkynyl that may be halogenated, (8) $C_{3-6}$ cycloalkyl that may be halogenated, (9) $C_{6-14}$ aryl, (10) $C_{1-6}$ alkoxy that may be halogenated, (11) $C_{1-6}$ alkylthio that may be halogenated or mercapto, (12) hydroxyl, (13) amino, (14) mono-$C_{1-6}$ alkylamino, (15) mono-$C_{6-14}$ arylamino, (16) di-$C_{1-6}$ alkylamino, (17) di-$C_{6-14}$ arylamino, (18) acyl selected from formyl, carboxyl, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5- or 6-membered heterocyclic carbonyl that contains, in addition to carbon atom, 1 to 4 hetero atoms selected from nitrogen atom, sulfur atom and oxygen atom, mono-$C_{1-6}$ alkyl-carbamoyl, di-$C_{1-6}$ alkyl-carbamoyl, thiocarbamoyl, $C_{6-14}$ aryl-carbamoyl, 5- or 6-membered heterocyclic carbamoyl that contains, in addition to carbon atom, 1 to 4 hetero atoms selected from nitrogen atom, sulfur atom and oxygen atom, $C_{1-6}$ alkylsulfonyl, $C_{6-14}$ arylsulfonyl, $C_{1-6}$ alkylsulfinyl and $C_{6-14}$ arylsulfinyl, (19) acylamino selected from formylamino, $C_{1-6}$ alkyl-carbonylamino, $C_{6-14}$ aryl-carbonylamino, $C_{1-6}$ alkoxy-carbonylamino, $C_{1-6}$ alkylsulfonylamino and $C_{6-14}$ arylsulfonylamino, (20) acyloxy selected from $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-14}$ aryl-carbamoyloxy and nicotinoyloxy, (21) 5- to 7-membered saturated-cyclic amino, which may have 1 to 3 substituents selected from $C_{1-6}$ alkyl, $C_{6-14}$ aryl, and a 5- to 10-membered aromatic heterocyclic group that contains, in addition to carbon atom, 1 to 4 hetero atoms selected from nitrogen atom, sulfur atom and oxygen atom, (22) a 5- to 10-membered aromatic heterocyclic group that contains, besides the carbon atom, 1 to 4 hetero atoms selected from nitrogen atom, sulfur atom and oxygen atom, (23) sulfo, and (24) a $C_{6-14}$ aryloxy;

$R^3$ is $C_{6-14}$ aryl, which respectively may have 1 to 5 substituents selected from (1) halogen, (2) $C_{1-3}$ alkylenedioxy, (3) nitro, (4) cyano, (5) $C_{1-6}$ alkyl that may be halogenated, (6) $C_{2-6}$ alkenyl that may be halogenated, (7) $C_{2-6}$ alkynyl that may be halogenated, (8) $C_{3-6}$ cycloalkyl that may be halogenated, (9) $C_{6-14}$ aryl, (10) $C_{1-6}$ alkoxy that may be halogenated, (11) $C_{1-6}$ alkylthio that may be halogenated or mercapto, (12) hydroxyl,

(13) amino, (14) mono-$C_{1-6}$ alkylamino, (15) mono-$C_{6-14}$ arylamino, (16) di-$C_{1-6}$ alkylamino, (17) di-$C_{6-14}$ arylamino, (18) acyl selected from formyl, carboxyl, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5- or 6-membered heterocyclic carbonyl that contains, in addition to carbon atom, 1 to 4 hetero atoms selected from nitrogen atom, sulfur atom and oxygen atom, mono-$C_{1-6}$ alkyl-carbamoyl, di-$C_{1-6}$ alkyl-carbamoyl, $C_{6-14}$ aryl-carbamoyl, thiocarbamoyl, 5- or 6-membered heterocyclic carbamoyl that contains, in addition to carbon atom, 1 to 4 hetero atoms selected from nitrogen atom, sulfur atom and oxygen atom, $C_{1-6}$ alkylsulfonyl, $C_{6-14}$ arylsulfonyl, $C_{1-6}$ alkylsulfinyl and $C_{6-14}$ arylsulfinyl, (19) acylamino selected from formylamino, $C_{1-6}$ alkyl-carbonylamino, $C_{6-14}$ aryl-carbonylamino, $C_{1-6}$ alkoxy-carbonylamino, $C_{1-6}$ alkylsulfonylamino and $C_{6-14}$ arylsulfonylamino, (20) acyloxy selected from $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-14}$ aryl-carbamoyloxy and nicotinoyloxy, (21) 5- to 7-membered saturated-cyclic amino, which may have 1 to 3 substituents selected from $C_{1-6}$ alkyl, $C_{6-14}$ aryl, and a 5- to 10-membered aromatic heterocyclic group that contains, in addition to carbon atom, 1 to 4 hetero atoms selected from nitrogen atom, sulfur atom and oxygen atom, (22) a 5- to 10-membered aromatic heterocyclic group that contains, in addition to carbon atom, 1 to 4 hetero atoms selected from nitrogen atom, sulfur atom and oxygen atom, (23) sulfo, and (24) $C_{6-14}$ aryloxy;

$R^4$ is (i) a $C_{1-6}$ alkyl group, a $C_{2-6}$ alkenyl group, a $C_{2-6}$ alkynyl group, or a $C_{3-6}$ cycloalkyl group, which have 1 to 3 groups of a $C_{6-14}$ aryl group and a 5- to 14-membered aromatic heterocyclic group that contains, in addition to carbon atom, 1 to 4 hetero atoms selected from nitrogen atom, sulfur atom and oxygen atom, which respectively may have 1 to 5 substituents selected from (1) halogen, (2) $C_{1-3}$ alkylenedioxy, (3) nitro, (4) cyano, (5) $C_{1-6}$ alkyl that may be halogenated, (6) $C_{2-6}$ alkenyl that may be halogenated, (7) $C_{2-6}$ alkynyl that may be halogenated, (8) $C_{3-6}$ cycloalkyl that may be halogenated, (9) $C_{6-14}$ aryl, (10) $C_{1-6}$ alkoxy that may be halogenated, (11) $C_{1-6}$ alkylthio that may be halogenated or mercapto, (12) hydroxyl, (13) amino, (14) mono-$C_{1-6}$ alkylamino, (15) mono-$C_{6-14}$ arylamino, (16) di-$C_{1-6}$ alkylamino, (17) di-$C_{6-14}$ arylamino, (18) acyl selected from formyl, carboxyl, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5- or 6-membered heterocyclic carbonyl that contains, in addition to carbon atom, 1 to 4 hetero atoms selected from nitrogen atom, sulfur atom and oxygen atom, mono-$C_{1-6}$ alkyl-carbamoyl, di-$C_{1-6}$ alkyl-carbamoyl, $C_{6-14}$ aryl-carbamoyl, thiocarbamoyl, 5- or 6-membered heterocyclic carbamoyl that contains, in addition to carbon atom, 1 to 4 hetero atoms selected from nitrogen atom, sulfur atom and oxygen atom, $C_{1-6}$ alkylsulfonyl, $C_{6-14}$ arylsulfonyl, $C_{1-6}$ alkylsulfinyl and $C_{6-14}$ arylsulfinyl, (19) acylamino selected from formylamino, $C_{1-6}$ alkyl-carbonylamino, $C_{6-14}$ aryl-carbonylamino, $C_{1-6}$ alkoxy-carbonylamino, $C_{1-6}$ alkylsulfonylamino and $C_{6-14}$ arylsulfonylamino, (20) acyloxy selected from $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-14}$ aryl-carbamoyloxy and nicotinoyloxy, (21) 5- to 7-membered saturated-cyclic amino, which may have 1 to 3 substituents selected from $C_{1-6}$ alkyl, $C_{6-14}$ aryl, and a 5- to 10-membered aromatic heterocyclic group that contains, in addition to carbon atom, 1 to 4 hetero atoms selected from nitrogen atom, sulfur atom and oxygen atom, (22) a 5- to 10-membered aromatic heterocyclic group that contains, in addition to carbon atom, 1 to 4 hetero atoms selected from nitrogen atom, sulfur atom and oxygen atom, (23) sulfo, and (24) $C_{6-14}$ aryloxy, or (ii) an acyl group that is selected from formyl, carboxyl, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5- or 6-membered heterocyclic carbonyl that contains, in addition to carbon atom, 1 to 4 hetero atoms selected from nitrogen atom, sulfur atom and oxygen atom, mono-$C_{1-6}$ alkyl-carbamoyl, di-$C_{1-6}$ alkyl-carbamoyl, $C_{6-14}$ aryl-carbamoyl, thiocarbamoyl, 5- or 6-membered heterocyclic carbamoyl that contains, in addition to carbon atom, 1 to 4 hetero atoms selected from nitrogen atom, sulfur atom and oxygen atom, $C_{1-6}$ alkylsulfonyl, $C_{6-14}$ arylsulfonyl, $C_{1-6}$ alkylsulfinyl and $C_{6-14}$ arylsulfinyl, which have 1 to 3 groups of a $C_{6-14}$ aryl group and a 5- to 14-membered aromatic heterocyclic group that contains, in addition to carbon atom, 1 to 4 hetero atoms selected from nitrogen atom, sulfur atom and oxygen atom, which respectively may have 1 to 5 substituents selected from (1) halogen, (2) $C_{1-3}$ alkylenedioxy, (3) nitro, (4) cyano, (5) $C_{1-6}$ alkyl that may be halogenated, (6) $C_{2-6}$ alkenyl that may be halogenated, (7) $C_{2-6}$ alkynyl that may be halogenated, (8) $C_{3-6}$ cycloalkyl that may be halogenated, (9) $C_{6-14}$ aryl, (10) $C_{1-6}$ alkoxy that may be halogenated, (11) $C_{1-6}$ alkylthio that may be halogenated or mercapto, (12) hydroxyl, (13) amino, (14) mono-$C_{1-6}$ alkylamino, (15) mono-$C_{6-14}$ arylamino, (16) di-$C_{1-6}$ alkylamino, (17) di-$C_{6-14}$ arylamino, (18) acyl selected from formyl, carboxyl, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5- or 6-membered, heterocyclic carbonyl that contains, in addition to carbon atom, 1 to 4 hetero atoms selected from nitrogen atom, sulfur atom and oxygen atom, mono-$C_{1-6}$ alkyl-carbamoyl, di-$C_{1-6}$ alkyl-carbamoyl, $C_{6-14}$ aryl-carbamoyl, thiocarbamoyl, 5- or 6-membered heterocyclic carbamoyl that contains, in addition to carbon atom, 1 to 4 hetero atoms selected from nitrogen atom, sulfur atom and oxygen atom, $C_{1-6}$ alkylsulfonyl, $C_{6-14}$ arylsulfonyl, $C_{1-6}$ alkylsulfinyl and $C_{6-14}$ arylsulfinyl, (19) acylamino selected from formylamino, $C_{1-6}$ alkyl-carbonylamino, $C_{6-14}$ aryl-carbonylamino, $C_{1-6}$ alkoxy-carbonylamino, $C_{1-6}$ alkylsulfonylamino and $C_{6-14}$ arylsulfonylamino, (20) acyloxy selected from $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-14}$ aryl-carbamoyloxy and nicotinoyloxy, (21) 5- to 7-membered, saturated-cyclic amino, which may have 1 to 3 substituents selected from $C_{1-6}$ alkyl, $C_{6-14}$ aryl, and a 5- to 10-membered aromatic heterocyclic group that contains, in addition to carbon atom, 1 to 4 hetero atoms selected from nitrogen atom, sulfur atom and oxygen atom, (22) a 5- to 10-membered aromatic heterocyclic group that contains, in addition to carbon atom, 1 to 4 hetero atoms selected from nitrogen atom, sulfur atom and oxygen atom, (23) sulfo, and (24) $C_{6-14}$ aryloxy.

4. The compound according to claim 1, wherein $R^1$ and $R^2$ are the same or different and each is hydrogen atom or a $C_{1-6}$ alkyl group which may be substituted.

5. The compound according to claim 1, wherein each of $R^1$ and $R^2$ is hydrogen atom or a $C_{1-6}$ alkyl group.

6. The compound according to claim 1, wherein each of $R^1$ and $R^2$ is hydrogen atom or methyl group.

7. The compound according to claim 1, wherein $R^3$ is phenyl group that may be substituted with halogen or $C_{1-6}$ alkyl.

8. The compound according to claim 1, wherein $R^3$ is phenyl group that may be substituted with fluorine, methyl or isopropyl.

9. The compound according to claim 1, wherein the substitution position on ring C of a group represented by the formula —$NR^4(R^5)$ is 5-position on the benzofuran ring or the dihydrobenzofuran ring.

10. The compound according to claim 1, wherein $R^4$ is (1) a $C_{1-6}$ alkyl group that is substituted with an aromatic group that may be substituted with halogen, $C_{1-6}$ alkoxy or $C_{1-3}$ alkylenedioxy, or (2) an acyl group, which contains an aromatic group that may be substituted with halogen, $C_{1-6}$ alkoxy or $C_{1-3}$ alkylenedioxy.

11. The compound according to claim 1, wherein $R^4$ is benzyl group or phenethyl group that may be substituted with fluorine, methoxy or methylenedioxy.

12. The compound according to claim 1, wherein $R^5$ is hydrogen atom, a $C_{1-6}$ alkyl group or a $C_{1-6}$ alkyl-carbonyl group.

13. The compound according claim 1, wherein $R^5$ is hydrogen atom or methyl group.

14. The compound according to claim 1, wherein ring C is benzene ring that may be further substituted with 1 to 3 $C_{1-6}$ alkyl groups.

15. The compound according to claim 1, wherein ring C is benzene ring that is further substituted with 3 methyl groups.

16. The compound according to claim 1, wherein $R^1$ and $R^2$ are the same or different and each is hydrogen atom or a $C_{1-6}$ alkyl group,
 $R^3$ is phenyl group that may be substituted with halogen or $C_{1-6}$ alkyl;
 $R^4$ is (1) a $C_{1-6}$ alkyl group that is substituted with $C_{6-14}$ aryl, thienyl or pyridyl, which may be substituted with halogen, $C_{1-6}$ alkoxy or $C_{1-3}$ alkylenedioxy, or (2) a $C_{6-14}$ aryl-carbonyl group, a $C_{7-16}$ aralkyl-carbonyl group, a $C_{6-14}$ arylsulfonyl group, nicotinoyl group or thenoyl group, which may be substituted with halogen, $C_{1-6}$ alkoxy or $C_{1-3}$ alkylenedioxy;
 $R^5$ is hydrogen atom, a $C_{1-6}$ alkyl group or a $C_{1-6}$ alkylcarbonyl group; and
 ring C is benzene ring that is further substituted with 1 to 3 $C_{1-6}$ alkyl groups.

17. The compound according to claim 1, wherein each of $R^1$ and $R^2$ is hydrogen atom or a $C_{1-3}$ alkyl group;
 $R^3$ is a $C_{6-14}$ aryl group that may be substituted with a halogen atom or $C_{1-6}$ alkyl;
 $R^4$ is a $C_{7-15}$ aralkyl group that may be substituted with a halogen atom, $C_{1-6}$ alkoxy or $C_{1-3}$ alkylenedioxy;
 $R^5$ is hydrogen atom or a $C_{1-6}$ alkyl group;

----- is a single bond; and
 ring C is benzene ring that is further substituted with 3 $C_{1-6}$ alkyl groups.

18. The compound according to claim 1, wherein each of $R^1$ and $R^2$ is methyl group;
 $R^3$ is phenyl group that may be substituted with fluorine, methyl or isopropyl;
 $R^4$ is benzyl group or phenethyl group that may be substituted with fluorine, methoxy or methylenedioxy;
 $R^5$ is hydrogen atom or methyl group;
 ----- is a single bond; and
 ring C is benzene ring that is further substituted with 3 methyl groups.

19. [1] N-(4-fluorobenzyl)-2,2,4,6,7-pentamethyl-3-phenyl-2,3-dihydro-1-benzofuran-5-amine, [2] N-benzyl-3-(4-isopropylphenyl)-2,2,4,6,7-pentamethyl-2,3-dihydro-1-benzofuran-5-amine, [3] 3-(4-isopropylphenyl)-N-(4-methoxybenzyl)-N,2,2,4,6,7-hexamethyl-2,3-dihydro-1-benzofuran-5-amine, [4] 3-(4-isopropylphenyl)-N-[2-(4-methoxyphenyl)ethyl]-2,2,4,6,7-pentamethyl-2,3-dihydro-1-benzofuran-5-amine, [5] N-(4-fluorobenzyl)-3-(4-isopropylphenyl)-2,2,4,6,7-pentamethyl-2,3-dihydro-1-benzofuran-5-amine, [6] N-(1,3-benzodioxol-5-ylmethyl)-3-(4-isopropylphenyl)-2,2,4,6,7-pentamethyl-2,3-dihydro-1-benzofuran-5-amine, [7] N-(4-fluorobenzyl)-3-(4-fluorophenyl)-2,2,4,6,7-pentamethyl-2,3-dihydro-1-benzofuran-5-amine, [8] N-(4-methoxybenzyl)-2,2,4,6,7-pentamethyl-3-(4-methylphenyl)-2,3-dihydro-1-benzofuran-5-amine, [9] N-(4-fluorobenzyl)-2,2,4,6,7- pentamethyl-3-(4-methylphenyl)-2,3-dihydro-1-benzofuran-5-amine, [10] 3-(4-isopropylphenyl)-N-(4-methoxybenzyl)-2,4,6,7-tetramethyl-1-benzofuran-5-amine, [11] N-(4-fluorobenzyl)-3-(4-isopropylphenyl)-2,4,6,7-tetramethyl-1-benzofuran-5-amine, [12] N-(4-fluorobenzyl)-3-(4-fluorophenyl)-2,4,6,7-tetramethyl-1- benzofuran-5-amine, [13] N-(4-fluorobenzyl)-3-(4-isopropylphenyl)-1',4,6,7-tetramethylspiro[benzofuran-2(3H),4'-piperidine]-5-amine, or [14] (+)-N-(4-fluorobenzyl)-3-(4-isopropylphenyl)-2,2,4,6,7-pentamethyl-2,3-dihydro-1-benzofuran-5-amine hydrochloride.

20. A pharmaceutical composition which comprises a compound represented by the formula:

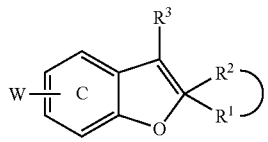

wherein $R^1$ and $R^2$ are the same or different and each is hydrogen atom, a hydrocarbon group that may be substituted or a heterocyclic group that may be substituted, ----- is a single bond or a double bond, W is
a group represented by the formula:

(Wb)

wherein $R^4$ is (1) an aliphatic hydrocarbon group which may be substituted with an aromatic group that may be substituted and, may further be substituted, or (2) an acyl group containing an aromatic group that may be substituted, $R^5$ is hydrogen atom, a $C_{1-6}$ alkyl group, or an acyl group, $R^3$ is a $C_{6-14}$ aryl group that may be substituted and ring C is benzene ring that may be further substituted, in addition to the group represented by Wb, or a salt thereof.

* * * * *